US007129259B2

(12) United States Patent
Chen et al.

(10) Patent No.: US 7,129,259 B2
(45) Date of Patent: Oct. 31, 2006

(54) HALOGENATED BIARYL HETEROCYCLIC COMPOUNDS AND METHODS OF MAKING AND USING THE SAME

(75) Inventors: Shili Chen, Cheshire, CT (US); Jiacheng Zhou, Hockessin, DE (US); Yusheng Wu, Lebanon, NJ (US); Deping Wang, Cheshire, CT (US); Joseph M. Salvino, Branford, CT (US); Adegboyega K. Oyelere, Hamden, CT (US); Rongliang Lou, Hamden, CT (US)

(73) Assignee: Rib-X Pharmaceuticals, Inc., New Haven, CT (US)

( * ) Notice: Subject to any disclaimer, the term of this patent is extended or adjusted under 35 U.S.C. 154(b) by 9 days.

(21) Appl. No.: 11/001,446

(22) Filed: Dec. 1, 2004

(65) Prior Publication Data

US 2005/0153971 A1 Jul. 14, 2005

Related U.S. Application Data

(60) Provisional application No. 60/576,267, filed on Jun. 2, 2004, provisional application No. 60/530,371, filed on Dec. 17, 2003.

(51) Int. Cl.
*C07D 261/04* (2006.01)
*C07D 263/04* (2006.01)
*C07D 263/08* (2006.01)
*A61K 31/42* (2006.01)
*A61K 31/421* (2006.01)

(52) U.S. Cl. ....................... 514/376; 548/225; 548/243

(58) Field of Classification Search ................ 514/376; 548/225, 243

See application file for complete search history.

(56) References Cited

U.S. PATENT DOCUMENTS

| | | | | |
|---|---|---|---|---|
| 4,348,393 | A | 9/1982 | Bourgery et al. | 424/248.57 |
| 4,948,801 | A | 8/1990 | Carlson et al. | 544/307 |
| 5,043,443 | A | 8/1991 | Carlson et al. | 544/112 |
| 5,130,316 | A | 7/1992 | Carlson et al. | 514/255 |
| 5,254,577 | A * | 10/1993 | Carlson et al. | 514/376 |
| 5,523,403 | A | 6/1996 | Barbachyn | 544/137 |
| 5,565,571 | A | 10/1996 | Barbachyn et al. | 546/144 |
| 5,627,181 | A | 5/1997 | Riedl et al. | 514/236.8 |
| 5,654,428 | A | 8/1997 | Barbachyn et al. | 544/235 |
| 5,654,435 | A | 8/1997 | Barbachyn et al. | 546/271.4 |
| 5,684,023 | A | 11/1997 | Riedl et al. | 514/337 |
| 5,756,732 | A | 5/1998 | Barbachyn et al. | 544/112 |
| 5,801,246 | A | 9/1998 | Barbachyn et al. | 548/152 |
| 5,843,967 | A | 12/1998 | Riedl et al. | 514/340 |
| 5,922,708 | A | 7/1999 | Riedl et al. | 514/236.8 |
| 5,929,248 | A | 7/1999 | Barbachyn et al. | 548/184 |
| 5,981,528 | A | 11/1999 | Gravestock | 514/252 |
| 6,239,152 | B1 | 5/2001 | Gordeev et al. | 514/340 |
| 6,271,383 | B1 | 8/2001 | Gravestock | 546/209 |
| 6,365,751 | B1 | 4/2002 | Gravestock | 548/229 |
| 6,441,005 | B1 | 8/2002 | Gordeev et al. | 514/340 |
| 6,495,551 | B1 | 12/2002 | Betts et al. | 514/249 |
| 6,531,470 | B1 | 3/2003 | Gordeev et al. | 514/236.8 |
| 6,562,844 | B1 | 5/2003 | Gordeev et al. | 514/340 |
| 6,605,630 | B1 | 8/2003 | Gravestock | 514/376 |
| 6,617,339 | B1 | 9/2003 | Gravestock | 514/340 |
| 6,638,955 | B1 | 10/2003 | Gravestock | 514/340 |
| 6,689,779 | B1 | 2/2004 | Lee et al. | 514/235.8 |
| 6,821,980 | B1 | 11/2004 | Guerry et al. | 514/275 |
| 2002/0169191 | A1 | 11/2002 | Gordev et al. | 514/376 |
| 2002/0183371 | A1 | 12/2002 | Gordev et al. | 514/376 |
| 2003/0144263 | A1 | 7/2003 | Gravestock | 514/210.2 |
| 2003/0166620 | A1 | 9/2003 | Lee et al. | 514/151 |
| 2004/0132764 | A1 | 7/2004 | Locher | 514/300 |
| 2005/0038092 | A1 | 2/2005 | Fukuda | 514/376 |

FOREIGN PATENT DOCUMENTS

| | | |
|---|---|---|
| DE | 100 34 627 | 1/2002 |
| EP | 0694543 | 1/1996 |
| EP | 1286998 | 6/2004 |
| GB | WO 2004/056818 | * 12/2003 |
| WO | WO 93/09103 A1 | 5/1993 |
| WO | WO 94/13649 A1 | 6/1994 |
| WO | WO 97/30995 A1 | 8/1997 |
| WO | WO 98/054161 | 12/1998 |
| WO | WO 99/10342 A1 | 3/1999 |
| WO | WO 99/28317 A1 | 6/1999 |
| WO | WO 99/033839 | 7/1999 |
| WO | WO 99/37630 A1 | 7/1999 |
| WO | WO 99/64416 A2 | 12/1999 |
| WO | WO 99/64417 A2 | 12/1999 |

(Continued)

OTHER PUBLICATIONS

Park, Chung-Ho, et al., "Antibacterials. Synthesis and Structure -Activity Studies of 3-Aryl-2-oxooxazoldines. 4. Multiply-Substituted Aryl Derivatives," J. Med. Chem., vol. 35(6), pp. 1156-1165 (1992).

(Continued)

*Primary Examiner*—Kamal A. Saeed
*Assistant Examiner*—Susannah L. Chung
(74) *Attorney, Agent, or Firm*—Ivor R. Elrifi; Mintz, Levin, Cohn, Ferris, Glovsky and Popeo, P.C.; Heidi A. Erlacher

(57) ABSTRACT

The present invention relates generally to the field of anti-infective, anti-proliferative, anti-inflammatory, and prokinetic agents. More particularly, the invention relates to a family of compounds having at least one halogenated hydrocarbon moiety, a biaryl moiety, and at least one heterocyclic moiety, that are useful as such agents.

111 Claims, No Drawings

FOREIGN PATENT DOCUMENTS

| | | | |
|---|---|---|---|
| WO | WO 00/10566 | | 3/2000 |
| WO | WO 00/21960 | A1 | 4/2000 |
| WO | WO 00/029396 | | 5/2000 |
| WO | WO 01/09107 | A1 | 2/2001 |
| WO | WO 01/32633 | A1 | 5/2001 |
| WO | WO 01/40236 | A2 | 6/2001 |
| WO | WO 01/042229 | | 6/2001 |
| WO | WO 01/81350 | A1 | 11/2001 |
| WO | WO 01/94342 | A1 | 12/2001 |
| WO | WO 02/080841 | A2 | 10/2002 |
| WO | WO 02/081468 | A1 | 10/2002 |
| WO | WO 02/081469 | A1 | 10/2002 |
| WO | WO 02/081470 | A1 | 10/2002 |
| WO | WO 02/096890 | A2 | 12/2002 |
| WO | WO 02/096916 | A1 | 12/2002 |
| WO | WO 03/022824 | A1 | 3/2003 |
| WO | WO 03/035648 | A1 | 5/2003 |
| WO | WO 03/072553 | A1 | 9/2003 |
| WO | WO 03/072575 | A1 | 9/2003 |
| WO | WO 03/084534 | | 10/2003 |
| WO | WO 04/029066 | A2 | 4/2004 |
| WO | WO 04/048392 | A1 | 6/2004 |
| WO | WO 04/056817 | A1 | 7/2004 |
| WO | WO 04/056818 | A1 | 7/2004 |
| WO | WO 04/056819 | A1 | 7/2004 |
| WO | WO 04/078753 | A1 | 9/2004 |
| WO | WO 04/089943 | A1 | 10/2004 |
| WO | WO 05/003087 | A2 | 1/2005 |
| WO | WO 05/012270 | A2 | 2/2005 |
| WO | WO 05/012271 | A2 | 2/2005 |
| WO | WO 05/019211 | A2 | 3/2005 |
| WO | WO 05/058886 | A1 | 6/2005 |
| WO | WO 05/070904 | A2 | 8/2005 |

OTHER PUBLICATIONS

Gregory, Walter, et al., “Antibacterials, Synthesis and Structure-Activity Studies of 3-Aryl-2-oxooxazoldines. 1 The “B”Group,” J. Med. Chem., vol. 32(8) pp. 1673-1681 (1989).
Brickner *Current Pharmaceutical Design*, 2:175-194 (1996).
Zurenko, G. E., et al., “Oxazolidinone Antibacterial Agents Development of the Clinical Candidates Eperezolid and Linezolid,” Expert Opinion on Investigational drugs, Ashley Publications LTD., London, GB, vol. 6 (2), 1997, pp. 151-158.
International Search Report amd Written Opinion for International Patent Application No. PCT/US04/039988, dated Apr. 21, 2005, 16 pages.

* cited by examiner

HALOGENATED BIARYL HETEROCYCLIC COMPOUNDS AND METHODS OF MAKING AND USING THE SAME

RELATED APPLICATION

This application claims the benefit of and priority to U.S. Patent Application Nos. 60/530,371, filed Dec. 17, 2003, and 60/576,267, filed Jun. 2, 2004, the disclosures of which are incorporated by reference herein.

FIELD OF THE INVENTION

The present invention relates generally to the field of anti-infective, anti-proliferative, anti-inflammatory, and prokinetic agents. More particularly, the invention relates to a family of halogenated biaryl heterocyclic compounds, comprising at least one halogenated hydrocarbon moiety, a biaryl moiety, and at least one heterocyclic moiety, that are useful as therapeutic agents.

BACKGROUND

Since the discovery of penicillin in the 1920s and streptomycin in the 1940s, many new compounds have been discovered or specifically designed for use as antibiotic agents. It was once believed that infectious diseases could be completely controlled or eradicated with the use of such therapeutic agents. However, such beliefs have been shaken by the fact that strains of cells or microorganisms resistant to currently effective therapeutic agents continue to evolve. In fact, virtually every antibiotic agent developed for clinical use has ultimately encountered problems with the emergence of resistant bacteria. For example, resistant strains of Gram-positive bacteria such as methicillin-resistant staphylocci, penicillin-resistant streptococci, and vancomycin-resistant enterococci have developed, which can cause serious and even fatal results for patients infected with such resistant bacteria. Bacteria that are resistant to macrolide antibiotics, i.e., antibiotics based on a 14- to 16-membered lactone ring, have developed. Also, resistant strains of Gram-negative bacteria such as *H. influenzae* and *M. catarrhalis* have been identified. See, e.g., F. D. Lowry, "Antimicrobial Resistance: The Example of *Staphylococcus aureus*," *J. Clin. Invest.*, vol. 111, no. 9, pp. 1265–1273 (2003); and Gold, H. S. and Moellering, R. C., Jr., "Antimicrobial-Drug Resistance," *N. Engl. J. Med.*, vol. 335, pp. 1445–53 (1996).

The problem of resistance is not limited to the area of anti-infective agents, because resistance has also been encountered with anti-proliferative agents used in cancer chemotherapy. Therefore, there exists a need for new anti-infective and anti-proliferative agents that are both effective against resistant bacteria and resistant strains of cancer cells.

In the antibiotic area, despite the problem of increasing antibiotic resistance, no new major classes of antibiotics have been developed for clinical use since the approval in the United States in 2000 of the oxazolidinone ring-containing antibiotic, N-[[(5S)-3-[3-fluoro-4-(4-morpholinyl)phenyl]-2-oxo-5-oxazolidinyl]methyl acetamide, which is known as linezolid and is sold under the tradename Zyvox® (see compound A). See, R. C. Moellering, Jr., "Linezolid: The First Oxazolidinone Antimicrobial," *Annals of Internal Medicine*, vol. 138, no. 2, pp. 135–142 (2003).

A

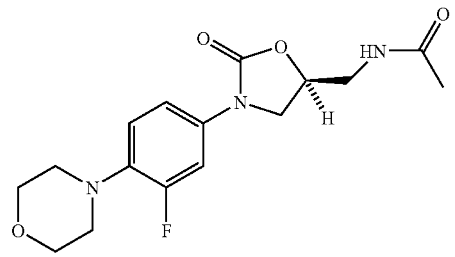

Linezolid was approved for use as an anti-bacterial agent active against Gram-positive organisms. Unfortunately, linezolid-resistant strains of organisms are already being reported. See, Tsiodras et al., *Lancet*, vol. 358, p. 207 (2001); Gonzales et al., *Lancet*, vol 357, p. 1179 (2001); Zurenko et al., *Proceedings Of The* 39*th* *Annual Interscience Conference On Antibacterial Agents And Chemotherapy* (*ICAAC*), San Francisco, Calif., USA (Sep. 26–29, 1999). Because linezolid is both a clinically effective and commercially significant anti-microbial agent, investigators have been working to develop other effective linezolid derivatives.

Notwithstanding the foregoing, there is an ongoing need for new anti-infective and anti-proliferative agents. Furthermore, because many anti-infective and anti-proliferative agents have utility as anti-inflammatory agents and prokinetic agents, there is also an ongoing need for new compounds useful as anti-inflammatory and prokinetic agents.

SUMMARY OF THE INVENTION

The invention provides a family of compounds useful as anti-infective agents and/or anti-proliferative agents, for example, chemotherapeutic agents, anti-microbial agents, anti-bacterial agents, anti-fungal agents, anti-parasitic agents, anti-viral agents, anti-inflammatory agents, and/or prokinetic (gastrointestinal modulatory) agents, having the formula:

$$M-X-L-\underset{|}{\overset{(R^1)_m}{A}}-\overset{(R^2)_n}{B}-Het-CH_2-R^3,$$

or a pharmaceutically acceptable salt, ester or prodrug thereof, wherein Het-$CH_2$—$R^3$ is selected from the group consisting of:

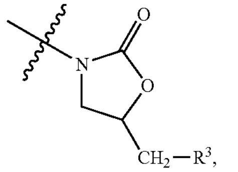

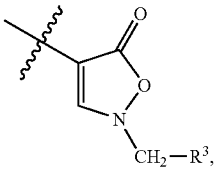

-continued

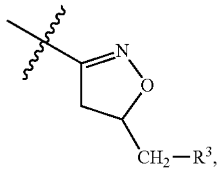

and

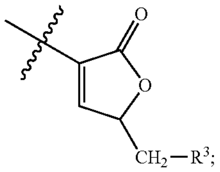

A and B independently are selected from the group consisting of phenyl, pyridyl, pyrazinyl, pyrimidinyl, and pyridazinyl; M is a halogenated $C_{1-6}$ alkyl, $C_{2-6}$ alkenyl, or $C_{2-6}$ alkynyl group; and the variables L, X, $R^1$, $R^2$, $R^3$, m, and n can be selected from the respective groups of chemical moieties or integers later defined in the detailed description.

Particular embodiments of compounds of the invention include those having the formula:

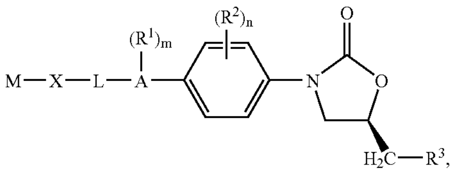

or a pharmaceutically acceptable salt, ester or prodrug thereof, wherein A is selected from the group consisting of phenyl and pyridyl, $R^2$ is selected from the group consisting of H and F, n is 0, 1, or 2, and the variables L, M, $R^1$, $R^3$, X, and m can be selected from the respective groups of chemical moieties or integers later defined in the detailed description.

Other embodiments of compounds of the invention include those having the formula:

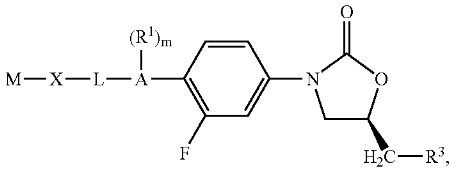

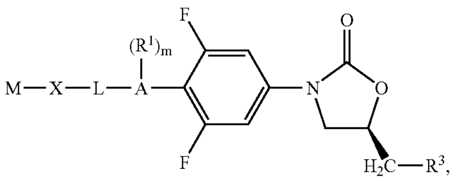

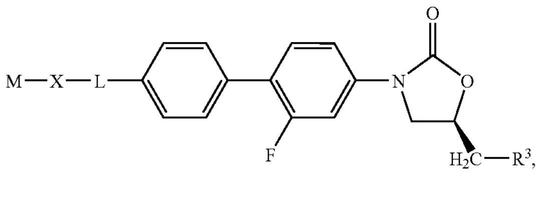

-continued

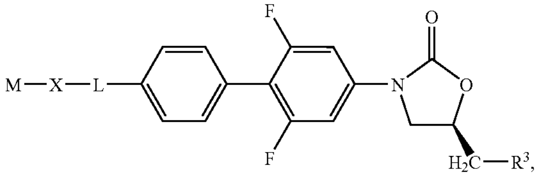

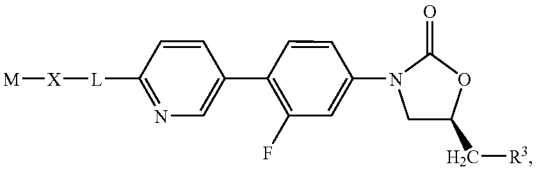

or

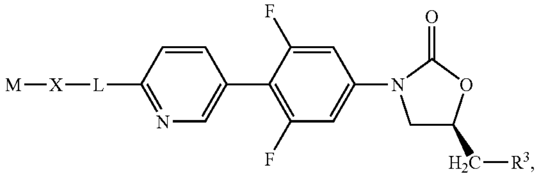

or a pharmaceutically acceptable salt, ester or prodrug thereof, wherein the variables A, L, M, $R^1$, $R^3$, X and m are selected from the respective groups of chemical moieties or integers later defined in the detailed description.

In addition, the invention provides methods of synthesizing the foregoing compounds. Following synthesis, an effective amount of one or more of the compounds can be formulated with a pharmaceutically acceptable carrier for administration to a mammal for use as an anti-cancer, anti-microbial, anti-biotic, anti-fungal, anti-parasitic or anti-viral agent, or to treat a proliferative disease, an inflammatory disease or a gastrointestinal motility disorder. The compounds or formulations can be administered, for example, via oral, parenteral, or topical routes, to provide an effective amount of the compound to the mammal.

The foregoing and other aspects and embodiments of the invention may be more fully understood by reference to the following detailed description and claims.

DETAILED DESCRIPTION OF THE INVENTION

The present invention provides a family of compounds that can be used as anti-proliferative agents and/or anti-infective agents. The compounds may be used without limitation, for example, as anti-cancer, anti-microbial, anti-bacterial, anti-fungal, anti-parasitic and/or anti-viral agents. Further, the present invention provides a family of compounds that can be used without limitation as anti-inflammatory agents, for example, for use in treating chronic inflammatory airway diseases, and/or as prokinetic agents, for example, for use in treating gastrointestinal motility disorders such as gastroesophageal reflux disease, gastroparesis (diabetic and post surgical), irritable bowel syndrome, and constipation.

1. Definitions

The term "substituted," as used herein, means that any one or more hydrogens on the designated atom is replaced with a selection from the indicated group, provided that the designated atom's normal valency is not exceeded, and that the substitution results in a stable compound. When the substituent is keto (i.e., =O), then 2 hydrogens on the atom are replaced. Ring double bonds, as used herein, are double bonds that are formed between two adjacent ring atoms (e.g., C=C, C=N, or N=N).

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The compounds described herein may have asymmetric centers. Compounds of the present invention containing an asymmetrically substituted atom can be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and can be isolated as a mixture of isomers or as separated isomeric forms. All chiral, diastereomeric, racemic, and geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

When any variable (e.g., $R^1$) occurs more than one time in any constituent or formula for a compound, its definition at each occurrence is independent of its definition at every other occurrence. Thus, for example, if a group is shown to be substituted with 0–2 $R^1$ moieties, then the group can optionally be substituted with up to two $R^1$ moieties and $R^1$ at each occurrence is selected independently from the definition of $R^1$. Also, combinations of substituents and/or variables are permissible, but only if such combinations result in stable compounds.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

Compounds of the present invention that contain one or more nitrogen atoms can be converted to N-oxides by treatment with an oxidizing agent (e.g., meta-chloroperoxybenzoic acid (m-CPBA) and/or hydrogen peroxide) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogen atom(s) in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_{1-6}$ alkyl, alkenyl, alkynyl, $C_{3-14}$ carbocycle, or 3–14-membered heterocycle) derivatives.

Similarly, compounds of the present invention that contain one or more sulfur atoms can be converted to S-oxides, i.e., sulfoxides or sulfones, by treatment with an oxidizing agent (e.g., m-CPBA and/or hydrogen peroxide) to afford other compounds of the present invention. Thus, all shown and claimed sulfur-containing compounds are considered, when allowed by valency and structure, to include both the compound as shown and its S-oxide derivatives (which can be designated as $S(O)_p$, where p=1 or 2).

When an atom or a chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1–6, 1–5, 1–4, 1–3, 1–2, 2–6, 2–5, 2–4, 2–3, 3–6, 3–5, 3–4, 4–6, 4–5, and 5–6 carbons.

As used herein, "alkyl" is intended to include both branched and straight-chain saturated aliphatic hydrocarbon groups having the specified number of carbon atoms. For example, $C_{1-6}$ alkyl is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, s-pentyl, and n-hexyl.

As used herein, "alkenyl" is intended to include hydrocarbon chains of either straight or branched configuration having one or more carbon-carbon double bonds occurring at any stable point along the chain. For example, $C_{2-6}$ alkenyl is intended to include $C_2$, $C_3$, $C_4$, $C_5$, and $C_6$ alkenyl groups. Examples of alkenyl include, but are not limited to, ethenyl and propenyl.

As used herein, "alkynyl" is intended to include hydrocarbon chains of either straight or branched configuration having one or more carbon-carbon triple bonds occurring at any stable point along the chain. For example, $C_{2-6}$ alkynyl is intended to include $C_2$, $C_3$, $C_4$, $C_5$, and $C_6$ alkynyl groups. Examples of alkynyl include, but are not limited to, ethynyl and propynyl.

Furthermore, "alkyl", "alkenyl", and "alkynyl" are intended to include moieties which are diradicals, i.e., having two points of attachment, an example of which in the present invention is when L is selected from these chemical groups. A nonlimiting example of such an alkyl moiety that is a diradical is $—CH_2CH_2—$, i.e., a $C_2$ alkyl group that is covalently bonded via each terminal carbon atom to the remainder of the molecule.

As used herein, "halo" or "halogen" refers to fluoro, chloro, bromo, and iodo. "Counterion" is used to represent a small, negatively charged species such as fluoride, chloride, bromide, iodide, hydroxide, acetate, and sulfate.

As used herein, "carbocycle" or "carbocyclic ring" is intended to mean any stable monocyclic, bicyclic, tricyclic, or higher order cyclic ring having the specified number of carbons, any of which can be saturated, unsaturated, or aromatic, recognizing that rings with certain numbers of members cannot be bicyclic or tricyclic, e.g., a 3-membered ring can only be a monocyclic ring. For example, a $C_{3-14}$ carbocycle is intended to mean a monocyclic, bicyclic, tricyclic, or higher order cyclic ring having 3, 4, 5, 6, 7, 8, 9, 10, 11, 12, 13, or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, cyclooctyl, cyclooctenyl, cyclooctadienyl, adamantyl, fluorenyl, phenyl, naphthyl, indanyl, anthryl, phenanthryl, and tetrahydronaphthyl. Bridged rings are also included in the definition of carbocycle, including, for example, [3.3.0]bicyclooctane, [4.3.0]bicyclononane, [4.4.0]bicyclodecane, and [2.2.2]bicyclooctane. A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring can also be present on the bridge. Fused (e.g., naphthyl and tetrahydronaphthyl) and spiro rings are also included.

It should be understood that included in the definition of "carbocycle" and "carbocyclic ring" are "aromatic carbocycles" and "aromatic carbocyclic rings," which are "aryl" groups. In the case of bicyclic aromatic carbocyclic rings, only one of the rings needs to be aromatic (e.g., tetrahydronaphthyl), though both can be (e.g., naphthyl). Similarly, in the case of tricyclic or higher order aromatic carbocyclic rings, only one of the rings needs to be aromatic, although tricyclic or higher order aromatic carbocycles having more than one aromatic ring are included (e.g., fluorenyl). Examples of aromatic carbocycles include, but are not limited to, phenyl, naphthyl, tetrahydronaphthyl; indanyl, indenyl, phenanthryl, anthryl, fluorenyl, pentalenyl, azulyl, chrysyl, pyryl, tetracyl, fluranthyl, coronyl, and hexahelicyl.

As used herein, the term "heterocycle" or "heterocyclic" is intended to mean any stable monocyclic, bicyclic, tricyclic, or higher order cyclic ring (recognizing that rings with certain numbers of members cannot be bicyclic or tricyclic, e.g., a 3-membered ring can only be a monocyclic ring), which is saturated, unsaturated, or aromatic and comprises carbon atoms and one or more ring heteroatoms, e.g., 1 or 1–2 or 1–3 or 1–4 or 1–5 or 1–6 heteroatoms, independently selected from the group consisting of nitrogen, oxygen, and sulfur. A bicyclic or tricyclic heterocycle can have one or more heteroatoms located in one ring, or the heteroatoms can be located in more than one ring. The nitrogen and sulfur heteroatoms can optionally be oxidized (i.e., N→O and $S(O)_p$, where p=1 or 2). When a nitrogen atom is included in the ring it is either N or NH, depending on whether or not it is attached to a double bond in the ring (i.e., a hydrogen is present if needed to maintain the tri-valency of the nitrogen atom). The nitrogen atom can be substituted or unsubstituted (e.g., N or NR wherein R is H or another substituent, as defined). The heterocyclic ring can be attached to its pendant group at any heteroatom or carbon atom that results in a stable structure. The heterocyclic rings described herein can be substituted on carbon or on a nitrogen atom if the resulting compound is stable. A nitrogen in the heterocycle can optionally be quaternized. It is preferred that when the total number of S and O atoms in the heterocycle exceeds 1, then these heteroatoms are not adjacent to one another. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring can also be present on the bridge. Spiro and fused rings are also included.

As used herein, the term "aromatic heterocycle" or "heteroaryl" is intended to mean a stable monocyclic, bicyclic, or higher order aromatic heterocyclic ring, which consists of carbon atoms and one or more heteroatoms, e.g., 1 or 1–2 or 1–3 or 1–4 or 1–5 or 1–6 heteroatoms, independently selected from the group consisting of nitrogen, oxygen, and sulfur. For example, an aromatic heterocycle or heteroaryl can be a 5, 6, 7, 8, 9, 10, 11, or 12-membered monocyclic or bicyclic aromatic heterocyclic ring, recognizing that rings with certain numbers of members cannot be a bicyclic aromatic, e.g., a 5-membered ring can only be a monocyclic aromatic ring. In the case of bicyclic heterocyclic aromatic rings, only one of the two rings needs to be aromatic (e.g., 2,3-dihydroindole), though both can be (e.g., quinoline). The second ring can also be fused or bridged as defined above for heterocycles. The nitrogen atom can be substituted or unsubstituted (i.e., N or NR wherein R is H or another substituent, as defined). The nitrogen and sulfur heteroatoms can optionally be oxidized (i.e., N→O and $S(O)_p$, where p=1 or 2). It is to be noted that total number of S and O atoms in the aromatic heterocycle is generally not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluene sulfonic.

The pharmaceutically acceptable salts of the present invention can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed. (Mack Publishing Company, 1990). For example, salts can include, but are not limited to, the hydrochloride and acetate salts of the aliphatic amine-containing, hydroxylamine-containing, and imine-containing compounds of the present invention. A nonlimiting example of a salt of a compound of the present invention is the monohydrochloride salt of compound 7. This salt is exemplified in the Examples.

Additionally, the compounds of the present invention, and particularly the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

As used herein, "treating" or "treatment" means the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

As used herein, "mammal" refers to human and non-human patients.

As used herein, the term "effective amount" refers to an amount of a compound, or a combination of compounds, of the present invention effective when administered alone or in combination as an anti-proliferative and/or anti-infective agent. In particular, an effective amount refers to an amount of the compound present in or on a recipient sufficient to elicit biological activity, for example, anti-infective activity (e.g., anti-microbial activity, anti-fungal activity, anti-viral activity, anti-parasitic activity) and/or anti-proliferative activity. The combination of compounds optionally is a synergistic combination. Synergy, as described, for example, by Chou and Talalay, *Adv. Enzyme Regul.* vol. 22, pp. 27–55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-proliferative and/or anti-infective effect, or some other beneficial effect of the combination compared with the individual components.

All percentages and ratios used herein, unless otherwise indicated, are by weight.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

2. Compounds of the Invention

In one aspect, the invention provides compounds having the formula:

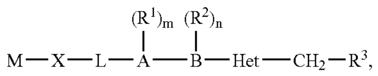

or a pharmaceutically acceptable salt, ester or prodrug thereof, wherein:

A is selected from the group consisting of:

phenyl, pyridyl, pyrazinyl, pyrimidinyl, and pyridazinyl;

B is selected from the group consisting of:

phenyl, pyridyl, pyrazinyl, pyrimidinyl, and pyridazinyl;

Het-$CH_2$—$R^3$ is selected from the group consisting of:

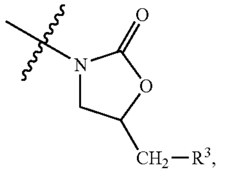
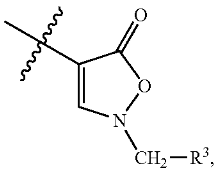
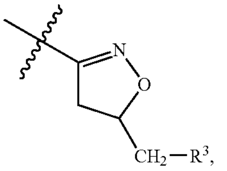
and
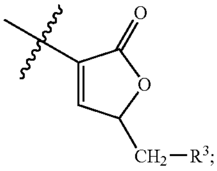

M is selected from the group consisting of:

a) $C_{1-6}$ alkyl, b) $C_{2-6}$ alkenyl, and c) $C_{2-6}$ alkynyl, wherein i) any of a)–c) is substituted with one or more moieties selected from the group consisting of F, Cl, Br, and I; and ii) any of a)–c) optionally is further substituted with one or more $R^4$ groups;

X is selected from the group consisting of:

a) —O—, b) —$NR^5$—, c) —N(O)—, d) —N($OR^5$)—, e) —$S(O)_p$—, f) —$NR^5$—N=, g) =N—$NR^5$—, h) —O—N=, i) =N—O—, j) —N=, k) =N—, l) —$NR_5$—$NR^5$—, m) —$NR^5$C(O)O—, n) —OC(O)$NR^5$—, o) —$NR^5$C(O)$NR^5$—, p) —$NR^5$C($NR^5$)$NR^5$—, and q)

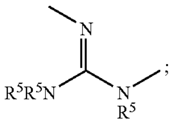
;

L is selected from the group consisting of:

a) $C_{1-6}$ alkyl, b) $C_{2-6}$ alkenyl, and c) $C_{2-6}$ alkynyl, wherein any of a)–c) optionally is substituted with one or more $R^4$ groups;

$R^1$, at each occurrence, independently is selected from the group consisting of:

a) F, b) Cl, c) Br, d) I, e) —$CF_3$, f) —$OR^7$, g) —CN, h) —$NO_2$, i) —$NR^7R^7$, j) —C(O)$R^7$, k) —C(O)$OR^7$, l) —OC(O)$R^7$, m) —C(O)$NR^7R^7$, n) —$NR^7$C(O)$R^7$, o) —OC(O)$NR^7R^7$, p) —$NR^7$C(O)$OR^7$, q) —$NR^7$C(O)$NR^7R^7$, r) —C(S)$R^7$, s) —C(S)$OR^7$, t) —OC(S)$R^7$, u) —C(S)$NR^7R^7$, v) —$NR^7$C(S)$R^7$, w) —OC(S)$NR^7$, $R^7$, x) —$NR^7$C(S)$OR^7$, y) —$NR^7$C(S)$NR^7$, $R^7$, z) —$NR^7$C($NR^7$)$NR^7R^7$, aa) —$S(O)_pR^7$, bb) —$SO_2NR^7R^7$, and cc) $R^7$;

$R^2$, at each occurrence, independently is selected from the group consisting of:

a) F, b) Cl, c) Br, d) I, e) —$CF_3$, f) —$OR^7$, g) —CN, h) —$NO_2$, i) —$NR^7R^7$, j) —C(O)$R^7$, k) —C(O)$OR^7$, l) —OC(O)$R^7$, m) —C(O)$NR^7R^7$, n) —$NR^7$C(O)$R^7$, o) —OC(O)$NR^7R^7$, p) —$NR^7$C(O)$OR^7$, q) —$NR^7$C(O)$NR^7R^7$, r) —C(S)$R^7$, s) —C(S)$OR^7$, t) —OC(S)$R^7$, u) —C(S)$NR^7R^7$, v) —$NR^7$C(S)$R^7$, w) —OC(S)$NR^7$, $R^7$, x) —$NR^7$C(S)$OR^7$, y) —$NR^7$C(S)$NR^7R^7$, z) —$NR^7$C($NR^7$)$NR^7R^7$, aa) —$S(O)_pR^7$, bb) —$SO_2NR^7R^7$, and cc) $R^7$;

$R^3$ is selected from the group consisting of:

a) —$OR^7$, b) —$NR^7R^7$, c) —C(O)$R^7$, d) —C(O)$OR^7$, e) —OC(O)$R^7$, f) —C(O)$NR^7R^7$, g) —$NR^7$C(O)$R^7$, h) —OC(O)$NR^7R^7$, i) —$NR^7$C(O)$OR^7$, j) —$NR^7$C(O)$NR^7R^7$, k) —C(S)$R^7$, l) —C(S)$OR^7$, m) —OC(S)$R^7$, n) —C(S)$NR^7R^7$, o) —$NR^7$C(S)$R^7$, p) —OC(S)$NR^7R^7$, q) —$NR^7$C(S)$OR^7$, r) —$NR^7$C(S)$NR^7R^7$, s) —$NR^7$C($NR^7$)$NR^7R^7$, t) —$S(O)_pR^7$, u) —$SO_2NR^7R^7$, and v) $R^7$;

$R^4$, at each occurrence, independently is selected from the group consisting of:

a) H, b) F, c) Cl, d) Br, e) I, f) =O, g) =S, h) =$NR^5$, i) =$NOR^5$, j) =N—$NR^5R^5$, k) —$CF_3$, l) —$OR^5$, m) —CN, n) —$NO_2$, o) —$NR^5R^5$, p) —C(O)$R^5$, q) —C(O)$OR^5$, r) —OC(O)$R^5$, s) —C(O)$NR^5R^5$, t) —$NR^5$C(O)$R^5$, u) —OC(O)$NR^5R^5$, v) —$NR^5$C(O)$OR^5$, w) —$NR^5$C(O)$NR^5R^5$, x) —C(S)$R^5$, y) —C(S)$OR^5$, z) —OC(S)$R^5$, aa) —C(S)$NR^5R^5$, bb) —$NR^5$C(S)$R^5$, cc) —OC(S)$NR^5R^5$, dd) —$NR^5$C(S)$OR^5$, ee) —$NR^5$C(S)$NR^5R^5$, ff) —$NR^5$C($NR^5$)$NR^5R^5$, gg) —$S(O)_pR^5$, and hh) $R^5$;

$R^5$, at each occurrence, independently is selected from the group consisting of:

a) H, b) $C_{1-6}$ alkyl, c) $C_{2-6}$ alkenyl, d) $C_{2-6}$ alkynyl, e) —C(O)$C_{1-6}$ alkyl, f) —C(O)—$C_{2-6}$ alkenyl, g) —C(O)—$C_{2-6}$ alkynyl, h) —C(O)O—$C_{1-6}$ alkyl, i) —C(O)O—$C_{2-6}$ alkenyl, and j) —C(O)O—$C_{2-6}$ alkynyl, wherein any of b)–j) optionally is substituted with one or more $R^6$ groups;

$R^6$, at each occurrence, independently is selected from the group consisting of:

a) F, b) Cl, c) Br, d) I, e) —$CF_3$, f) —OH, g) —$OC_{1-6}$ alkyl, h) —SH, i) —$SC_{1-6}$ alkyl, j) —CN, k) —$NO_2$, l) —$NH_2$, m) —$NHC_{1-6}$ alkyl, n) —N($C_{1-6}$ alkyl)$_2$, o) —C(O)$C_{1-6}$ alkyl, p) —C(O)$OC_{1-6}$ alkyl, q) —C(O)$NH_2$, r) —C(O)$NHC_{1-6}$ alkyl, s) —C(O)N($C_{1-6}$ alkyl)$_2$, t) —NHC(O)$C_{1-6}$ alkyl, and u) —$S(O)_pC_{1-6}$ alkyl;

$R^7$, at each occurrence, independently is selected from the group consisting of:

a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3–14 membered saturated, unsaturated, or aromatic heterocycle comprising one or more heteroatoms selected from the group consisting of nitrogen, oxygen, and sulfur, g) —C(O)$C_{1-6}$ alkyl, h) —C(O)—$C_{2-6}$ alkenyl, i) —C(O)—$C_{2-6}$ alkynyl, j) —C(O)—$C_{3-14}$ saturated, unsaturated, or aromatic carbocycle, k) —C(O)-3–14 membered saturated, unsaturated, or aromatic heterocycle comprising one or more heteroatoms selected from the group consisting of nitrogen, oxygen, and sulfur, l) —C(O)O—$C_{1-6}$ alkyl, m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3–14 membered saturated, unsaturated, or aromatic heterocycle comprising one or more heteroatoms selected from the group consisting of nitrogen, oxygen, and sulfur, wherein any of b)–p) optionally is substituted with one or more $R^8$ groups;

$R^8$, at each occurrence, is independently selected from the group consisting of:

a) F, b) Cl, c) Br, d) I, e) =O, f) =S, g) =$NR^9$, h) =$NOR^9$, i) =N—$NR^9R^9$, j) —$CF_3$, k) —$OR^9$, l) —CN, m) —$NO_2$, n) —$NR^9R^9$, o) —C(O)$R^9$, p)

—C(O)OR$^9$, q) —OC(O)R$^9$, r) —C(O)NR$^9$R$^9$, s) —NR$^9$C(O)R$^9$, t) —OC(O)NR$^9$R$^9$, u) —NR$^9$C(O)OR$^9$, v) —NR$^9$C(O)NR$^9$R$^9$, w) —C(S)R$^9$, x) —C(S)OR$^9$, y) —OC(S)R$^9$, z) —C(S)NR$^9$R$^9$, aa) —NR$^9$C(S)R$^9$, bb) —OC(S)NR$^9$R$^9$, cc) —NR$^9$C(S)OR$^9$, dd) —NR$^9$C(S)NR$^9$R$^9$, ee) —NR$^9$C(NR$^9$)NR$^9$R$^9$, ff) —S(O)$_p$R$^9$, gg) —SO$_2$NR$^9$R$^9$, and hh) R$^9$;

R$^9$, at each occurrence, independently is selected from the group consisting of:

a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3–14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated, unsaturated, or aromatic carbocycle, k) —C(O)-3–14 membered saturated, unsaturated, or aromatic heterocycle comprising one or more heteroatoms selected from the group consisting of nitrogen, oxygen, and sulfur, l) —C(O)O—$C_{1-6}$ alkyl, m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3–14 membered saturated, unsaturated, or aromatic heterocycle comprising one or more heteroatoms selected from the group consisting of nitrogen, oxygen, and sulfur, wherein any of b)–p) optionally is substituted with one or more moieties selected from the group consisting of:

a) F, b) Cl, c) Br, d) I, e) —CF$_3$, f) —OH, g) —O$C_{1-6}$ alkyl, h) —SH, i) —S$C_{1-6}$ alkyl, j) —CN, k) —NO$_2$, l) —NH$_2$, m) —NH$C_{1-6}$ alkyl, n) —N($C_{1-6}$ alkyl)$_2$, o) —C(O)$C_{1-6}$ alkyl, p) —C(O)O$C_{1-6}$ alkyl, q) —C(O)NH$_2$, r) —C(O)NH$C_{1-6}$ alkyl, s) —C(O)N($C_{1-6}$ alkyl)$_2$, t) —NHC(O)$C_{1-6}$ alkyl, u) —SO$_2$NH$_2$—, v) —SO$_2$NH$C_{1-6}$ alkyl, w) —SO$_2$N($C_{1-6}$ alkyl)$_2$, and x) —S(O)$_p$$C_{1-6}$ alkyl;

m is 0, 1, 2, 3, or 4;

n is 0, 1, 2, 3, or 4; and p, at each occurrence, independently is 0, 1, or 2.

Particular embodiments of the invention include compounds having the formula:

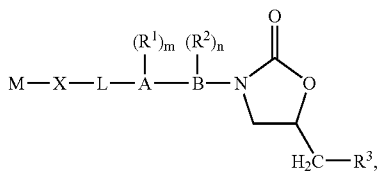

or a pharmaceutically acceptable salt, ester or prodrug thereof, wherein A, B, L, M, R$^1$, R$^2$, R$^3$, X, m, and n are defined as described above.

Other embodiments include compounds having the formula:

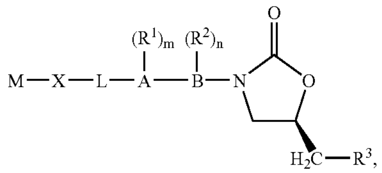

or a pharmaceutically acceptable salt, ester or prodrug thereof, wherein A, B, L, M, R$^1$, R$^2$, R$^3$, X, m, and n are defined as described above.

Particular compounds include those where A and B independently are selected from the group consisting of phenyl and pyridyl, and m and n independently are 0, 1, or 2.

In some embodiments, A-B is:

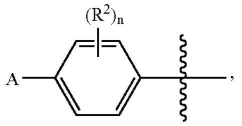

wherein A, R$^2$, and n are defined as described above. Particular compounds according to these embodiments include those where R$^2$ is selected from the group consisting of H and F, and n is 0, 1, or 2. In particular embodiments, A-B is:

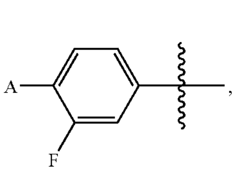
, or
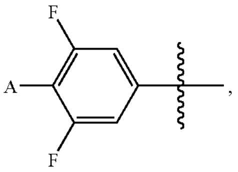

wherein A is defined as described above.

In various embodiments, A-B is:

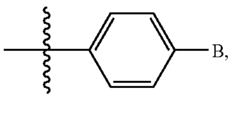
or
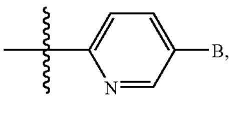

wherein B is defined as described in above.

In some embodiments, R$^3$ is —NR$^7$C(O)R$^7$. In other embodiments, R$^3$ is —NHC(O)R$^7$. Particular compounds according to these embodiments include those where R$^7$ is a $C_{1-6}$ alkyl group optionally substituted with one or more substituents independently selected from F or Cl. Examples of such alkyl groups include, but are not limited to, —CH$_3$, —CH$_2$F, —CHF$_2$, —CF$_3$, —CH$_2$Cl, —CHCl$_2$, —CCl$_3$, —CHFCl, —CF$_2$Cl, and —CFCl$_2$. In other embodiments, R$^3$ is:

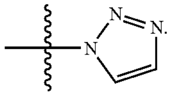

Particular embodiments of the invention include compounds having the formula:

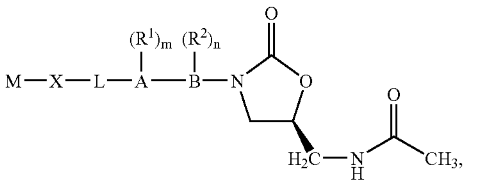

or a pharmaceutically acceptable salt, ester or prodrug thereof, wherein A, B, L, M, $R^1$, $R^2$, X, m, and n are defined as described above.

Other embodiments of the invention include compounds having the formula:

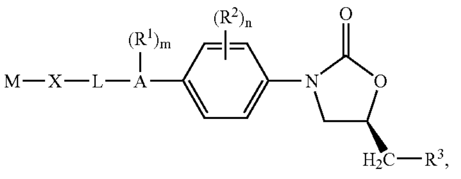

or a pharmaceutically acceptable salt, ester or prodrug thereof, wherein L, M, $R^1$, $R^3$, X, and m are defined as described above, A is selected from the group consisting of phenyl and pyridyl, R is selected from the group consisting of H and F, and n is 0, 1, or 2.

Still other embodiments of the invention include compounds having the formula:

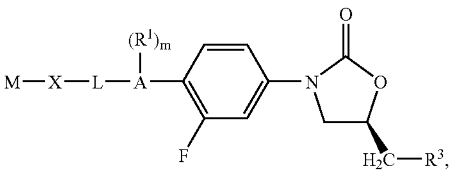

or a pharmaceutically acceptable salt, ester or prodrug thereof, wherein A, L, M, $R^1$, $R^3$, X, and m are defined as described above. Particular compounds according to these embodiments include those having the formula:

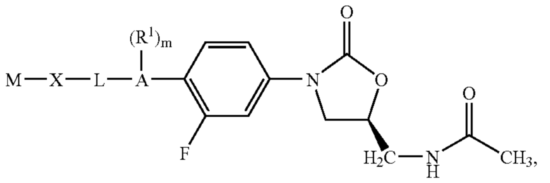

or a pharmaceutically acceptable salt, ester or prodrug thereof, wherein A, L, M, $R^1$, X, and m are defined as described above.

Some embodiments of the invention include compounds having the formula:

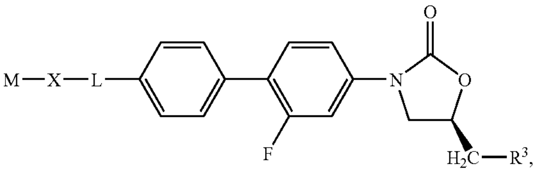

or

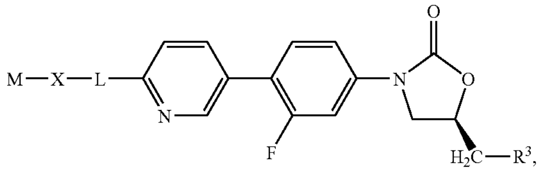

or a pharmaceutically acceptable salt, ester or prodrug thereof, wherein L, M, $R^3$, and X are defined as described above. Particular compounds according to these embodiments include those having the formula:

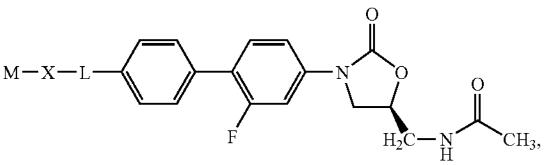

or

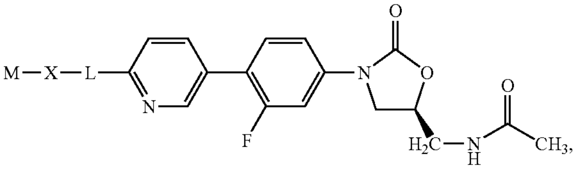

or a pharmaceutically acceptable salt, ester or prodrug thereof, wherein L, M, and X are defined as described above.

Other embodiments of the invention include compounds having the formula:

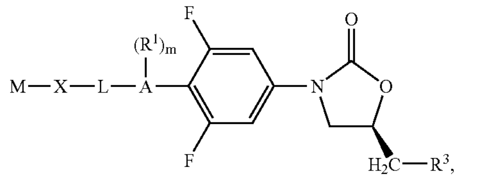

or a pharmaceutically acceptable salt, ester or prodrug thereof, wherein A, L, M, $R^1$, $R^3$, X, and m are defined as described above. Particular compounds according to these embodiments include those having the formula:

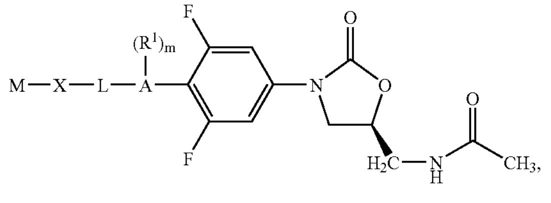

or a pharmaceutically acceptable salt, ester or prodrug thereof, wherein A, L, M, $R^1$, X, and m are defined as described above.

Some embodiments of the invention include compounds having the formula:

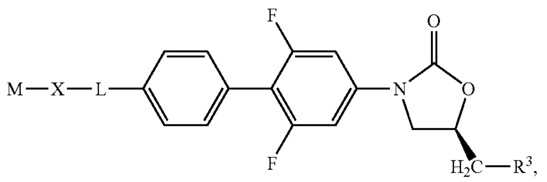

or

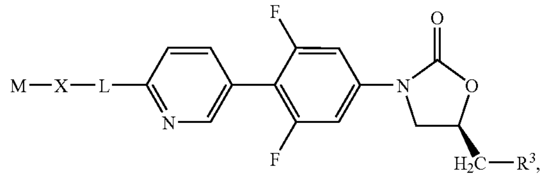

or a pharmaceutically acceptable salt, ester or prodrug thereof, wherein L, M, X, and $R^3$ are defined as described above. Particular compounds according to these embodiments include those having the formula:

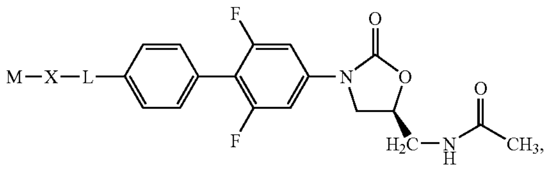

or

-continued

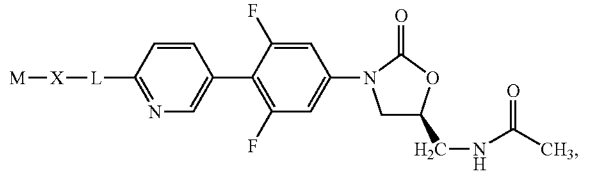

or a pharmaceutically acceptable salt, ester or prodrug thereof, wherein L, M, and X are defined as described above.

In any of the foregoing embodiments, L can be $C_{1-6}$ alkyl, for example, —$CH_2$—. Further, X can be selected from the group consisting of —$NR^5$—, —N(O), and —$N(OR^5)$—, wherein $R^5$ is, for example, H or a $C_{1-6}$ alkyl group, for example, a halogenated $C_{1-6}$ alkyl group. M can be, for example, a $C_{1-6}$ alkyl group substituted with one or more moieties selected from the group consisting of F, Cl, Br, and I. Examples of suitable M groups include, but are not limited to, —$CH_2CH_2CH_2F$ and —$CH_2CH(OH)CH_2F$.

Other embodiments of the invention include compounds having a structure corresponding to any one of the compounds listed in Table 1 hereinbelow, or a pharmaceutically acceptable salt, ester, or prodrug thereof.

In another aspect, the invention provides a pharmaceutically acceptable salt, ester, or prodrug of a compound listed in Table 1 hereinbelow. Particular embodiments of the invention include pharmaceutically acceptable salts of a compound corresponding to any one of structures 1–14, 20–22, 24–42, 44–49, and 53–83 listed in Table 1 hereinbelow. An example of a suitable pharmaceutically acceptable salt, for example, is a monohydrochloride salt.

The invention further provides methods for synthesizing any one of the foregoing compounds, including pharmaceutically acceptable salts of these compounds.

Yet another aspect of the invention provides a pharmaceutical composition comprising an effective amount of one or more of the foregoing compounds and a pharmaceutically acceptable carrier. Suitable formulating agents are described in detail in section 4 hereinbelow.

One or more of the foregoing compounds can also be incorporated into a medical device. For example, a medical device, such as a medical stent, can contain or be coated with one or more of the compounds of the invention.

In still another aspect, the invention provides a method for treating a microbial infection, a fungal infection, a viral infection, a parasitic disease, a proliferative disease, an inflammatory disease, or a gastrointestinal motility disorder in a mammal. The method involves administering an effective amount of one or more compounds or pharmaceutical compositions of the invention, for example, via oral, parenteral or topical routes.

The invention provides a method of treating a disorder in a mammal comprising the step of administering to the mammal an effective amount of one or more compounds of the invention thereby to ameliorate a symptom of a particular disorder. Such a disorder can be selected from the group consisting of a skin infection, nosocomial pneumonia, post-viral pneumonia, an abdominal infection, a urinary tract infection, bacteremia, septicemia, endocarditis, an atrio-ventricular shunt infection, a vascular access infection, meningitis, surgical prophylaxis, a peritoneal infection, a bone infection, a joint infection, a methicillin-resistant *Sta-*

*phylococcus aureus* infection, a vancomycin-resistant Enterococci infection, a linezolid-resistant organism infection, and tuberculosis.

3. Characterization of Compounds of the Invention

Compounds designed, selected and/or optimized by methods described above, after being produced, can be characterized using a variety of assays known to those skilled in the art to determine whether the compounds have biological activity. For example, the compounds can be characterized by conventional assays, including but not limited to those assays described below, to determine whether the compounds have a predicted activity, binding activity and/or binding specificity.

Furthermore, high-throughput screening can be used to speed up analysis using such assays. As a result, it can be possible to screen rapidly the molecules described herein for activity, for example, as anti-cancer, anti-bacterial, anti-fungal, anti-parasitic or anti-viral agents. Also, it can be possible to assay how the compounds interact with a ribosome or ribosomal subunit and/or are effective as modulators (for example, inhibitors) of protein synthesis using techniques known in the art. General methodologies for performing high-throughput screening are described, for example, in Devlin, *High Throughput Screening*, (Marcel Dekker, 1998); and U.S. Pat. No. 5,763,263. High-throughput assays can use one or more different assay techniques including, but not limited to, those described below.

(1) Surface Binding Studies. A variety of binding assays can be useful in screening new molecules for their binding activity. One approach includes surface plasmon resonance (SPR) that can be used to evaluate the binding properties of molecules of interest with respect to a ribosome, ribosomal subunit or a fragment thereof.

SPR methodologies measure the interaction between two or more macromolecules in real-time through the generation of a quantum-mechanical surface plasmon. One device, (BIAcore Biosensor RTM from Pharmacia Biosensor, Piscataway, N.J.) provides a focused beam of polychromatic light to the interface between a gold film (provided as a disposable biosensor "chip") and a buffer compartment that can be regulated by the user. A 100 nm thick "hydrogel" composed of carboxylated dextran that provides a matrix for the covalent immobilization of analytes of interest is attached to the gold film. When the focused light interacts with the free electron cloud of the gold film, plasmon resonance is enhanced. The resulting reflected light is spectrally depleted in wavelengths that optimally evolved the resonance. By separating the reflected polychromatic light into its component wavelengths (by means of a prism), and determining the frequencies that are depleted, the BIAcore establishes an optical interface which accurately reports the behavior of the generated surface plasmon resonance. When designed as above, the plasmon resonance (and thus the depletion spectrum) is sensitive to mass in the evanescent field (which corresponds roughly to the thickness of the hydrogel). If one component of an interacting pair is immobilized to the hydrogel, and the interacting partner is provided through the buffer compartment, the interaction between the two components can be measured in real time based on the accumulation of mass in the evanescent field and its corresponding effects of the plasmon resonance as measured by the depletion spectrum. This system permits rapid and sensitive real-time measurement of the molecular interactions without the need to label either component.

(2) Fluorescence Polarization. Fluorescence polarization (FP) is a measurement technique that can readily be applied to protein-protein, protein-ligand, or RNA-ligand interactions in order to derive $IC_{50}$s and Kds of the association reaction between two molecules. In this technique one of the molecules of interest is conjugated with a fluorophore. This is generally the smaller molecule in the system (in this case, the compound of interest). The sample mixture, containing both the ligand-probe conjugate and the ribosome, ribosomal subunit or fragment thereof, is excited with vertically polarized light. Light is absorbed by the probe fluorophores, and re-emitted a short time later. The degree of polarization of the emitted light is measured. Polarization of the emitted light is dependent on several factors, but most importantly on viscosity of the solution and on the apparent molecular weight of the fluorophore. With proper controls, changes in the degree of polarization of the emitted light depends only on changes in the apparent molecular weight of the fluorophore, which in-turn depends on whether the probe-ligand conjugate is free in solution, or is bound to a receptor. Binding assays based on FP have a number of important advantages, including the measurement of $IC_{50}$s and Kds under true homogenous equilibrium conditions, speed of analysis and amenity to automation, and ability to screen in cloudy suspensions and colored solutions.

(3) Protein Synthesis. It is contemplated that, in addition to characterization by the foregoing biochemical assays, the compound of interest may also be characterized as a modulator (for example, an inhibitor of protein synthesis) of the functional activity of the ribosome or ribosomal subunit.

Furthermore, more specific protein synthesis inhibition assays may be performed by administering the compound to a whole organism, tissue, organ, organelle, cell, a cellular or subcellular extract, or a purified ribosome preparation and observing its pharmacological and inhibitory properties by determining, for example, its inhibition constant ($IC_{50}$) for inhibiting protein synthesis. Incorporation of $^{3}$H leucine or $^{35}$S methionine, or similar experiments can be performed to investigate protein synthesis activity. A change in the amount or the rate of protein synthesis in the cell in the presence of a molecule of interest indicates that the molecule is a modulator of protein synthesis. A decrease in the rate or the amount of protein synthesis indicates that the molecule is a inhibitor of protein synthesis.

Furthermore, the compounds can be assayed for anti-proliferative or anti-infective properties on a cellular level. For example, where the target organism is a microorganism, the activity of compounds of interest can be assayed by growing the microorganisms of interest in media either containing or lacking the compound. Growth inhibition can be indicative that the molecule could be acting as a protein synthesis inhibitor. More specifically, the activity of the compounds of interest against bacterial pathogens can be demonstrated by the ability of the compound to inhibit growth of defined strains of human pathogens. For this purpose, a panel of bacterial strains can be assembled to include a variety of target pathogenic species, some containing resistance mechanisms that have been characterized. Use of such a panel of organisms permits the determination of structure-activity relationships not only in regards to potency and spectrum, but also with a view to obviating resistance mechanisms. The assays can be performed in microtiter trays according to conventional methodologies as published by The National Committee for Clinical Laboratory Standards (NCCLS) guidelines (NCCLS. M7-A5-Methods for Dilution Antimicrobial Susceptibility Tests for Bacteria That Grow Aerobically; Approved Standard-Fifth Edition. NCCLS Document M100-S12/M7 (ISBN 1-56238-394-9)).

4. Formulation and Administration

The compounds of the invention can be useful in the prevention or treatment of a variety of human or other animal disorders, including for example, bacterial infection, fungal infections, viral infections, parasitic diseases, and cancer. It is contemplated that, once identified, the active molecules of the invention can be incorporated into any suitable carrier prior to use. The dose of active molecule, mode of administration and use of suitable carrier will depend upon the intended recipient and target organism. The formulations, both for veterinary and for human medical use, of compounds according to the present invention typically include such compounds in association with a pharmaceutically acceptable carrier.

The carrier(s) should be "acceptable" in the sense of being compatible with the other ingredients of the formulations and not deleterious to the recipient. Pharmaceutically acceptable carriers, in this regard, are intended to include any and all solvents, dispersion media, coatings, anti-bacterial and anti-fungal agents, isotonic and absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified or designed according to the invention and/or known in the art) also can be incorporated into the compositions. The formulations can conveniently be presented in dosage unit form and can be prepared by any of the methods well known in the art of pharmacy/microbiology. In general, some formulations are prepared by bringing the compound into association with a liquid carrier or a finely divided solid carrier or both, and then, if necessary, shaping the product into the desired formulation.

A pharmaceutical composition of the invention should be formulated to be compatible with its intended route of administration. Examples of routes of administration include oral or parenteral, for example, intravenous, intradermal, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Useful solutions for oral or parenteral administration can be prepared by any of the methods well known in the pharmaceutical art, described, for example, in *Remington's Pharmaceutical Sciences,* 18th ed. (Mack Publishing Company, 1990). Formulations for parenteral administration can also include glycocholate for buccal administration, methoxysalicylate for rectal administration, or citric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, and hydrogenated naphthalenes. Formulations for direct administration can include glycerol and other compositions of high viscosity. Other potentially useful parenteral carriers for these drugs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present invention suitable for oral administration can be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug can also be administered in the form of a bolus, electuary or paste. A tablet can be made by compressing or molding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Molded tablets may be made by molding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the drug with a dermatologically acceptable carrier such as a lotion, cream, ointment or soap. Particularly useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents and bile salts. Transmucosal administration can be accomplished through the use of nasal sprays or suppositories. For transdermal administration, the active compounds typically are formulated into ointments, salves, gels, or creams as generally known in the art.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

Where adhesion to a tissue surface is desired the composition can include the drug dispersed in a fibrinogen-thrombin composition or other bioadhesive. The compound then can be painted, sprayed or otherwise applied to the desired tissue surface. Alternatively, the drugs can be formulated for parenteral or oral administration to humans or other mammals, for example, in effective amounts, e.g., amounts that provide appropriate concentrations of the drug to target tissue for a time sufficient to induce the desired effect.

Where the active compound is to be used as part of a transplant procedure, it can be provided to the living tissue or organ to be transplanted prior to removal of tissue or organ from the donor. The compound can be provided to the donor host. Alternatively or, in addition, once removed from the donor, the organ or living tissue can be placed in a preservation solution containing the active compound. In all cases, the active compound can be administered directly to the desired tissue, as by injection to the tissue, or it can be provided systemically, either by oral or parenteral administration, using any of the methods and formulations described herein and/or known in the art. Where the drug comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution.

Active compound as identified or designed by the methods described herein can be administered to individuals to treat disorders (prophylactically or therapeutically). In conjunction with such treatment, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a drug as well as tailoring the dosage and/or therapeutic regimen of treatment with the drug.

In therapeutic use for treating, or combating, bacterial infections in mammals, the compounds or pharmaceutical compositions thereof will be administered orally, parenterally and/or topically at a dosage to obtain and maintain a concentration, that is, an amount, or blood-level or tissue level of active component in the animal undergoing treatment which will be anti-microbially effective. The term "effective amount" is understood to mean that the compound of the invention is present in or on the recipient in an amount sufficient to elicit biological activity, for example, anti-microbial activity, anti-fungal activity, anti-viral activity, anti-parasitic activity, and/or anti-proliferative activity. Generally, an effective amount of dosage of active component will be in the range of from about 0.1 to about 100, more preferably from about 1.0 to about 50 mg/kg of body weight/day. The amount administered will also likely depend on such variables as the type and extent of disease or indication to be treated, the overall health status of the particular patient, the relative biological efficacy of the compound delivered, the formulation of the drug, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum and the daily dosage can be progressively increased during the course of treatment depending on the particular situation. If desired, the daily dose can also be divided into multiple doses for administration, for example, two to four times per day.

5. EXAMPLES

In the following examples, nuclear magnetic resonance (NMR) spectra were obtained on a Bruker Avance 300 or Avance 500 spectrometer, or in some cases a GE-Nicolet 300 spectrometer. Common reaction solvents were either high performance liquid chromatography (HPLC) grade or American Chemical Society (ACS) grade, and anhydrous as obtained from the manufacturer unless otherwise noted. "Chromatography" or "purified by silica gel" refers to flash column chromatography using silica gel (EM Merck, Silica Gel 60, 230–400 mesh) unless otherwise noted.

Exemplary compounds synthesized in accordance with the invention are listed in Table 1. A straight, unbolded or unhatched bond from a chiral center indicates that the substituent can be either an enantiomer, i.e., R or S, or a mixture of both. In the table, a (±) symbol preceding a chemical name means that the compound is racemic with respect to any undesignated chiral centers. A wavy bond indicates that the substituent can be either cis or trans, or a mixture of both. Furthermore, the chemical names are provided for convenience and are not intended to limit the indicated chemical structures. To the extent that there is a discrepancy between the chemical name and the structure of a compound, the structure of the compound shall govern. Also, depending on the conventions and choices available, more than one chemical name can be given to a particular chemical structure. As a nonlimiting example, Compound 1, below, is drawn with stereochemistry indicated for the methyl acetamide substituent on the oxazolidinone ring, but with no stereochemistry indicated for the hydroxy substituent. Compound 1 is named indicating the "5S" stereochemistry at the chiral carbon center at which the acetamide substituent is attached. However, Compound 1 is also named with a "(±)" designation, indicating that the stereochemistry is undefined or the compound is racemic with respect to the hydroxyl substituent, where no stereochemistry is indicated.

The compounds of the present invention can be prepared, formulated, and delivered as salts, esters, and prodrugs. For convenience, the compounds in Table 1 are generally shown without indicating a particular salt, ester, or prodrug form and are generally named in the table without further limitation to such salts, esters, or prodrugs. As a nonlimiting example, Compound 2, having a propyl amino group, is depicted as the free base compound, although it can be prepared as the hydrochloride salt, as indicated from the synthetic procedure provided for the compound.

TABLE 1

| Compound Number | Structure |
|---|---|
| 1 | 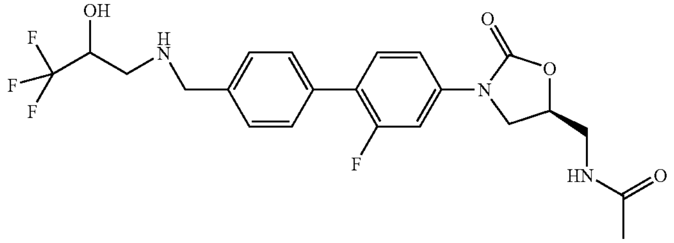<br>(±) (5S)-N-(3-{2-Fluoro-4'-[(3,3,3-trifluoro-2-hydroxy-propylamino)-methyl]-biphenyl-4-yl}-2-oxo-oxazolidin-5-ylmethyl)-acetamide |

TABLE 1-continued

| Compound Number | Structure |
| --- | --- |
| 2 | 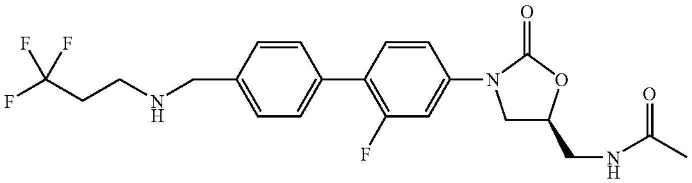 (5S)-N-(3-{2-Fluoro-4'-[(3,3,3-trifluoro-propylamino)-methyl]-biphenyl-4-yl}-2-oxo-oxazolidin-5-ylmethyl)-acetamide |
| 3 | 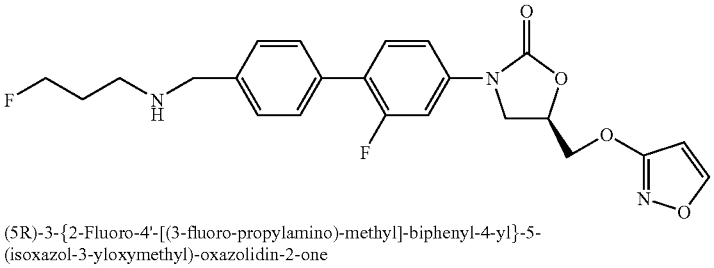 (5R)-3-{2-Fluoro-4'-[(3-fluoro-propylamino)-methyl]-biphenyl-4-yl}-5-(isoxazol-3-yloxymethyl)-oxazolidin-2-one |
| 4 | 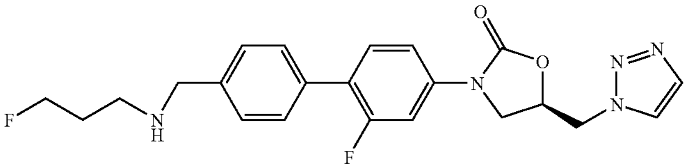 (5R)-3-{2-Fluoro-4'-[(3-fluoro-propylamino)-methyl]-biphenyl-4-yl}-5-[1,2,3]triazol-1-ylmethyl-oxazolidin-2-one |
| 5 | 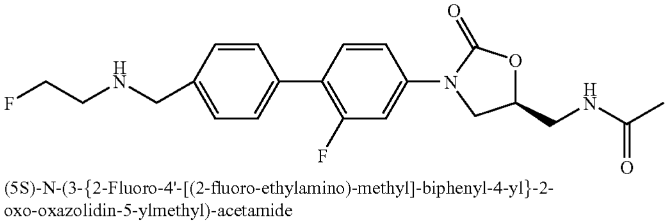 (5S)-N-(3-{2-Fluoro-4'-[(2-fluoro-ethylamino)-methyl]-biphenyl-4-yl}-2-oxo-oxazolidin-5-ylmethyl)-acetamide |
| 6 | 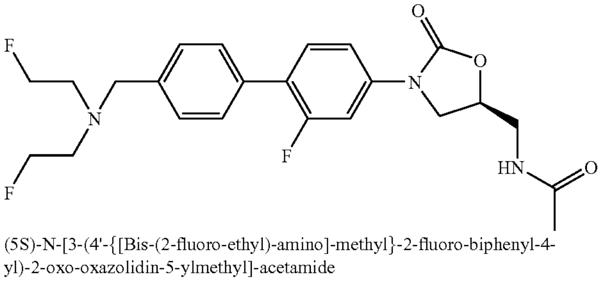 (5S)-N-[3-(4'-{[Bis-(2-fluoro-ethyl)-amino]-methyl}-2-fluoro-biphenyl-4-yl)-2-oxo-oxazolidin-5-ylmethyl]-acetamide |
| 7 | 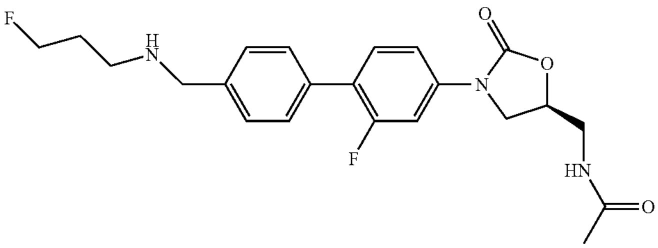 (5S)-N-(3-{2-Fluoro-4'-[(3-fluoro-propylamino)-methyl]-biphenyl-4-yl}-2-oxo-oxazolidin-5-ylmethyl)-acetamide |

TABLE 1-continued

| Compound Number | Structure |
| --- | --- |
| 8 | 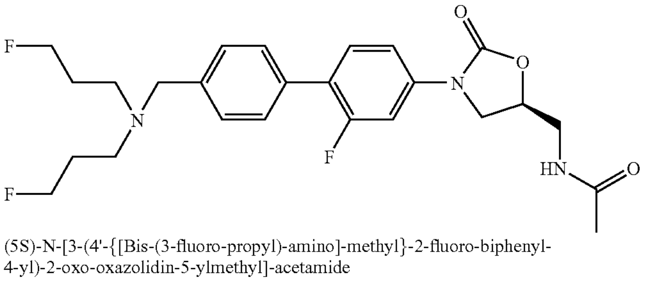 (5S)-N-[3-(4'-{[Bis-(3-fluoro-propyl)-amino]-methyl}-2-fluoro-biphenyl-4-yl)-2-oxo-oxazolidin-5-ylmethyl]-acetamide |
| 9 | 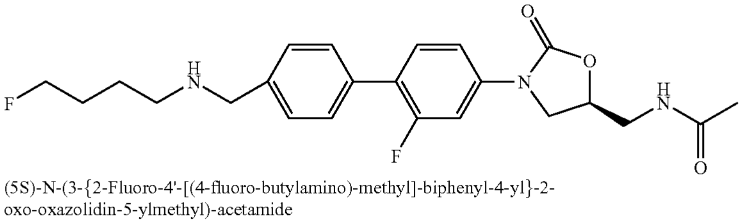 (5S)-N-(3-{2-Fluoro-4'-[(4-fluoro-butylamino)-methyl]-biphenyl-4-yl}-2-oxo-oxazolidin-5-ylmethyl)-acetamide |
| 10 | 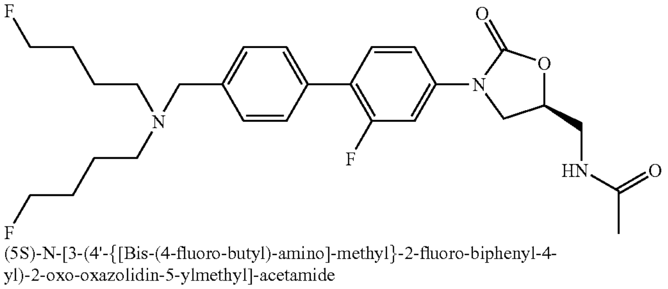 (5S)-N-[3-(4'-{[Bis-(4-fluoro-butyl)-amino]-methyl}-2-fluoro-biphenyl-4-yl)-2-oxo-oxazolidin-5-ylmethyl]-acetamide |
| 11 | 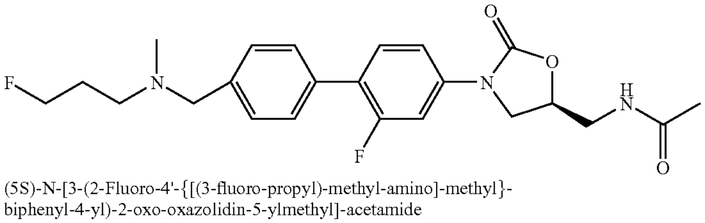 (5S)-N-[3-(2-Fluoro-4'-{[(3-fluoro-propyl)-methyl-amino]-methyl}-biphenyl-4-yl)-2-oxo-oxazolidin-5-ylmethyl]-acetamide |
| 12 | 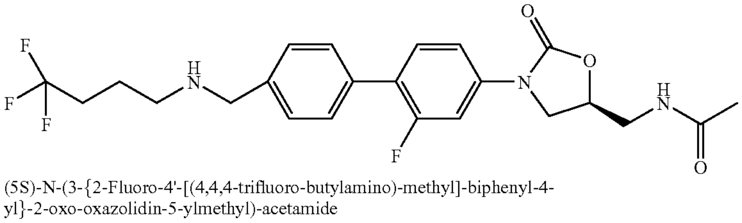 (5S)-N-(3-{2-Fluoro-4'-[(4,4,4-trifluoro-butylamino)-methyl]-biphenyl-4-yl}-2-oxo-oxazolidin-5-ylmethyl)-acetamide |
| 13 | 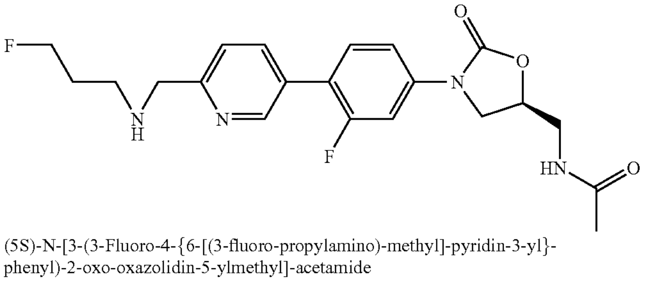 (5S)-N-[3-(3-Fluoro-4-{6-[(3-fluoro-propylamino)-methyl]-pyridin-3-yl}-phenyl)-2-oxo-oxazolidin-5-ylmethyl]-acetamide |

TABLE 1-continued

| Compound Number | Structure |
|---|---|
| 14 | 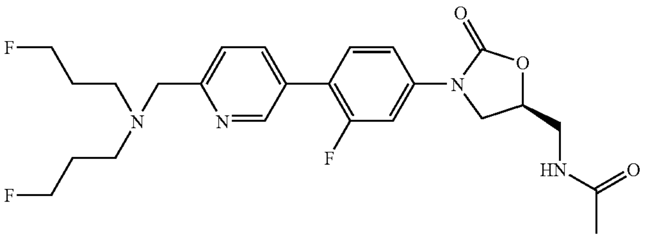 (5S)-N-{3-[4-(6-{[Bis-(3-fluoro-propyl)-amino]-methyl}-pyridin-3-yl)-3-fluoro-phenyl]-2-oxo-oxazolidin-5-ylmethyl}-acetamide |
| 15 | 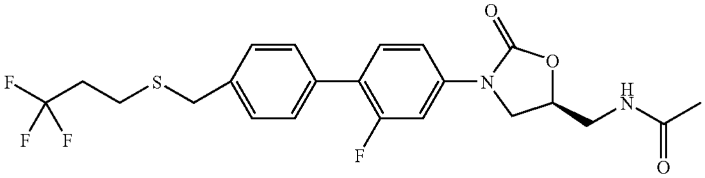 (5S)-N-{3-[2-Fluoro-4'-(3,3,3-trifluoro-propylsulfanylmethyl)-biphenyl-4-yl]-2-oxo-oxazolidin-5-ylmethyl}-acetamide |
| 16 | 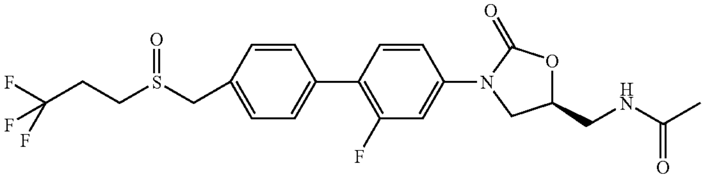 (5S)-N-{3-[2-Fluoro-4'-(3,3,3-trifluoro-propane-1-sulfinylmethyl)-biphenyl-4-yl]-2-oxo-oxazolidin-5-ylmethyl}-acetamide |
| 17 | 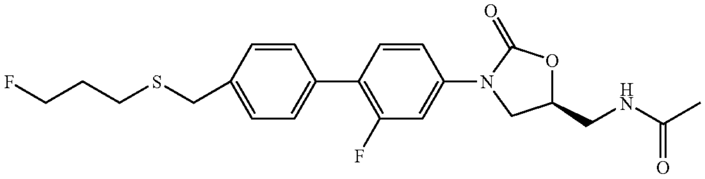 (5S)-N-{3-[2-Fluoro-4'-(3-fluoro-propylsulfanylmethyl)-biphenyl-4-yl]-2-oxo-oxazolidin-5-ylmethyl}-acetamide |
| 18 | 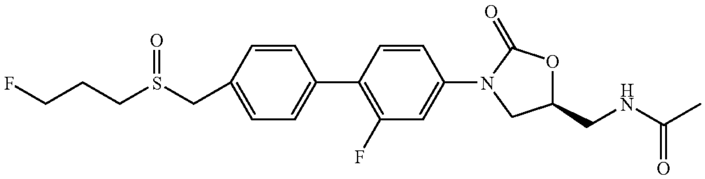 (5S)-N-{3-[2-Fluoro-4'-(3-fluoro-propane-1-sulfinylmethyl)-biphenyl-4-yl]-2-oxo-oxazolidin-5-ylmethyl}-acetamide |
| 19 | 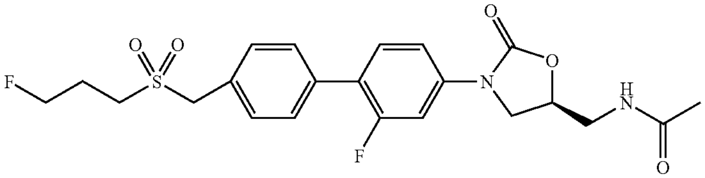 (5S)-N-{3-[2-Fluoro-4'-(3-fluoro-propane-1-sulfonylmethyl)-biphenyl-4-yl]-2-oxo-oxazolidin-5-ylmethyl}-acetamide |

TABLE 1-continued

| Compound Number | Structure |
| --- | --- |
| 20 | 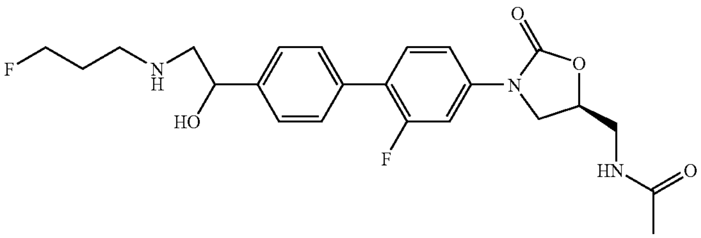<br>(±) (5S)-N-(3-{2-Fluoro-4'-[2-(3-fluoro-propylamino)-1-hydroxy-ethyl]-biphenyl-4-yl}-2-oxo-oxazolidin-5-ylmethyl)-acetamide |
| 21 | 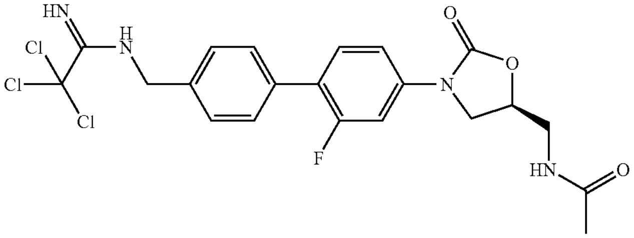<br>(5S)-N-[3-(2-Fluoro-4'-{[(2,2,2-trichloro-acetimidoyl)-amino]-methyl}-biphenyl-4-yl)-2-oxo-oxazolidin-5-ylmethyl]-acetamide |
| 22 | 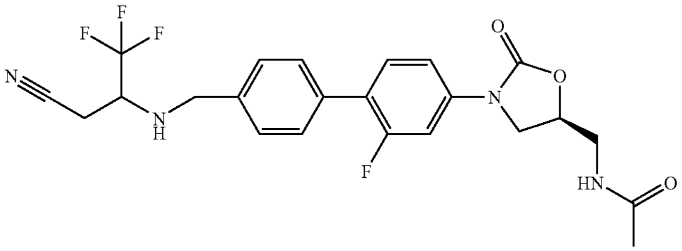<br>(±) (5S)-N-{3-[2-Fluoro-4'-(1-methyl-1H-tetrazole-5-sulfonylmethyl)-biphenyl-4-yl]-2-oxo-oxazolidin-5-ylmethyl}-acetamide |
| 23 | 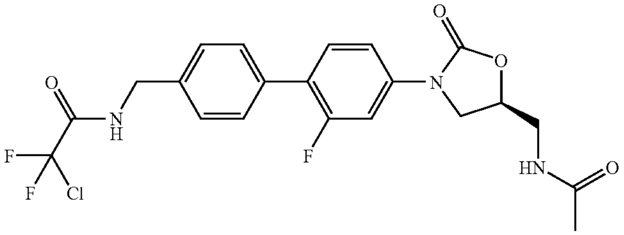<br>(5S)-N-{4'-[5-(Acetylamino-methyl)-2-oxo-oxazolidin-3-yl]-2'-fluoro-biphenyl-4-ylmethyl}-2-chloro-2,2-difluoro-acetamide |
| 24 | 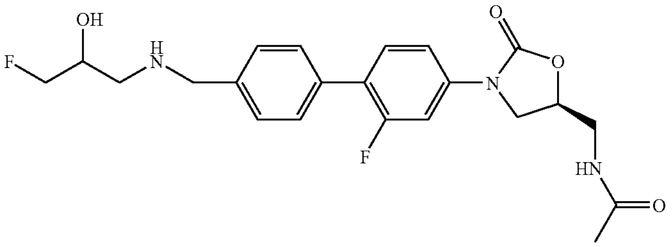<br>(±) (5S)-N-(3-{2-Fluoro-4'-[(3-fluoro-2-hydroxy-propylamino)-methyl]-biphenyl-4-yl}-2-oxo-oxazolidin-5-ylmethyl)-acetamide |

TABLE 1-continued

| Compound Number | Structure |
|---|---|
| 25 | 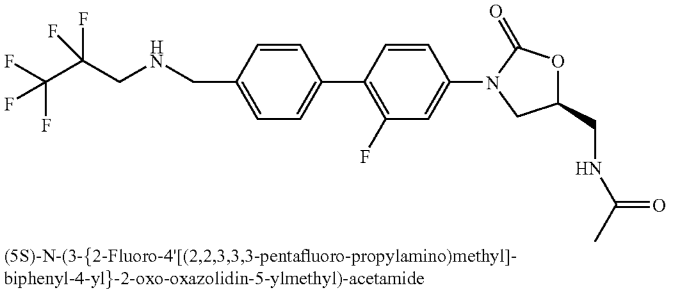 (5S)-N-(3-{2-Fluoro-4'[(2,2,3,3,3-pentafluoro-propylamino)methyl]-biphenyl-4-yl}-2-oxo-oxazolidin-5-ylmethyl)-acetamide |
| 26 | 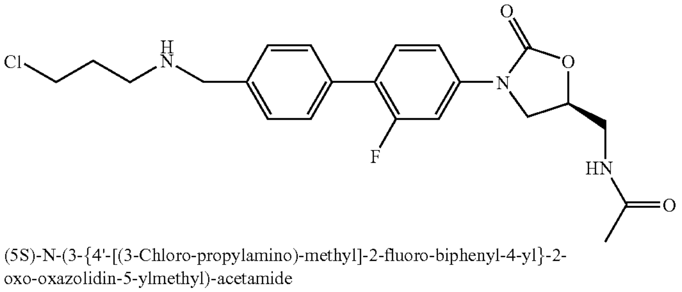 (5S)-N-(3-{4'-[(3-Chloro-propylamino)-methyl]-2-fluoro-biphenyl-4-yl}-2-oxo-oxazolidin-5-ylmethyl)-acetamide |
| 27 | 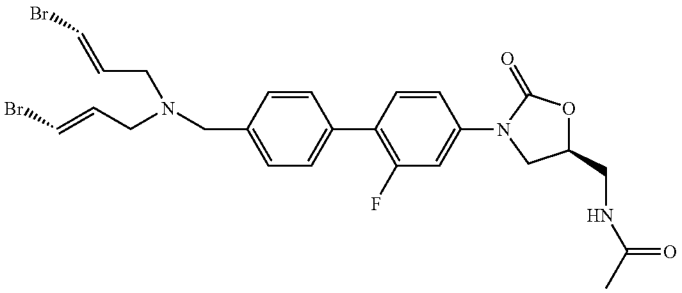 (5S)-N-[3-(4'-{[Bis-(3-bromo-allyl)-amino]-methyl}-2-fluoro-biphenyl-4-yl)-2-oxo-oxazolidin-5-ylmethyl]-acetamide |
| 28 | 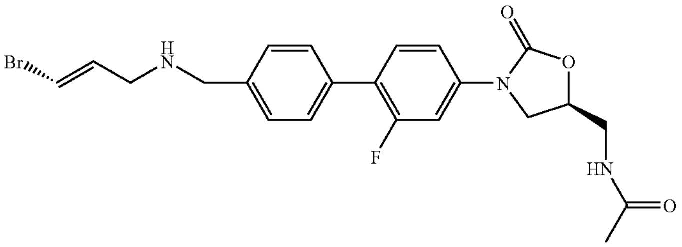 (5S)-N-(3- {4'-[(3-Bromo-allylamino)-methyl]-2-fluoro-biphenyl-4-yl}-2-oxo-oxazolidin-5-ylmethyl)-acetamide |
| 29 | 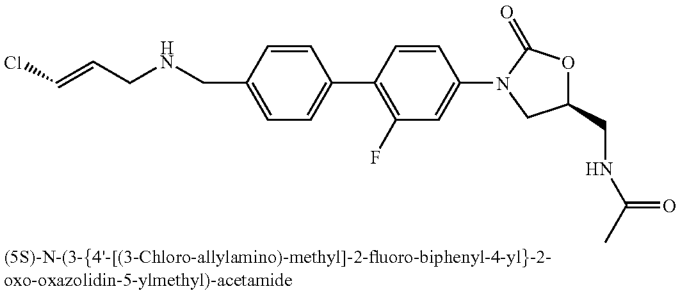 (5S)-N-(3-{4'-[(3-Chloro-allylamino)-methyl]-2-fluoro-biphenyl-4-yl}-2-oxo-oxazolidin-5-ylmethyl)-acetamide |

TABLE 1-continued

| Compound Number | Structure |
|---|---|
| 30 | 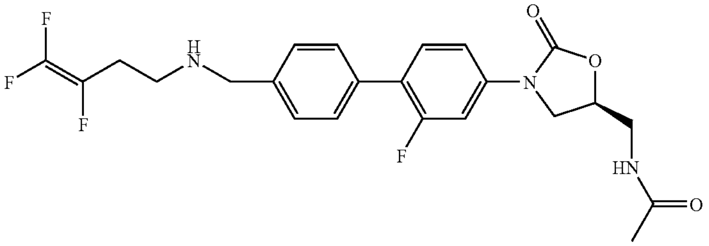<br>(5S)-N-(3-{2-Fluoro-4'-[(3,4,4-trifluoro-but-3-enylamino)-methyl]-biphenyl-4-yl}-2-oxo-oxazolidin-5-ylmethyl)-acetamide |
| 31 | 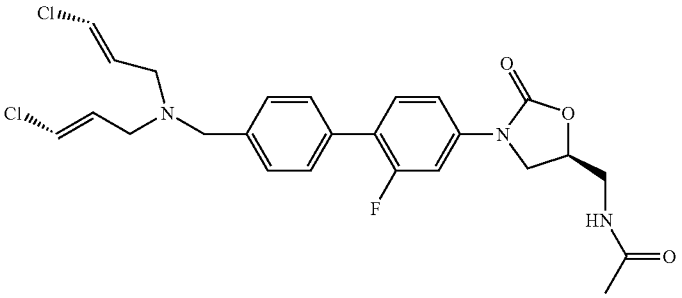<br>(5S)-N-[3-(4'-{[Bis-(3-chloro-allyl)-amino]-methyl}-2-fluoro-biphenyl-4-yl)-2-oxo-oxazolidin-5-ylmethyl]-acetamide |
| 32 | 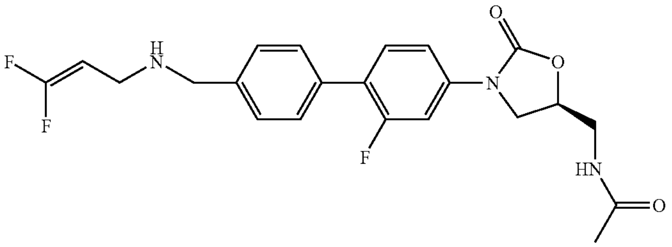<br>(5S)-N-(3-{4'-[(3,3-Difluoro-allylamino)-methyl]-2-fluoro-biphenyl-4-yl}-2-oxo-oxazolidin-5-ylmethyl)-acetamide |
| 33 | 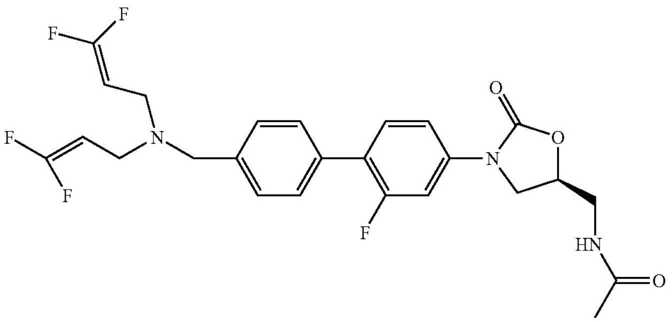<br>(5S)-N-[3-(4'-{[Bis-(3,3-difluoro-allyl)-amino]-methyl}-2-fluoro-biphenyl-4-yl)-2-oxo-oxazolidin-5-ylmethyl]-acetamide |

TABLE 1-continued

| Compound Number | Structure |
|---|---|
| 34 | 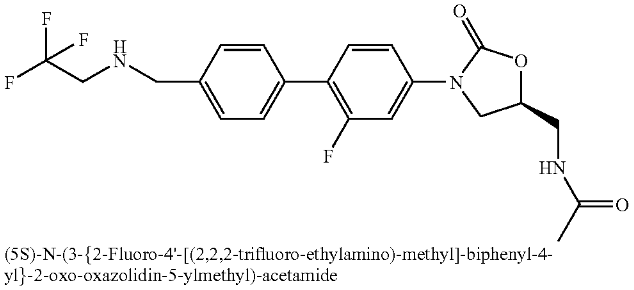 (5S)-N-(3-{2-Fluoro-4'-[(2,2,2-trifluoro-ethylamino)-methyl]-biphenyl-4-yl}-2-oxo-oxazolidin-5-ylmethyl)-acetamide |
| 35 | 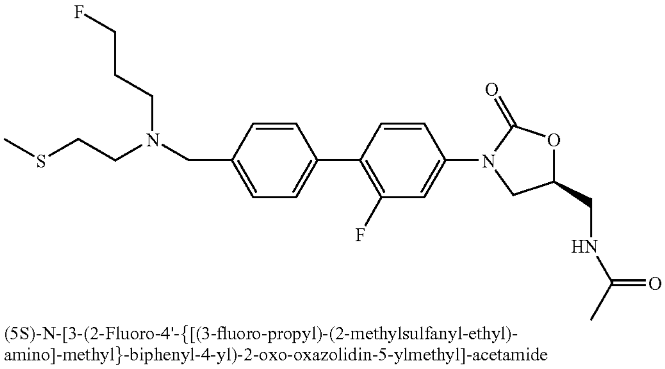 (5S)-N-[3-(2-Fluoro-4'-{[(3-fluoro-propyl)-(2-methylsulfanyl-ethyl)-amino]-methyl}-biphenyl-4-yl)-2-oxo-oxazolidin-5-ylmethyl]-acetamide |
| 36 | 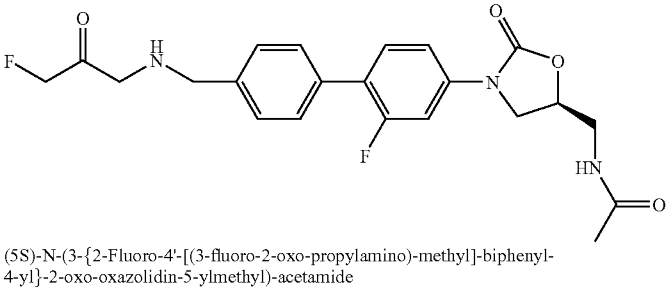 (5S)-N-(3-{2-Fluoro-4'-[(3-fluoro-2-oxo-propylamino)-methyl]-biphenyl-4-yl}-2-oxo-oxazolidin-5-ylmethyl)-acetamide |
| 37 | 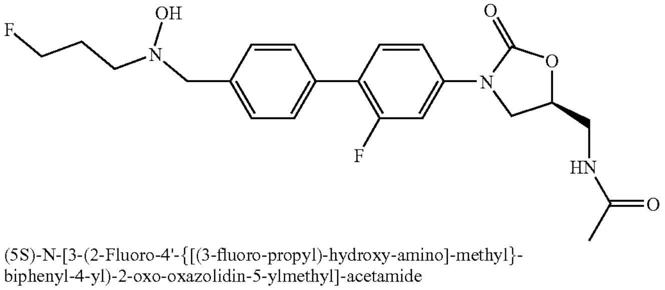 (5S)-N-[3-(2-Fluoro-4'-{[(3-fluoro-propyl)-hydroxy-amino]-methyl}-biphenyl-4-yl)-2-oxo-oxazolidin-5-ylmethyl]-acetamide |
| 38 | 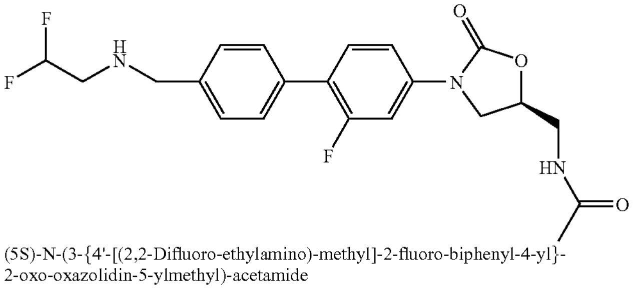 (5S)-N-(3-{4'-[(2,2-Difluoro-ethylamino)-methyl]-2-fluoro-biphenyl-4-yl}-2-oxo-oxazolidin-5-ylmethyl)-acetamide |

TABLE 1-continued

| Compound Number | Structure |
| --- | --- |
| 39 | 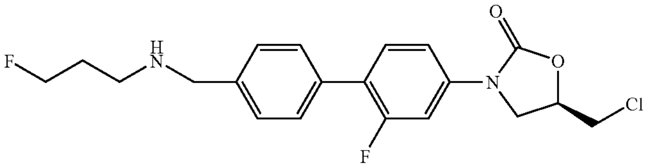 (5R)-5-Chloromethyl-3-{2-fluoro-4'-[(3-fluoro-propylamino)-methyl]-biphenyl-4-yl}-oxazolidin-2-one |
| 40 | 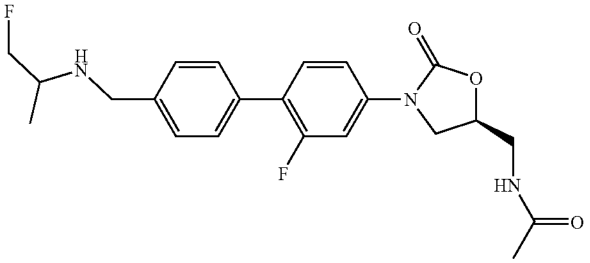 (±) (5S)-N-(3-{2-Fluoro-4'-[(2-fluoro-1-methyl-ethylamino)-methyl]-biphenyl-4-yl}-2-oxo-oxazolidin-5-ylmethyl)-acetamide |
| 41 | 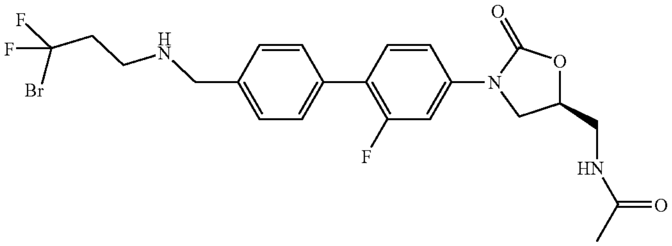 (5S)-N-(3-{4'-[(3-Bromo-3,3-difluoro-propylamino)-methyl]-2-fluoro-biphenyl-4-yl}-2-oxo-oxazolidin-5-ylmethyl)-acetamide |
| 42 | 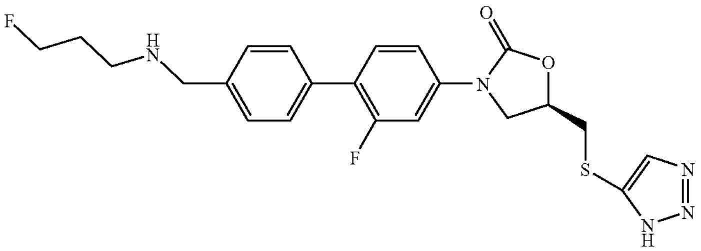 (5R)-3-{2-Fluoro-4'-[(3-fluoro-propylamino)-methyl]-biphenyl-4-yl}-5-(3H-[1,2,3]triazol-4-ylsulfanylmethyl)-oxazolidin-2-one |
| 43 | 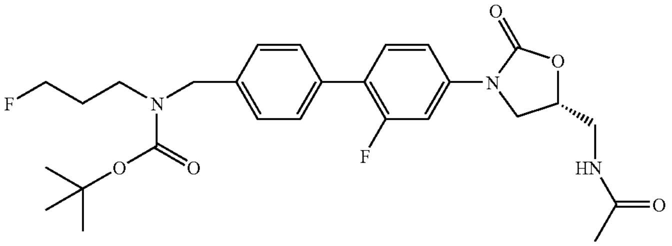 (5R)-{4'-[5-(Acetylamino-methyl)-2-oxo-oxazolidin-3-yl]-2'-fluoro-biphenyl-4-ylmethyl}-(3-fluoro-propyl)-carbamic acid tert-butyl ester |

TABLE 1-continued

| Compound Number | Structure |
|---|---|
| 44 | 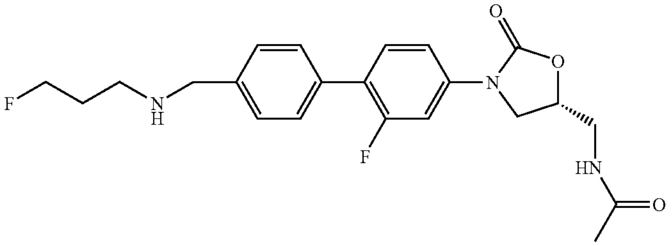 (5R)-N-(3-{2-Fluoro-4'-[(3-fluoro-propylamino)-methyl]-biphenyl-4-yl}-2-oxo-oxazolidin-5-ylmethyl)-acetamide |
| 45 | 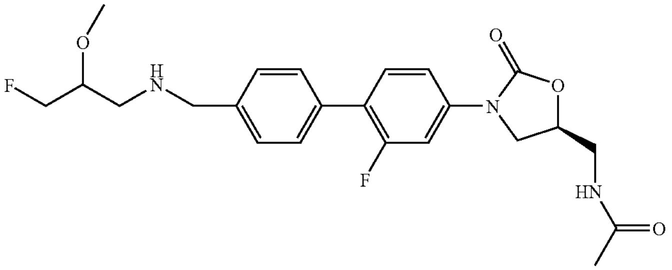 (±) (5S)-N-(3-{2-Fluoro-4'-[(3-fluoro-2-methoxy-propylamino)-methyl]-biphenyl-4-yl}-2-oxo-oxazolidin-5-ylmethyl)-acetamide |
| 46 | 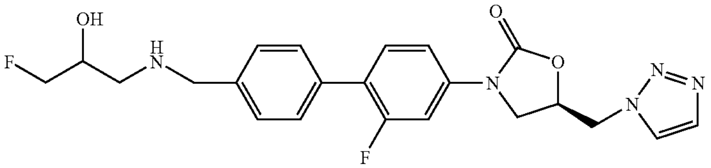 (±) (5R)-3-{2-Fluoro-4'-[(3-fluoro-2-hydroxy-propylamino)-methyl]-biphenyl-4-yl}-5-[1,2,3]triazol-1-ylmethyl-oxazolidin-2-one |
| 47 | 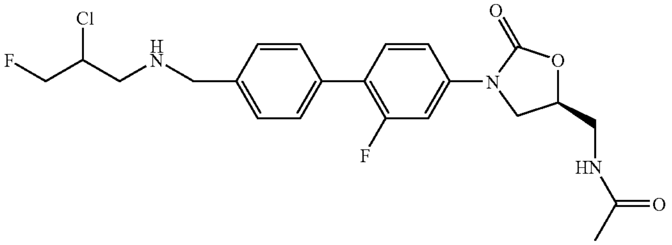 (±) (5S)-N-(3-{4'-[(2-Chloro-3-fluoro-propylamino)-methyl]-2-fluoro-biphenyl-4-yl}-2-oxo-oxazolidin-5-ylmethyl)-acetamide |
| 48 | 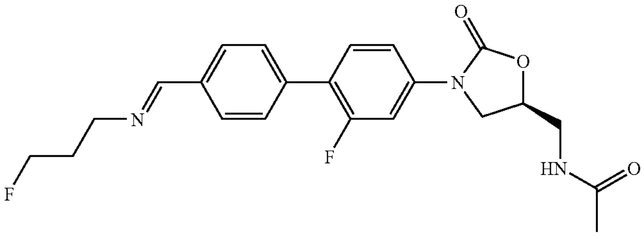 (5S)-N-(3-{2-Fluoro-4'-[(3-fluoro-propylimino)-methyl]-biphenyl-4-yl}-2-oxo-oxazolidin-5-ylmethyl)-acetamide |

TABLE 1-continued

| Compound Number | Structure |
| --- | --- |
| 49 | 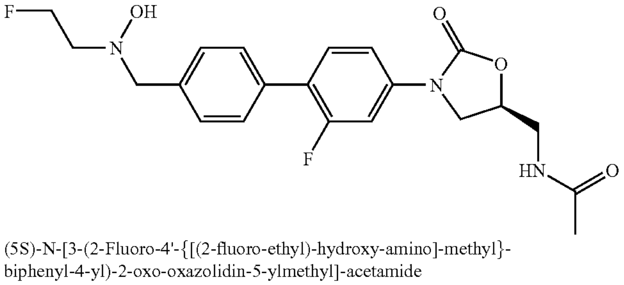 (5S)-N-[3-(2-Fluoro-4'-{[(2-fluoro-ethyl)-hydroxy-amino]-methyl}-biphenyl-4-yl)-2-oxo-oxazolidin-5-ylmethyl]-acetamide |
| 50 | 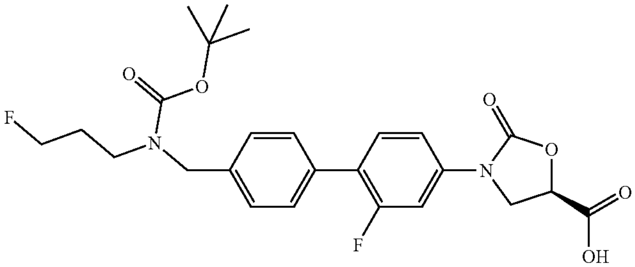 (5R)-3-(4'-{[tert-Butoxycarbonyl-(3-fluoro-propyl)-amino]-methyl}-2-fluoro-biphenyl-4-yl)-2-oxo-oxazolidine-5-carboxylic acid |
| 51 | 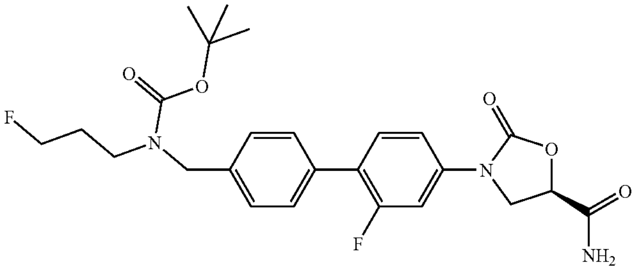 (5R)-[4'-(5-Carbamoyl-2-oxo-oxazolidin-3-yl)-2'-fluoro-biphenyl-4-ylmethyl]-(3-fluoro-propyl)-carbamic acid tert-butyl ester |
| 52 | 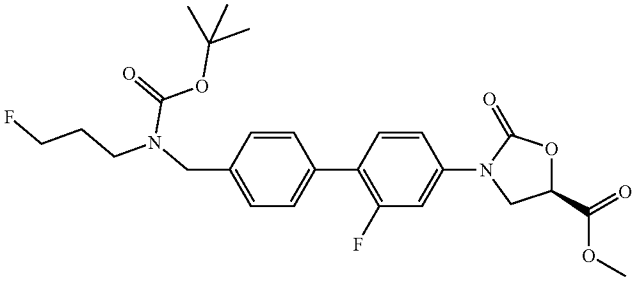 (5R)-3-(4'-{[tert-Butoxycarbonyl-(3-fluoro-propyl)-amino]-methyl}-2-fluoro-biphenyl-4-yl)-2-oxo-oxazolidine-5-carboxylic acid methyl ester |
| 53 | 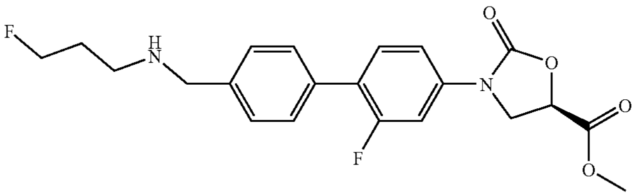 (5R)-3-{2-Fluoro-4'-[(3-fluoro-propylamino)-methyl]-biphenyl-4-yl}-2-oxo-oxazolidine-5-carboxylic acid methyl ester |

TABLE 1-continued

| Compound Number | Structure |
|---|---|
| 54 | 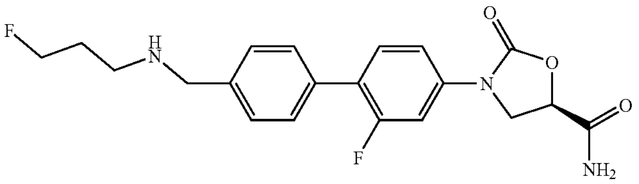 (5R)-3-{2-Fluoro-4'-[(3-fluoro-propylamino)-methyl]-biphenyl-4-yl}-2-oxo-oxazolidine-5-carboxylic acid amide |
| 55 | 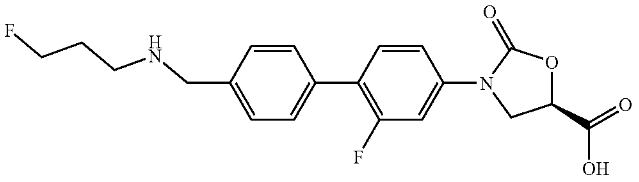 (5R)-3-{2-Fluoro-4'-[(3-fluoro-propylamino)-methyl]-biphenyl-4-yl}-2-oxo-oxazolidine-5-carboxylic acid |
| 56 | 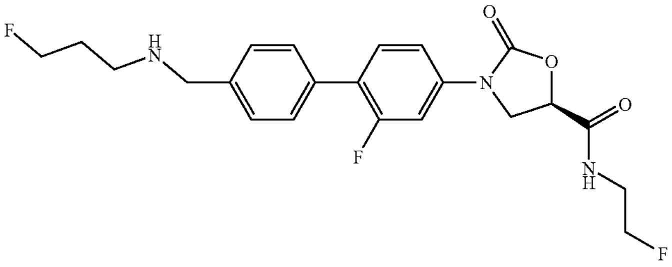 (5R)-3-{2-Fluoro-4'-[(3-fluoro-propylamino)-methyl]-biphenyl-4-yl}-2-oxo-oxazolidine-5-carboxylic acid (2-fluoro-ethyl)-amide |
| 57 | 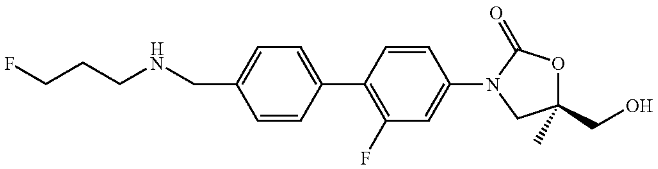 (5R)-3-{2-Fluoro-4'-[(3-fluoro-propylamino)-methyl]-biphenyl-4-yl}-5-hydroxymethyl-5-methyl-oxazolidin-2-one |
| 58 | 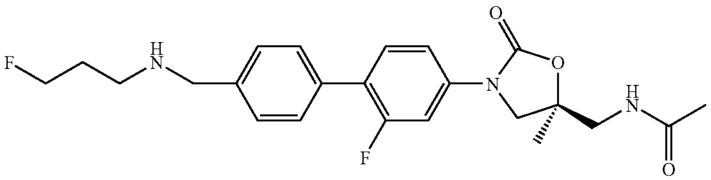 (5S)-N-(3-{2-Fluoro-4'-[(3-fluoro-propylamino)-methyl]-biphenyl-4-yl}-5-methyl-2-oxo-oxazolidin-5-ylmethyl)-acetamide |
| 59 | 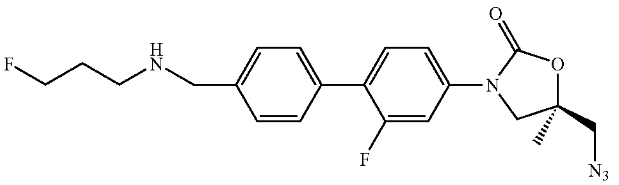 (5R)-5-Azidomethyl-3-{2-fluoro-4'-[(3-fluoro-propylamino)-methyl]-biphenyl-4-yl}-5-methyl-oxazolidin-2-one |

TABLE 1-continued

| Compound Number | Structure |
|---|---|
| 60 | 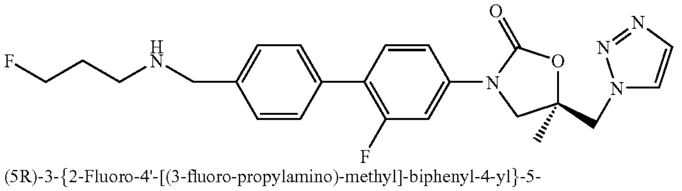 (5R)-3-{2-Fluoro-4'-[(3-fluoro-propylamino)-methyl]-biphenyl-4-yl}-5-methyl-5-[1,2,3]triazol-1-ylmethyl-oxazolidin-2-one |
| 61 | 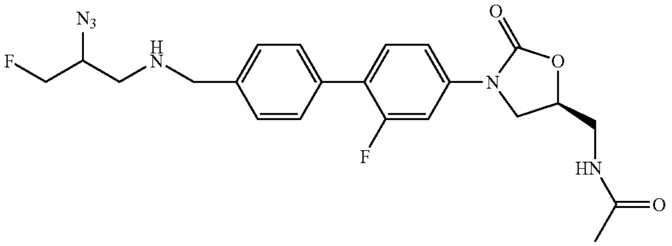 (±) (5S)-N-(3-{4'-[(2-Azido-3-fluoro-propylamino)-methyl]-2-fluoro-biphenyl-4-yl}-2-oxo-oxazolidin-5-ylmethyl)-acetamide |
| 62 | 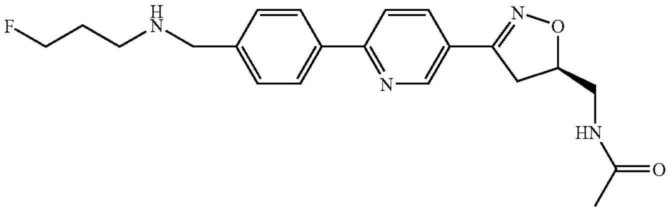 (5R)-N-[3-(6-{4-[(3-Fluoro-propylamino)-methyl]-phenyl}-pyridin-3-yl)-4,5-dihydro-isoxazol-5-ylmethyl]-acetamide |
| 63 | 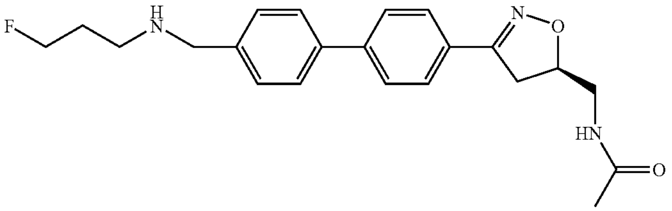 (5R)-N-(3-{4'-[(3-Fluoro-propylamino)-methyl]-biphenyl-4-yl}-4,5-dihydro-isoxazol-5-ylmethyl)-acetamide |
| 64 | 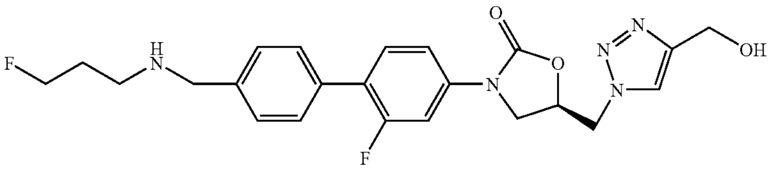 (5R)-3-{2-Fluoro-4'-[(3-fluoro-propylamino)-methyl]-biphenyl-4-yl}-5-(4-hydroxymethyl-[1,2,3]triazol-1-ylmethyl)-oxazolidin-2-one |
| 65 | 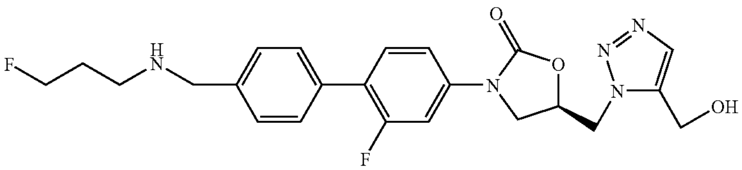 (5R)-3-{2-Fluoro-4'-[(3-fluoro-propylamino)-methyl]-biphenyl-4-yl}-5-(5-hydroxymethyl-[1,2,3]triazol-1-ylmethyl)-oxazolidin-2-one |

TABLE 1-continued

| Compound Number | Structure |
| --- | --- |
| 66 | 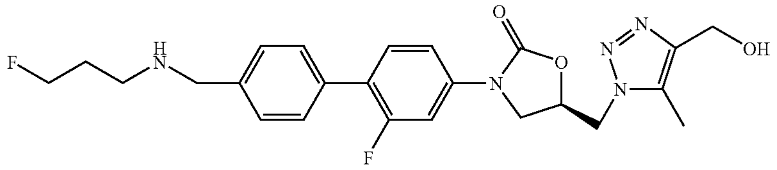 (5R)-3-{2-Fluoro-4'-[(3-fluoro-propylamino)-methyl]-biphenyl-4-yl}-5-(4-hydroxymethyl-5-methyl-[1,2,3]triazol-1-ylmethyl)-oxazolidin-2-one |
| 67 | 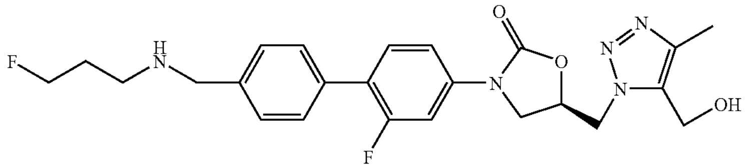 (5R)-3-{2-Fluoro-4'-[(3-fluoro-propylamino)-methyl]-biphenyl-4-yl}-5-(5-hydroxymethyl-4-methyl-[1,2,3]triazol-1-ylmethyl)-oxazolidin-2-one |
| 68 | 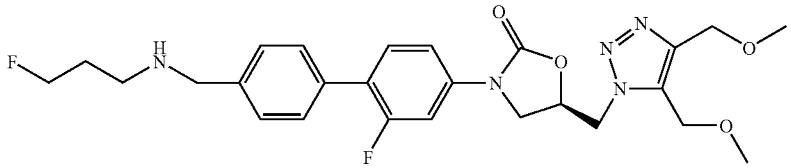 (5R)-5-(4,5-Bis-methoxymethyl-[1,2,3]triazol-1-ylmethyl)-3-{2-fluoro-4'-[(3-fluoro-propylamino)-methyl]-biphenyl-4-yl}-oxazolidin-2-one |
| 69 | 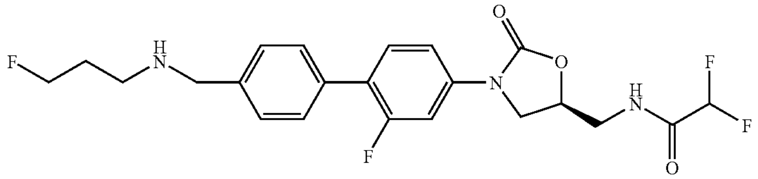 (5S)-2,2-Difluoro-N-(3-{2-fluoro-4'-[(3-fluoro-propylamino)-methyl]-biphenyl-4-yl}-2-oxo-oxazolidin-5-ylmethyl)-acetamide |
| 70 | 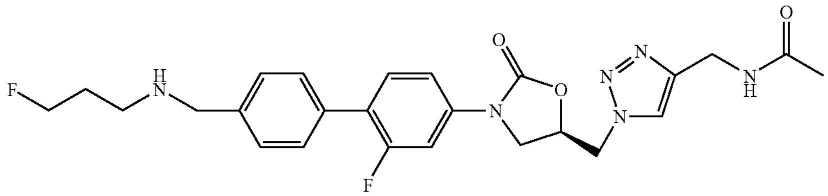 (5R)-N-[1-(3-{2-Fluoro-4'-[(3-fluoro-propylamino)-methyl]-biphenyl-4-yl}-2-oxo-oxazolidin-5-ylmethyl)-1H-[1,2,3]triazol-4-ylmethyl]-acetamide |
| 71 | 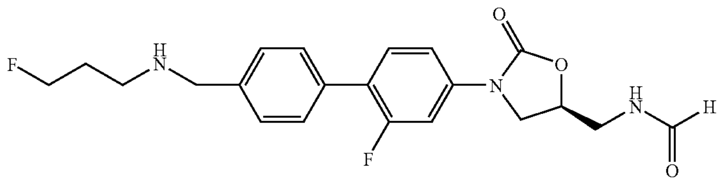 (5S)-N-(3-{2-Fluoro-4'-[(3-fluoro-propylamino)-methyl]-biphenyl-4-yl}-2-oxo-oxazolidin-5-ylmethyl)-formamide |

TABLE 1-continued

| Compound Number | Structure |
| --- | --- |
| 72 | 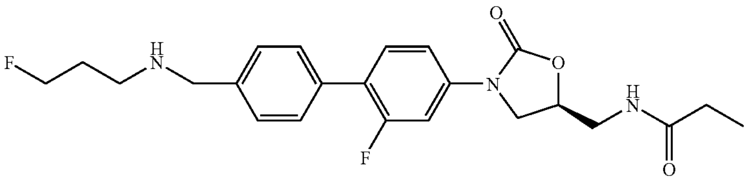<br>(5S)-N-(3-{2-Fluoro-4'-[(3-fluoro-propylamino)-methyl]-biphenyl-4-yl}-2-oxo-oxazolidin-5-ylmethyl)-propionamide |
| 73 | 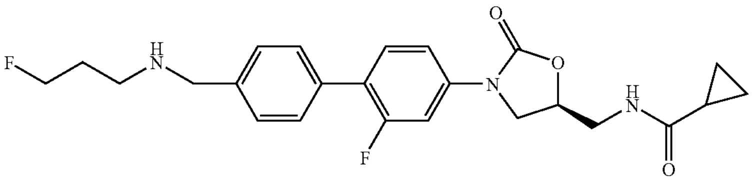<br>(5S)-Cyclopropanecarboxylic acid (3-{2-fluoro-4'-[(3-fluoro-propylamino)-methyl]-biphenyl-4-yl}-2-oxo-oxazolidin-5-ylmethyl)-amide |
| 74 | 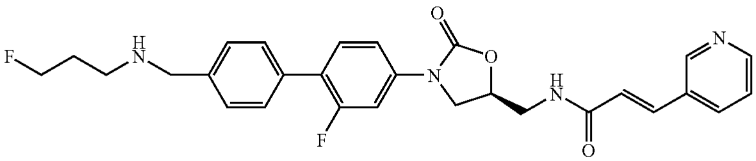<br>(5S)-N-(3-{2-Fluoro-4'-[(3-fluoro-propylamino)-methyl]-biphenyl-4-yl}-2-oxo-oxazolidin-5-ylmethyl)-3-pyridin-3-yl-acrylamide |
| 75 | 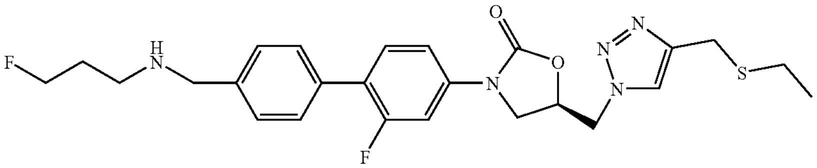<br>(5R)-5-(4-Ethylsulfanylmethyl-[1,2,3]triazol-1-ylmethyl)-3-{2-fluoro-4'-[(3-fluoro-propylamino)-methyl]-biphenyl-4-yl}-oxazolidin-2-one |
| 76 | 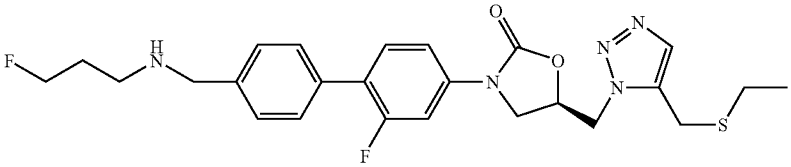<br>(5R)-5-(5-Ethylsulfanylmethyl-[1,2,3]triazol-1-ylmethyl)-3-{2-fluoro-4'-[(3-fluoro-propylamino)-methyl]-biphenyl-4-yl}-oxazolidin-2-one |
| 77 | 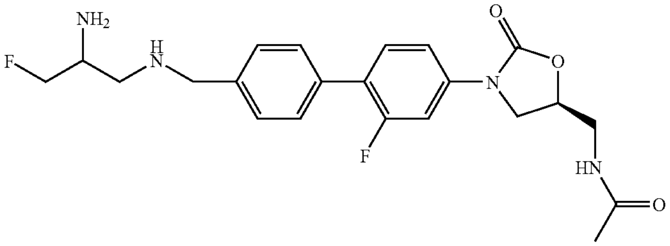<br>(±) (5S)-N-(3-{4'-[(2-Amino-3-fluoro-propylamino)-methyl]-2-fluoro-biphenyl-4-yl}-2-oxo-oxazolidin-5-ylmethyl)-acetamide |

TABLE 1-continued

| Compound Number | Structure |
| --- | --- |
| 78 | 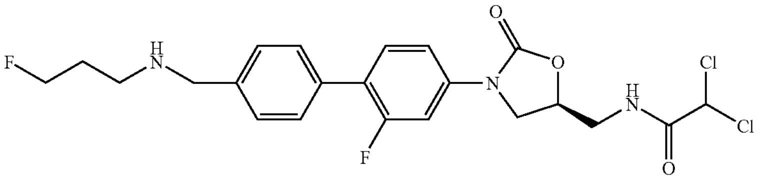<br>(5S)-2,2-Dichloro-N-(3-{2-fluoro-4'-[(3-fluoro-propylamino)-methyl]-biphenyl-4-yl}-2-oxo-oxazolidin-5-ylmethyl)-acetamide |
| 79 | 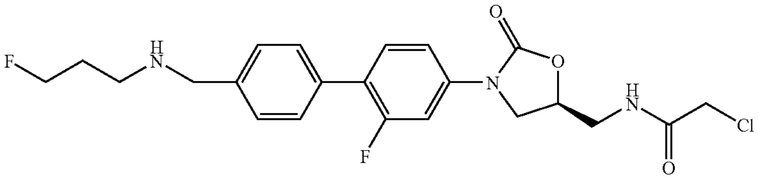<br>(5S)-2-Chloro-N-(3-{2-fluoro-4'-[(3-fluoro-propylamino)-methyl]-biphenyl-4-yl}-2-oxo-oxazolidin-5-ylmethyl)-acetamide |
| 80 | 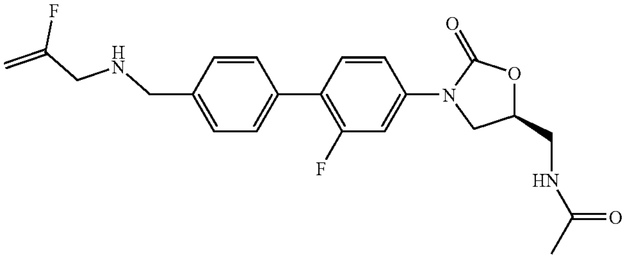<br>(5S)-N-(3-{2-Fluoro-4'-[(2-fluoro-allylamino)-methyl]-biphenyl-4-yl}-2-oxo-oxazolidin-5-ylmethyl)-acetamide |
| 81 | 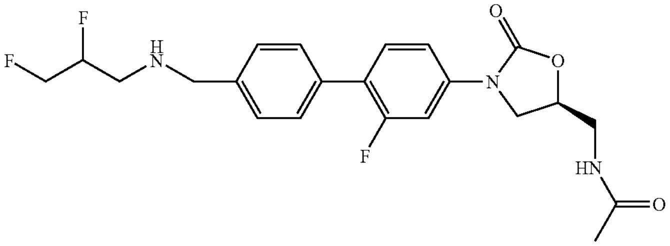<br>(±) (5S)-N-(3-{4'-[(2,3-Difluoro-propylamino)-methyl]-2-fluorobiphenyl-4-yl}-2-oxo-oxazolidin-5-ylmethyl)-acetamide |
| 82 | 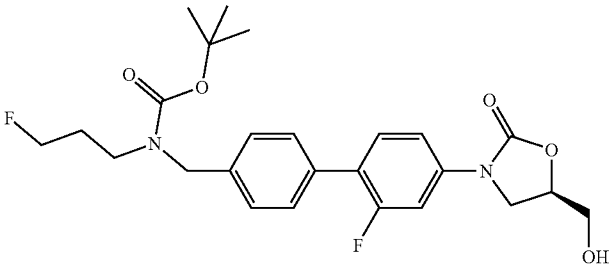<br>(5R)-[2'-fluoro-4'-(5-hydroxymethyl-2-oxo-oxazolidin-3-yl)-biphenyl-4-ylmethyl]-(3-fluoro-propyl)-carbamic acid tert-butyl ester |

The following schemes depict some exemplary chemistries available for synthesizing the compounds of the invention. It will be appreciated, however, that the desired compounds may be synthesized using other alternative chemistries known in the art.

Example 1

Synthesis of Aryl Iodide 101

Method A

Scheme 1 depicts the synthesis of aryl iodide 101, an intermediate useful in producing compounds of the present invention.

Scheme 1

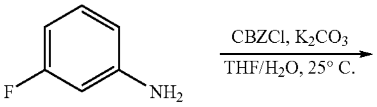

90

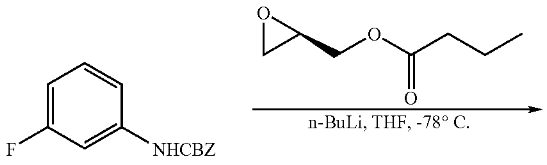

91

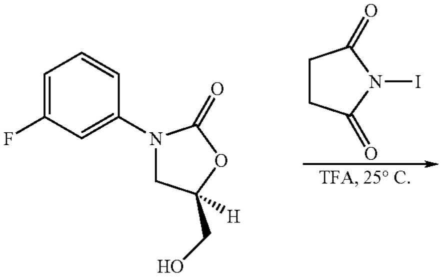

92

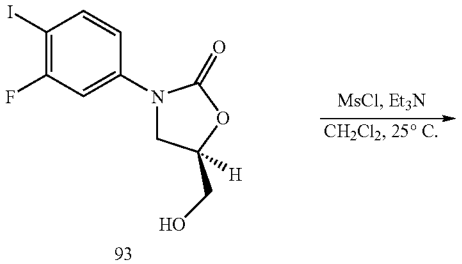

93

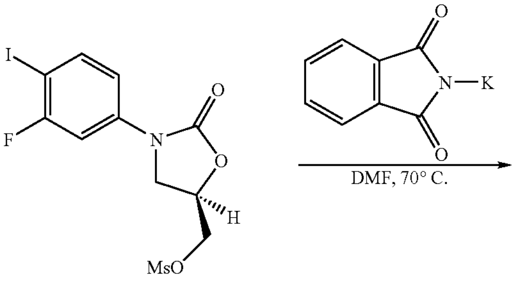

94

-continued

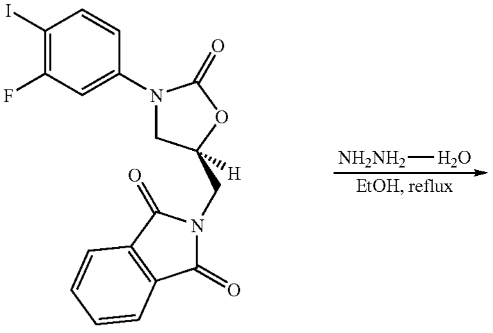

95

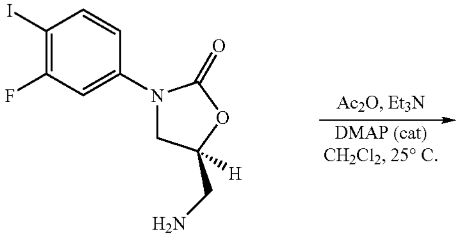

96

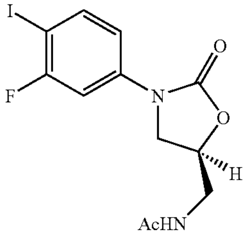

101

Synthesis of Amine 91

A solution of 3-fluoroanaline 90 (18.7 g, 168.3 mmol) in tetrahydrofuran (THF, 150 mL) was treated with potassium carbonate ($K_2CO_3$, 46.45 g, 336.6 mmol, 2.0 equiv) and water ($H_2O$) (150 mL) before a solution of benzyl chloroformate (CBZCl, 31.58 g, 185.1 mmol, 26.1 mL, 1.1 equiv) in THF (50 mL) was dropwise added into the reaction mixture at room temperature under nitrogen ($N_2$). The resulting reaction mixture was stirred at room temperature for 2 hours (h). When thin layer chromatography (TLC) showed the reaction was complete, the reaction mixture was treated with $H_2O$ (100 mL) and ethyl acetate (EtOAc, 100 mL). The two layers were separated, and the aqueous layer was extracted with EtOAc (2×100 mL). The combined organic extracts were washed with $H_2O$ (2×100 mL) and saturated aqueous sodium chloride (NaCl, 100 mL), dried over magnesium sulfate ($MgSO_4$), and concentrated in vacuo. The residue was further dried in vacuo to afford the desired (3-fluoro-phenyl)-carbamic acid benzyl ester (amine 91, 39.2 g, 95% yield) as pale-yellow oil. This product was directly used in subsequent reactions without further purification. $^1H$ NMR (300 MHz, $CDCl_3$) δ 5.23 (s, 2H, $OCH_2Ph$), 6.75–6.82 (m, 2H), 7.05 (dd, 1H, J=1.4, 8.2 Hz), 7.22–7.45 (m, 6H). $C_{14}H_{12}FNO_2$, LCMS (EI) m/e 246 ($M^+$+H).

Synthesis of Alcohol 92

A solution of amine 91 (39.2 g, 160.0 mmol) in anhydrous THF (300 mL) was cooled to −78° C. in a dry-ice/acetone bath before a solution of n-butyl lithium (n-BuLi, 2.5 M solution in hexane, 70.4 mL, 176 mmol, 1.1 equiv) was dropwise added under $N_2$. The resulting reaction mixture was subsequently stirred at −78° C. for 1 h before a solution of (R)-(−)-glycidyl butyrate (25.37 g, 24.6 mL, 176 mmol, 1.1 equiv) in anhydrous THF (100 mL) was dropwise added into the reaction mixture at −78° C. under $N_2$. The resulting reaction mixture was stirred at −78° C. for 30 minutes (min) before being gradually warmed to room temperature for 12 h under $N_2$. When TLC and high performance liquid chromatography/mass spectrometry (HPLC/MS) showed the reaction was complete, the reaction mixture was quenched with $H_2O$ (200 mL), and the resulting mixture was stirred at room temperature for 1 h before EtOAc (200 mL) was added. The two layers were separated, and the aqueous layer was extracted with EtOAc (2×100 mL). The combined organic extracts were washed with $H_2O$ (2×100 mL) and saturated aqueous NaCl (100 mL), dried over $MgSO_4$, and concentrated in vacuo. White crystals precipitated from the concentrated solution when most of the solvent was evaporated. The residue was then treated with 20% EtOAc/hexane (100 mL) and the resulting slurry was stirred at room temperature for 30 min. The solids were collected by filtration and washed with 20% EtOAc/hexane (2×50 mL) to afford the desired (5R)-(3-(3-fluoro-phenyl)-5-hydroxymethyl-oxazolidin-2-one (alcohol 92, 24.4 g, 72.3% yield) as white crystals. This product was directly used in subsequent reactions without further purification. $^1H$ NMR (300 MHz, DMSO-$d_6$) δ 3.34–3.72 (m, 2H), 3.83 (dd, 1H, J=6.2, 9.0 Hz), 4.09 (t, 1H, J=12.0 Hz), 4.68–4.75 (m, 1H), 5.23 (t, 1H, J=5.6 Hz, OH), 6.96 (m, 1H), 7.32–7.56 (m, 3H). $C_{10}H_{10}FNO_3$, LCMS (EI) m/e 212 ($M^+$+H).

Synthesis of Iodo-Alcohol 93

A solution of alcohol 92 (10.74 g, 50.9 mmol) in trifluoroacetic acid (TFA, 50 mL) was treated with N-iodosuccinimide (12.03 g, 53.45 mmol, 1.05 equiv) at 25° C. and stirred for 2 h. When TLC and HPLC/MS showed the reaction was complete, the reaction mixture was concentrated in vacuo. The residue was then treated with $H_2O$ (100 mL) and 20% EtOAc/hexane (100 mL) at 25° C., and the resulting mixture was stirred at 25° C. for 30 min before being cooled to 0–5° C. for 2 h. The white solids were collected by filtration, washed with $H_2O$ (2×25 mL) and 20% EtOAc/hexane (2×25 mL), and dried in vacuo to afford the desired (5R)-3-(3-fluoro-4-iodo-phenyl)-5-hydroxymethyl-oxazolidin-2-one (iodo-alcohol 93, 15; 1 g, 88% yield) as an off-white powder. This product was directly used in subsequent reactions without further purification. $^1H$ NMR (300 MHz, DMSO-$d_6$) δ 3.58 (dd, 1H, J=4.2, 12.6 Hz), 3.67 (dd, 1H, J=3.0, 12.6 Hz), 3.67 (dd, 1H, J=6.3, 9.0 Hz), 4.07(t, 1H, J=9.0 Hz), 4.72 (m, 1H), 5.21 (br. s, 1H, OH), 7.22 (dd, 1H, J=2.4, 8.4 Hz), 7.58 (dd, 1H, J=2.4, 11.1 Hz), 7.81 (dd, 11H, J=7.8, 8.7 Hz). $C_{10}H_9FINO_3$, LCMS (EI) m/e 338 ($M^+$+H).

Synthesis of Mesylate 94

A solution of iodo-alcohol 93 (25.2 g, 74.8 mmol) in methylene chloride ($CH_2Cl_2$, 150 mL) was treated with triethylamine (TEA or $Et_3N$, 15.15 g, 20.9 mL, 150 mmol, 2.0 equiv) at 25° C., and the resulting mixture was cooled to 0–5° C. before methanesulfonyl chloride (MsCl, 10.28 g, 6.95 mL, 89.7 mmol, 1.2 equiv) was dropwise introduced into the reaction mixture at 0–5° C. under $N_2$. The resulting reaction mixture was subsequently stirred at 0–5° C. for 1 h under $N_2$. When TLC and HPLC/MS showed the reaction was complete, the reaction mixture was quenched with $H_2O$ (100 mL) and $CH_2Cl_2$ (100 mL). The two layers were separated, and the aqueous layer was extracted with $CH_2Cl_2$ (100 mL). The combined organic extracts were washed with $H_2O$ (2×100 mL) and saturated aqueous NaCl (100 mL), dried over $MgSO_4$, and concentrated in vacuo. The residue was further dried in vacuo to afford the desired (5R)-methanesulfonic acid 3-(3-fluoro-4-iodo-phenyl)-2-oxo-oxazolidin-5-ylmethyl ester (mesylate 94, 30.71 g, 98.9% yield) as an off-white powder. This product was directly used in subsequent reactions without further purification. $C_{11}H_{11}FINO_5S$, LCMS (EI) m/e 416 ($M^+$+H).

Synthesis of Phthalimide 95

A solution of mesylate 94 (26.38 g, 63.57 mmol) in anhydrous N,N-dimethylformamide (DMF, 120 mL) was treated with solid potassium phthalimide (12.95 g, 70.0 mmol, 1.1 equiv) at 25° C., and the resulting reaction mixture was warmed to 70° C. for 2 h. When TLC and HPLC showed the reaction was complete, the reaction mixture was cooled to room temperature before being quenched with $H_2O$ (400 mL). The resulting mixture was stirred at room temperature for 10 min before being cooled to 0–5° C. for 1 h. The white precipitate was collected by filtration, washed with water (3×100 mL), and dried in vacuo to afford the desired (5R)-2-[3-(3-fluoro-4-iodo-phenyl)-2-oxo-oxazolidin-5-ylmethyl]-isoindole-1,3-dione (phthalimide 95, 27.85 g, 94%) as an off-white powder. This product was directly used in subsequent reactions without further purification. $C_{18}H_{12}FIN_2O_4$, LCMS (EI) m/e 467 ($M^+$+H).

Synthesis of Amine 96

A solution of phthalimide 95 (23.3 g, 50.0 mmol) in ethanol (EtOH, 150 mL) was treated with hydrazine monohydrate (12.52 g, 12.1 mL, 250 mmol, 5.0 equiv) at 25° C., and the resulting reaction mixture was warmed to reflux for 2 h. A white precipitate formed as the reaction mixture refluxed. When TLC and HPLC showed that the reaction was complete, the reaction mixture was cooled to room temperature before being quenched with $H_2O$ (100 mL). The aqueous solution was then extracted with $CH_2Cl_2$ (3×200 mL), and the combined organic extracts were washed with $H_2O$ (2×100 mL) and saturated aqueous NaCl (100 mL), dried over $MgSO_4$, and concentrated in vacuo. The residue was further dried in vacuo to afford the desired (5S)-5-aminomethyl-3-(3-fluoro-4-iodo-phenyl)-oxazolidin-2-one (amine 96, 16.0 g, 95.2% yield) as a white powder. This product was directly used in the subsequent reactions without further purification. $C_{10}H_{10}FIN_2O_2$, LCMS (EI) m/e 337 ($M^+$+H).

Synthesis of Aryl Iodide 101

A suspension of amine 96 (16.0 g, 47.6 mmol) in $CH_2Cl_2$ (150 mL) was treated with TEA (9.62 g, 13.2 mL, 95.2 mmol, 2.0 equiv) at 25° C., and the resulting reaction mixture was cooled to 0–5° C. before being treated with acetic anhydride ($Ac_2O$, 7.29 g, 6.75 mL, 71.4 mmol, 1.5 equiv) and 4-N,N-dimethylaminopyridine (DMAP, 58 mg, 0.5 mmol, 0.01 equiv) at 0–5° C. under $N_2$. The resulting reaction mixture was subsequently stirred at 0–5° C. for 2 h. When TLC and HPLC showed the reaction was complete, the reaction mixture was quenched with $H_2O$ (100 mL). The two layers were separated, and the aqueous layer was extracted with $CH_2Cl_2$ (2×50 mL). The combined organic extracts were washed with $H_2O$ (2×100 mL) and saturated aqueous NaCl (100 mL), dried over $MgSO_4$, and concentrated in vacuo. The residue was further dried in vacuo to afford the desired (5S)-N-[3-(3-fluoro-4-iodo-phenyl)-2-oxo-oxazolidin-5-ylmethyl]-acetamide (aryl iodide 101, 17.36 g, 96.5% yield) as a white powder. This product was directly used in subsequent reactions without further purification. $^1$H NMR (300 MHz, DMSO-$d_6$) δ 1.63 (s, 3H, $NHCOCH_3$), 3.25 (t, 2H, J=5.4 Hz), 3.56 (dd, 1H, J=6.4, 9.2 Hz), 3.95 (t, 1H, J=9.1 Hz), 4.58 (m, 1H), 5.16 (t, 1H, J=5.7 Hz, OH), 7.02 (dd, 1H, J=2.4, 8.2 Hz), 7.38 (dd, 1H, J=2.4, 10.8 Hz), 7.66 (t, 1H, J=7.5, 8.4 Hz), 8.08 (t, 1H, J=5.8 Hz, $NHCOCH_3$). $C_{12}H_{12}FIN_2O_3$, LCMS (EI) m/e 379 ($M^+$+H).

Method B

Scheme 2 depicts an alternate synthesis of aryl iodide 101 from alcohol 92.

Scheme 2

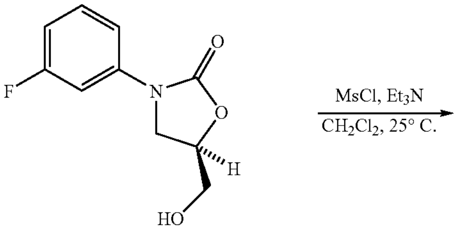

92

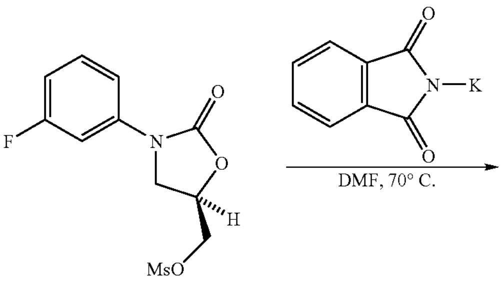

97

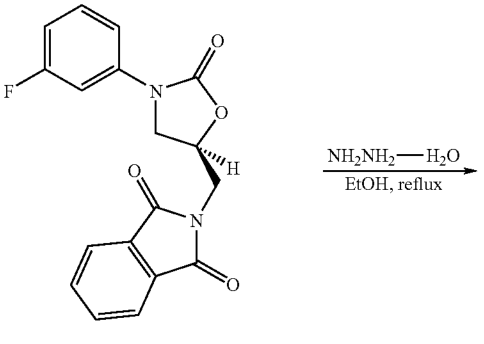

98

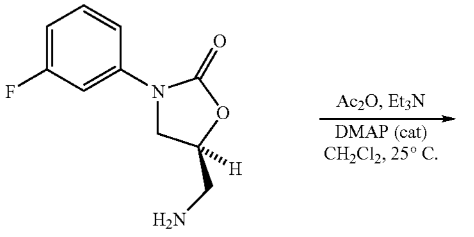

99

-continued

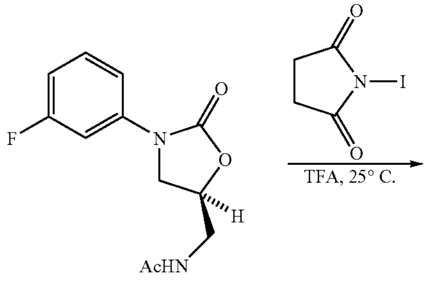

100

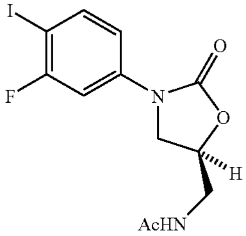

101

Synthesis of Mesylate 97

A solution of alcohol 92 (6.33 g, 30.0 mmol) in $CH_2Cl_2$ (60 mL) was treated with TEA (6.07 g, 8.36 mL, 60 mmol, 2.0 equiv) at 25° C., and the resulting mixture was cooled to 0–5° C. before MsCl (3.78 g, 2.55 mL, 33.0 mmol, 1.1 equiv) was dropwise introduced into the reaction mixture at 0–5° C. under $N_2$. The resulting reaction mixture was subsequently stirred at 0–5° C. for 1 h under $N_2$. When TLC and HPLC/MS showed the reaction was complete, the reaction mixture was quenched with $H_2O$ (40 mL) and $CH_2Cl_2$ (40 mL). The two layers were separated, and the aqueous layer was extracted with $CH_2Cl_2$ (40 mL). The combined organic extracts were washed with $H_2O$ (2×40 mL) and saturated aqueous NaCl (40 mL), dried over $MgSO_4$, and concentrated in vacuo. The residue was further dried in vacuo to afford the desired (5R)-methanesulfonic acid 3-(3-fluoro-phenyl)-2-oxo-oxazolidin-5-ylmethyl ester (mesylate 97, 7.69 g, 88.7% yield) as an off-white powder. This product was directly used in subsequent reactions without further purification. $C_{11}H_{12}FNO_5S$, LCMS (EI) m/e 290 ($M^+$+H).

Synthesis of Phthalimide 98

A solution of mesylate 97 (2.89 g, 10.0 mmol) in anhydrous DMF (20 mL) was treated with solid potassium phthalimide (2.22 g, 70.0 mmol, 1.2 equiv) at 25° C., and the resulting reaction mixture was warmed to 70° C. for 4 h. When TLC and HPLC showed the reaction was complete, the reaction mixture was cooled to room temperature before being quenched with $H_2O$ (60 mL). The resulting mixture was stirred at room temperature for 10 min before being cooled to 0–5° C. for 1 h. The white precipitate was collected by filtration, washed with water (2×40 mL), and dried in vacuo to afford the desired (5R)-2-[3-(3-fluoro-phenyl)-2-oxo-oxazolidin-5-ylmethyl]-isoindole-1,3-dione (phthalimide 98, 3.12 g, 91.8% yield) as an off-white powder. This product was directly used in subsequent reactions without further purification. $C_{18}H_{13}FN_2O_4$, LCMS (EI) m/e 341 ($M^+$+H).

Synthesis of Amine 99

A solution of phthalimide 98 (3.0 g, 8.82 mmol) in EtOH (30 mL) was treated with hydrazine monohydrate (2.20 g, 2.2 mL, 44.12 mmol, 5.0 equiv) at 25° C., and the resulting reaction mixture was warmed to reflux for 2 h. White precipitates formed as the reaction mixture was refluxed. When TLC and HPLC showed the reaction was complete, the reaction mixture was cooled to room temperature before being quenched with $H_2O$ (20 mL). The aqueous solution was then extracted with $CH_2Cl_2$ (3×40 mL), and the combined organic extracts were washed with $H_2O$ (2×20 mL) and saturated aqueous NaCl (20 mL), dried over $MgSO_4$, and concentrated in vacuo. The residue was further dried in vacuo to afford the desired (5S)-5-aminomethyl-3-(3-fluoro-phenyl)-oxazolidin-2-one (amine 99, 1.79 g, 96.6% yield) as a white powder. This product was directly used in the subsequent reactions without further purification. $C_{10}H_{11}FN_2O_2$, LCMS (EI) m/e 211 ($M^+$+H).

Synthesis of Acetamide 100

A suspension of amine 99 (2.60 g, 12.38 mmol) in $CH_2Cl_2$ (40 mL) was treated with TEA (2.50 g, 3.4 mL, 24.76 mmol, 2.0 equiv) at 25° C., and the resulting reaction mixture was cooled to 0–5° C. before being treated with $Ac_2O$ (1.90 g, 1.75 mL, 18.75 mmol, 1.5 equiv) and DMAP (15 mg, 0.12 mmol, 0.01 equiv) at 0–5° C. under $N_2$. The resulting reaction mixture was subsequently stirred at 0–5° C. for 2 h. When TLC and HPLC showed the reaction was complete, the reaction mixture was quenched with $H_2O$ (20 mL). The two layers were separated, and the aqueous layer was then extracted with $CH_2Cl_2$ (2×20 mL). The combined organic extracts were washed with $H_2O$ (2×20 mL) and saturated aqueous NaCl (20 mL), dried over $MgSO_4$, and concentrated in vacuo. The residue was further dried in vacuo to afford the desired (5S)-N-[3-(3-fluoro-4-phenyl)-2-oxo-oxazolidin-5-ylmethyl]-acetamide (acetamide 100, 2.93 g, 94% yield) as a white powder. This product was directly used in the subsequent reactions without further purification. $C_{12}H_{13}FN_2O_3$, LCMS (EI) m/e 253 ($M^+$+H).

Synthesis of Aryl Iodide 101

A solution of acetamide 100 (2.3 g, 9.1 mmol) in TFA (20 mL) was treated with N-iodosuccinimide (2.3 g, 10.0 mmol, 1.1 equiv) at 25° C., and the resulting reaction mixture was stirred at 25° C. for 2 h. When TLC and HPLC/MS showed the reaction was complete, the reaction mixture was concentrated in vacuo. The residue was treated with $H_2O$ (20 mL) and 20% EtOAc/hexane (20 mL) at 25° C., and the resulting mixture was stirred at 25° C. for 30 min before being cooled to 0–5° C. for 2 h. The white solids were collected by filtration, washed with $H_2O$ (2×20 mL) and 20% EtOAc/hexane (2×20 mL), and dried in vacuo to afford the desired (5S)-N-[3-(3-fluoro-4-iodo-phenyl)-2-oxo-oxazolidin-5-ylmethyl]-acetamide (aryl iodide 101, 3.34 g, 96.8% yield) as an off-white powder. This product was found to be identical with the material obtained from Method A.

The synthesis of aryl iodide 101 is also described, for example, in U.S. Pat. Nos. 5,523,403 and 5,565,571.

Example 2

Synthesis of Compounds 1 and 2

Scheme 3 illustrates the synthesis of amine 105, an intermediate used in the synthesis of compounds 1 and 2. Aryl iodide 101 is coupled to a substituted aryl boronic acid (the Suzuki reaction) to produce N-[3-(2-fluoro-4'-hydroxymethyl-biphenyl-4-yl)-2-oxo-oxazolidin-5-ylmethyl]-acetamide (biaryl alcohol 102). Other coupling reactions (for example, the Stille reaction), using alternate coupling intermediates easily obtained or synthesized by those skilled in the art, could also be employed to synthesize target biaryl intermediates similar to biaryl alcohol 102. Biaryl alcohol 102 is then converted to amine 105 by chemistry well known to those skilled in the art.

Scheme 3

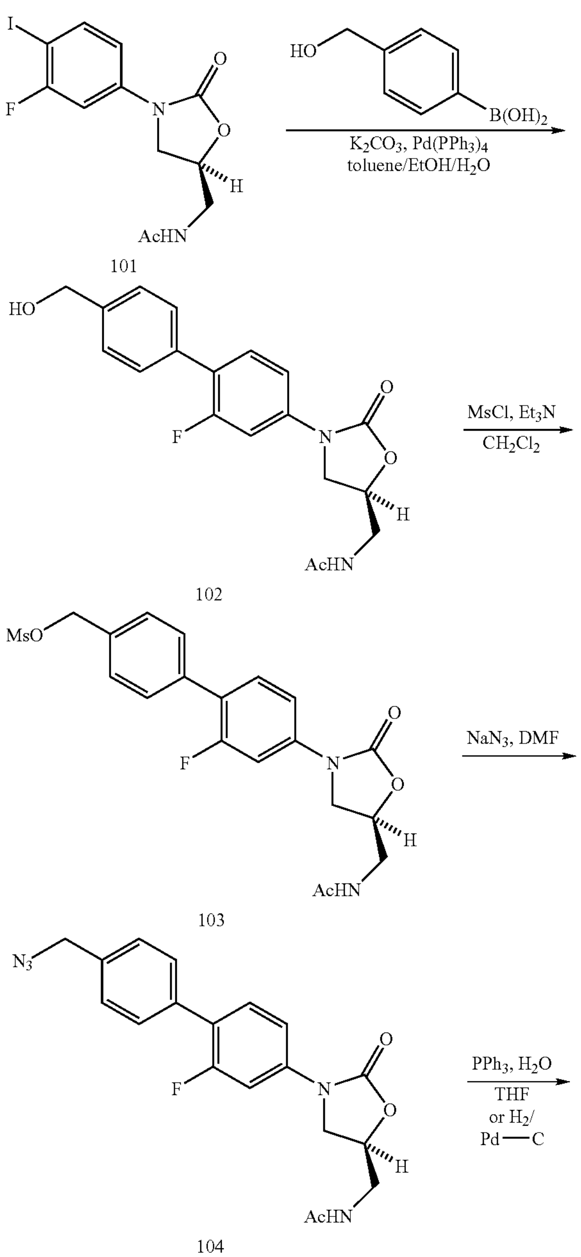

101
102
103
104

-continued

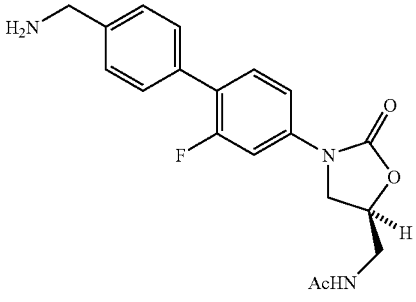

105

Scheme 4 illustrates the synthesis of compounds 1 and 2. Amine 105 is alkylated with the requisite bromides to afford compounds 1 and 2.

Scheme 4

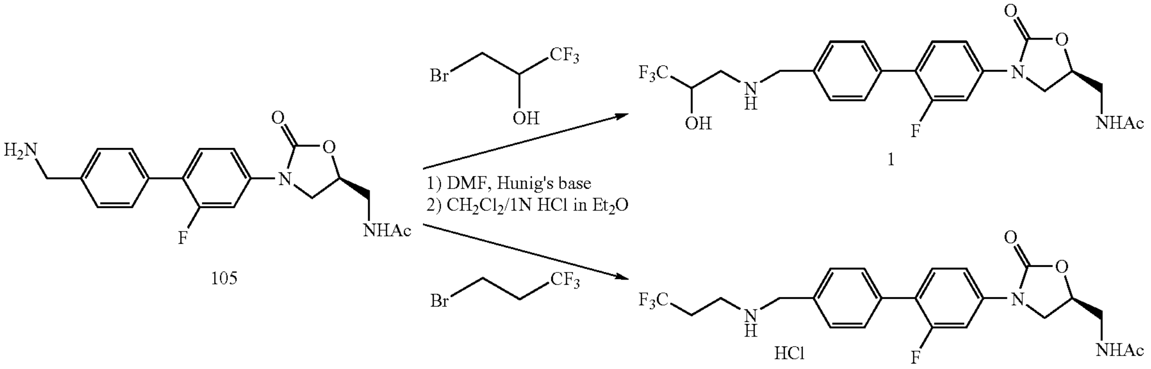

105

1

2

Synthesis of Amine 105

A suspension of aryl iodide 101 (14.0 g, 37 mmol) in toluene (120 mL) was treated with 4-(hydroxymethyl)phenylboronic acid (7.87 g, 51.8 mmol), $K_2CO_3$ (15.32 g, 111 mmol), EtOH (40 mL), and $H_2O$ (40 mL) at 25° C., and the resulting mixture was degassed three times under a steady stream of argon at 25° C. Tetrakis (triphenylphosphine) palladium(0) ($Pd(PPh_3)_4$, 2.14 g, 1.85 mmol) was subsequently added to the reaction mixture, and the resulting reaction mixture was degassed three times before being warmed to gentle reflux for 6 h. When TLC and HPLC showed the coupling reaction was complete, the reaction mixture was cooled to room temperature before being treated with $H_2O$ (240 mL). The resulting mixture was then stirred at room temperature for 10 min before being cooled to 0–5° C. for 1 h. The solid precipitates were collected by filtration, washed with $H_2O$ (2×100 mL) and 20% EtOAc/hexane (2×50 mL), and dried in vacuo. The crude desired biaryl alcohol 102 (12.50 g; 94% yield) was obtained as an off-white solid. This material was found to be essentially pure by HPLC and $^1H$ NMR and was directly used in the subsequent reaction without further purification. $^1H$ NMR (300 MHz, DMSO-$d_6$) δ 1.76 (s, 3H, $COCH_3$), 3.35 (t, 2H, J=5.4 Hz), 3.69 (dd, 1H, J=6.4, 9.2 Hz), 4.08 (t, 1H, J=9.1 Hz), 4.46 (d, 2H, J=5.7 Hz, $CH_2OH$), 4.68 (m, 1H), 5.16 (t, 1H, J=5.7 Hz, Oh), 7.25–7.52 (m, 7H, aromatic-H), 8.18 (t, 1H, J=5.8 Hz, $NHCOCH_3$). LCMS (ESI) m/z 359 $(M+H)^+$.

A suspension of alcohol 102 (12.49 g, 34.90 mmol) in $CH_2Cl_2$ (150 mL) was treated with TEA (7.07 g, 9.7 mL, 70 mmol) at 25° C., and the resulting mixture was cooled to 0–5° C. before being treated dropwise with MsCl (4.80 g, 3.24 mL, 41.9 mmol) at 0–5° C. The resulting reaction mixture was subsequently stirred at 0–5° C. for 2 h. When TLC and HPLC showed the reaction was complete, the reaction mixture was treated with $H_2O$ (100 mL) at 0–5° C. The mixture was then concentrated in vacuo to remove most of the $CH_2Cl_2$, and the resulting slurry was treated with $H_2O$ (150 mL). The mixture was stirred at room temperature for 10 min before being cooled to 0–5° C. for 30 min. The solid precipitates were collected by filtration, washed with $H_2O$ (2×100 mL) and 20% EtOAc/hexane (2×50 mL), and dried in vacuo. The crude mesylate 103 (11.84 g; 78% yield) was obtained as an off-white solid, which by TLC and HPLC was found to be essentially pure and was directly used in the subsequent reaction without further purification. LCMS (ESI) m/z 437 $(M+H)^+$.

A solution of mesylate 103 (9.27 g, 21.26 mmol) in anhydrous DMF (50 mL) was treated with sodium azide ($NaN_3$, 5.53 g, 85.04 mmol) at 25° C., and the resulting reaction mixture was warmed to 70–80° C. for 4 h. When TLC and HPLC showed the reaction was complete, the reaction mixture was cooled to room temperature before being treated with $H_2O$ (150 mL). The resulting mixture was stirred at room temperature for 10 min before being cooled to 0–5° C. for 1 h. The solid precipitate was collected by filtration, washed with $H_2O$ (2×100 mL) and 20% EtOAc/hexane (2×50 mL), and dried in vacuo. The crude azide 104 (7.16 g; 88% yield) was obtained as an off-white solid. The material was found to be essentially pure by TLC and HPLC and was directly used in the subsequent reaction without further purification. LCMS (ESI) m/z 384 $(M+H)^+$.

A solution of azide 104 (7.16 g, 18.69 mmol) in THF (100 mL) was treated with triphenylphosphine (5.88 g, 22.43 mmol) and $H_2O$ (3.6 g, 3.6 mL, 0.2 mmol) at 25° C., and the resulting reaction mixture was warmed to 50–55° C. for 12 h. When TLC and HPLC showed the reduction reaction was complete, the reaction mixture was cooled to room temperature before the solvents were removed in vacuo. The residue was directly purified by flash column chromatography (0–15% methanol (MeOH)/$CH_2Cl_2$ gradient elution) to afford amine 105 (5.82 g; 87% yield) as off-white crystals, which was of sufficient purity to be directly used in subsequent reactions. $^1H$ NMR (300 MHz, DMSO-$d_6$) δ 1.85 (s, 3H, $COCH_3$), 3.04 (br. s, 2H, $NH_2$), 3.44 (t, 2H, J=5.4 Hz), 3.78 (m, 3H), 4.18 (t, 1H, J=9.1 Hz), 4.77 (m, 1H), 7.25–7.60 (m, 7H, aromatic-H), 8.20 (t, 1H, J=5.8 Hz, $NHCOCH_3$). LCMS (ESI) m/e 359 $(M+2H)^{2+}$.

Synthesis of Compound 1

Amine 105 (1.0 g, 2.8 mmol) was dissolved in DMF (15 mL) and N,N-diisopropylethylamine (Hunig's base or i-$Pr_2NEt$, 3 mL). To this solution was added 3-bromo-1,1,1-trifluoro-2-propanol (0.33 mL, 3.0 mmol) and the mixture was heated at 60° C. for 24 h. The solvent was evaporated off and the crude was suspended in $H_2O$ (150 mL) and filtered. The residue was washed with $H_2O$ (50 mL), the combined aqueous layer was basified with concentrated ammonium hydroxide ($NH_4OH$), and a white precipitate resulted. The suspension was filtered; the residue was dissolved in $CH_2Cl_2$/MeOH 7:1 (50 mL) and dried over sodium sulfate ($Na_2SO_4$). The solvent was evaporated and the crude was purified on silica gel eluting with $CH_2Cl_2$/MeOH 16:1 to 12:1 to give compound 1 as white solid (0.265 g; 20% yield). LCMS (ESI) m/z 470 $(M+H)^+$.

Synthesis of Compound 2

Amine 105 (0.50 g, 1.40 mmol) was dissolved in DMF (10 mL) and Hunig's base (1 mL). To this solution was added 3-bromo-1,1,1-trifluoropropane (0.15 mL, 1.4 mmol) and the mixture was heated at 60° C. for 24 h. The solvent was evaporated and the crude was suspended in $H_2O$ (40 mL) and filtered. The residue was washed with $H_2O$ (50 mL) and dissolved in 10% MeOH in $CH_2Cl_2$ (60 mL). The solution was dried over $Na_2SO_4$ and the solvent evaporated. The crude was purified on silica gel eluting with 1–6% MeOH in $CH_2Cl_2$ to give a white solid (0.33 g; 52% yield). The isolated product was dissolved in $CH_2Cl_2$ (30 mL) and 1N hydrochloric acid (HCl) in diethyl ether ($Et_2O$, 1.5 mL, 1.5 mmol) and the mixture was stirred at room temperature for 20 min during which precipitation occurred. The solvent was evaporated to give a hydrochloride salt of compound 2 in quantitative yield. LCMS (ESI) m/z 454 $(M+H)^+$.

Example 3

Synthesis of Amine 3

Scheme 5 illustrates the synthesis of amine 3. 3-fluoropropylamine hydrochloride (amine hydrochloride 106) was synthesized from 1-bromo-3-fluoropropane 139, and then alkylated with benzyl chloride 107 to afford amine 3.

Scheme 5

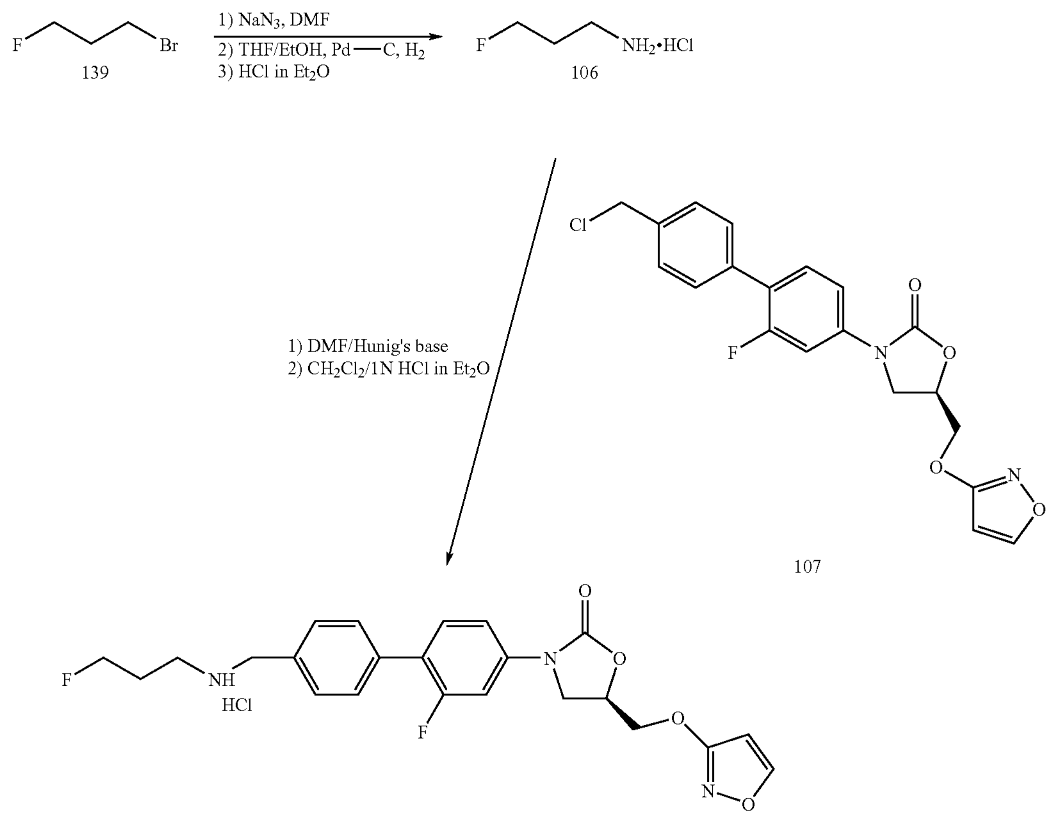

139, 106, 107, 3

Synthesis of Benzyl Chloride 107

To a solution of 3-(3-fluoro-4-iodo-phenyl)-5-hydroxymethyl-oxazolidin-2-one (1.0 g, 2.97 mmol), isoxazol-3-ol (0.30 g, 3.56 mmol) and triphenylphosphine (1.02 g, 3.86 mmol) in THF (15 mL) was added diisopropyl azodicarboxylate (DIAD, 0.74 mL, 3.56 mmol) dropwise at 0° C.

The reaction was warmed to room temperature and stirring was continued for 2 h. The solvent was evaporated and the crude was purified on silica gel, eluting with hexanes/EtOAc 2:1 to 3:2, to give 3-(3-fluoro-4-iodo-phenyl)-5-(isoxazol-3-yloxymethyl)-oxazolidin-2-one (1.01 g; 84% yield).

A degassed mixture containing 3-(3-fluoro-4-iodo-phenyl)-5-(isoxazol-3-yloxymethyl)-oxazolidin-2-one (1.0 g, 2.48 mmol), 4-(hydroxymethyl)phenylboronic acid (0.46 g, 3.00 mmol) and $Pd(PPh_3)_4$ in toluene (24 mL), EtOH (8 mL) and $H_2O$ (8 mL) was heated to reflux for 15 h. The reaction was concentrated, the crude residue was suspended in $H_2O$, filtered and dried in vacuo to give 3-(2-fluoro-4'-hydroxymethyl-biphenyl-4-yl)-5-(isoxazol-3-yloxymethyl)-oxazolidin-2-one. This crude material was dissolved in $CH_2Cl_2$ (10 mL) and Hunig's base (0.88 mL, 5.3 mmol), then MsCl (0.32 mL, 2.65 mmol) was added and the mixture was stirred at room temperature for 15 h. The reaction was partitioned between dilute sodium bicarbonate ($NaHCO_3$, 20 mL) and $CH_2Cl_2$ (30 mL). The two layers were separated and the organic phase was washed with saturated ammonium chloride ($NH_4Cl$, 1×20 mL) and $H_2O$ (1×20 mL) and dried over $Na_2SO_4$. The solvent was evaporated and the crude was purified on silica gel eluting with 0–3% MeOH in $CH_2Cl_2$ to give benzyl chloride 107 as white crystalline solid (0.46 g; 43% yield over the last two steps). LCMS (ESI) m/z 403 $(M+H)^+$.

Synthesis of Amine Hydrochloride 106

A mixture of 3-fluoro-1-bromopropane (1.0 g, 7.1 mmol) and $NaN_3$ (1.2 g, 17.7 mmol) in DMF (10 mL) was heated at 60° C. overnight. The reaction was poured into $Et_2O$ (40 mL) and extracted with $H_2O$ (3×30 mL). The organic layer was dried over $Na_2SO_4$ and carefully concentrated to about 0.6 mL. Half of the volatile material was dissolved in THF (5 mL) and EtOH (2 mL) mixture. Palladium on carbon (Pd—C, 10 wt %, 60 mg) was added and the mixture was kept under a hydrogen balloon overnight. The reaction was filtered to remove the Pd—C, and 1 N HCl in $Et_2O$ (3.5 mL, 3.5 mmol) was added to the filtrate. The solution was stirred at room temperature for 10 min, and the solvent was evaporated to give amine hydrochloride 106 as a thick yellow oil that solidified upon standing (0.224 g; 56% yield).

Synthesis of Monohydrochloride Salt of Compound 3

A mixture of amine hydrochloride 106 (0.11 g, 0.96 mmol) and benzyl chloride 107 (0.097 g, 0.24 mmol) in DMF (5 mL) and Hunig's base (1 mL) was heated at 60° C. for 24 h. The solvent was evaporated and the crude was suspended in dilute aqueous $NH_4OH$ and filtered. The residue was dissolved in $CH_2Cl_2$ and dried over $Na_2SO_4$. The solvent was evaporated and the crude was purified on silica gel eluting with $CH_2Cl_2$/MeOH/$NH_4OH$ 16:1:0.05 to give a brown-white solid (0.041 g; 39%). The isolated product was dissolved in $CH_2Cl_2$ (5 mL) and 1 N HCl in $Et_2O$ (0.25 mL, 0.25 mmol) and the mixture was stirred at room temperature for 5 min during which time precipitation occurred. The solvent was evaporated to give a monohydrochloride salt of compound 3 in quantitative yield. LCMS (ESI) m/z 444 $(M+H)^+$.

Example 4

Synthesis of Triazole 4

Scheme 6 illustrates the synthesis of triazole 4. Known alcohol 108 is converted to known azide 110 which is then treated with trimethylsilylacetylene (TMS acetylene) to afford a silylated triazole. The silyl group is removed with tetrabutylammonium fluoride (TBAF) to afford triazole intermediate 111. Suzuki coupling of triazole intermediate 111 with 4-hydroxymethylboronic acid yields alcohol 112 which is converted to mesylate 113. Displacement of the mesylate of 113 with amine 106 yields triazole 4.

Scheme 6

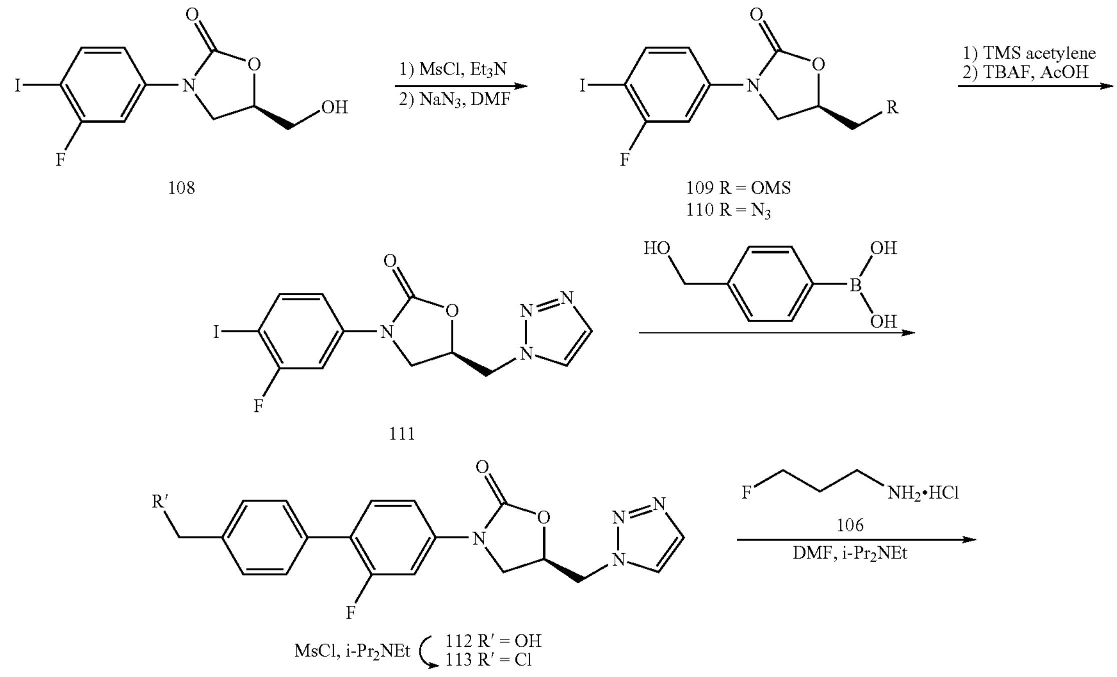

-continued

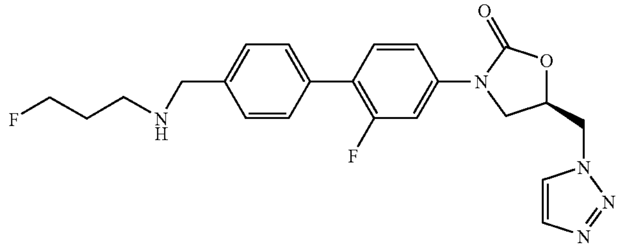

4

Synthesis of Azide 110

To a suspension of alcohol 108 (5 g, 14.84 mmol) in $CH_2Cl_2$ (80 mL) was added TEA (2.5 mL, 17.8 mmol) and MsCl (1.4 mL, 17.8 mmol) at 0° C. and the clear solution was stirred for 1 h at the same temperature. The reaction mixture was poured into brine solution (100 mL) and the aqueous phase was extracted with $CH_2Cl_2$ (2×50 mL). The combined organic layer was washed with brine solution (3×100 mL), dried over anhydrous $Na_2SO_4$, and concentrated to yield mesylate 109. To this was added $NaN_3$ (2 g, 29.7 mmol) and DMF (50 mL) and the mixture was heated to 80° C. overnight. The solution was poured into a mixture of EtOAc (150 mL) and $H_2O$ (100 mL). The organic layer was separated and the aqueous part was extracted with EtOAc (3×50 mL). The combined organic layer was washed with brine (1×150 mL), dried over anhydrous $Na_2SO_4$, and concentrated to yield 5.4 g of the azide 110.

A solution of azide 110 (5.4 g, 14.84 mmol) and TMS acetylene (10.48 mL, 74.2 mmol) in DMF (20 mL) was heated to 90° C. for 12 h. The reaction mixture was concentrated and treated with 1 M TBAF in THF (60 mL) and acetic acid (AcOH, 2 mL, 29.7 mmol) and stirred at ambient temperature for 12 h. The solution was concentrated and poured into a mixture of saturated $NH_4Cl$ (50 mL), EtOAc (150 mL) and brine solution (50 mL). The organic layer was separated and the aqueous phase was extracted with EtOAc (3×50 mL). The combined organic layer was dried over anhydrous $Na_2SO_4$, concentrated and the solid thus obtained was washed with $H_2O$ (5×200 mL) to yield 5.7 g of tetrazole intermediate 111. LCMS (ESI) m/z 389 $(M+H)^+$.

Synthesis of Alcohol 112

To a mixture of tetrazole intermediate 111 (5.7 g, 14.84 mmol), 4-hydroxymethylboronic acid (2.9 g, 19.29 mmol), $K_2CO_3$ (6.0 g, 44.52 mmol) and $Pd(PPh_3)_4$ (857 mg, 5 mol %) was added toluene (120 mL), EtOH (40 mL) and $H_2O$ (40 mL). The reaction mixture was degassed and flushed with argon and refluxed for 4 h. The solvent was concentrated under reduced pressure and residue thus obtained was poured into $H_2O$ (2000 mL). The pale yellow solid was filtered, and dried at 40° C. under vacuum to yield 4.76 g of alcohol 112. LCMS (ESI) m/z 369 $(M+H)^+$.

Synthesis of Benzyl Chloride 113

To a solution of alcohol 112 (4.6 g, 12.5 mmol) and Hunig's base (6.4 mL, 38.75 mmol) in DMF (40 mL) and $CH_2Cl_2$ (30 mL) was added MsCl (2.9 mL, 37.5 mmol) at 0° C. and the resulting solution was stirred at ambient temperature for 3 h. The solution was concentrated to remove $CH_2Cl_2$ and poured into $H_2O$ (1000 mL). The pale yellow solid was filtered and successively washed with $H_2O$ (5×200 mL), 10% EtOAc in hexanes (5×100 mL) and 50% ether in hexanes (5×100 mL). The resulting solid was dried at 40° C. under vacuum to yield 4.5 g of benzyl chloride 113. LCMS (ESI) m/z 387 $(M+H)^+$.

Synthesis of Triazole 4

A mixture of benzyl chloride 113 (100 mg, 0.258 mmol), amine hydrochloride 106 (100 mg, 0.881 mmol) and Hunig's base (1 mL) in DMF (4 mL) was heated to 60° C. overnight. The solution was concentrated and purified by flash chromatography over silica gel (12:1:0.01 $CH_2Cl_2$/MeOH/$NH_4OH$) to yield 37 mg of triazole 4. LCMS (ESI) m/z 328 (M+H).

Example 5

Synthesis of Compounds 5–14

Scheme 7 illustrates the general approach used to synthesize compounds 5–14. Amines 105, 114, and 115 were alkylated with fluorinated alkyl bromides to provide compounds 5–14.

Scheme 7

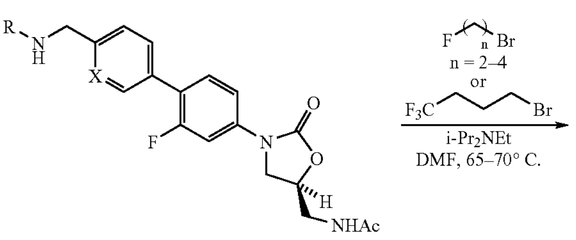

105 R = H, X = CH
114 R = $CH_3$, X = CH
115 R = H, X = N

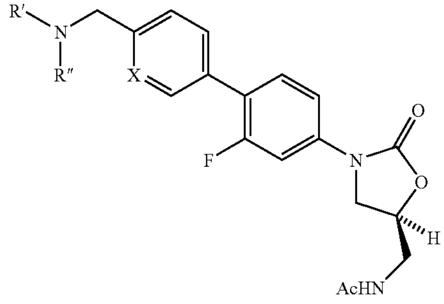

5-14

Scheme 8 depicts the synthesis of amine 114 used in the synthesis of compound 11. The Suzuki coupling of aryl iodide 101 and 4-formylphenylboronic acid produced aldehyde 116, which was converted via reductive amination chemistry to amine 114.

Scheme 8

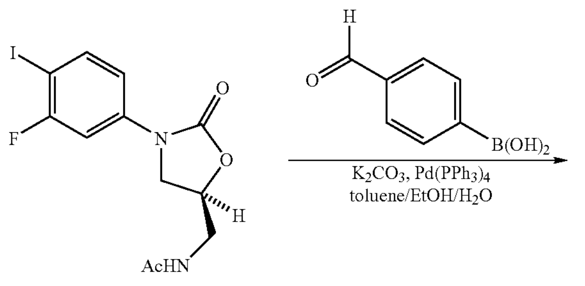

101

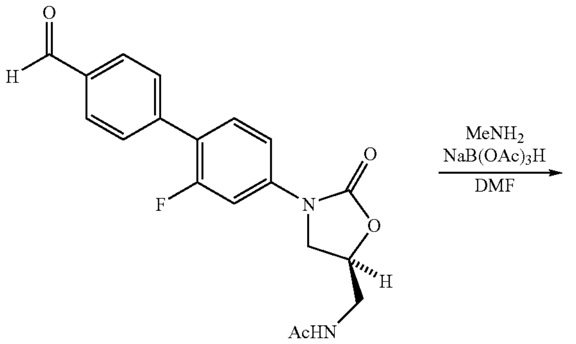

116

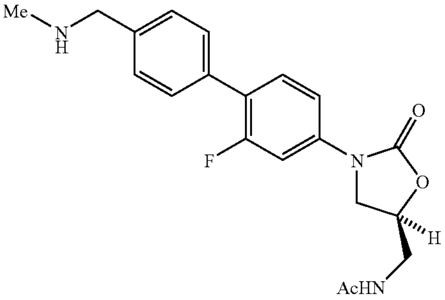

114

Scheme 9 illustrates the synthesis of amine 115 used in the synthesis of compounds 13 and 14. Pyridyl aldehyde 117 was reduced to alcohol 118 which was coupled to boronic ester 119 to afford alcohol 120. Alcohol 120 was converted via mesylate 121 to azide 122, which was subsequently reduced to amine 115.

Scheme 9

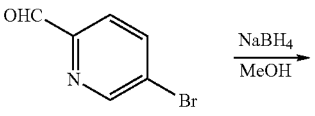

117

-continued

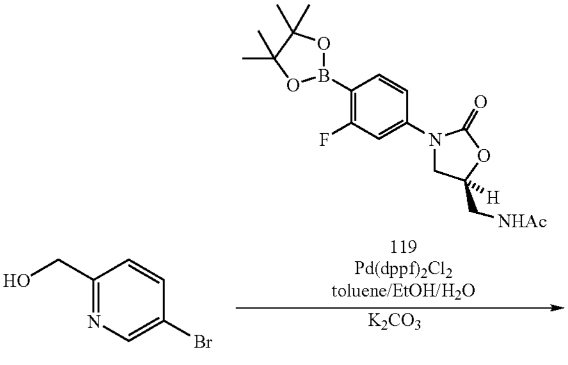

118

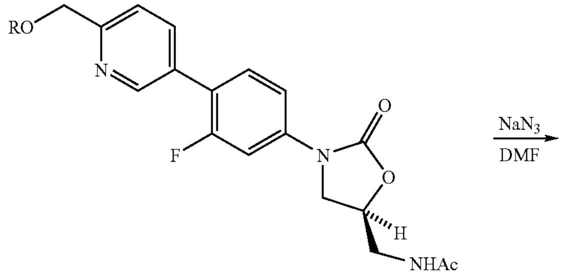

MsCl, i-Pr$_2$NEt 120 R = H
121 R = CH$_3$SO$_2$

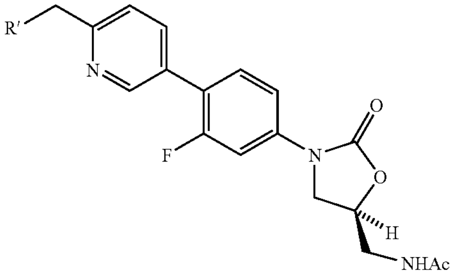

PPh$_3$ THF, H$_2$O 122 R' = N$_3$
115 R' = NH$_2$

Synthesis of Aldehyde 116

Aldehyde 116 was synthesized from aryl iodide 101 and 4-formylphenylboronic acid using the same procedure as described above for the synthesis of alcohol 112 from triazole intermediate 111.

Synthesis of Amine 114

A solution of aldehyde 116 (3.56 g, 10.0 mmol) in anhydrous DMF (20 mL) was treated with a 2 N solution of methylamine in THF (25 mL, 50.0 mmol) and sodium triacetoxyborohydride (NaB(OAc)$_3$H, 3.20 g, 15.0 mmol) at room temperature, and the resulting reaction mixture was stirred at room temperature for 6 h. When TLC and LCMS showed that the reaction was complete, the reaction mixture was quenched with $H_2O$ (40 mL), and the resulting mixture was stirred at room temperature for 30 min. The solid precipitate was then collected by filtration, washed with $H_2O$ (2×50 mL), and dried in vacuo. This crude material was subsequently purified by flash column chromatography (5–15% MeOH/$CH_2Cl_2$ gradient elution) to afford amine 114 (2.26 g; 61% yield) as an off-white solid. $^1$H NMR (300

MHz, DMSO-$d_6$) δ 2.03 (s, 3H, $COCH_3$), 2.46 (s, 3H, NMe), 3.62 (t, 2H, J=5.4 Hz), 3.86 (s, 2H, Ar—$CH_2$)), 3.96 (dd, 1H, J=6.4, 9.2 Hz), 4.35 (t, 1H, J=9.2 Hz), 4.90–4.99 (m, 1H), 7.58–7.80 (m, 7H, aromatic-H), 8.45 (t, 1H, J=5.8 Hz, $NHCOCH_3$). LCMS (ESI) m/z 372 $(M+H)^+$.

Synthesis of Aldehyde 117

A solution of 2,5-dibromopyridine (25 g, 105.5 mmol) in toluene (1.24 L) was cooled to −78° C. before being treated dropwise with a 2.5 M solution of n-BuLi in hexane (50.6 mL, 126.6 mmol) at −78° C. under $N_2$. The resulting reaction mixture was stirred at −78° C. for 1 h before being treated with anhydrous DMF (11.6 g, 12.2 mL, 158.0 mmol) at −78° C. The reaction mixture was stirred at −78° C. for an additional 1 h before being gradually warmed to room temperature for 6 h. When TLC and LCMS showed that the reaction was complete, the reaction mixture was quenched with $H_2O$ (200 mL). The two layers were separated, and the aqueous layer was extracted with EtOAc (2×50 mL). The combined organic extracts were then washed with $H_2O$ (2×200 mL), and saturated aqueous NaCl (100 mL), and dried over $MgSO_4$. The solvents were then removed in vacuo, and the residual pale-yellow oil was purified by flash column chromatography (0–15% EtOAc/hexane gradient elution) to afford pyridyl aldehyde 117 (10.2 g; 52% yield) as a pale-yellow solid.

Synthesis of Alcohol 118

A solution aldehyde 117 (4.91 g, 26.4 mmol) in MeOH (120 mL) was treated with sodium borohydride ($NaBH_4$, 1.18 g, 31.7 mmol) at 0–5° C., and the resulting reaction mixture was stirred at 0–5° C. for an additional 1 h. When TLC and LCMS showed that the reaction was complete, the reaction mixture was quenched with $H_2O$ (20 mL). The solvents were then removed in vacuo, and the residue was directly purified by flash column chromatography (5–25% EtOAc/hexane gradient elution) to afford alcohol 118 (4.23 g; 85% yield) as a white solid.

Synthesis of Boronic Ester 119

A solution of aryl iodide 101 (1.11 g, 2.55 mmol) in 1,4-dioxane (25 mL) was treated with 4,4,5,5-tetramethyl-[1,3,2]dioxaborolane (489 mg, 0.56 mL, 3.82 mmol) and TEA (772 mg, 1.07 mL, 7.65 mmol) at room temperature, and the resulting reaction mixture was degassed three times under a steady stream of argon before being treated with dichloro[1,1'-bis(diphenylphosphino)ferrocene]palladium (II) ($Pd(dppf)_2Cl_2$, 107 mg, 0.13 mmol) at room temperature. The reaction mixture was then degassed three times again under a steady stream of argon before being warmed to reflux for 6 h. When TLC and LCMS showed that the reaction was complete, the reaction mixture was cooled to room temperature before being treated with $H_2O$ (20 mL) and EtOAc (20 mL). The two layers were separated, and the aqueous layer was extracted with EtOAc (2×20 mL). The combined organic extracts were washed with $H_2O$ (2×20 mL) and saturated aqueous NaCl solution (20 mL), dried over $MgSO_4$, and concentrated in vacuo. The residual brown oil was then purified by flash column chromatography (10–30% EtOAc/hexanes gradient elution) to afford boronic ester 119 (646 mg; 58% yield) as a brown oil, which solidified upon standing at room temperature in vacuo and was of suitable purity for use in subsequent reactions.

Synthesis of Alcohol 120

A solution of boronic ester 119 (11.05 g, 29.2 mmol) and alcohol 118 (4.227 g, 22.5 mmol) in toluene (150 mL) was treated with solid $K_2CO_3$ (9.315 g, 67.5 mmol), EtOH (50 mL) and $H_2O$ (50 mL) at room temperature, and the resulting reaction mixture was degassed three times under a steady stream of argon before being treated with $Pd(dppf)_2Cl_2$ (564 mg, 0.675) at room temperature. The reaction mixture was then degassed three times again under a steady stream of argon before being warmed to reflux for 1 h. When LCMS showed that the reaction was complete, the reaction mixture was cooled to room temperature before being treated with $H_2O$ (200 mL) and EtOAc (100 mL). The two layers were separated, and the aqueous layer was extracted with ethyl EtOAc (2×50 mL). The combined organic extracts were washed with water (2×50 mL) and saturated aqueous NaCl solution (50 mL), dried over $MgSO_4$, and concentrated in vacuo. The residue was then purified by flash column chromatography (0–5% MeOH/$CH_2Cl_2$ gradient elution) to afford alcohol 120 (6.16 g; 76%) as a grey solid.

Synthesis of Azide 122

A suspension of alcohol 120 (2.15 g, 6.0 mmol) in $CH_2Cl_2$ (25 mL) was treated with Hunig's base (1.551 g, 2.10 mL, 12.0 mmol) and MsCl (756 mg, 0.511 mL, 6.6 mmol) at 0–5° C., and the resulting reaction mixture was stirred at 0–5° C. for an additional 2 h. When TLC and LCMS showed that the reaction was complete, the reaction mixture was treated with $H_2O$ (20 mL) and $CH_2Cl_2$ (40 mL). The two layers were separated, and the aqueous layer was extracted with $CH_2Cl_2$ (20 mL). The combined organic extracts were washed with $H_2O$ (20 mL) and saturated aqueous NaCl solution (20 mL), dried over $MgSO_4$, and concentrated in vacuo. The residue was then purified by flash column chromatography (0–5% MeOH/$CH_2Cl_2$ gradient elution) to afford mesylate 121 (2.47 g; 94% yield) as a yellow solid.

A solution of mesylate 121 (874 mg, 2.0 mmol) in DMF (8.0 mL) was treated with $NaN_3$ (260 mg, 4.0 mmol) at room temperature, and the resulting reaction mixture was warmed to 40–45° C. for 3 h. When TLC and LCMS showed that the reaction was complete, the reaction mixture was treated with $H_2O$ (20 mL), and the precipitate was collected by filtration, washed with $H_2O$ (2×10 mL), and dried in vacuo to afford crude azide 122 (699 mg; 91% yield) as a grey solid, which was of suitable purity for use in subsequent reactions.

Synthesis of Amine 115

A suspension of azide 122 (2.611 g, 6.8 mmol) in THF (25 mL) was treated with $H_2O$ (0.13 mL, 68 mmol) and triphenylphosphine ($PPh_3$, 2.14 g, 8.2 mmol) at room temperature, and the resulting reaction mixture was subsequently stirred at room temperature for 12 h. When TLC and LCMS showed that the reaction was complete, the solvents were removed in vacuo, and the residue was directly purified by flash column chromatography (0–15% MeOH/$CH_2Cl_2$ gradient elution) to afford amine 115 (2.233 g; 92% yield) as a yellow solid.

Synthesis of Compounds 5 and 6

A solution of amine 105 (700.0 mg, 1.96 mmol) in anhydrous DMF (10 mL) was treated with Hunig's base (380 mg, 0.51 mL, 2.94 mmol) at 25° C. under $N_2$, and the resulting mixture was treated with 1-bromo-2-fluoroethane (250 mg, 1.96 mmol) at 25° C. under $N_2$. The resulting reaction mixture was subsequently warmed to 65–70° C. for 6 h. When TLC and LCMS showed that the alkylation reaction was complete, the reaction mixture was concentrated in vacuo. The residue was then directly purified by flash column chromatography (0–5% MeOH/$CH_2Cl_2$ gradient elution) to afford compound 5 (395 mg; 50% yield) as an off-white solid and compound 6 (33.0 mg; 4% yield) as a pale-yellow oil, which solidified upon standing at room temperature in vacuo. For compound 5: LCMS (ESI) m/z 404 $(M+H)^+$. For compound 6: LCMS (ESI) m/z 450 $(M+H)^+$.

Synthesis of Compounds 7 and 8

A solution of amine 105 (5.712 g, 16.0 mmol) in anhydrous DMF (40 mL) was treated with Hunig's base (6.20 g, 8.4 mL, 48.0 mmol) at 25° C. under $N_2$, and the resulting mixture was treated with 3-fluoro-1-bromopropane (2.71 g, 19.2 mmol) at 25° C. under $N_2$. The resulting reaction mixture was subsequently warmed to 65–70° C. for 6 h. When TLC and LCMS showed that the alkylation reaction was complete, the reaction mixture was concentrated in vacuo. The residue was then directly purified by flash column chromatography (0–5% $MeOH/CH_2Cl_2$ gradient elution) to afford compound 7 (2.30 g; 35% yield) as an off-white solid and compound 8 (2.14 g; 28% yield) as a pale-yellow oil, which solidified upon standing at room temperature in vacuo. For compound 7: LCMS (ESI) m/z 418 $(M+H)^+$. For compound 8: LCMS (ESI) m/z 478 $(M+H)^+$.

Synthesis of Compounds 9 and 10

A solution of amine 105 (380 mg, 1.06 mmol) in anhydrous DMF (4.0 mL) was treated with Hunig's base (210 mg, 0.25 mL, 1.59 mmol) at 25° C. under $N_2$, and the resulting mixture was treated with 1-bromo-4-fluorobutane (165 mg, 1.06 mmol, 1.0 equiv) at 25° C. under $N_2$. The resulting reaction mixture was subsequently warmed to 65–70° C. for 6 h. When TLC and LCMS showed that the alkylation reaction was complete, the reaction mixture was concentrated in vacuo. The residue was then directly purified by flash column chromatography (0–5% $MeOH/CH_2Cl_2$ gradient elution) to afford compound 9 (119 mg; 26% yield) as an off-white solid and compound 10 (48.2 mg, 9% yield) as a pale-yellow oil, which solidified upon standing at room temperature in vacuo. For compound 9: LCMS (ESI) m/z 432 $(M+H)^+$. For compound 10: LCMS (ESI) m/z 506 $(M+H)^+$.

Synthesis of Compound 11

A solution of amine 114 (100.0 mg, 0.27 mmol) in anhydrous DMF (3.0 mL) was treated with Hunig's base (105 mg, 0.14 mL, 0.81 mmol) at 25° C. under $N_2$, and the resulting mixture was treated with 3-fluoro-1-bromopropane (46 mg, 0.32 mmol) at 25° C. under $N_2$. The resulting reaction mixture was subsequently warmed to 65–70° C. for 6 h. When TLC and LCMS showed that the alkylation reaction was complete, the reaction mixture was concentrated in vacuo. The residue was then directly purified by flash column chromatography (0–5% $MeOH/CH_2Cl_2$ gradient elution) to afford compound 11 (45 mg; 39% yield) as an off-white solid. LCMS (ESI) m/z 432 $(M+H)^+$.

Synthesis of Compound 12

A solution of amine 105 (150.0 mg, 0.42 mmol) in anhydrous DMF (4.0 mL) was treated with Hunig's base (163 mg, 0.22 mL, 1.26 mmol) at 25° C. under $N_2$, and the resulting mixture was treated with 4-bromo-1,1,1-trifluorobutane (120 mg, 0.60 mmol) at 25° C. under $N_2$. The resulting reaction mixture was subsequently warmed to 65–70° C. for 6 h. When TLC and LCMS showed that the alkylation reaction was complete, the reaction mixture was concentrated in vacuo. The residue was then directly purified by flash column chromatography (0–5% $MeOH/CH_2Cl_2$ gradient elution) to afford compound 12 (76.5 mg; 39% yield) as an off-white solid. LCMS (ESI) m/z 468 $(M+H)^+$.

Synthesis of Compounds 13 and 14

A solution of amine 115 (500.0 mg, 1.4 mmol) in anhydrous DMF (7.0 mL) was treated with Hunig's base (542 mg, 0.732 mL, 4.2 mmol) at 25° C. under $N_2$, and the resulting mixture was treated with 3-fluoro-1-bromopropane (197 mg, 1.4 mmol) at 25° C. under $N_2$. The resulting reaction mixture was subsequently warmed to 65–70° C. for 6 h. When TLC and LCMS showed that the alkylation reaction was complete, the reaction mixture was concentrated in vacuo. The residue was then directly purified by flash column chromatography (0–5% $MeOH/CH_2Cl_2$ gradient elution) to afford compound 13 (247.0 mg; 42% yield) as an off-white solid and compound 14 (121.0 mg; 18% yield) as a pale-yellow oil, which solidified upon standing at room temperature in vacuo. For compound 13: LCMS (ESI) m/z 419 $(M+H)^+$. For compound 14: LCMS (ESI) m/z 479 $(M+H)^+$.

Example 6

Synthesis of Compounds 15 and 16

Scheme 10 shows the synthesis of sulfide 15 and sulfoxide 16. Benzyl chloride 123 is displaced with thiolacetic acid to afford thioester 124 which is subsequently hydrolyzed to thiol 125. Alkylation of thiol 125 with 3-bromo-1,1,1-trifluoropropane to afford sulfide 15 which was oxidized to sulfoxide 16.

Scheme 10

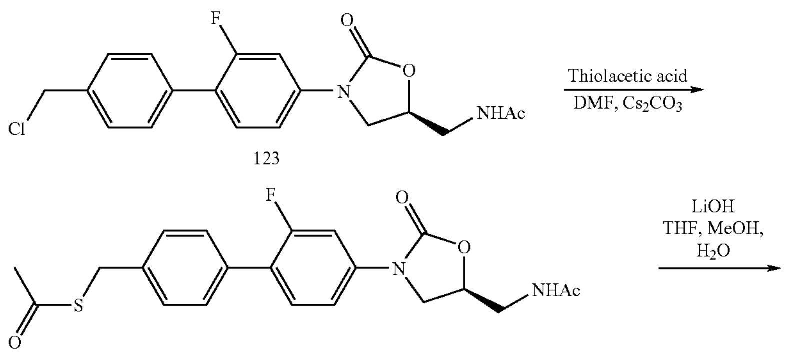

123

124

-continued

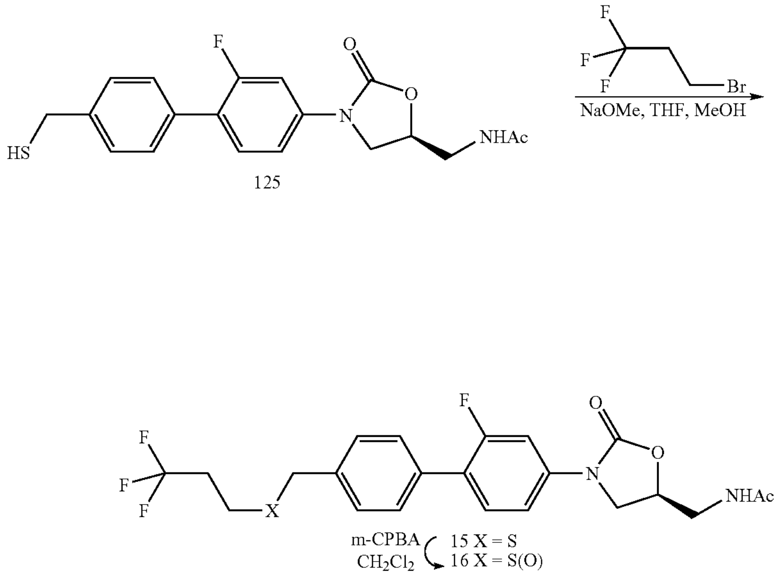

125

Synthesis of Benzyl Chloride 123

Alcohol 102 (3.0 g, 8.4 mmol) was dissolved in $CH_2Cl_2$ (20 mL) and Hunig's base (2 mL). MsCl (1.4 mL, 12.6 mmol) was added dropwise and the resulting solution stirred at room temperature for 4 h. The mixture was poured into 100 mL saturated aqueous $NaHCO_3$ and extracted with $CH_2Cl_2$ (3×50 mL). The combined organic extracts were washed with brine, dried over $MgSO_4$, filtered, and concentrated to give 3.9 g of an oily yellow solid. The crude material was purified by silica gel chromatography to give benzyl chloride 123 as an off-white solid (2.7 g, 7.2 mmol). LCMS (ESI) m/z 377 $(M+H)^+$, 418 $(M+CH_3CN+H)^+$, 440 $(M+CH_3CN+Na)^+$.

Synthesis of Thioester 124

Under an argon atmosphere, thiolacetic acid (1.55 mL, 21.7 mmol) was added to a mixture of benzyl chloride 123 (4.08 g, 10.8 mmol) and cesium carbonate ($Cs_2CO_3$, 3.52 g, 10.8 mmol) in DMF (25 mL). The reaction was stirred at room temperature for 2 h. Then 50 mL of $H_2O$ was added. The off-white thioester product 124 (4.3 g) was collected by filtration in a yield of 96%. LCMS (ESI) m/z 417 $(M+H)^+$.

Synthesis of Thiol 125

Lithium hydroxide (LiOH, 360 mg, 15 mmol) was added to a solution of thioester 124 (4.3 g, 10.3 mmol) in a mixture of THF (50 mL), MeOH (50 mL) and $H_2O$ (20 mL). After stirring for 30 minutes at room temperature under argon atmosphere, the insoluble solid was removed by filtration. The filtrate was diluted with $H_2O$ (50 mL), concentrated to remove organic solvents, then neutralized with 10% HCl. The off-white thio]product 125 (3.5 g) was collected by filtration in a yield of 91%. LCMS (ESI) m/z 375 $(M+H)^+$.

Synthesis of Sulfide 15

Under an argon atmosphere, sodium methoxide (NaOMe, 25% by wt. in MeOH, 238 mg, 1.1 mmol) was added to a solution of thiol 125 (374 mg, 1 mmol) and 3-bromo-1,1,1-trifluoropropane (186 mg, 1.05 mmol) in MeOH (4 mL) and THF (4 mL). After stirring at room temperature for 2 h, the reaction was concentrated. The residue was dissolved in $CH_2Cl_2$, washed with brine, dried over $MgSO_4$ and concentrated. The crude product was purified by chromatography (25:1:0.05 $CH_2Cl_2$/MeOH/$NH_3$.$H_2O$) to afford 220 mg of sulfide 15 in a yield of 47%. LCMS (ESI) m/z 471 $(M+H)^+$.

Synthesis of Sulfoxide 16

A mixture of sulfide 15 (135 mg 0.29 mmol) and mCPBA (70%, 71 mg, 0.29 mmol) in $CH_2Cl_2$ was stirred at room temperature for 1 h. The $CH_2Cl_2$ solution was washed with brine, dried over $MgSO_4$ and concentrated. The crude product was purified by chromatography on silica gel (25:1:0.05 $CH_2Cl_2$/MeOH/$NH_3$.$H_2O$) to afford 105 mg of a diastereomeric mixture of sulfoxide 16 in a yield of 75%. LCMS (ESI) m/z 487 $(M+H)^+$, 509 $(M+Na)^+$.

Example 7

Synthesis of Compounds 17–19

Synthesis of Sulfide 17

Under argon atmosphere, NaOMe (25% by wt. in MeOH, 216 mg, 1 mmol) was added to a solution of thiol 125 (340 mg, 0.91 mmol) and 1-bromo-3-fluoropropane (141 mg, 1 mmol) in MeOH (4 mL) and THF (4 mL). After stirring at room temperature for 2 h, the reaction was concentrated. The residue was dissolved $CH_2Cl_2$, washed with brine, dried over $MgSO_4$ and concentrated. The crude product was purified by preparative TLC (15:1:0.05 $CH_2Cl_2$/MeOH/$NH_3$.$H_2O$) to afford 220 mg of sulfide 17 in a yield of 56%. LCMS (ESI) m/z 435 $(M+H)^+$.

Synthesis of Sulfoxide 18

A mixture of sulfide 17 (140 mg 0.32 mmol) and mCPBA (70%, 79 mg, 0.32 mmol) in $CH_2Cl_2$ (10 mL) was stirred at room temperature for 1 h. The $CH_2Cl_2$ solution was washed with brine, dried over $MgSO_4$ and concentrated under vacuum. The crude product was purified by chromatography on silica gel (25:1:0.05 $CH_2Cl_2$/MeOH/$NH_3$.$H_2O$) to afford 140 mg of sulfoxide 18 (as a diastereomeric mixture) in a yield of 97%. LCMS (ESI) m/z 451 $(M+H)^+$, 473 $(M+Na)^+$.

Synthesis of Sulfone 19

A mixture of sulfoxide 18 (68 mg 0.15 mmol) and mCPBA (70%, 38 mg, 0.15 mmol) in $CH_2Cl_2$ (5 mL) was stirred at room temperature for 1 h. The reaction was concentrated and the residue was washed with $H_2O$ to afford 57 mg of sulfone 19 in a yield of 82%. LCMS (ESI) m/z 467 $(M+H)^+$.

Example 8

Synthesis of Compound 20

Scheme 11 depicts the synthesis of compound 20. Epoxide 126 served as the alkylating agent for benzylamine to provide aryl bromide 127. Aryl bromide 127 was coupled to boronic ester 119 to yield benzylamine 128. Benzylamine 128 was alkylated with 3-fluoro-1-bromopropane to afford the expected tertiary amine which was subsequently deprotected by hydrogenation to afford compound 20.

Scheme 11

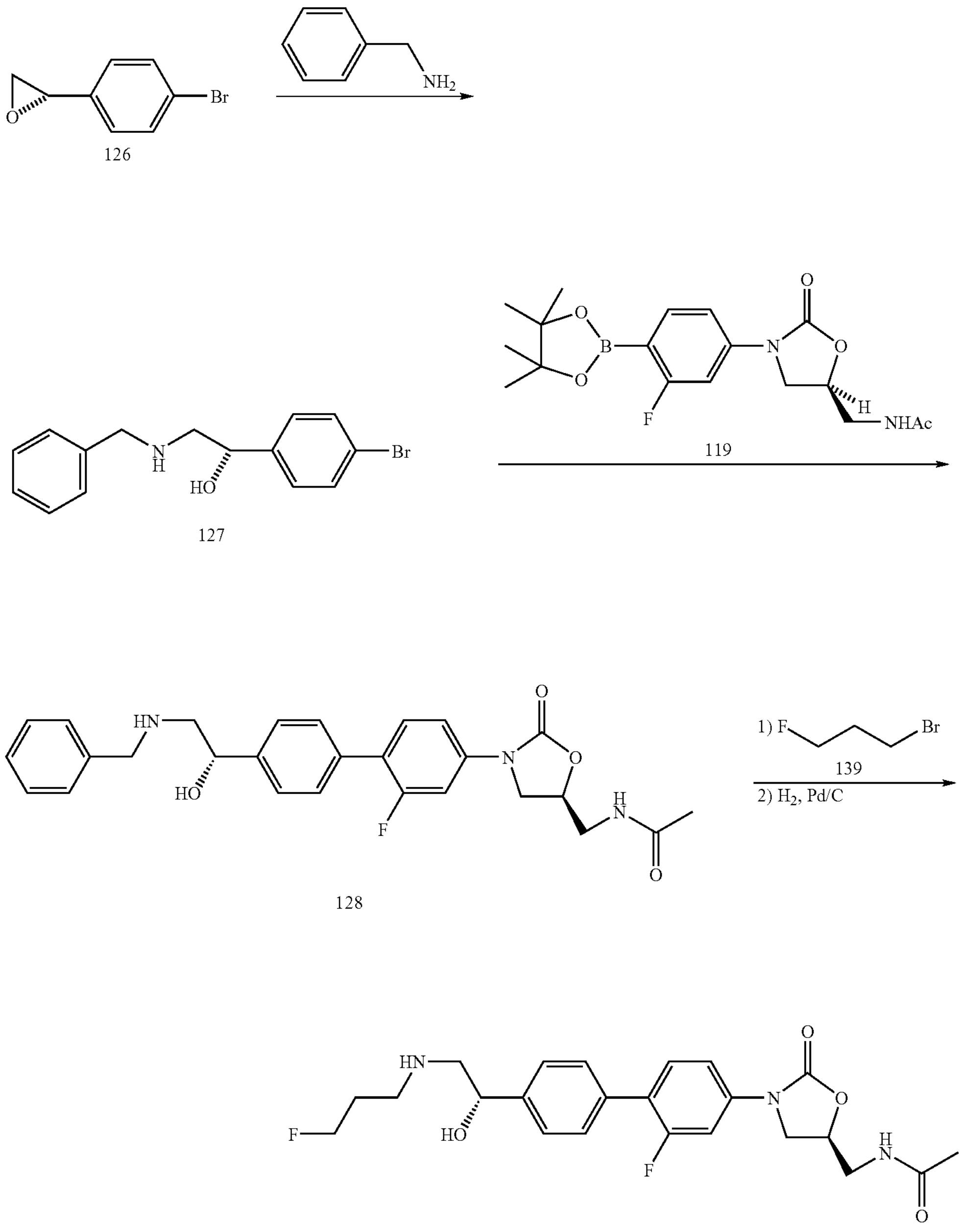

126

127

128

20

Synthesis of Epoxide 126

To a solution of 4-bromostyrene (5.00 g, 26.8 mmol) in $CH_2Cl_2$ (130 mL) was added 4-methylmorpholine N-oxide (NMO, 12.90 g, 107.1 mmol, anhydrous) and Jacobsen catalyst ((1S,2S)-(+)-[1,2-(cyclohexanodiamino-N,N'-bis(3, 5-di-t-butyl-salicylidene)]manganese(III) chloride, 850 mg, 1.34 mmol). The solution was cooled to −78° C., then mCPBA (7.40 g, 42.8 mmol) was added in four portions every 10 min. The mixture was stirred at −78° C. for 2 h. The reaction was quenched by addition of a solution of sodium thiosulfate ($Na_2S_2O_3$, 10.0 g in 30 mL $H_2O$), then the cooling bath was removed, and $H_2O$ (70 mL) and 1N sodium hydroxide (NaOH, 60 mL) was added. The aqueous phase was extracted with $CH_2Cl_2$ (30 mL×3), dried over $Na_2SO_4$, and evaporated. The residue was purified by flash chromatography (4:100 $Et_2O$/Hexane) to yield 5.20 g epoxide 126 (98% yield).

Synthesis of Aryl Bromide 127

To a suspension of epoxide 126 (1 mmol, 1 eq) in acetonitrile ($CH_3CN$, 3.0 mL) at room temperature was added lithium perchlorate ($LiClO_4$, 1.05 mmol, 1.05 eq). After the formation of clear solution, benzylamine (1.5 mmol, 1.5 eq) was added. The mixture was stirred at 80° C. for 4.5 h. The solvent was removed in vacuo and the residue was separated by chromatography on silica gel (3.5:100 $MeOH/CH_2Cl_2$) to afford aryl bromide 127 (460 mg; 50% yield). LCMS (ESI) m/z 307 $(M+H)^+$.

Synthesis of Amine 128

A suspension of aryl bromide 127 (1 eq), boronic ester 119 (1 eq), $Pd(dppf)_2Cl_2$ (0.05 eq), and $K_2CO_3$ (4 eq) in a 3:1:1 mixture of dioxane/EtOH/$H_2O$ was degassed by passing a steady stream of argon through the mixture. The mixture was stirred at 80° C. for 3 h. The solvent was removed in vacuo and the residue was purified by chromatography on silica gel (3:100 $MeOH/CH_2Cl_2$) to yield amine 128 (690 mg; 96% yield). LCMS (ESI) m/z 439 $(M+H)^+$.

Synthesis of Compound 20

A mixture of amine 128 (80 mg, 0.168 mmol), 3-fluoro-1-bromopropane (47 mg, 0.335 mmol) and Hunig's base (117 μL, 0.670 mmol) in DMF (1.5 mL) was stirred at 55–60° C. for 15 h. The solvent was removed in vacuo and residue was purified by chromatography on silica gel (2:100 $MeOH/CH_2Cl_2$) to give 87 mg of the alkylation product (96% yield). LCMS (ESI) m/z 538 $(M+H)^+$.

To a solution of the above alkylation product (80 mg, 0.149 mmol), in EtOH (1.5 mL) at room temperature was added 3N aqueous HCl (120 μL, 0.360 mmol), followed by 10% Pd—C (15 mg). The mixture was stirred under $H_2$ (1 atm.) for 18 h. The mixture was passed through a pad of celite, and the cake was washed with MeOH (10 mL×3). The filtrate was evaporated to give compound 20 (57 mg HCl salt; 79% yield). LCMS (ESI) m/z 448 $(M+H)^+$.

Example 9

Synthesis of Compound 21

A solution of amine 105 (0.178 g, 0.5 mmol) in anhydrous DMF (5.0 mL) was treated with 2,2,2-trichloro-acetimidic acid methyl ester (0.106 g, 0.075 mL, 0.6 mmol, 1.2 equiv) at 25° C. under $N_2$, and the resulting mixture was stirred at 25° C. for 24 h. When TLC and LCMS showed that the reaction was complete, the reaction mixture was concentrated in vacuo. The residue was directly purified by flash column chromatography (0–5% $MeOH/CH_2Cl_2$ gradient elution) to afford compound 21 (52.0 mg, 20.7% yield) as white solids. $C_{21}H_{20}Cl_3FN_4O_3$, LCMS (EI) m/e 501/503/505/507 $(M^++H)$.

Example 10

Synthesis of Compound 22

A mixture of amine 105 (50 mg, 0.14 mmol), 4,4,4 trifluoro crotononitrile (0.17 mL, 0.14 mmol) and catalytic amount of p-toluenesulfonic acid was stirred at ambient temperature for 12 h. The reaction mixture was concentrated and purified by flash chromatography over silica gel (15:1:0.01 $CH_2Cl_2/MeOH/NH_4OH$) to yield 18 mg of compound 22. LCMS (ESI) m/e 479 $(M+H^+)$.

Example 11

Synthesis of Compound 24

A mixture of amine 105 (357 mg, 1 mmol), 1-bromo-3-fluoropropan-2-ol (157 mg, 1 mmol), Hunig's base (0.4 mL, 2.3 mmol) and potassium iodide (KI, 10 mg) in DMF (5 mL) was heated at 70° C. for 3 h. The reaction was diluted with EtOAc (25 mL), washed with $H_2O$, dried over $MgSO_4$ and concentrated in vacuo. The crude product was purified by preparative TLC (15:1:0.05 $CH_2Cl_2/MeOH/NH_3.H_2O$) to afford 165 mg of compound 24 in a yield of 38%. MS (ESI): 434.1(100%, $(M+H)^+$), 456.0 $(M+Na)^+$.

Example 12

Synthesis of Compound 26

A solution of amine 105 (0.357 g, 1.0 mmol) in anhydrous DMF (6 mL) was treated with Hunig's base (0.13 g, 0.18 mL, 1.0 mmol, 1.0 equiv) at 25° C. under $N_2$, and the resulting mixture was treated with 1-chloro-3-iodo-propane (0.204 g, 0.105 mL, 1.0 mmol, 1.0 equiv) at 25° C. under $N_2$. The resulting reaction mixture was subsequently warmed to 50–60° C. for 6 h. When TLC and LCMS showed that the alkylation reaction was complete, the reaction mixture was concentrated in vacuo. The residue was directly purified by flash column chromatography (0–5% $MeOH/CH_2Cl_2$ gradient elution) to afford compound 26 (97.4 mg, 22.5% yield) as off-white solids. $C_{22}H_{25}ClFN_3O_3$, LCMS (EI) m/e 434 $(M^++H)$.

Example 13

Synthesis of Compound 28

A solution of amine 105 (0.357 g, 1.0 mmol) in anhydrous DMF (5 mL) was treated with Hunig's base (0.13 g, 0.18 mL, 1.0 mmol, 1.0 equiv) at 25° C. under $N_2$, and the resulting mixture was treated with 1,3-dibromo-propene (0.2 g, 1.0 mmol, 1.0 equiv) at 25° C. under $N_2$. The resulting reaction mixture was stirred at room temperature for 2 h.

When TLC and LCMS showed that the reaction was complete, the reaction mixture was concentrated in vacuo. The residue was directly purified by preparative HPLC to afford compound 28 (107.0 mg, 16% yield) as off-white solids. $C_{22}H_{23}BrFN_3O_3$, LCMS (EI) m/e 476 ($M^+$+H).

Example 14

Synthesis of Compound 29

A mixture of amine 105 (178.5 mg, 0.5 mmol), 1,3-dichloropropene (55.5 mg, 0.5 mmol), Hunig's base (0.2 mL, 1.15 mmol) and KI (5 mg) in DMF (3 mL) was heated at 70° C. for 6 h. The reaction was diluted with EtOAc (25 mL), washed with $H_2O$, dried over $MgSO_4$ and concentrated in vacuo. The crude product was purified by preparative TLC (15:1:0.05 $CH_2Cl_2$/MeOH/$NH_3$.$H_2O$) to afford 97 mg of desired compound 29 in a yield of 45%. MS (ESI): 432.0(100%, $(M+H)^+$), 473.2, 495.1.

Example 15

Synthesis of Compound 30

A mixture of amine 105 (178.5 mg, 0.5 mmol), 4-bromo-1,1,2-trifluoro-1-butene (94.5 mg, 0.5 mmol), Hunig's base (0.2 mL, 1.15 mmol) and KI (5 mg) DMF (3 mL) was heated at 70° C. for 6 h. The reaction was diluted with EtOAc (25 mL), washed with $H_2O$, dried over $MgSO_4$ and concentrated in vacuo. The crude product was purified by preparative TLC (15:1:0.05 $CH_2Cl_2$/MeOH/$NH_3$.$H_2O$) to afford 75 mg of desired compound 30 in a yield of 32%. MS (ESI): 466.1 $(M+H)^+$, 488.2.

Example 16

Synthesis of Compound 32

A mixture of amine 105 (178.5 mg, 0.5 mmol), 1-bromo-1,1-difluoroprop-2-ene (94.5 mg, 0.5 mmol), Hunig's base (0.2 mL, 1.15 mmol) and KI (5 mg) in DMF (3 mL) was heated at 70° C. for 2 h. The reaction was diluted with EtOAc (25 mL), washed with $H_2O$, dried over $MgSO_4$ and concentrated in vacuo. The crude product was purified by preparative TLC (15:1:0.05 $CH_2Cl_2$/MeOH/$NH_3$.$H_2O$) to afford 70 mg of compound 32 in a yield of 32%. MS (ESI): 434.1 $(M+H)^+$, 456.0.

Example 17

Synthesis of Compound 34

A suspension of aldehyde 116 (356 mg, 1.0 mmol) in anhydrous THF (5 mL) and anhydrous DMF (2 mL) was treated with 2,2,2-trifluoro-ethylamine (99.0 mg, 1.0 mmol, 1.0 equiv) and $NaB(OAc)_3H$ (450 mg, 2.0 mmol, 2.0 equiv) at room temperature, and stirred for 6 h. When TLC and HPLC/MS showed that the reaction was complete, the reaction mixture was concentrated in vacuo. This residue was directly purified by flash column chromatography (0–10% MeOH/$CH_2Cl_2$ gradient elution) to afford compound 34 (25.5 mg, 5.8% yield) as off-white solids. LCMS (EI), $C_{21}H_{21}F_4N_3O_3$, m/e 439 ($M^+$+H).

Example 18

Synthesis of Compound 35

The synthesis of compound 35 from benzyl chloride 123 is depicted in Scheme 12 below.

Scheme 12

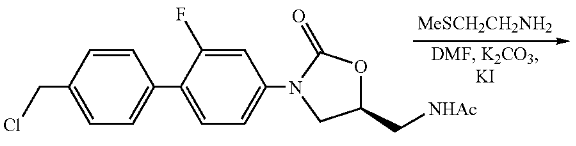

123

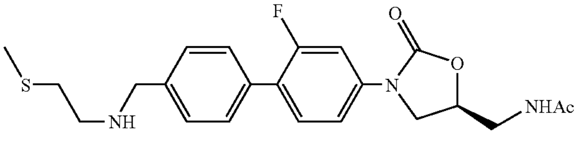

129

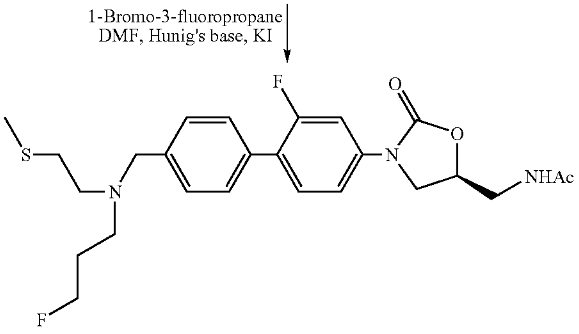

35

A mixture of benzyl chloride 123 (149 mg, 0.395 mmol), 2-(methylthio)ethylamine ($MeSCH_2CH_2NH_2$, 148 mg, 1.626 mmol), $K_2CO_3$ (55 mg, 0.395 mmol) and KI (5 mg) in DMF (2 mL) was heated at 70° C. for 2 h. The reaction was diluted with EtOAc (25 mL), washed with $H_2O$, dried over $MgSO_4$ and concentrated in vacuo. The crude product was purified by preparative TLC (15:1:0.05 $CH_2Cl_2$/MeOH/$NH_3$.$H_2O$) to afford 138 mg of amine 129 in a yield of 81%. MS (ESI): 432.1 (100%, $(M+H)^+$), 473.1.

A mixture of amine 129 (144 mg, 0.33 mmol), 1-bromo-3-fluoropropane (70.5 mg, 0.5 mmol), Hunig's base (0.2 mL, 1.15 mmol) and KI (5 mg) in DMF (3 mL) was heated at 70° C. for 24 h. The reaction was diluted with EtOAc (25 mL), washed with $H_2O$, dried over $MgSO_4$ and concentrated in vacuo. The crude product was purified by preparative TLC (25:1:0.05 $CH_2Cl_2$/MeOH/$NH_3$.$H_2O$) to afford 105 mg of compound 35 in a yield of 64%. MS (ESI): 492.1 (100%, $(M+H)^+$), 514.0.

Example 19

Synthesis of Compound 36

Scheme 13 depicts the synthesis of compound 36 from compound 24.

Scheme 13

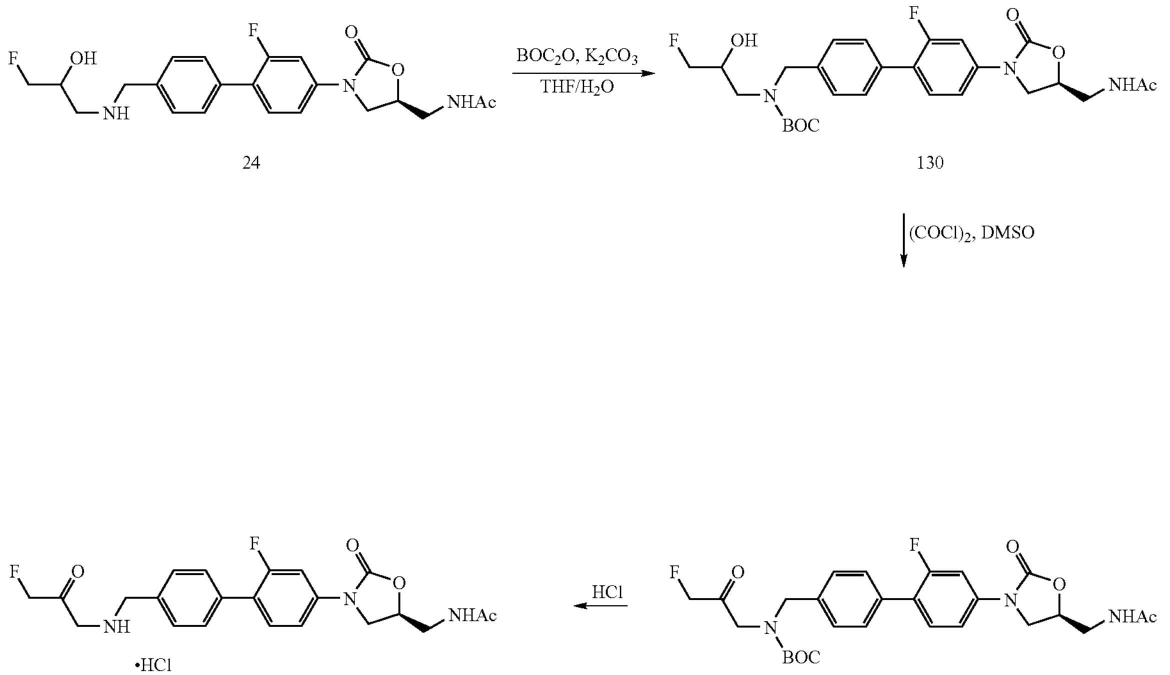

24 130 36 131

A mixture of compound 24 (1.1 g, 2.5 mmol, prepared as described in Example 10, above), di-tert-butyl dicarbonate ($BOC_2O$, 1.1 g, 5 mmol) and $K_2CO_3$ in 10 mL THF and 1 mL $H_2O$ was stirred at room temperature for 12 h. The reaction was diluted with EtOAc (25 mL), washed with $H_2O$, dried over $MgSO_4$ and concentrated in vacuo. The crude product was purified by column chromatography (25:1:0.05 $CH_2Cl_2$/MeOH/$NH_3.H_2O$) to afford 1.24 g of protected amine 130 in a yield of 93%. MS (ESI): 434.1, 556.1.

Dimethyl sulfoxide (DMSO, 0.05 mL) was added to a solution of oxalyl chloride ($(COCl)_2$, 0.42 mmol) in $CH_2Cl_2$ (1 mL) at −78° C. under argon atmosphere. After stirring for 5 minutes, protected amine 130 (142 mg, 0.27 mmol) in $CH_2Cl_2$ (2 mL) was added. The resulting mixture was stirred for 15 min at −78° C., at which point TEA (0.17 mL. 1.22 mmol) was added. After stirring at −78° C. for an additional 15 min, the reaction was allowed to warm to room temperature and stand overnight. The reaction was quenched with $H_2O$, diluted with EtOAc, washed with saturated $NaHCO_3$, dried over $MgSO_4$, and concentrated in vacuo. The crude product was purified by preparative TLC (15:1:0.05 $CH_2Cl_2$/MeOH/$NH_3.H_2O$) to afford 90 mg of ketone 131 in a yield of 63%. MS (ESI): 554.0 (100%, $(M+Na)^+$).

To a solution of ketone 131 in $CH_2Cl_2$ (10 mL) and MeOH (1 mL) was added 2 mL of 4.0 M HCl in dioxane. After stirring at room temperature for 1 h, the reaction was concentrated and washed with EtOAc/MeOH to give 56 mg of a mono hydrochloride salt of compound 36 in a yield of 90%. MS (ESI): 554.0(100%, $(M+H_3O)^+$).

Example 20

Synthesis of Compound 37

Method A

Scheme 14 depicts the synthesis of compound 37 from compound 7.

Scheme 14

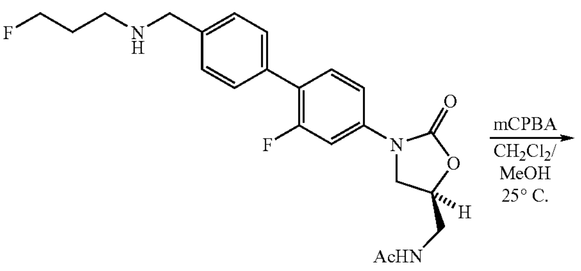

7

-continued

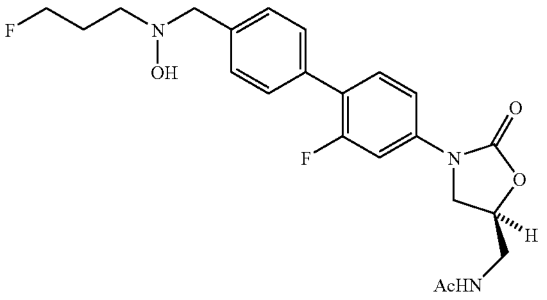

37

A solution of compound 7 (417 mg, 1.0 mmol, prepared as described in Example 4 above) in $CH_2Cl_2$ (10 mL) and MeOH (10 mL) was treated with mCPBA (207.1 mg, 1.2 mmol, 1.2 equiv) at room temperature and stirred for 4 h. The reaction mixture was then quenched with $H_2O$ (10 mL) and $CH_2Cl_2$ (10 mL). The two layers were separated, and the aqueous layer was extracted with $CH_2Cl_2$ (2×10 mL), dried over $MgSO_4$, and concentrated in vacuo. The residue was purified by flash column chromatography (0–5% MeOH/$CH_2Cl_2$ gradient elution) to afford compound 37 (22.5 mg, 5.2% yield) as white solids. LCMS (EI), $C_{22}H_{25}F_2N_3O_4$, m/e 434 ($M^+$+H).

Method B

Scheme 15 depicts the synthesis of compound 37 from aldehyde 116.

Scheme 15

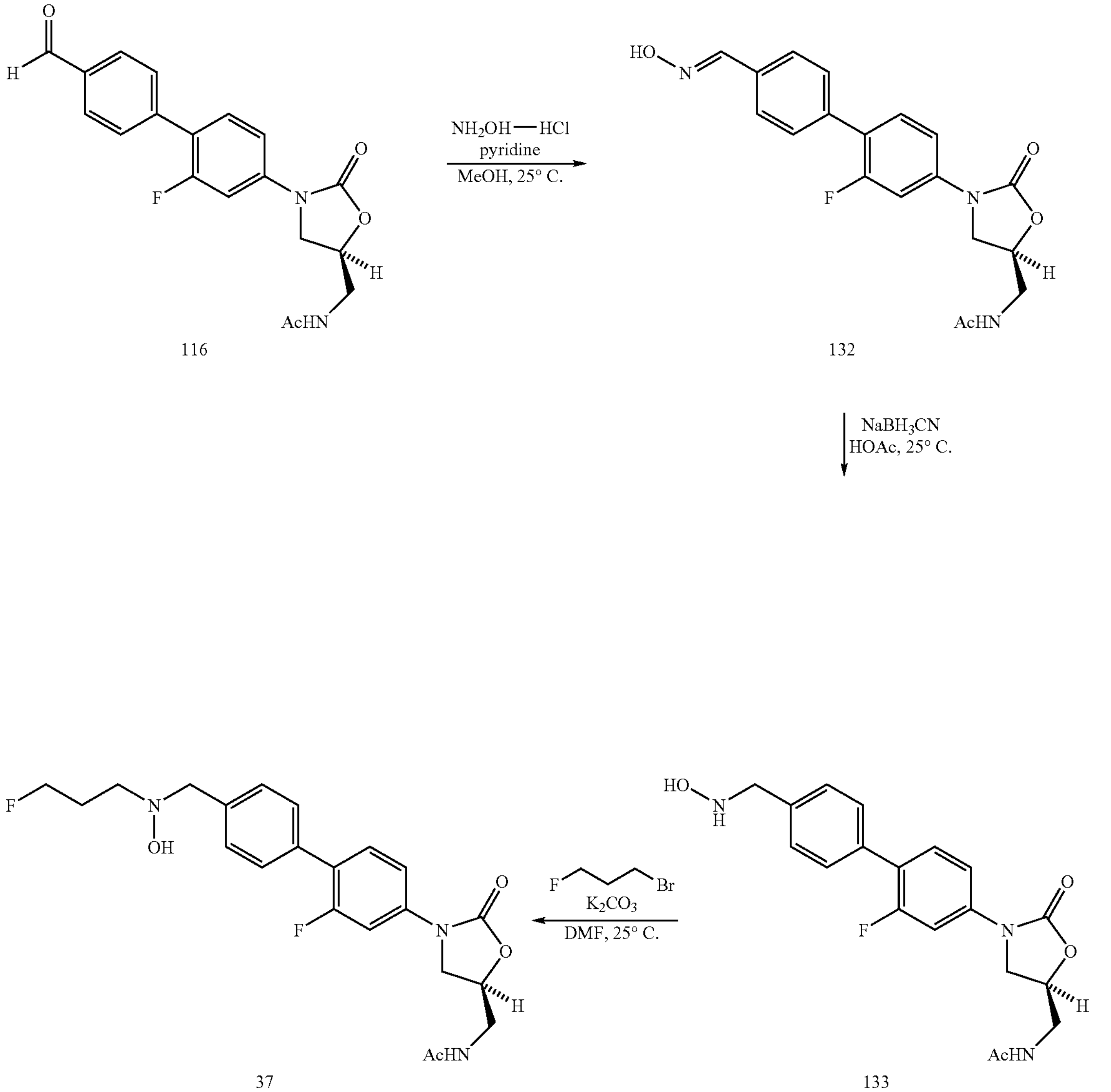

116

132

37

133

A suspension of aldehyde 116 (3.56 g, 10.0 mmol) in MeOH (40 mL) was treated with hydroxylamine hydrochloride ($NH_2OH.HCl$, 843 mg, 12.0 mmol, 1.2 equiv) and pyridine (948 mg, 12.0 mmol, 1.2 equiv) at room temperature and stirred at 25° C. for 12 h. When TLC and HPLC/MS showed that the reaction was complete, the reaction mixture was concentrated in vacuo. This residue was treated with $H_2O$ (100 mL) and the resulting suspension was stirred at room temperature for 30 min. The solids were collected by filtration, washed with $H_2O$ (2×20 mL), and dried in vacuo to afford the desired (5S)-N-{3-[2-fluoro-4'-(hydroxyimino-methyl)-biphenyl-4-yl]-2-oxo-oxazolidin-5-ylmethyl}-acetamide (acetamide 132, 3.58 g, 96.5% yield) as off-white solids, which was directly used in the subsequent reaction without further purification.

A solution of acetamide 132 (1.113 g, 3.0 mmol) in AcOH (10 mL) was treated with sodium cyanoborohydride ($NaBH_3CN$, 378 mg, 6.0 mmol, 2.0 equiv) at room temperature and stirred for 1 h. When TLC and LCMS showed that the reaction was complete, the reaction mixture was concentrated in vacuo. The residue was then directly purified by flash column chromatography (0–5% $MeOH/CH_2Cl_2$ gradient elution) to afford compound 133 (856 mg, 76.5% yield) as white solids. $C_{19}H_{20}FN_3O_4$, LCMS (EI) m/e 374 ($M^+$+H).

A solution of compound 133 (373 mg, 1.0 mmol) in anhydrous DMF (8 mL) was treated with solid $K_2CO_3$ (414 mg, 3.0 mmol, 3.0 equiv) and 3-fluoro-1-bromopropane (282 mg, 2.0 mmol, 2.0 equiv) at room temperature and stirred for 12 h. When TLC and LCMS showed that the reaction was complete, the reaction mixture was concentrated in vacuo. The residue was then directly purified by flash column chromatography (0–5% $MeOH/CH_2Cl_2$ gradient elution) to afford compound 37 (195 mg, 45% yield) as white solids. This product was found by HPLC/MS and $^1H$ NMR to be identical to the material obtained by Method A.

Example 21

Synthesis of Compound 38

A suspension of benzyl chloride 123 (750.0 mg, 2.0 mmol) anhydrous DMF (10 mL) was treated with 2,2- difluoro-ethylamine (162.0 mg, 2.0 mmol, 1.0 equiv) and KI (in a catalytic amount) at room temperature. The resulting reaction mixture was warmed to 50° C. and stirred overnight. When TLC and HPLC/MS showed that the reaction was complete, the reaction mixture was concentrated in vacuo. The residue was directly purified by flash column chromatography (0–10% $MeOH/CH_2Cl_2$ gradient elution) to afford compound 38 (68.5 mg, 8.1% yield) as off-white solids. LCMS (EI), $C_{21}H_{22}F_3N_3O_3$, m/e 422 ($M^+$+H).

Example 22

Synthesis of Compound 40

To a solution of amine 105 (0.100 g, 0.28 mmol) and fluoroacetone (0.021 g, 0.28 mmol) in 2 mL of DMF was added $NaB(OAc)_3H$ (0.119 g, 0.56 mmol) at 25° C. The reaction mixture was stirred for 2 h. The solvent was removed via rotary evaporation, and the solid residue was purified by preparative TLC to give 0.080 g of compound 40. MS(M+1): 418.

Example 23

Synthesis of Compound 41

A suspension of aldehyde 116 (200 mg, 0.56 mmol) in anhydrous THF (5 mL) and anhydrous DMF (2 mL) was treated with 2,2,2-trifluoro-ethylamine (120.0 mg, 0.56 mmol, 1.0 equiv) and $NaB(OAc)_3H$ (240 mg, 2.0 mmol, 2.0 equiv) at room temperature. The resulting reaction mixture was warmed to 50° C. and stirred for 12 h. When TLC and HPLC/MS showed that the reaction was complete, the reaction mixture was concentrated in vacuo. The residue was directly purified by flash column chromatography (0–10% $MeOH/CH_2Cl_2$ gradient elution) to afford compound 41 (18.2 mg, 3.5% yield) as off-white solids. LCMS (EI), $C_{22}H_{23}BrF_3N_3O_3$, m/e 515 ($M^+$+H).

Example 24

Synthesis of Compound 42

Scheme 16 depicts the synthesis of compound 42 from mesylate 134.

Scheme 16

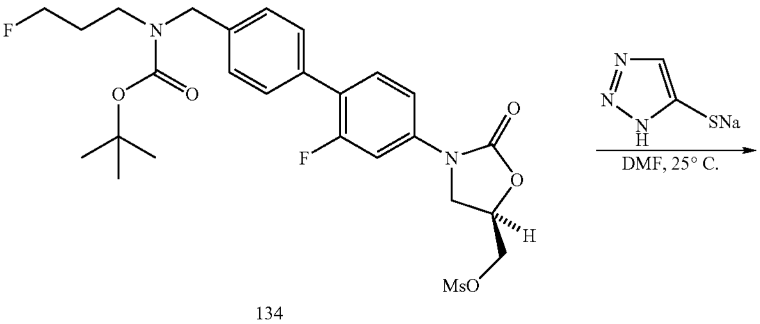

134

-continued

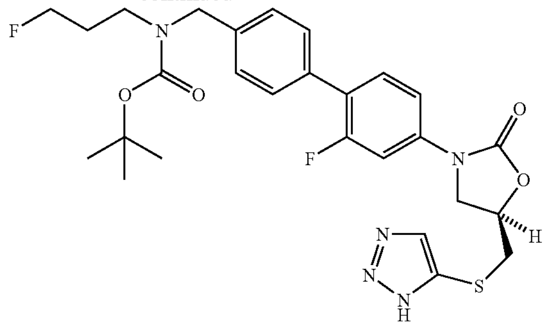

135

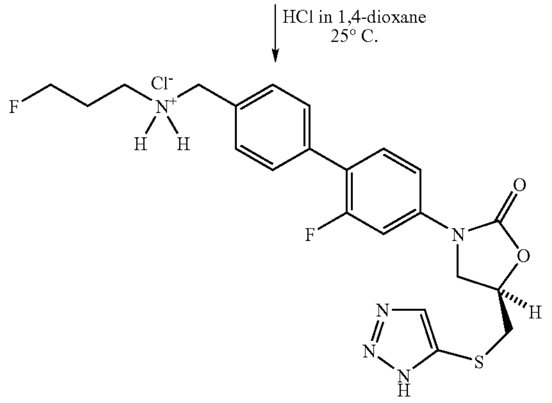

42

A solution of (5R)-methanesulfonic acid 3-(4'-{[tert-butoxycarbonyl-(3-fluoro-propyl)-amino]-methyl}-2-fluoro-biphenyl-4-yl)-2-oxo-oxazolidin-5-ylmethyl ester (mesylate 134, 162 mg, 0.3 mmol) in anhydrous DMF (8 mL) was treated with 1,2,3-triazole-5-thiol sodium salt (74 mg, 0.6 mmol, 2.0 equiv) at 25° C. under $N_2$ and stirred for 4 h. When TLC and LCMS showed that the reaction was complete, the reaction mixture was concentrated in vacuo. The residue was directly purified by flash column chromatography (0–5% MeOH/$CH_2Cl_2$ gradient elution) to afford the desired (5R)-{2'-fluoro-4'-[2-oxo-5-(3H-[1,2,3]triazol-4-ylsulfanylmethyl)-oxazolidin-3-yl]-biphenyl-4-ylmethyl}-(3-fluoro-propyl)-carbamic acid tert-butyl ester (compound 135, 146 mg, 87% yield) as pale-yellow solids, which was directly used in the subsequent reaction.

A solution of compound 135 (140 mg, 0.25 mmol) in $CH_2Cl_2$ (3 mL) and MeOH (1 mL) was treated with a solution of 4.0 N HCl in 1,4-dioxane (1 mL, 4.0 mmol, 16.0 equiv) at 25° C. and stirred for 2 h. The solvents were then removed in vacuo, and the residue was slurried in $CH_3CN$ (10 mL) at 25° C. for 30 min. The solids were then collected by filtration, washed with $CH_3CN$ (5 mL), and dried in vacuo to afford compound 42 (117 mg, 94.4%) as pale-yellow crystals. $C_{22}H_{23}F_2N_5O_2S$, LCMS (EI) m/e 460 ($M^+$+H).

Example 25

Alternate Synthesis of Compound 7 (Method 1)

Scheme 17 depicts the synthesis of compound 7 from aryl iodide 101 and aryl boronic acid 141.

Scheme 17

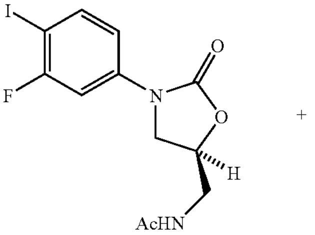

101

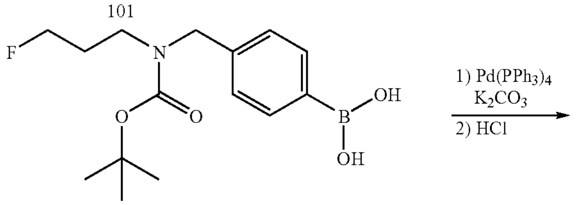

141

-continued

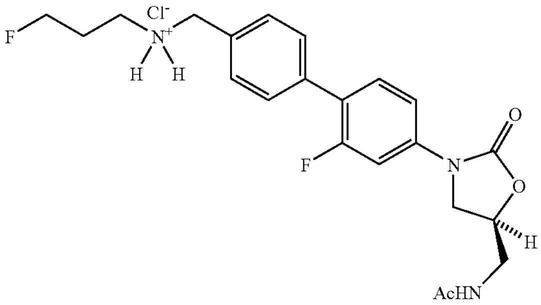

7

Synthesis of Aryl Boronic Acid 120

Scheme 18 depicts three synthetic routes to 4-(N-tert-butylcarbonyl-3-fluoropropylaminomethyl)phenyl boronic acid (aryl boronic acid 141).

Synthesis of Amine Hydrochloride 106

A solution of 3-fluoro-propan-1-ol (31.2 g, 400 mmol) in 300 mL of $CH_2Cl_2$ was treated with MsCl (55 g, 38 mL, 480 mmol, 1.2 equiv) at 0° C. The resulting reaction mixture was gradually warmed to room temperature and stirred for 1–2 hours. When $^1H$ NMR showed the reaction was complete, the reaction mixture was treated with $H_2O$ (100 mL), and the two layers were separated. The aqueous layer was extracted with $CH_2Cl_2$ (2×100 mL). The combined organic layers were washed with $H_2O$ (3×100 mL) and dried over $MgSO_4$. The solvent was removed in vacuo to afford the desired methanesulfonic acid 3-fluoro-propyl ester (57.2 g, 91% yield) as a yellow oil.

A solution of methanesulfonic acid 3-fluoro-propyl ester (34.5 g, 221 mmol) in 250 mL of anhydrous DMF was treated with solid potassium phthalimide (49 g, 265 mmol, 1.2 equiv) at 25° C. The resulting suspension was warmed to 70–80° C. for 2 hours. When $^1H$ NMR showed that the reaction was complete, the reaction mixture was treated with $H_2O$ (200 mL). The aqueous solution was extracted with EtOAc (3×100 mL). The combined organic layers were Scheme 18

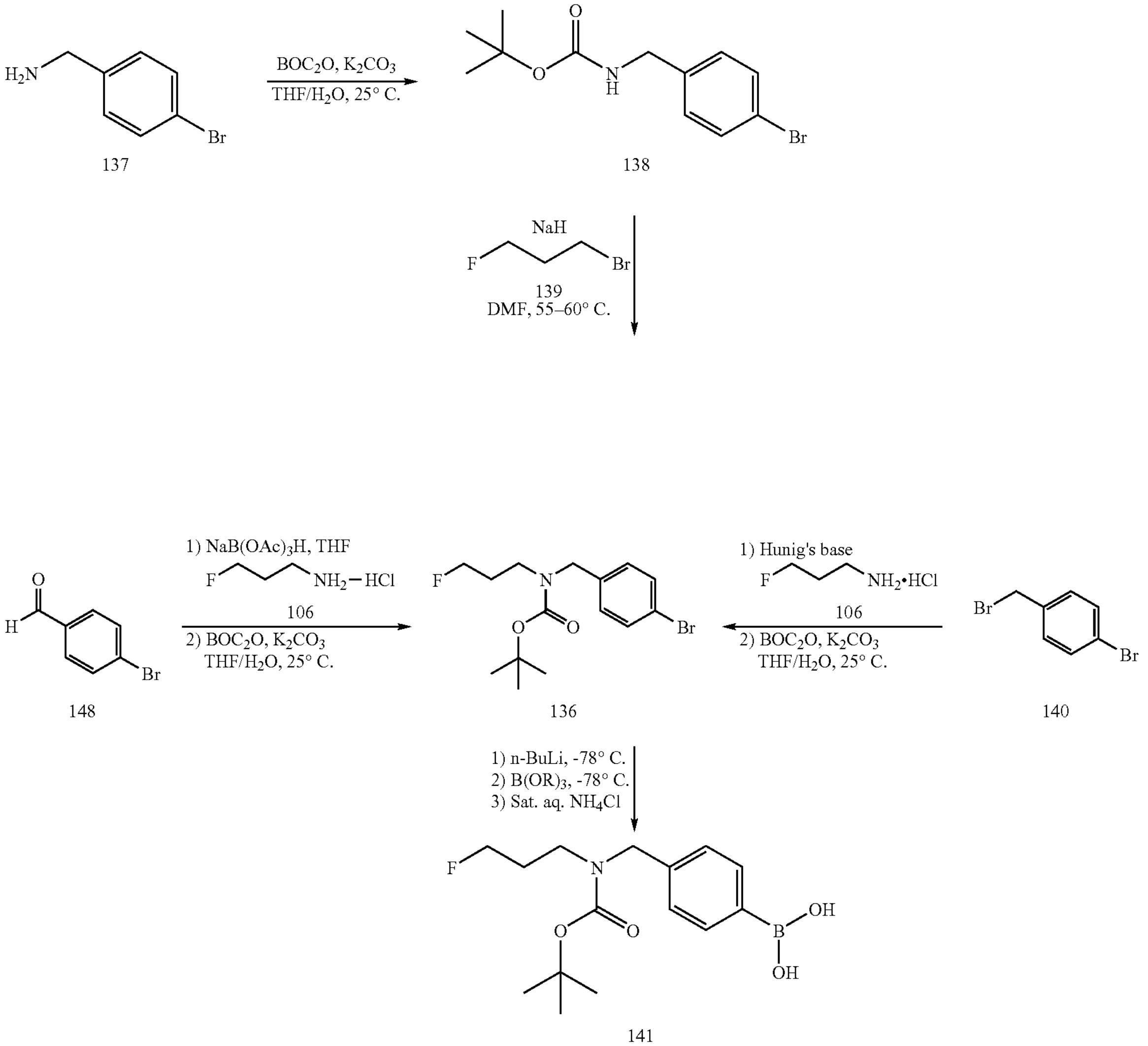

137 138 139 106 148 136 140 141 washed with $H_2O$ (3×100 mL) and dried over $MgSO_4$. The solvent was removed in vacuo to afford the desired 2-(3-fluoro-propyl)-isoindole-1,3-dione (45.4 g, 45.5 g theoretical, 99.7% yield) as a white powder.

A suspension of 2-(3-fluoro-propyl)-isoindole-1,3-dione (45.4 g, 221 mmol) in 400 mL of 95% aqueous EtOH was treated with hydrazine monohydrate (11.3 g, 11.1 mL, 223 mmol, 1.0 equiv). The solution was refluxed for 3 h. When $^1H$ NMR showed the reaction was complete, the reaction mixture was cooled to room temperature before being treated with concentrated aqueous HCl (250 mL) to pH 1–2. The white phthalhydrazide precipitate was collected by filtration and washed with 95% aqueous EtOH (4×100 mL). The combined filtrates were then concentrated to about 100 mL before 250 mL of $H_2O$ was added. The insoluble material was removed by filtration and the filtrates were concentrated to dryness in vacuo. The filtrates were recrystallized from $EtOH/Et_2O$ and dried in vacuo to afford amine hydrochloride 106 (20.83 g, 83.8% yield) as white crystals. This product was used directly in subsequent reactions without further purification. $^1H$ NMR (DMSO-$d_6$, 300 MHz) δ 1.89–2.07 (m, 2H), 2.52–2.90 (m, 2H), 4.47(t, 1H, J=5.8 Hz), 4.63(t, 1H, J=5.8 Hz), 8.19 (s, 3H).

Alternate Synthesis of Amine Hydrochloride 106

Amine hydrochloride 106 can be prepared using the general procedure described above in Example 3, using 1-bromo-3-fluoropropane 139 instead of the methanesulfonic acid 3-fluoro-propyl ester.

Synthesis of Bromide 136

Method A

To a solution of amine hydrochloride 106 (6.0 g, 52.8 mmol, 1.16 equiv) in DMF (200 mL) was added 4-bromobenzaldehyde 148 (8.50 g, 45.5 mmol) at room temperature. The resulting reaction mixture was then treated with $NaB(OAc)_3H$ (16.10 g, 72.0 mmol, 1.6 equiv) at room temperature and stirred for 2 h. When TLC and HPLC/MS showed the reaction was complete, the reaction mixture was quenched with $H_2O$ (100 mL). The resulting aqueous mixture was treated with solid $Na_2CO_3$ (99.64 g, 91.0 mmol, 2.0 equiv) and $BOC_2O$ (12.9 g, 59.1 mmol, 1.3 equiv) at room temperature. The mixture was then stirred at room temperature for 1.5 h before being quenched with $H_2O$ (100 mL). The reaction mixture was then extracted with EtOAc (3×60 mL). The combined organic extracts were washed with 0.5 M aqueous HCl (100 mL) and $H_2O$ (3×100 mL), dried over anhydrous $Na_2SO_4$ and concentrated in vacuo. The residue was then purified by flash column chromatography (3–4% EtOAc/hexane) to afford the desired (4-bromo-benzyl)-(3-fluoro-propyl)-carbamic acid tert-butyl ester (bromide 136, 11.38 g, 72% yield) as a colorless oil. $C_{15}H_{21}BrFNO_2$, HPLC/MS (ESI) m/e 347 ($M^+$+H).

Method B

A solution of 4-bromobenzylamine hydrochloride 137 (2.225 g, 10.0 mmol) and $K_2CO_3$ (2.07 g, 15.0 mmol, 1.5 equiv) in THF (20 mL) and $H_2O$ (5 mL) was treated with $BOC_2O$ (2.40 g, 11.0 mmol, 1.1 equiv) at room temperature and stirred for 12 h. When TLC and HPLC/MS showed the reaction was complete, the reaction mixture was treated with $H_2O$ (10 mL) and EtOAc (40 mL). The two layers were separated, and the aqueous layer was extracted with EtOAc (20 mL). The combined organic extracts were washed with $H_2O$ (2×20 mL) and saturated aqueous NaCl (20 mL), dried over $MgSO_4$, and concentrated in vacuo. The residue was further dried in vacuo to afford the desired (4-bromo-benzyl)-carbamic acid tert-butyl ester (compound 138, 2.60 g, 90.9% yield) as a colorless oil.

To a solution of compound 138 (286 mg, 1.0 mmol) in anhydrous DMF (3.0 mL) was added sodium hydride (NaH, 60% oil dispersion, 48.0 mg, 1.2 mmol, 1.2 equiv) at 0° C. The resulting mixture was stirred at 0° C. for 30 min before 1-bromo-3-fluoropropane 139 (170 mg, 1.2 mmol, 1.2 equiv) was added. The reaction mixture was subsequently warmed to 50–60° C. and stirred for 24 hours. The reaction mixture was then quenched with $H_2O$ (10 mL), and the resulting aqueous solution was extracted with EtOAc (2×20 mL). The combined organic extracts were washed with $H_2O$ (10 mL) and saturated aqueous NaCl (10 mL), dried over $MgSO_4$ and concentrated in vacuo. The residue was purified by column chromatography (10–15% EtOAc/hexane gradient elution) to afford bromide 136 (158 mg, 46% yield) as a colorless oil.

Method C

A solution of 4-bromobenzylbromide 140 (0.30 g, 1.20 mmol) and amine hydrochloride 106 (0.272 g, 2.40 mmol, 2.0 equiv) in anhydrous DMF (8.0 mL) was treated with Hunig's base (2.0 mL) at room temperature. The resulting reaction mixture was warmed to 60° C. for 24 h. When TLC and HPLC showed the reaction was complete, the reaction mixture was cooled to 25° C. before being treated with $H_2O$ (8.0 mL). The resulting aqueous solution was then treated with solid $NaHCO_3$ (0.30 g, 3.60 mmol, 3.0 equiv) and $BOC_2O$ (0.524 g, 2.40 mmol, 2.0 equiv) at 25° C. and stirred for 24 h. When TLC and HPLC/MS showed the reaction was complete, the reaction mixture was treated with $H_2O$ (20 mL) and EtOAc, 20 mL. The two layers were separated, and the aqueous layer was extracted with EtOAc (2×30 mL). The combined organic extracts were washed with $H_2O$ (4×10 mL) and saturated aqueous NaCl (10 mL), dried over $MgSO_4$, and concentrated in vacuo. The residue was purified by column chromatography (3% EtOAc/hexanes) to afford bromide 136 (0.24 g, 57.8% yield) as a colorless oil.

Synthesis of Boronic Acid 141

To a solution of bromide 136 (3.0 g, 8.7 mmol) in anhydrous THF (30 mL) at −78° C. was added a 2.5 M solution of n-BuLi in hexane (3.64 mL, 9.1 mmol, 1.05 equiv). The resulting reaction mixture was stirred at −78° C. for 1 h before trimethyl borate ($B(OMe)_3$, 1.2 mL, 10.4 mmol, 1.2 equiv) was added dropwise. The resulting reaction mixture was stirred at −78° C. for 0.5 h before being gradually warmed to room temperature overnight. The reaction mixture was poured into $H_2O$ (60 mL), and the aqueous solution was treated with 1.0 N aqueous HCl to pH 4.0. The aqueous mixture was then extracted with EtOAc (4×30 mL). The combined organic extracts were washed with saturated aqueous NaCl (30 mL), dried over anhydrous $Na_2SO_4$, and concentrated in vacuo to obtain the desired aryl boronic acid 141 (2.5 g). This product was directly used in subsequent reactions without further purification. $C_{15}H_{23}BFNO_4$, HPLC/MS (ESI) m/e 312 ($M^+$+H).

Synthesis of Compound 7

Scheme 19 depicts the synthesis of compound 7 from aryl iodide 101 and aryl boronic acid 141.

Scheme 19

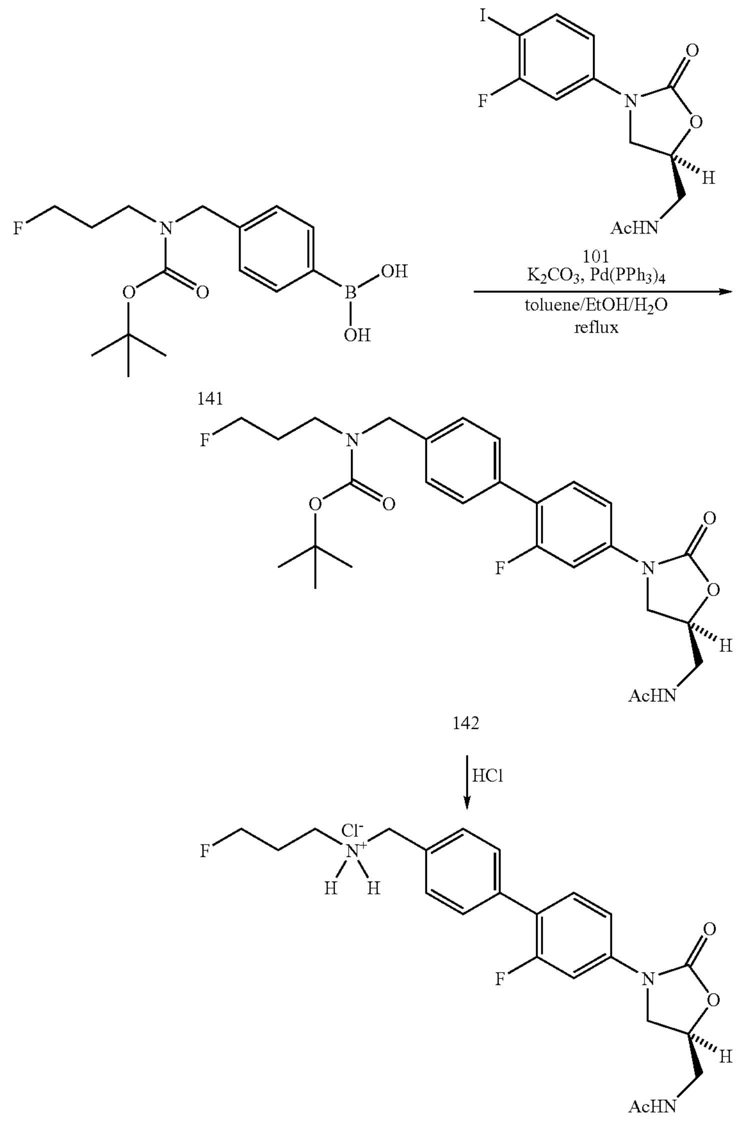

141

142

7

A suspension of aryl boronic acid 141 (2.50 g, 8.03 mmol) in a mixture of toluene (24 mL), EtOH (8 mL), and $H_2O$ (8 mL) was treated with aryl iodide 101 (2.53 g, 6.7 mmol, 0.83 equiv) and solid $K_2CO_3$ (2.80 g, 20.1 mmol, 3.0 equiv) at room temperature. The resulting reaction mixture was degassed three times under a steady stream of argon before $Pd(PPh_3)_4$ (387 mg, 0.335 mmol, 0.05 equiv) was added. The resulting reaction mixture was degassed three times under a steady stream of argon before being warmed to reflux for 8 h. When TLC and HPLC/MS showed the reaction was complete, the reaction mixture was cooled to room temperature before being poured into $H_2O$ (60 mL) and EtOAc (60 mL). The two layers were separated, and the organic phase was washed with $H_2O$ (30 mL) and saturated aqueous NaCl (2×30 mL), dried over anhydrous $Na_2SO_4$, and concentrated in vacuo. The product was then recrystallized from EtOAc/hexanes and dried in vacuo to afford the desired (5S)-{4'-[5-(acetylamino-methyl)-2-oxo-oxazolidin-3-yl]-2'-fluoro-biphenyl-4-ylmethyl}-(3-fluoro-propyl)-carbamic acid tert-butyl ester (BOC-amine 142, 1.3 g, 30%) as an off-white powder.

A solution of BOC-amine 142 (15.65 g, 30.3 mmol) in $CH_2Cl_2$ (30 mL) was treated with a solution of 4 N HCl in 1,4-dioxane (37.5 mL, 150.0 mmol, 5.0 equiv) at room temperature and stirred for 12 h. When TLC and HPLC/MS showed that the reaction was complete, the solvents were removed in vacuo. The residue was suspended in a mixture of $CH_3CN$ (200 mL) and MeOH (50 mL), and the resulting slurry was stirred at room temperature for 1 h. The solids were collected by filtration, washed with 20% MeOH/$CH_3CN$ (2×50 mL), and dried in vacuo to afford the hydrochloride salt of compound 7 (13.0 g, 95.3% yield) as white crystals. $^1H$ NMR (300 MHz, DMSO-$d_6$) δ 1.90 (s, 3H, $COCH_3$), 2.11–2.20 (m, 2H), 3.10 (m, 2H), 3.50 (t, 2H, J=5.4 Hz), 3.87 (dd, 1H, J=6.4, 9.2 Hz), 4.24 (t, 1H, J=9.1 Hz), 4.27 (s, 2H, $ArCH_2$), 4.54 (t, 1H, J=5.8 Hz), 4.70 (t, 1H, J=5.8 Hz), 4.83 (m, 1H), 7.50 (dd, 1H, J=2.2, 8.6 Hz), 7.65–7.74 (m, 6H, aromatic-H), 8.37 (t, 1H, J=5.8 Hz, $NHCOCH_3$), 9.43 (br. s, 2H, $RArN^+H_2$). $C_{22}H_{25}F_2N_3O_3$ HCl, LCMS (EI) m/e 418 ($M^+$+H).

Example 26

Alternate Synthesis of Compound 7 (Method 2)

Scheme 20 depicts an alternate synthesis of aryl boronic acid 141, which is coupled to aryl iodide 101 to yield compound 7.

for 3 h. When TLC and HPLC/MS showed the reaction was complete, the reaction mixture was poured into $H_2O$ (500 mL) and EtOAc (500 mL). The two layers were separated and the aqueous layer was treated with a 2 N aqueous HCl (130 mL) to pH 4. The aqueous layer was then extracted with EtOAc (160 mL), and the combined organic layers were washed with $H_2O$ (2×100 mL) and saturated aqueous NaCl (2×100 mL), dried over $Na_2SO_4$, and concentrated in vacuo. The residue was further dried in vacuo to afford the desired aryl boronic acid 141 (25.0 g) as a pale-yellow oil. This product was found to be identical with the material Scheme 20

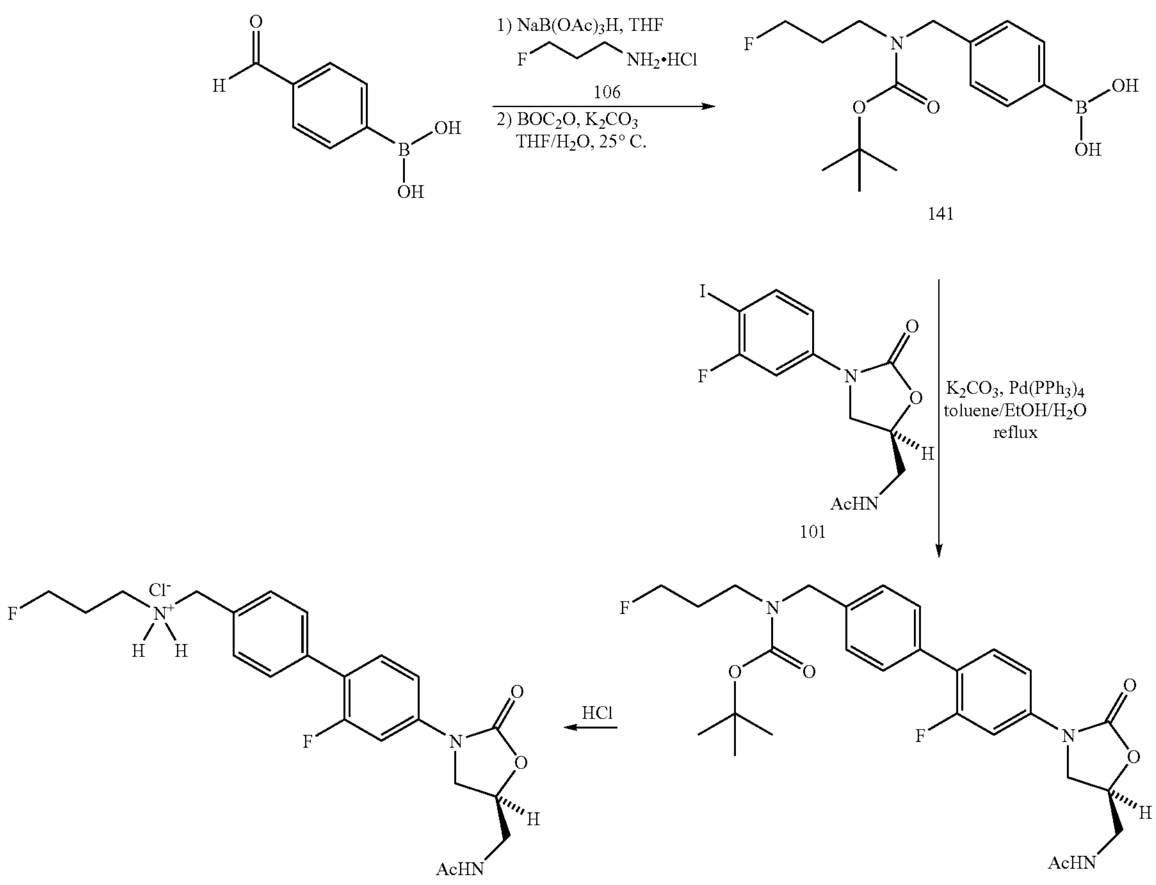

141

101

7

142

Synthesis of Aryl Boronic Acid 141

A solution of 4-formylphenyl boronic acid (10.0 g, 66.69 mmol) in anhydrous DMF (150 mL) was treated with amine hydrochloride 106 (8.70 g, 76.70 mmol, 1.15 equiv, prepared as described in Example 1, above) at room temperature. The resulting mixture was treated with $NaB(OAc)_3H$ (28.30 g, 133.39 mmol, 2.0 equiv) at room temperature and stirred for 3 h. When TLC and HPLC/MS showed the reaction was complete, the reaction mixture was treated with $H_2O$ (150 mL), solid $Na_2CO_3$ (14.14 g, 133.39 mmol, 2.0 equiv), and $BOC_2O$ (22.05 g, 100.04 mmol, 1.5 equiv). The resulting reaction mixture was stirred at room temperature obtained from Example 1 above and was directly used in the subsequent reaction without further purification.

Synthesis of Compound 7

A suspension of aryl boronic acid 141 (25.0 g, 64.30 mmol, 1.45 equiv) in a mixture of toluene (120 mL), EtOH (40 mL), and $H_2O$ (40 mL) was treated with aryl iodide 101 (16.80 g, 44.44 mmol, prepared as described in Example 1, above) and solid $K_2CO_3$ (18.40 g, 133.4 mmol, 3.0 equiv) at room temperature. The resulting reaction mixture was degassed three times under a steady stream of argon before being treated with $Pd(PPh_3)_4$ (2.57 g, 2.23 mmol, 0.05 equiv). The resulting reaction mixture was degassed three times under a steady stream of argon before being warmed to reflux for 8 h. When TLC and HPLC/MS showed the reaction was complete, the reaction mixture was cooled to room temperature before being poured into $H_2O$ (300 mL) and EtOAc (300 mL). The two layers were separated, and the organic phase was washed with $H_2O$ (60 mL) and saturated aqueous NaCl (2×50 mL), dried over anhydrous $Na_2SO_4$, and concentrated in vacuo. The product was recrystallized from EtOAc/hexanes and dried in vacuo to afford BOC-protected amine 142 (21.2 g, 61.5% yield for three steps) as an off-white powder.

BOC-protected amine 142 was subsequently treated with 4 N HCl in 1,4-dioxane as in Example 25 to afford a mono hydrochloride salt of compound 7. The product obtained from this process was identical by NMR and LCMS to the material obtained in Example 25.

Example 27

Alternate Synthesis of Compound 7 (Method 3)

Scheme 21 depicts the synthesis of compound 7 from aryl bromide 136 and aryl boronic ester 119.

Scheme 21

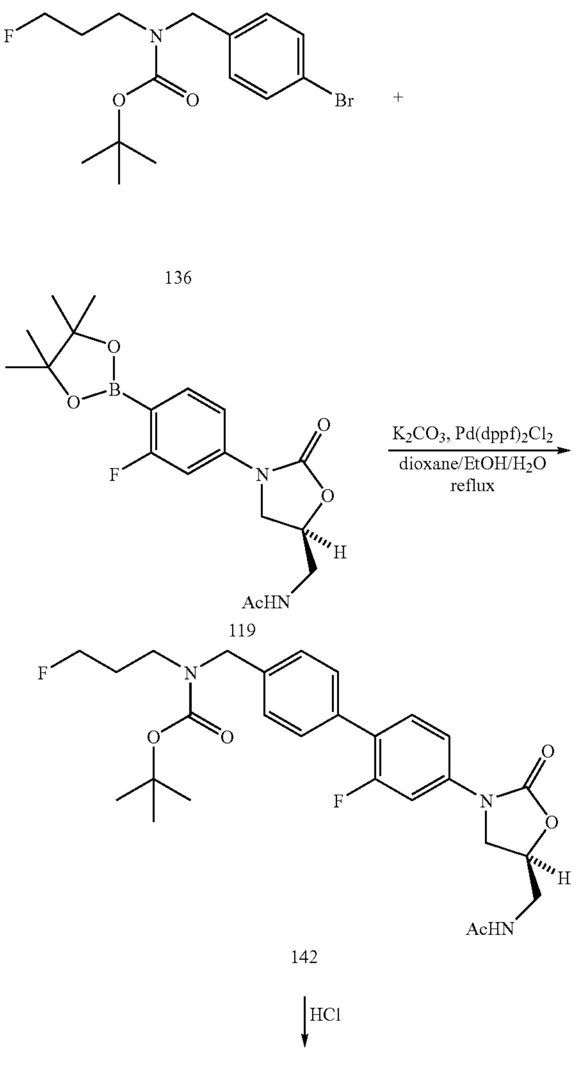

136

119

142

-continued

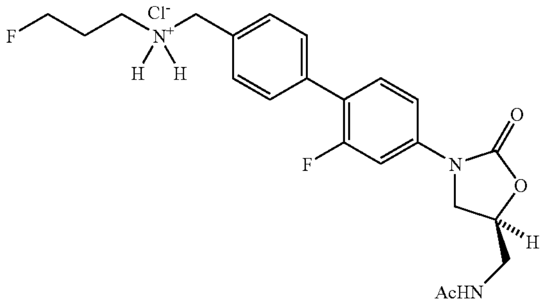

7

Synthesis of Boronic Ester 119

A suspension of aryl iodide 101 (20.0 g, 52.8 mmol) in anhydrous 1,4-dioxane (130 mL) was treated with 4,4,5,5-tetramethyl-[1,3,2]dioxaborolane (10.2 g, 11.6 mL, 80.0 mmol, 1.5 equiv) and TEA (16.0 g, 22.4 mL, 158.4 mmol, 3.0 equiv) at room temperature. The resulting reaction mixture was degassed three times under a steady stream of argon before being treated with $Pd(dppf)_2Cl_2$ (1.32 g, 1.6 mmol, 0.03 equiv) at room temperature. The resulting reaction mixture was degassed three times under a steady stream of argon before being warmed to reflux for 7 h. When HPLC/MS showed the reaction was complete, the reaction mixture was cooled to room temperature before being treated with $H_2O$ (100 mL) and EtOAc (100 mL). The two layers were separated, and the aqueous layer was extracted with EtOAc (2×50 mL). The combined organic extracts were washed with $H_2O$ (2×50 mL) and saturated aqueous NaCl (50 mL), dried over $MgSO_4$, and concentrated in vacuo. The residual brown oil was further dried in vacuo to afford the desired boronic ester 119 (18.8 g, 94%) as brown solids. This product was directly used in subsequent reactions without further purification. $C_{18}H_{24}BFN_2O_5$, HPLC/MS (ESI) m/e 379 ($M^+$+H).

Synthesis of Compound 7

A solution of boronic ester 119 (1.40 g, 3.7 mmol, 1.3 equiv) and bromide 136 (1.0 g, 2.89 mmol, prepared as described in Example 25, above) in a mixture of 1,4-dioxane (21 mL), EtOH (7.0 mL) and $H_2O$ (7.0 mL) was treated with solid $K_2CO_3$ (1.2 g, 8.7 mmol, 3.0 equiv) at room temperature. The resulting reaction mixture was degassed three times under a steady stream of argon before being treated with $Pd(dppf)_2Cl_2$ (118 mg, 0.144 mmol, 0.05 equiv) at room temperature. The reaction mixture was degassed three times under a steady stream of argon before being warmed to reflux for 2 h. When TLC and HPLC/MS showed the reaction was complete, the reaction mixture was cooled to room temperature before being treated with $H_2O$ (60 mL). The aqueous solution was then extracted with $CH_2Cl_2$ (3×20 mL), and the combined organic extracts were washed with $H_2O$ (2×20 mL) and saturated aqueous NaCl (20 mL), dried over $MgSO_4$, and concentrated in vacuo. The residue was purified by flash column chromatography (0–5% MeOH—$CH_2Cl_2$ gradient elution) to afford BOC-protected amine 142 (1.36 g, 91% yield) as a colorless oil, which solidified upon standing at room temperature in vacuo.

BOC-protected amine 142 was subsequently treated with 4 N HCl in 1,4-dioxane as in Example 1 to afford a mono hydrochloride salt of compound 7. The product obtained from this process was identical by NMR and LCMS to the material obtained in Example 25.

Example 28

Alternate Synthesis of Compound 7 (Method 4)

Scheme 22 depicts the synthesis of compound 7 from benzyl chloride 123 and amine salt 106.

Scheme 22

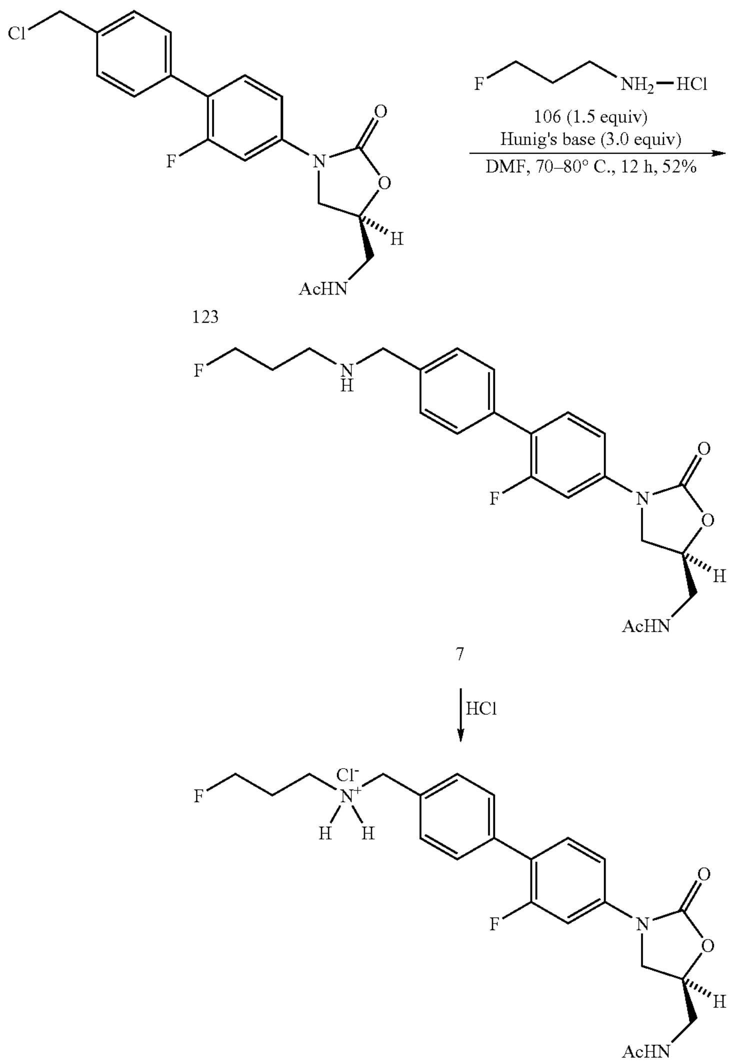

123

7

7, Mono Hydrochloride Salt

Synthesis of Compound 7

A solution of benzyl chloride 123 (190.0 mg, 0.5 mmol) in anhydrous DMF (5.0 mL) was treated with Hunig's base (194 mg, 0.26 mL, 1.5 mmol, 3.0 equiv) at 25° C. under $N_2$, and the resulting mixture was treated with amine salt 106 (85 mg, 0.75 mmol, 1.5 equiv) at 25° C. under $N_2$. The resulting reaction mixture was subsequently warmed up to 0.60° C. for 12 h. When TLC and HPLC/MS showed the reaction was complete, the reaction mixture was concentrated in vacuo. The residue was then directly purified by flash column chromatography ($SiO_2$, 0–5% MeOH—$CH_2Cl_2$ gradient elution) to afford compound 7 (108.4 mg, 208.5 mg theoretical, 52%) as white solid. LCMS (EI) m/e 418 ($M^+$+H).

Synthesis of Monohydrochloride Salt of Compound 7

A solution of compound 7 (834 mg, 2.0 mmol) in a mixture of MeOH (2 mL) and $CH_2Cl_2$ (18 mL) was treated with a solution of 4 N HCl in 1,4-dioxane (1.0 mL, 4.0 mmol, 2.0 equiv) at room temperature, and the resulting reaction mixture was stirred at room temperature for 2 h. When TLC showed that the salt formation reaction was complete, the solvents were removed in vacuo. The residue then was suspended in a mixture of $CH_3CN$ (16 mL) and MeOH (4 mL), and the resulting slurry was stirred at room temperature for 1 h. The solids were collected by filtration, washed with 20% MeOH—$CH_3CN$ (2×5 mL), and dried in vacuo to afford the monohydrochloride salt of compound 7 (871 mg, 907 mg theoretical, 96%) as white crystals.

Example 29

Alternate Synthesis of Compound 7 (Method 5)

Scheme 23 depicts the synthesis of compound 7 from aldehyde 116 and amine salt 106.

Scheme 23

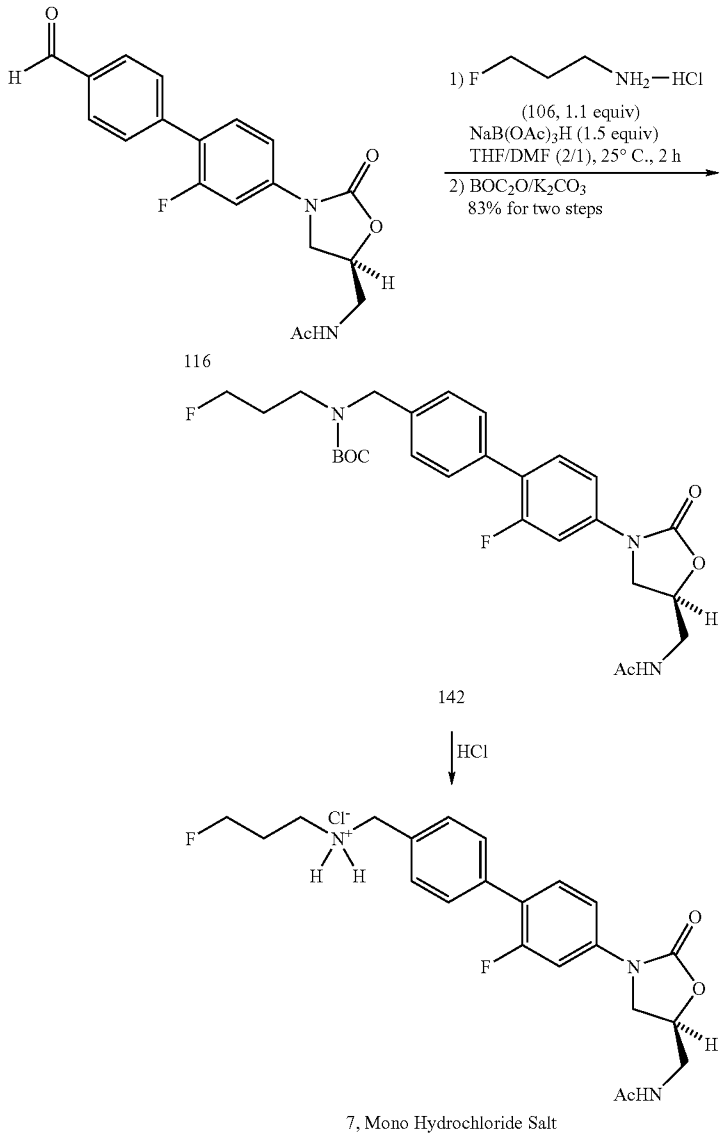

116

142

7, Mono Hydrochloride Salt

Synthesis of BOC-Protected Amine 142

A solution of N-[3-(2-fluoro-4'-formyl-biphenyl-4-yl)-2-oxo-oxazolidin-5-ylmethyl]-acetamide (aldehyde 116, 24.54 g, 68.9 mmol) in a mixture of anhydrous THF (250 mL) and anhydrous DMF (125 mL) was treated with amine salt 106 (10.17 g, 89.6 mmol, 1.3 equiv) at 25° C. under $N_2$, and the resulting mixture was treated with $NaB(OAc)_3H$ (21.9 g, 103.4 mmol, 1.5 equiv) at 25° C. under $N_2$. The resulting reaction mixture was subsequently stirred at 25° C. for 2 h. When TLC and HPLC/MS showed the reductive amination reaction was complete, the reaction mixture was treated with $H_2O$ (375 mL). The resulting solution was subsequently treated with $K_2CO_3$ (38.0 g, 275.6 mmol, 4.0 equiv) and $BOC_2O$ (18.0 g, 82.7 mmol, 1.2 equiv) at room temperature, and the resulting reaction mixture was stirred at room temperature for 2 h. When TLC and HPLC/MS showed the N-BOC protection reaction was complete, the reaction mixture was treated with EtOAc (200 mL) and $H_2O$ (100 mL). The two layers were separated, and the aqueous layer was extracted with EtOAc (2×200 mL). The combined organic extracts were then washed with $H_2O$ (100 mL), 1 N aqueous HCl solution (2×200 mL), $H_2O$ (2×200 mL), and the saturated aqueous NaCl solution (200 mL), dried over $MgSO_4$, and concentrated in vacuo. The residual oil was purified by flash column chromatography ($SiO_2$, 0–3% MeOH—$CH_2Cl_2$ gradient elution) to afford the desired BOC-protected amine 142 (29.57 g, 35.62 g theoretical, 83%) as colorless oil, which solidified upon standing at room temperature in vacuo.

Synthesis of Monohydrochloride Salt of Compound 7

A solution containing BOC-protected amine 142 (15.65 g, 30.3 mmol) in $CH_2Cl_2$ (30 mL) was treated with a solution of 4 N HCl in 1,4-dioxane (37.5 mL, 150.0 mmol, 5.0 equiv) at room temperature, and the resulting reaction mixture was stirred at room temperature for 12 h. When TLC and HPLC/MS showed that the N-BOC deprotection reaction was complete, the solvents were removed in vacuo. The residue then was suspended in a mixture of $CH_3CN$ (200 mL) and MeOH (50 mL), and the resulting slurry was stirred at room temperature for 1 h. The solids were collected by filtration, washed with 20% MeOH—$CH_3CN$ (2×50 mL), and dried in vacuo to afford the monohydrochloride salt of compound 7 (13.0 g, 13.64 g theoretical, 95.3%) as white crystals. LCMS (EI) m/e 418 ($M^+$+H).

Example 30

Alternate Synthesis of Compound 7 (Method 6)

Scheme 24 depicts the synthesis of compound 7 via a reaction in which the oxazolidinone ring is prepared via a cyclization reaction of (4'-{[tert-butoxycarbonyl-(3-fluoro-propyl)-amino]-methyl}-2-fluoro-biphenyl-4-yl)-carbamic acid tert-butyl ester (carbamate 146) and (R)-(−)-glycidyl burate.

Scheme 24

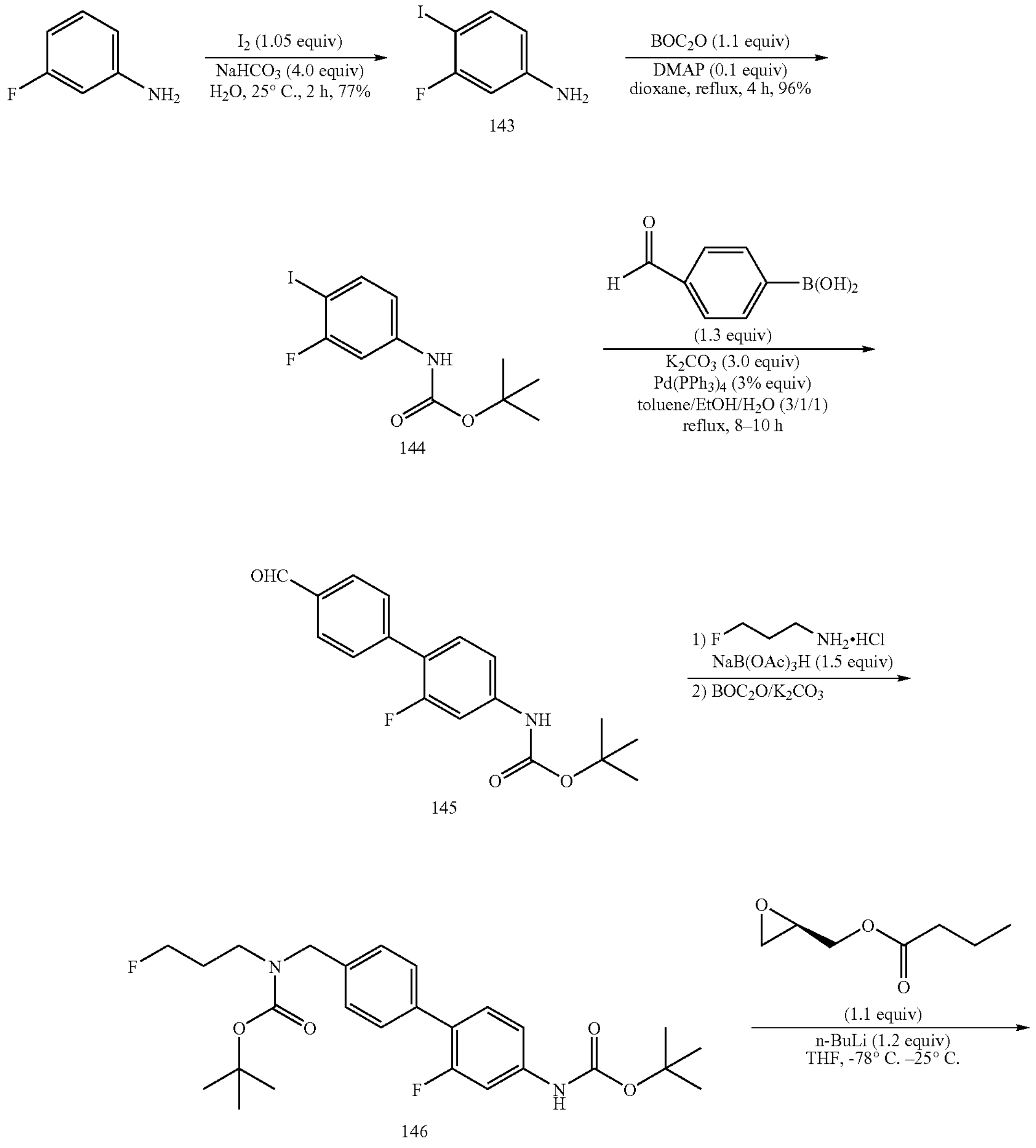

-continued

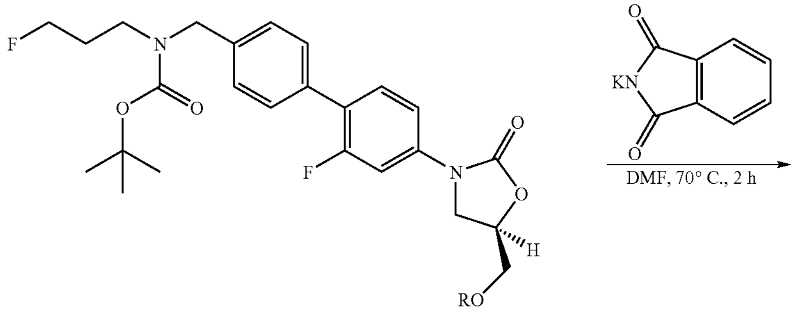

82, R = H
134, R = Ms
MsCl/TEA

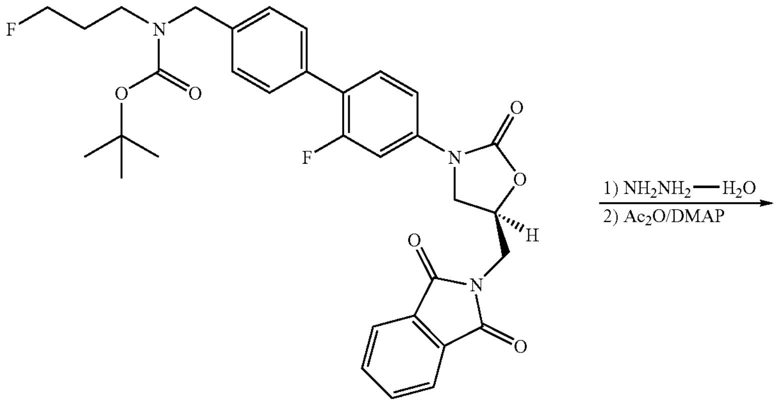

147

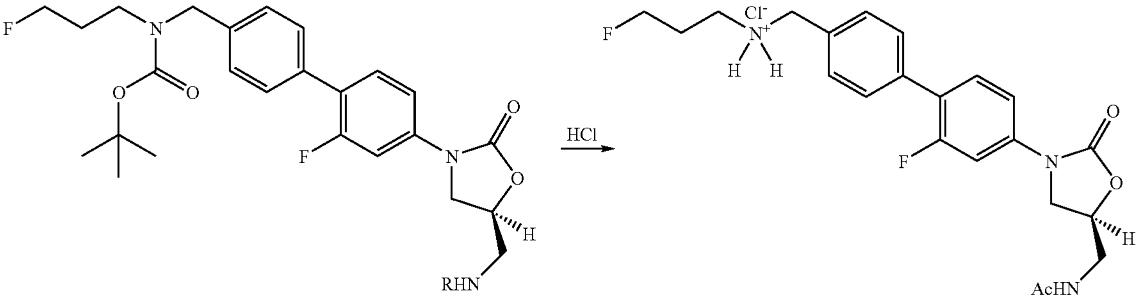

51, R = H
142, R = Ac
$Ac_2O$ 7 mono hydrochloride salt

Synthesis of Compound 143

A solution of $NaHCO_3$ (75.6 g, 0.90 mol, 4.0 equiv) in $H_2O$ (600 mL) was treated with solid iodine ($I_2$, 60.0 g, 0.236 mol, 1.05 equiv) and liquid 3-fluoroaniline (25.0 g, 0.225 mol) at room temperature, and the resulting reaction mixture was stirred at room temperature for 3 h. When TLC showed that the reaction was complete, the yellow to brown solids were collected by filtration, washed with $H_2O$ (2×200 mL) and hexane (2×100 mL), and dried in vacuo to afford the crude, desired 3-fluoro-4-iodophenylamine (compound 143, 47.81 g, 53.325 g theoretical, 89.7% yield). This crude product was recrystallized in EtOAc/hexane to afford the pure, desired compound 143 (41.2 g, 53.325 g theoretical, 77.3% yield) as pale-yellow crystals. For compound 143: $^1$H NMR (300 MHz, DMSO-d$_6$) δ 5.61 (br.s, 2H, $NH_2$), 6.25 (dd, 1H, J=2.4, 8.2 Hz), 6.41 (dd, 1H, J=2.4, 8.2 Hz), 7.32 (t, 1H, J=8.4 Hz); $C_6H_5FIN$, LCMS (EI) m/e 238 ($M^+$+H).

Synthesis of Compound 144

A solution of compound 143 (13.67 g, 57.7 mmol) in 1,4-dioxane (100 mL) was treated with $BOC_2O$ (13.83 g, 63.4 mmol, 1.1 equiv) and DMAP (700.0 mg, 5.8 mmol, 0.1 equiv) at room temperature. The resulting reaction mixture was then warmed up to refluxing for 4 h. When TLC and HPLC/MS showed that the reaction was complete, the reaction mixture was treated with $H_2O$ (100 mL) and EtOAc (100 mL). The two layers were separated, and the aqueous layer was extracted with EtOAc (2×100 mL). The combined organic extracts were washed with $H_2O$ (2×100 mL) and saturated NaCl aqueous solution (100 mL), dried over $MgSO_4$, and concentrated in vacuo. The residue was further dried in vacuo to afford the crude, desired (3-fluoro-4-iodo-phenyl)-carbamic acid tert-butyl ester (compound 144, 18.67 g, 19.44 g theoretical, 96%) as pale-yellow oil, which solidified upon standing in vacuo at room temperature and was found to be essentially pure and was directly used in the subsequent reactions without further purifications. For compound 144: $C_{11}H_{13}FINO_2$, LCMS (EI) m/e 338 ($M^+$+H).

Synthesis of Compound 145

A solution of compound 144 (18.50 g, 54.8 mmol) and 4-formylphenylboronic acid 143 (10.70 g, 71.4 mmol, 1.3 equiv) in toluene (150 mL), EtOH (50 mL), and $H_2O$ (50 mL) was treated with $K_2CO_3$ (22.7 g, 164.4 mmol, 3.0 equiv) at 25° C., and the resulting mixture was degassed three times under a steady stream of argon at 25° C. $Pd(PPh_3)_4$ (3.17 g, 2.74 mmol, 0.05 equiv) was subsequently added to the reaction mixture, and the resulting reaction mixture was degassed three times again under a steady stream of argon at 25° C. before being warmed up to gentle reflux for 10 h. When TLC and HPLC/MS showed the coupling reaction was complete, the reaction mixture was cooled down to room temperature before being treated with $H_2O$ (100 mL) and EtOAc (100 mL) at room temperature. The resulting mixture was then stirred at room temperature for 10 min before the two layers were separated. The aqueous layer was extracted with EtOAc (2×100 mL), and the combined organic extracts were washed with $H_2O$ (2×100 mL) and the saturated aqueous NaCl solution (100 mL), dried over $MgSO_4$, and concentrated in vacuo. The residue was directly purified by flash column chromatography ($SiO_2$, 0–2% MeOH/$CH_2Cl_2$ gradient elution) to afford the desired (2-fluoro-4'-formyl-biphenyl-4-yl)-carbamic acid tert-butyl ester (compound 145, 14.6 g, 17.26 g theoretical, 85.2% yield) as pale-yellow oil, which solidified upon standing in vacuo at room temperature. For compound 145: $^1$H NMR (300 MHz, $CDCl_3$) δ 1.47 (s, 9H, $NHCO_2C(CH_3)_3$), 6.60 (s, 1H, NHBOC), 7.04 (dd, 1H, J=2.0, 8.4 Hz), 7.32 (t, 1H, J=8.6 Hz), 7.40 (dd, 1H, J=2.0, 13.0 Hz), 7.62 (dd, 2H, J=1.5, 8.3 Hz), 7.87 (dd, 2H, J=1.5, 8.3 Hz), 9.98 (s, 1H, CHO); $C_{18}H_{18}FNO_3$, LCMS (EI) m/e 316 ($M^+$+H).

Synthesis of Carbamate 146

A solution of compound 145 (7.0 g, 22.22 mmol) in a mixture of anhydrous THF (40 mL) and anhydrous DMF (40 mL) was treated with amine salt 106 (3.03 g, 26.66 mmol, 1.2 equiv) at 25° C. under $N_2$, and the resulting mixture was treated with $NaB(OAc)_3H$ (7.07 g, 33.33 mmol, 1.5 equiv) at 25° C. under $N_2$. The resulting reaction mixture was subsequently stirred at 25° C. for 2 h. When TLC and HPLC/MS showed the reductive amination reaction was complete, the reaction mixture was treated with $H_2O$ (80 mL). The resulting solution was subsequently treated with $K_2CO_3$ (12.3 g, 88.88 mmol, 4.0 equiv) and $BOC_2O$ (5.82 g, 26.66 mmol, 1.2 equiv) at room temperature, and the resulting reaction mixture was stirred at room temperature for 2 h. When TLC and HPLC/MS showed the N-BOC protection reaction was complete, the reaction mixture was treated with EtOAc (100 mL) and $H_2O$ (100 mL). The two layers were separated, and the aqueous layer was extracted with EtOAc (2×100 mL). The combined organic extracts were then washed with $H_2O$ (100 mL), 1 N aqueous HCl solution (2×100 mL), $H_2O$ (2×100 mL), and the saturated aqueous NaCl solution (100 mL), dried over $MgSO_4$, and concentrated in vacuo. The residual oil was purified by flash column chromatography ($SiO_2$, 5–10% EtOAc-hexane gradient elution) to afford carbamate 146, 9.8 g, 10.6 g theoretical, 92.5%) as colorless oil, which solidified upon standing at room temperature in vacuo. For carbamate 146: $^1$H NMR (300 MHz, $CDCl_3$) δ 1.51 (s, 9H, $NHCO_2C(CH_3)_3$), 1.59 (s, 9H, $NHCO_2C(CH_3)_3$), 1.88–2.08 (m, 2H), 3.30–3.37 (m, 2H), 4.42–4.67 (m, 4H), 6.59 (s, 1H, NHBOC), 7.09 (dd, 1H, J=2.0, 8.4 Hz), 7.30–7.99 (m, 6H); $C_{26}H_{34}F_2N_2O_4$, LCMS (EI) m/e 477 ($M^+$+H).

Synthesis of Compound 82

A solution of compound 146 (7.155 g, 15.0 mmol) in anhydrous THF (50 mL) was cooled down to −78° C. in a dry-ice-acetone bath before a solution of n-BuLi (1.6 M solution in hexane, 11.25 mL, 18 mmol, 1.2 equiv) in hexane was dropwise added at −78° C. under $N_2$. The resulting reaction mixture was subsequently stirred at −78° C. for 1 h before a solution of (R)-(−)-glycidyl butyrate (2.38 g, 2.32 mL, 16.5 mmol, 1.1 equiv) in anhydrous THF (10 mL) was dropwise added into the reaction mixture at −78° C. under $N_2$. The resulting reaction mixture was stirred at −78° C. for 30 min before being gradually warmed up to room temperature for 12 h under $N_2$. When TLC and HPLC/MS showed that the reaction was complete, the reaction mixture was quenched with $H_2O$ (50 mL), and the resulting mixture was stirred at room temperature for 1 h before EtOAc (100 mL) was added. The two layers were separated, and the aqueous layer was extracted with EtOAc (2×50 mL). The combined organic extracts were washed with $H_2O$ (2×50 mL) and saturated NaCl aqueous solution (50 mL), dried over $MgSO_4$, and concentrated in vacuo. The white crystals were precipitated out from the concentrated solution when most of the solvents were evaporated. The residual oil was purified by flash column chromatography ($SiO_2$, 10–30% EtOAc-hexane gradient elution) to afford the desired (5R)-[2'-fluoro-4'-(5-hydroxymethyl-2-oxo-oxazolidin-3-yl)-biphenyl-4-ylmethyl]-(3-fluoro-propyl)-carbamic acid tert-butyl ester (compound 82, 5.82 g, 7.14 g theoretical, 81.5%) as colorless oil, which solidified upon standing at room temperature in vacuo. For compound 82: $C_{25}H_{30}F_2N_2O_5$, LCMS (EI) m/e 540 ($M^+$+Na+$CH_3CN$).

Synthesis of Mesylate 134

A solution of compound 82, 1.725 g, 3.6 mmol) in $CH_2Cl_2$ (25 mL) was treated with TEA (727 mg, 1.0 mL, 7.2 mmol, 2.0 equiv) at 25° C., and the resulting mixture was cooled down to 0–5° C. before MsCl (95 mg, 0.335 mL, 4.32 mmol, 1.2 equiv) was dropwise introduced into the reaction mixture at 0–5° C. under $N_2$. The resulting reaction mixture was subsequently stirred at 0–5° C. for 1 h under $N_2$. When TLC and HPLC/MS showed that the reaction was complete, the reaction mixture was quenched with $H_2O$ (40 mL) and $CH_2Cl_2$ (40 mL). The two layers were separated, and the aqueous layer was extracted with $CH_2Cl_2$ (40 mL). The combined organic extracts were washed with $H_2O$ (2×20 mL) and saturated NaCl aqueous solution (20 mL), dried over $MgSO_4$, and concentrated in vacuo. The residue was further dried in vacuo to afford mesylate 134, 1.82 g, 1.994 g theoretical, 91.3%) as off-white powders, which was found to be essentially pure and was directly used in the subsequent reactions without further purifications. For mesylate 134: $C_{26}H_{32}F_2N_2O_7S$, LCMS (EI) m/e 555 ($M^+$+H).

Synthesis of Compound 147

A solution of mesylate 134 (1.662 g, 3.0 mmol) in anhydrous DMF (30 mL) was treated with solid potassium pathilimide (667 mg, 3.6 mmol, 1.2 equiv) at 25° C., and the resulting reaction mixture was warmed up to 70° C. for 2 h. When TLC and HPLC showed that the reaction was complete, the reaction mixture was cooled down to room temperature before being quenched with $H_2O$ (50 mL). The resulting aqueous mixture was then extracted with EtOAc (2×50 mL), and the combined organic extracts were washed with water (40 mL) and saturated aqueous NaCl solution (20 mL), dried over $MgSO_4$, and concentrated in vacuo to afford the crude, desired (5R)-{4'-[5-(1,3-dioxo-1,3-dihydro-isoindol-2-ylmethyl)-2-oxo-oxazolidin-3-yl]-2'-fluoro-biphenyl-4-ylmethyl}-(3-fluoro-propyl)-carbamic acid tert-butyl ester (compound 147, 1.74 g, 1.815 g theoretical, 95.9%) as pale-yellow oil, which solidified upon standing in vacuo at room temperature. This crude product was found to be essentially pure and was directly used in the subsequent reactions without further purifications. For compound 147: $C_{33}H_{33}F_2N_3O_6$, LCMS (EI) m/e 606 ($M^+$+H).

Synthesis of Compound 51

A solution of compound 147 (1.50 g, 2.48 mmol) in EtOH (30 mL) was treated with hydrazine monohydrate (250.5 mg, 0.25 mL, 5.0 mmol, 2.0 equiv) at 25° C., and the resulting reaction mixture was warmed up to reflux for 6 h. The white precipitates were formed during the reaction mixture was refluxed. When TLC and HPLC showed that the reaction was complete, the reaction mixture was cooled down to room temperature before being quenched with $H_2O$ (20 mL). The white precipitates were totally dissolved when water was introduced into the reaction mixture and a homogeneous solution was generated. The aqueous solution was then extracted with $CH_2Cl_2$ (2×40 mL), and the combined organic extracts were washed with $H_2O$ (2×20 mL) and saturated NaCl aqueous solution (20 mL), dried over $MgSO_4$, and concentrated in vacuo. The residue was then purified by flash column chromatography ($SiO_2$, 0–5% $MeOH/CH_2Cl_2$ gradient elution) to afford the desired (2-fluoro-4'-formyl-biphenyl-4-yl)-carbamic acid tert-butyl ester (compound 51, 14.6 g, 17.26 g theoretical, 85.2% yield) as pale-yellow oil, which solidified upon standing in vacuo at room temperature. For compound 51: $C_{25}H_{31}F_2N_3O_4$, LCMS (EI) m/e 476 ($M^+$+H).

Synthesis of Compound 142

A suspension of compound 51 (180 mg, 0.38 mmol) in $CH_2Cl_2$ (6.0 mL) was treated with TEA (76.5 mg, 0.115 mL, 0.76 mmol, 2.0 equiv) at 25° C., and the resulting reaction mixture was cooled down to 0–5° C. before being treated with $Ac_2O$ (77.6 mg, 0.072 mL, 0.76 mmol, 2.0 equiv) and DMAP (10 mg, cat.) at 0–5° C. under $N_2$. The resulting reaction mixture was subsequently stirred at 0–5° C. for 2 h. When TLC and HPLC showed that the reaction was complete, the reaction mixture was quenched with $H_2O$ (10 mL). The two layers were separated, and the aqueous layer was then extracted with $CH_2Cl_2$ (2×10 mL), and the combined organic extracts were washed with $H_2O$ (2×10 mL) and saturated NaCl aqueous solution (10 mL), dried over $MgSO_4$, and concentrated in vacuo. The residue was then purified by flash column chromatography ($SiO_2$, 0–5% $MeOH/CH_2Cl_2$ gradient elution) and was further dried in vacuo to afford the crude, desired (5S)-{4'-[5-(acetylamino-methyl)-2-oxo-oxazolidin-3-yl]-2'-fluoro-biphenyl-4-ylmethyl}-(3-fluoro-propyl)-carbamic acid tert-butyl ester (compound 142, 196.5 mg theoretical, 93%) as colorless oil, which solidified upon standing at room temperature in vacuo.

Synthesis of Monohydrochloride Salt of Compound 7

The monohydrochloride salt of compound 7 was prepared from compound 142 as described in Example 29.

Example 31

Synthesis of Compound 50

Scheme 25 depicts the synthesis of compound 50 from the oxidation of compound 82.

Scheme 25

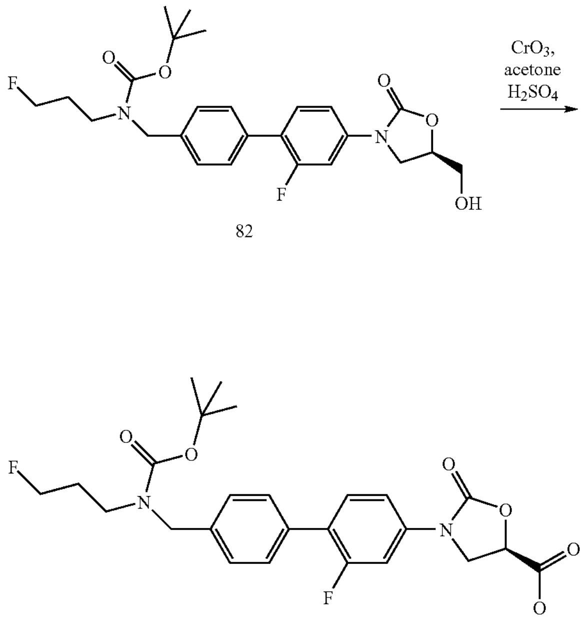

82

50

To a solution of 0.230 g (0.48 mmol) of compound 82 in 10 mL of acetone at 0° C. was added 0.145 g (1.45 mmol) of chromium trioxide ($CrO_3$) in 0.40 mL of $H_2SO_4$. The reaction mixture was then warmed up to 25° C., and allowed to stir for 20 h. Sulfuric acid was neutralized with excess $Na_2CO_3$. Subsequently, the mixture was diluted with 10 mL of THF, followed by the addition of 0.158 g (0.72 mmol) of $BOC_2O$. The reaction was monitored through LC/MS until the reaction was completed. The reaction mixture was extracted with $CH_2Cl_2$ (50 mL×3), combined $CH_2Cl_2$ layers were washed with brine (40 mL), dried over $MgSO_4$, and concentrated, purified via preparative TLC to give 0.082 g (53% yield) of compound 50 plus 0.080 g of starting material. MS (M+1): 491.

Example 32

Synthesis of Compound 51

Scheme 26 depicts the synthesis of compound 51 from compound 50.

Scheme 26

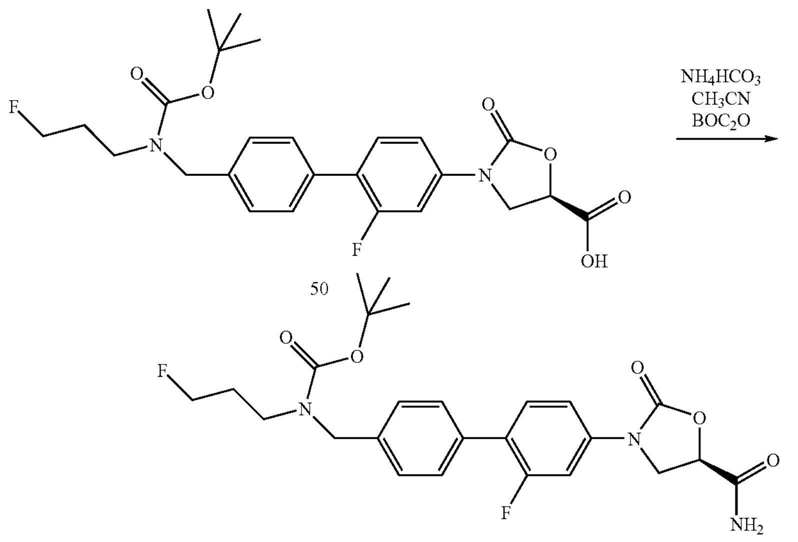

50

51

A solution of 0.029 g (0.059 mmol) of compound 50, 0.024 g (0.30 mmol) of ammonium bicarbonate ($NH_4HCO_3$), and 0.019 g (0.089 mmol) of $(BOC)_2O$ in 5 mL of $CH_3CN$ with one drop of pyridine was stirred at 25° C. for 10 h. $CH_3CN$ was removed, and the residue purified through preparative TLC to give 0.025 g of compound 51. MS (M+1): 490.

Example 33

Synthesis of Compound 52

Scheme 27 depicts the synthesis of compound 52 from compound 50.

Scheme 27

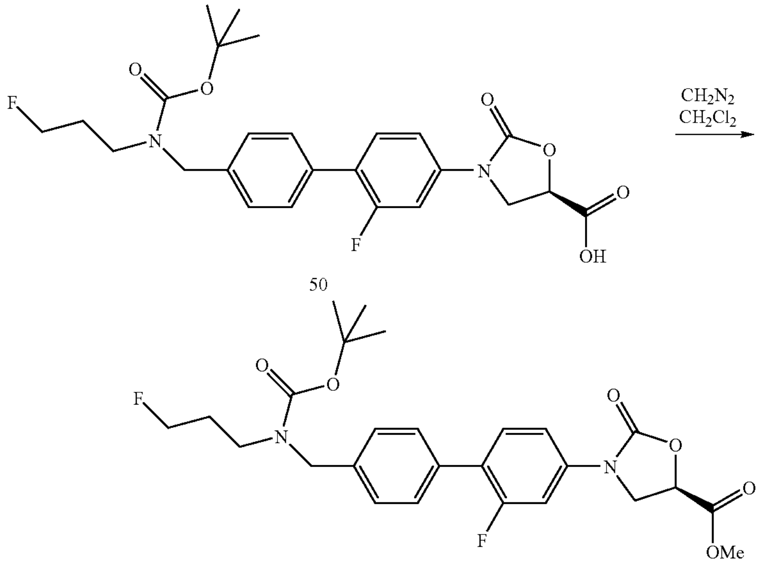

50

52

To a solution of 0.020 g (0.04 mmol) of compound 50 in 5 mL of $CH_2Cl_2$ and 1 mL of MeOH at 0° C. was added an excess of diazomethane ($CH_2N_2$) in ether. The reaction mixture was then warmed to 25° C. and stirred for 4 additional hours. Excess $CH_2N_2$ was quenched with AcOH, and the solvents were removed by rotary evaporation. The residue was purified through preparative TLC to give 0.015 g (71% yield) of compound 52. MS (M+1): 505.

Example 34

Synthesis of Monohydrochloride Salt of Compound 53

Scheme 28 depicts the synthesis of the mono hydrochloride salt of compound 53 from compound 52.

Scheme 28

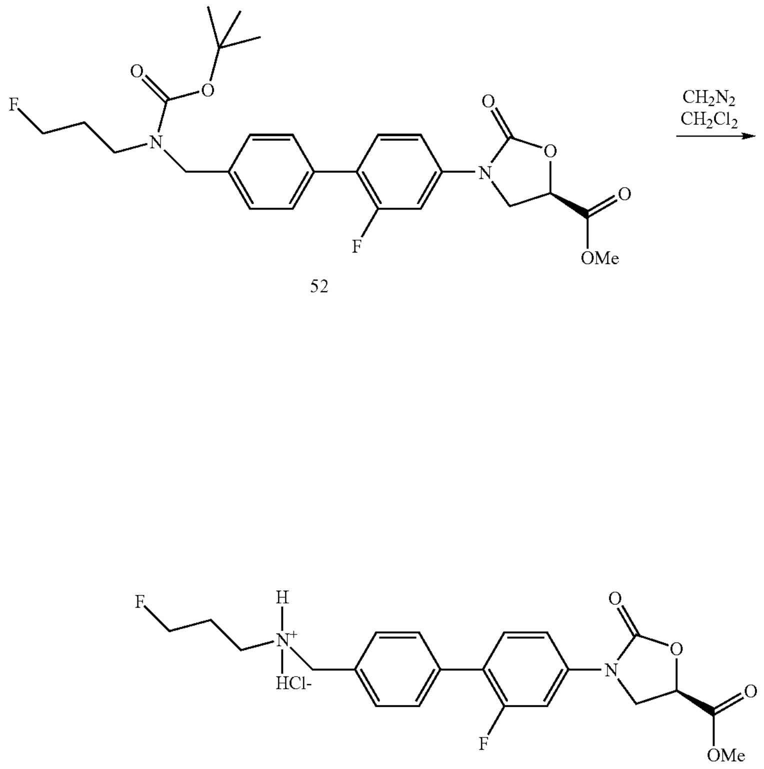

52

53

A solution of 0.010 g (0.02 mmol) of compound 52 in 2 mL of $CH_2Cl_2$, 1 mL of MeOH and 2 mL of 4 N HCl was stirred at 25° C. for 3 h. The solvents were removed, and the residue dried under vacuum to give compound 53 as the monohydrochloride salt in 100% yield. MS (M+1): 405.

Example 35

Synthesis of Monohydrochloride Salt of Compound 54

Scheme 29 depicts the synthesis of compound 54 from compound 51.

Scheme 29

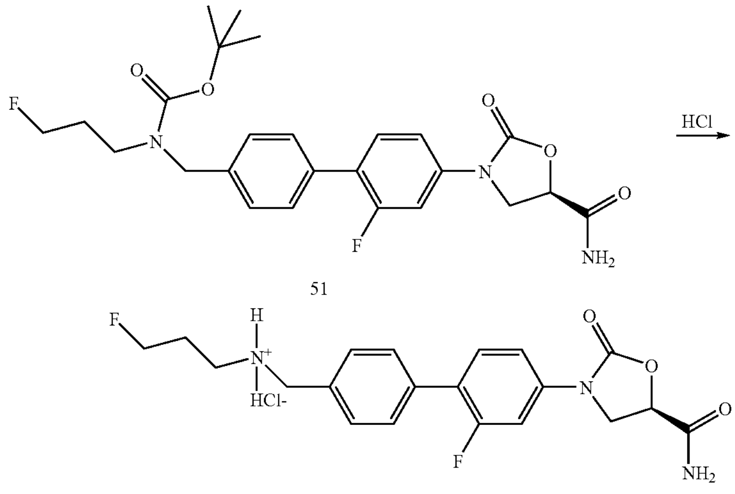

51

54

A solution of 0.022 g (0.05 mmol) of compound 51 and 1 mL of 4 N HCl in 3 mL of dioxane was stirred at 25° C. for 6 h. The dioxane was removed, and the residue dried to give the compound 54 as the monohydrochloride salt in 100% yield. MS (M+1): 390.

Example 36

Synthesis of Monohydrochloride Salt of Compound 55

Scheme 30 depicts the synthesis of the monohydrochloride salt of compound 55 from compound 50.

Scheme 30

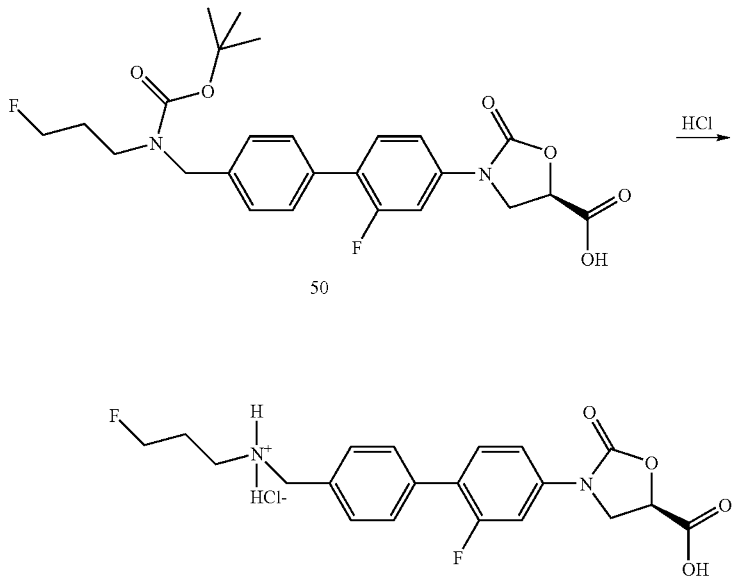

50

55

A solution of 0.025 g (0.05 mmol) of compound 50 and 1 mL of 4 N HCl in 3 mL of dioxane was stirred at 25° C. for 6 h. The dioxane was removed, and the residue dried to give the compound 55 as the monohydrochloride salt in 100% yield. MS (M+1): 391.

Example 37

Synthesis of Compound 56

Scheme 31 depicts the synthesis of compound 56 from compound 50.

Scheme 31

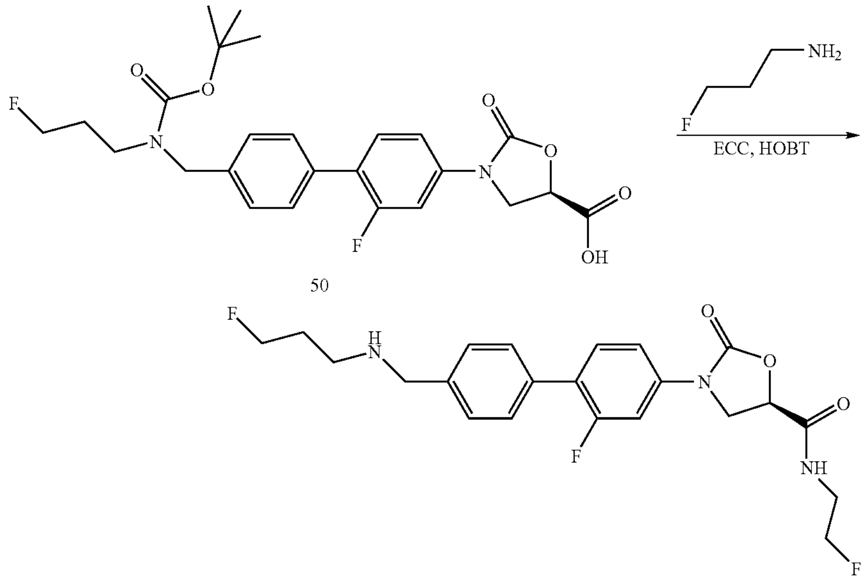

50

56

To a solution of 0.030 g (0.06 mmol) of compound 50, 0.007 g (0.07 mmol) of 2-fluoroethylamine, and 0.010 g (0.07 mmol) of N-hydroxy benzotriazole (HOBT) in 2 mL of DMF was added 0.014 g (0.07 mmol) of diethylene chloride (EDC). The reaction mixture was allowed to stir for 6 h, DMF was then removed, and the residue purified by preparative TLC to give 0.010 g of compound 56. MS (M+1): 436.

Example 38

Synthesis of Compound 23

Compound 23 can be made from amine 105 via a condensation reaction with difluorochloroacetic acid under conditions known in the art.

Example 39

Synthesis of Compounds 25, 27, 31, 33, 45, 47, 61, 77, 80, and 81

Compounds 25, 27, 31, 33, 45, 47, 61, 77, 80, and 81 can be made by reacting amine 105 with the appropriate alkylating agents via alkylation reactions analogous to the chemistries described in, for example, Schemes 4 and 7 above. It is to be understood that alternative chemistries could be employed by those skilled in the art to prepare these compounds.

Example 40

Synthesis of Compound 39

Compound 40, which has a 5-chloromethyl substituent on the oxazolidinone ring, can be made via chlorination of the corresponding hydroxymethyl oxazolidione intermediate 93, followed by coupling with an aryl boronic acid or ester to form the biaryl system under conditions known in the art.

Example 41

Synthesis of Compounds 43 and 44

Compounds 43 and 44, both of which have the R stereochemistry at the 5-position of the oxazolidinone ring, can be made via a cyclization reaction analogous to the chemistries described in Scheme 1 above to prepare intermediate alcohol 92, by replacing (R)-(−)-glycidyl butyrate with (S)-(−)-glycidyl butyrate.

Example 42

Synthesis of Compound 48

Compound 48 can be made from the corresponding aldehyde 116 by reaction with 3-fluoropropylamine under conditions known in the art.

Example 43

Synthesis of Compound 49

Compound 49 can be made from compound 5 using a procedure analogous to that for making compound 37 from compound 7 as described in Scheme 14 above.

Example 44

Synthesis of Compounds 57, 58, 59, and 60

Compounds 57, 58, 59, and 60, which have a methyl substituent at the 5-position of the oxazolidinone ring, can be made via a cyclization reaction analogous to the chemistries described in Scheme 1 above to prepare intermediate alcohol 92, by replacing (R)-(−)-glycidyl butyrate with (R)-2-methyl-oxiranyl methanol.

Example 45

Synthesis of Compounds 62 and 63

Compounds 62 and 63 can be made by following the general procedures depicted in Scheme 32 below under conditions known in the art.

Scheme 32

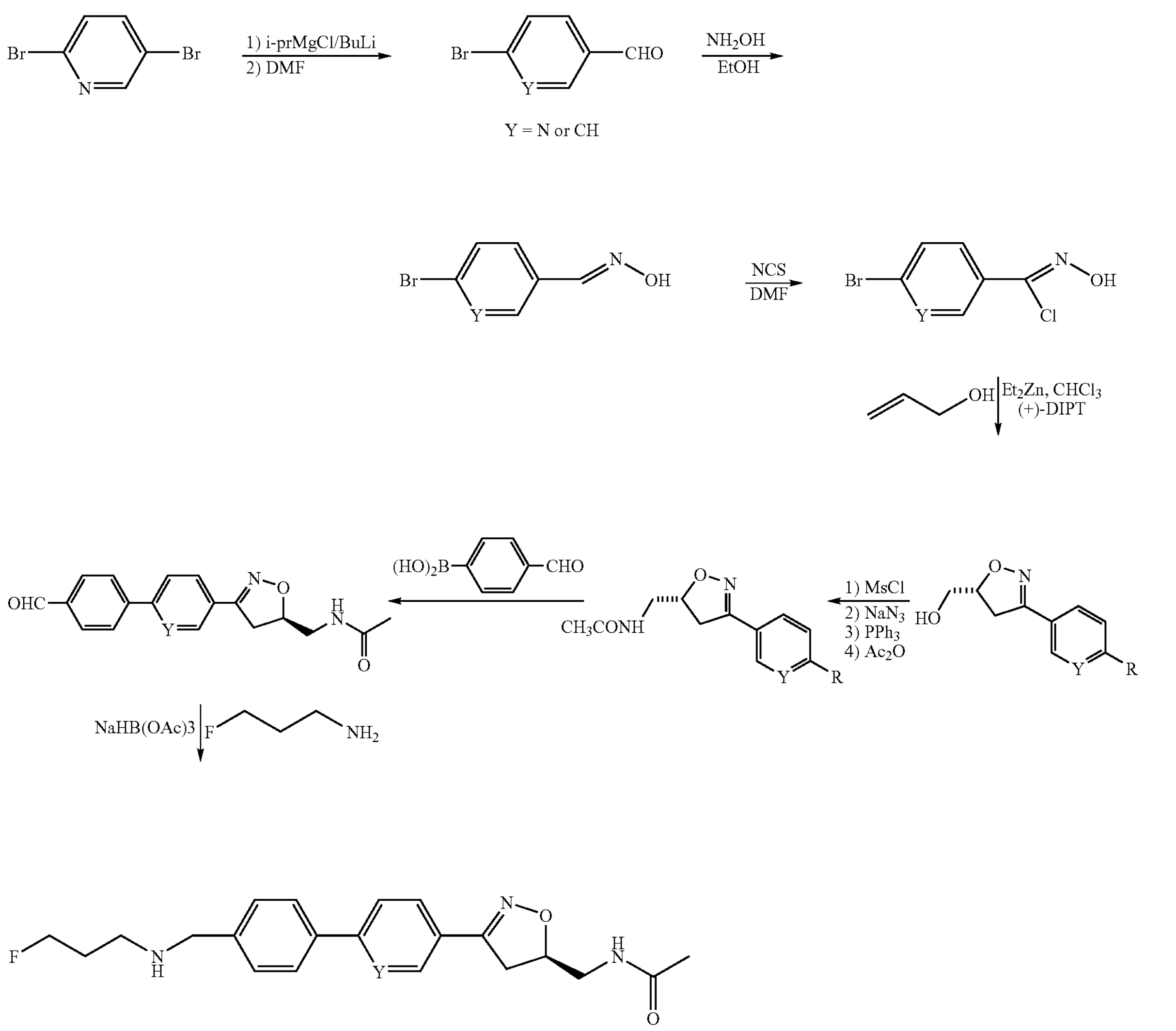

62 Y = N
63 Y = CH

Example 46

Synthesis of Compounds 46, 64, 65, 66, 67, 68, 70, 75, and 76

Compounds 46, 64, 65, 66, 67, 68, 70, 75, and 76, which have a heterocyclic ring substituent on the 5 methyl group of the oxazolidinone ring, can be made via cycloaddition reactions analogous to the chemistries described in Scheme 6 for making compound 111 from azide 110.

Example 47

Synthesis of Compounds 69, 71, 72, 73, 74, 78, and 79

Compounds 69, 71, 72, 73, 74, 78, and 79 can be made from the corresponding 5-yl methyl amino oxazolidinone compound by reaction with the appropriate carboxylic acid or derivatives thereof (e.g., anhydrides and acid chlorides).

INCORPORATION BY REFERENCE

The entire disclosure of each of the patent documents and scientific articles referred to herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound having the formula:

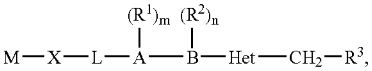

or a pharmaceutically acceptable salt, ester or prodrug thereof, wherein:

A is phenyl

B is selected from the group consisting of:
phenyl, pyridyl, pyrazinyl, pyrimidinyl, and pyridazinyl;

Het-$CH_2$—$R^3$ is selected from the group consisting of:

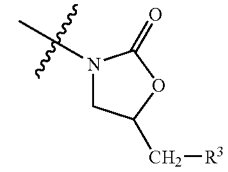
,
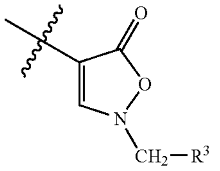
,
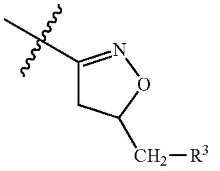
, and
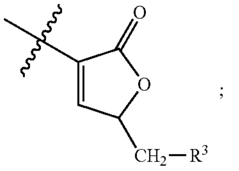
;

M is selected from the group consisting of:
a) $C_{1-6}$ alkyl, b) $C_{2-6}$ alkenyl, and c) $C_{2-6}$ alkynyl, wherein
i) any of a)–c) is substituted with one or more moieties selected from the group consisting of F, Cl, Br, and I; and
ii) any of a)–c) optionally is further substituted with one or more $R^4$ groups;

X is selected from the group consisting of:
a) —O—, b) —$NR^5$—, c) —N(O)—, d) —N($OR^5$)—, e) —$S(O)_p$—, f) —$NR^5$—N═, g) ═N—$NR^5$—, h) —O—N═, i) ═N—O—, j) —N═, k) ═N—, l) —$NR^5$—$NR^5$—, m) —$NR^5$C(O)O—, n) —OC(O)$NR^5$—, o) —$NR^5$C(O)$NR^5$—, p) —$NR^5$C($NR^5$)$NR^5$—, and

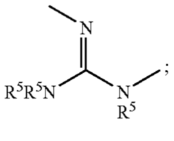
;

L is selected from the group consisting of:
a) $C_{1-6}$ alkyl, b) $C_{2-6}$ alkenyl, and c) $C_{2-6}$ alkynyl, wherein any of a)–c) optionally is substituted with one or more $R^4$ groups;

$R^1$, at each occurrence, independently is selected from the group consisting of:
a) F, b) Cl, c) Br, d) I, e) —$CF_3$, f) —$OR^7$, g) —CN, h) —$NO_2$, i) —$NR^7R^7$, j) —C(O)$R^7$, k) —C(O)$OR^7$, l) —OC(O)$R^7$, m) —C(O)$NR^7R^7$, n) —$NR^7$C(O)$R^7$, o) —OC(O)$NR^7R^7$, p) —$NR^7$C(O)$OR^7$, q) —$NR^7$C(O)$NR^7R^7$, r) —C(S)$R^7$, s) —C(S)$OR^7$, t) —OC(S)$R^7$, u) —C(S)$NR^7R^7$, v) —$NR^7$C(S)$R^7$, w) —OC(S)$NR^7R^7$, x) —$NR^7$C(S)$OR^7$, y) —$NR^7$C(S)$NR^7$, $R^7$, z) —$NR^7$C($NR^7$)$NR^7R^7$, aa) —$S(O)_pR^7$, bb) —$SO_2NR^7R^7$, and cc) $R^7$;

$R^2$, at each occurrence, independently is selected from the group consisting of:
a) F, b) Cl, c) Br, d) I, e) —$CF_3$, f) —$OR^7$, g) —CN, h) —$NO_2$, i) —$NR^7R^7$, j) —C(O)$R^7$, k) —C(O)$OR^7$, l) —OC(O)$R^7$, m) —C(O)$NR^7R^7$, n) —$NR^7$C(O)$R^7$, o) —OC(O)$NR^7R^7$, p) —$NR^7$C(O)$OR^7$, q) —$NR^7$C(O)$NR^7R^7$, r) —C(S)$R^7$, s) —C(S)$R^7$, t) —OC(S)$R^7$, u) —C(S)$NR^7R^7$, v) —$NR^7$C(S)$R^7$, w) —OC(S)$NR^7R^7$, x) —$NR^7$C(S)$OR^7$, y) —$NR^7$C(S)$NR^7R^7$, z) —$NR^7$C($NR^7$)$NR^7R^7$, aa) —$S(O)_pR^7$, bb) —$SO_2NR^7R^7$, and cc) $R^7$;

$R^3$ is selected from the group consisting of:
a) —$OR^7$, b) —$NR^7R^7$, c) —C(O)$R^7$, d) —C(O)$OR^7$, e) —OC(O)$R^7$, f) —C(O)$NR^7R^7$, g) —$NR^7$C(O)$R^7$, h) —OC(O)$NR^7R^7$, i) —$NR^7$C(O)$OR^7$, j) —$NR^7$C(O)$NR^7R^7$, k) —C(S)$R^7$, l) —C(S)$OR^7$, m) —OC(S)$R^7$, n) —C(S)$NR^7R^7$, o) —$NR^7$C(S)$R^7$, p) —OC(S)$NR^7R^7$, q) —$NR^7$C(S)$OR^7$, r) —$NR^7$C(S)$NR^7R^7$, s) —$NR^7$C($NR^7$)$NR^7R^7$, t) —$S(O)_pR^7$, u) —$SO_2NR^7R^7$, and v) $R^7$;

$R^4$, at each occurrence, independently is selected from the group consisting of:
a) H, b) F, c) Cl, d) Br, e) I, f) ═O, g) ═S, h) ═$NR^5$, i) ═$NOR^5$, j) ═N—$NR^5R^5$, k) —$CF_3$, l) —$OR^5$, m) —CN, n) —$NO_2$, o) —$NR^5R^5$, p) —C(O)$R^5$, q) —C(O)$OR^5$, r) —OC(O)$R^5$, s) —C(O)$NR^5R^5$, t) —$NR^5$C(O)$R^5$, u) —OC(O)$NR^5R^5$, v) —$NR^5$C(O)$OR^5$, w) —$NR^5$C(O)$NR^5R^5$, x) —C(S)$R^5$, y) —C(S)$OR^5$, z) —OC(S)$R^5$, aa) —C(S)$NR^5R^5$, bb) —$NR^5$C(S)$R^5$, cc) —OC(S)$NR^5R^5$, dd) —$NR^5$C(S)$OR^5$, ee) —$NR^5$C(S)$NR^5R^5$, ff) —$NR^5$C($NR^5$)$NR^5$, $R^5$, gg) —$S(O)_pR^5$, and hh) $R^5$;

$R^5$, at each occurrence, independently is selected from the group consisting of:
a) H, b) $C_{1-6}$ alkyl, c) $C_{2-6}$ alkenyl, d) $C_{2-6}$ alkynyl, e) —C(O)—$C_{1-6}$ alkyl, f) —C(O)—$C_{2-6}$ alkenyl, g) —C(O)—$C_{2-6}$ alkynyl, h) —C(O)O—$C_{1-6}$ alkyl, i) —C(O)O—$C_{2-6}$ alkenyl, and j) —C(O)O—$C_{2-6}$ alkynyl,
wherein any of b)–j) optionally is substituted with one or more $R^6$ groups;

$R^6$, at each occurrence, independently is selected from the group consisting of:
a) F, b) Cl, c) Br, d) I, e) —$CF_3$, f) —OH, g) —$OC_{1-6}$ alkyl, h) —SH, i) —$SC_{1-6}$ alkyl, j) —CN, k) —$NO_2$, l) —$NH_2$, m) —$NHC_{1-6}$ alkyl, n) —N($C_{1-6}$ alkyl)$_2$, o) —C(O)$C_{1-6}$ alkyl, p) —C(O)$OC_{1-6}$ alkyl, q) —C(O)$NH_2$, r) —C(O)$NHC_{1-6}$ alkyl, s) —C(O)N($C_{1-6}$ alkyl)$_2$, t) —NHC(O)$C_{1-6}$ alkyl, and u) —$S(O)_pC_{1-6}$ alkyl;

$R^7$, at each occurrence, independently is selected from the group consisting of:
a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3–14 membered saturated, unsaturated, or aromatic heterocycle consisting one or more heteroatoms selected from the group consisting of nitrogen, oxygen, and sulfur, g) —C(O)$C_{1-6}$ alkyl, h) —C(O)—$C_{2-6}$ alkenyl, i) —C(O)—$C_{2-6}$ alkynyl, j) —C(O)$C_{3-14}$ saturated, unsaturated, or aromatic carbocycle, k) —C(O)-3–14 membered saturated, unsaturated, or aromatic heterocycle consisting one or more heteroatoms selected from the group consisting of nitrogen, oxygen, and sulfur, l) —C(O)O—$C_{1-6}$ alkyl, m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3–14 membered saturated, unsaturated, or aromatic heterocycle consisting one or more heteroatoms selected from the group consisting of nitrogen, oxygen, and sulfur, wherein any of b)–p) optionally is substituted with one or more $R^8$ groups;

$R^8$, at each occurrence, is independently selected from the group consisting of:

a) F, b) Cl, c) Br, d) I, e) =O, f) =S, g) =$NR^9$, h) =$NOR^9$, i) =N—$NR^9R^9$, j) —$CF_3$, k) —$OR^9$, l) —CN, m) —$NO_2$, n) —$NR^9R^9$, o) —C(O)$R^9$, p) —C(O)$OR^9$, q) —OC(O)$R^9$, r) —C(O)$NR^9R^9$, s) —$NR^9$C(O)$R^9$, t) —OC(O)$NR^9R^9$, u) —$NR^9$C(O)$OR^9$, v) —$NR^9$C(O)$NR^9R^9$, w) —C(S)$R^9$, x) —C(S)$OR^9$, y) —OC(S)$R^9$, z) —C(S)$NR^9R^9$, aa) —$NR^9$C(S)$R^9$, bb) —OC(S)$NR^9R^9$, cc) —$NR^9$C(S)$OR^9$, dd) —$NR^9$C(S)$NR^9R^9$, ee) —$NR^9$C($NR^9$)$NR^9R^9$, ff) —$S(O)_pR^9$, gg) —$SO_2NR^9R^9$, and hh) $R^9$;

$R^9$, at each occurrence, independently is selected from the group consisting of:

a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3–14 membered saturated, unsaturated, or aromatic heterocycle consisting one or more heteroatoms selected from the group consisting of nitrogen, oxygen, and sulfur, g) —C(O)—$C_{1-6}$ alkyl, h) —C(O)$C_{2-6}$ alkenyl, i) —C(O)—$C_{2-6}$ alkynyl, j) —C(O)$C_{3-14}$ saturated, unsaturated, or aromatic carbocycle, k) —C(O)—C3–14 membered saturated, unsaturated, or aromatic heterocycle consisting one or more heteroatoms selected from the group consisting of nitrogen, oxygen, and sulfur, l) —C(O)O—$C_{1-6}$ alkyl, m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3–14 membered saturated, unsaturated, or aromatic heterocycle consisting one or more heteroatoms selected from the group consisting of nitrogen, oxygen, and sulfur, wherein any of b)–p) optionally is substituted with one or more moieties selected from the group consisting of:

a) F, b) Cl, c) Br, d) I, e) —$CF_3$, f) —OH, g) —O$C_{1-6}$ alkyl, h) —SH, i) —S$C_{1-6}$ alkyl, j) —CN, k) —$NO_2$, l) —$NH_2$, m) —NH$C_{1-6}$ alkyl, n) —N($C_{1-6}$ alkyl)$_2$, o) —C(O)$C_{1-6}$ alkyl, p) —C(O)O$C_{1-6}$ alkyl, q) —C(O)$NH_2$, r) —C(O)NH$C_{1-6}$ alkyl, s) —C(O)N($C_{1-6}$ alkyl)$_2$, t) —NHC(O)$C_{1-6}$ alkyl, u) —$SO_2NH_2$—, v) —$SO_2$NH$C_{1-6}$ alkyl, w) —$SO_2$N($C_{1-6}$ alkyl)$_2$, and x) —$S(O)_p C_{1-6}$ alkyl;

m is 0, 1, 2, 3, or 4;

n is 0, 1, 2, 3, or 4; and p, at each occurrence, independently is 0, 1, or 2.

2. The compound according to claim 1, having the formula:

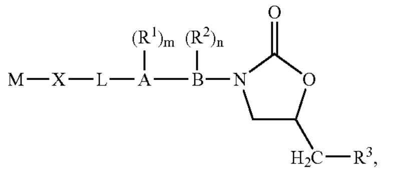

or a pharmaceutically acceptable salt, ester or prodrug thereof, wherein A, B, L, M, $R^1$, $R^2$, $R^3$, X, m, and n are defined as described in claim 1.

3. The compound according to claim 1, having the formula:

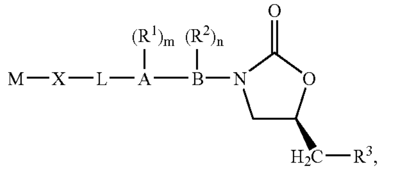

or a pharmaceutically acceptable salt, ester or prodrug thereof, wherein A, B, L, M, $R^1$, $R^2$, $R^3$, X, m, and n are defined as described in claim 1.

4. The compound according to claim 1, wherein

A is phenyl

B is selected from the group consisting of phenyl and pyridyl;

m is 0, 1, or 2; and n is 0, 1, or 2.

5. The compound according to claim 1, wherein A-B is:

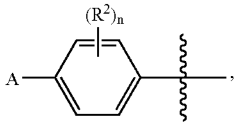

wherein A, $R^2$, and n are defined as described in claim 1.

6. The compound according to claim 5, wherein $R^2$ is selected from the group consisting of H and F, and n is 0, 1, or 2.

7. The compound according to claim 5, wherein A-B is:

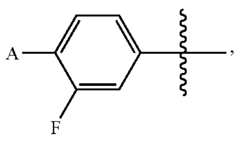

wherein A is defined as described in claim 1.

8. The compound according to claim 5, wherein A-B is:

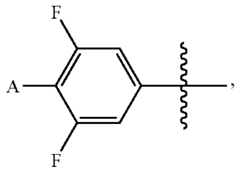

wherein A is defined as described in claim 1.

9. The compound according to claim 1, wherein A-B is:

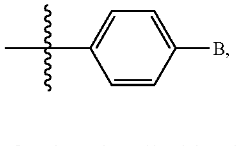

wherein B is defined as described in claim 1.

10. The compound according to claim 1, wherein $R^3$ is —$NR^7C(O)R^7$.

11. The compound according to claim 1, wherein $R^3$ is —$NHC(O)R^7$.

12. The compound according to claim 10, wherein $R^7$ is $C_{1-6}$ alkyl, optionally substituted with one or more substituents independently selected from F or Cl.

13. The compound according to claim 10 wherein $R^7$ is selected from the group consisting of —$CH_3$, —$CH_2F$, —$CHF_2$, —$CF_3$, —$CH_2Cl$, —$CHCl_2$, —$CCl_3$, —CHFCl, —$CF_2Cl$, and —$CFCl_2$.

14. The compound according to claim 13, wherein $R^7$ is —$CH_3$.

15. The compound according to claim 1, wherein $R^3$ is:

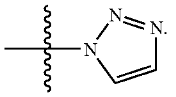

16. The compound according to claim 1, having the formula:

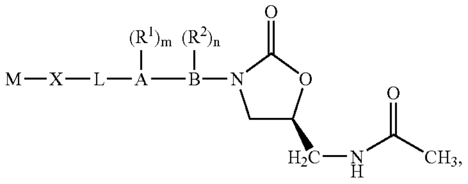

or a pharmaceutically acceptable salt, ester or prodrug thereof, wherein A, B, L, M, $R^1$, $R^2$, X, m, and n are defined as described in claim 1.

17. The compound according to claim 1, having the formula:

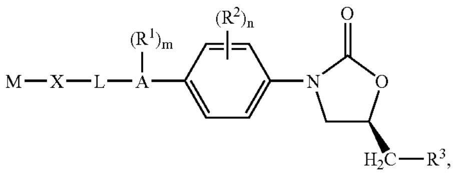

or a pharmaceutically acceptable salt, ester or prodrug thereof, wherein A, L, M, $R^1$, $R^3$, X, and m are defined as described in claim 1, A is selected from the group consisting of H and F, and n is 0, 1, or 2.

18. The compound according to claim 1, having the formula:

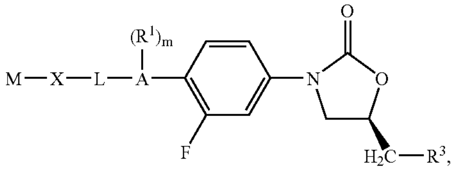

or a pharmaceutically acceptable salt, ester or prodrug thereof, wherein A, L, M, $R^1$, $R^3$, X, and m are defined as described in claim 1.

19. The compound according to claim 18, having the formula:

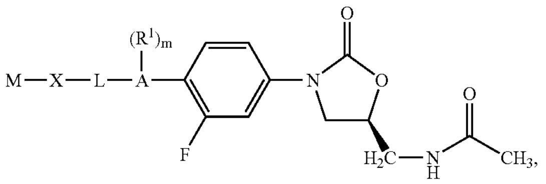

or a pharmaceutically acceptable salt, ester or prodrug thereof, wherein A, L, M, $R^1$, X, and m are defined as described in claim 1.

20. The compound according to claim 18, having the formula:

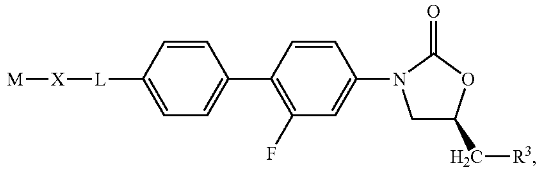

or a pharmaceutically acceptable salt, ester or prodrug thereof, wherein L, M, $R^3$, and X are defined as described in claim 1.

21. The compound according to claim 20, having the formula:

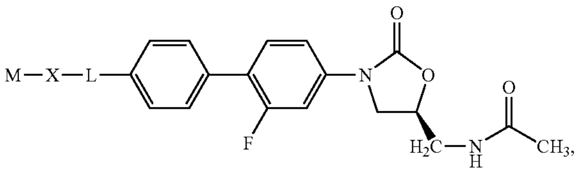

or a pharmaceutically acceptable salt, ester or prodrug thereof, wherein L, M, and X are defined as described in claim 1.

22. The compound according to claim 1, having the formula:

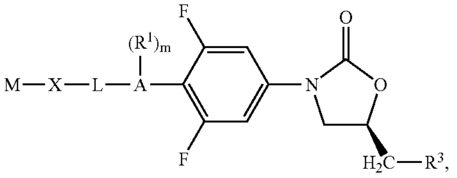

or a pharmaceutically acceptable salt, ester or prodrug thereof, wherein A, L, M, $R^1$, $R^3$, X, and m are defined as described in claim 1.

23. The compound according to claim 22, having the formula:

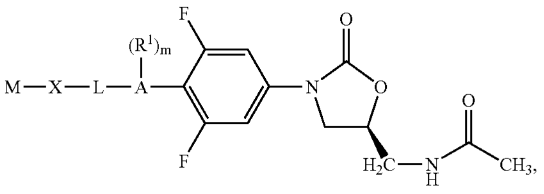

or a pharmaceutically acceptable salt, ester or prodrug thereof, wherein A, L, M, $R^1$, X, and m are defined as described in claim 1.

24. The compound according to claim 22, having the formula:

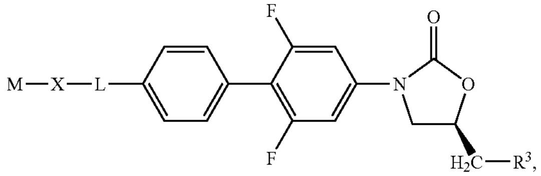

or a pharmaceutically acceptable salt, ester or prodrug thereof, wherein L, M, $R^3$, and X are defined as described in claim 1.

25. The compound according to claim 24, having the formula:

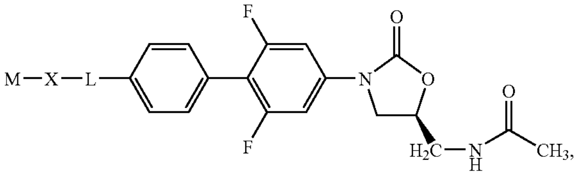

or a pharmaceutically acceptable salt, ester or prodrug thereof, wherein L, M and X are defined as described in claim 1.

26. The compound according to claim 1, wherein L is $C_{1-6}$ alkyl.

27. The compound according to claim 26, wherein L is $—CH_2—$.

28. The compound according to claim 1, wherein X is selected from the group consisting of-$NR^5$—, —N(O)—, and —N($OR^5$)—, and $R^5$ is selected from the group consisting of H and $C_{1-6}$ alkyl.

29. The compound according to claim 1, wherein X is —$NR^5$—, and $R^5$ is selected from the group consisting of H and $C_{1-6}$ alkyl.

30. The compound according to claim 29, wherein X is —NH—.

31. The compound according to claim 29, wherein X is —$NC_{1-6}$ alkyl, wherein the $C_{1-6}$ alkyl group is substituted with one or more moieties selected from the group consisting of F, Cl, Br, and I.

32. The compound according to claim 1, wherein M is $C_{1-6}$ alkyl substituted with one or more moieties selected from the group consisting of F, Cl, Br, and I.

33. The compound according to claim 32, wherein M is $C_{1-6}$ alkyl substituted with one or more F atoms.

34. The compound according to claim 33, wherein M is $—CH_2CH_2CH_2F$.

35. The compound according to claim 1, wherein M is $—CH_2CH(OH)CH_2F$.

36. A compound having a structure corresponding to any one of the compounds listed below:

| Compound Number | Structure |
|---|---|
| 1 | 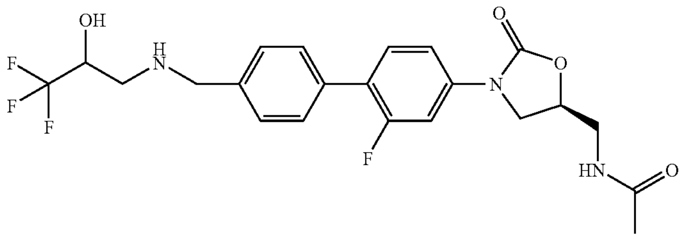 |
| 2 | 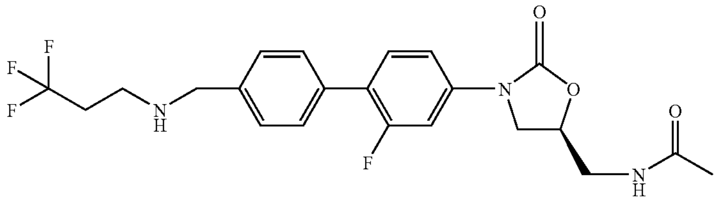 |
| 3 | 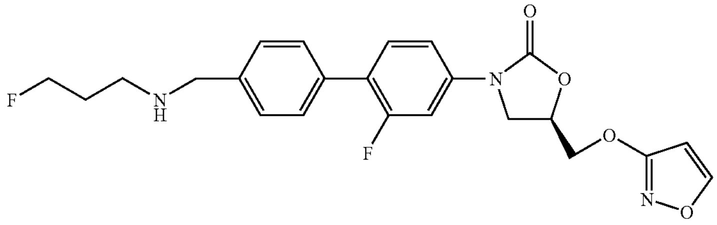 |
| 4 | 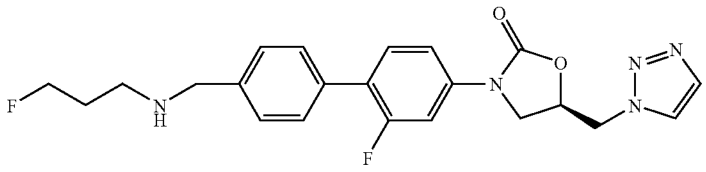 |
| 5 | 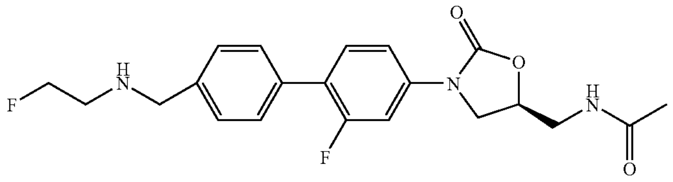 |
| 6 | 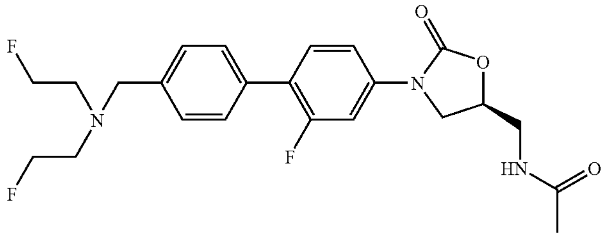 |
| 7 | 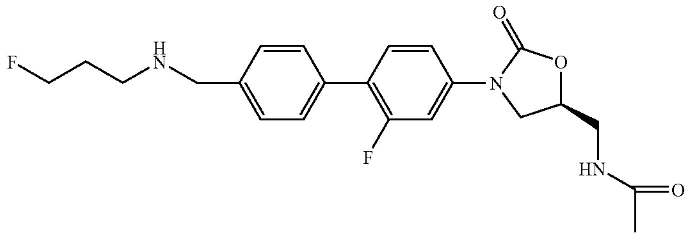 |

-continued
| Compound Number | Structure |
| --- | --- |
| 8 | 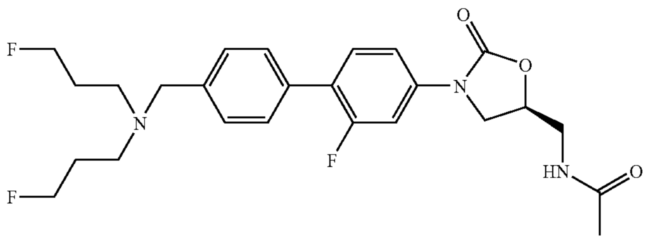 |
| 9 | 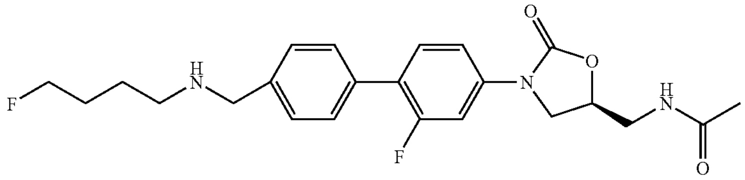 |
| 10 | 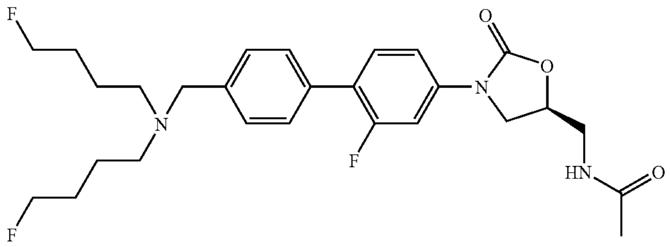 |
| 11 | 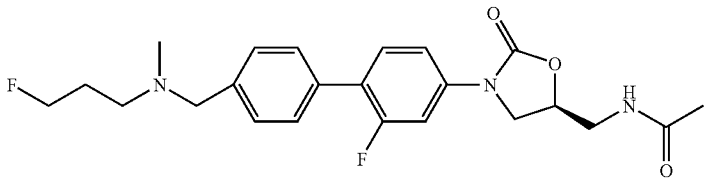 |
| 12 | 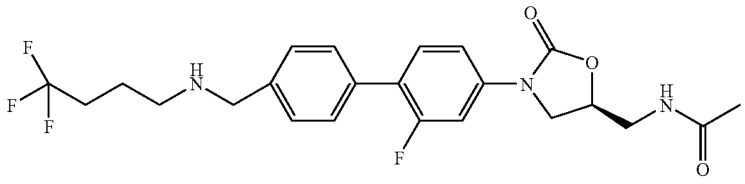 |
| 15 | 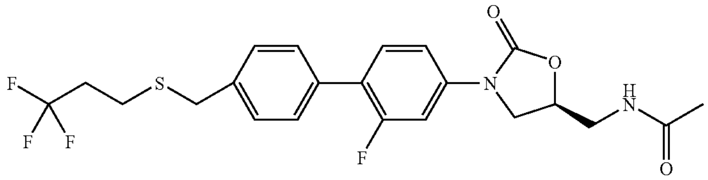 |
| 16 | 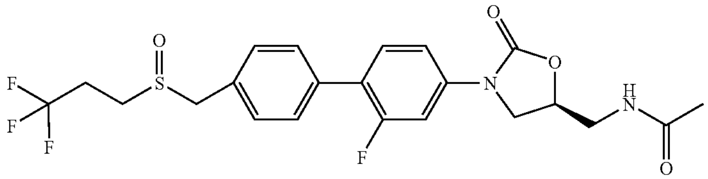 |

-continued
| Compound Number | Structure |
|---|---|
| 17 | 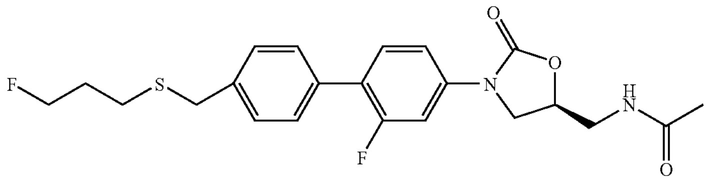 |
| 18 | 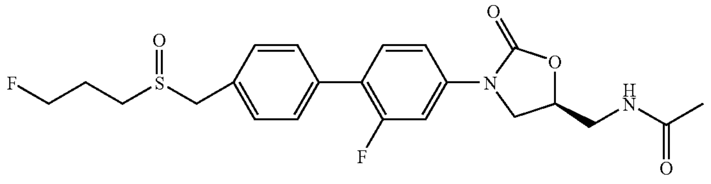 |
| 19 | 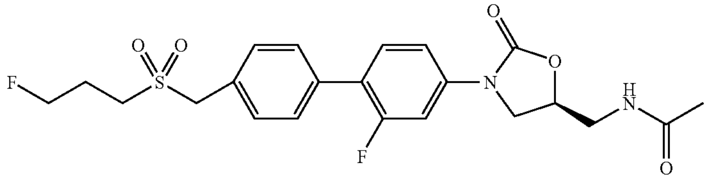 |
| 20 | 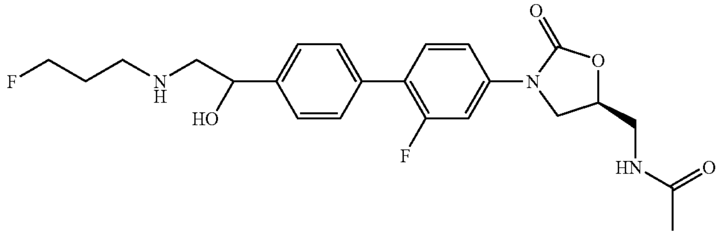 |
| 21 | 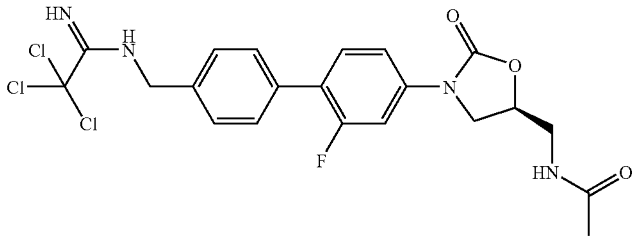 |
| 22 | 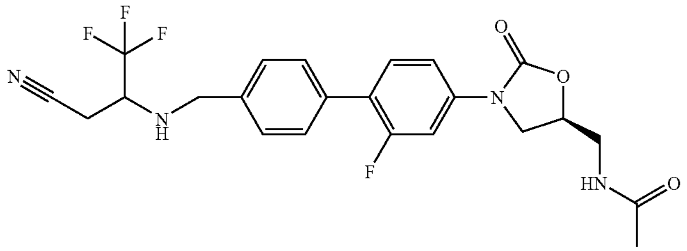 |
| 23 | 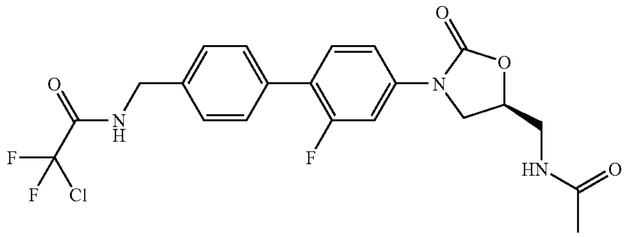 |

-continued
| Compound Number | Structure |
|---|---|
| 24 | 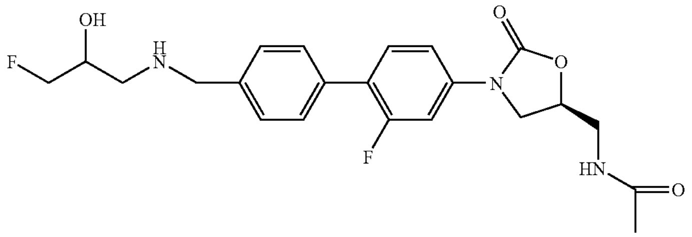 |
| 25 | 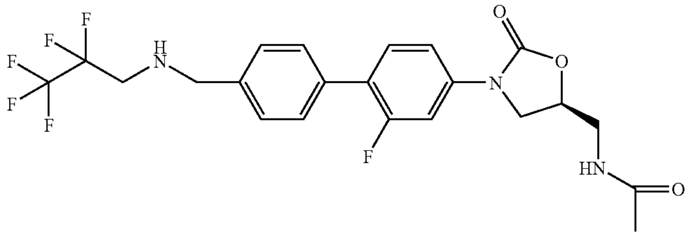 |
| 26 | 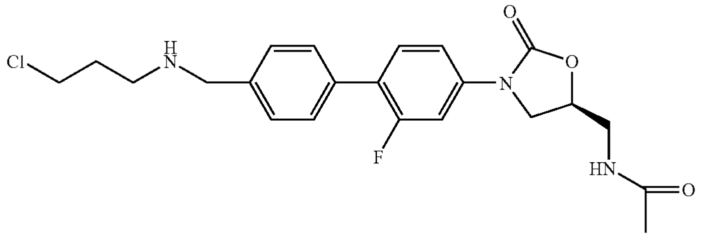 |
| 27 | 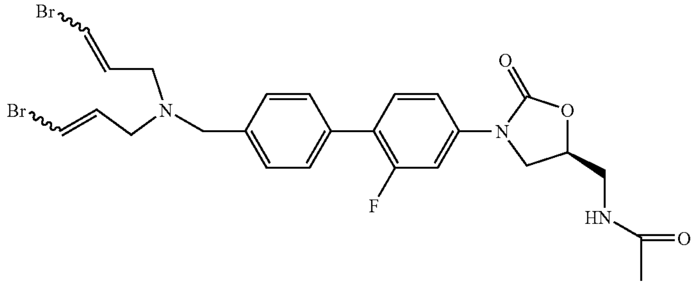 |
| 28 | 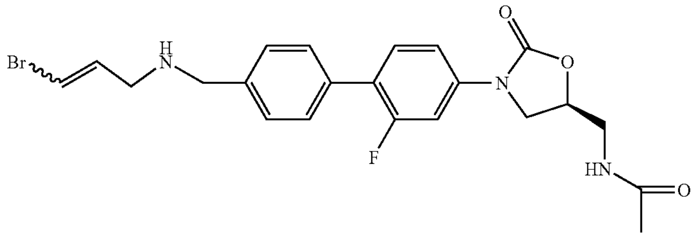 |
| 29 | 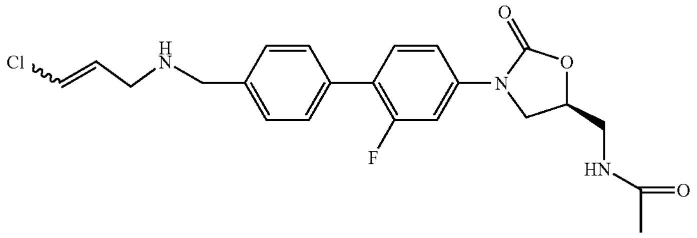 |

-continued
| Compound Number | Structure |
| --- | --- |
| 30 | 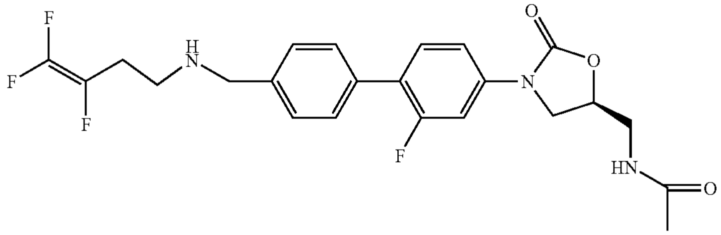 |
| 31 | 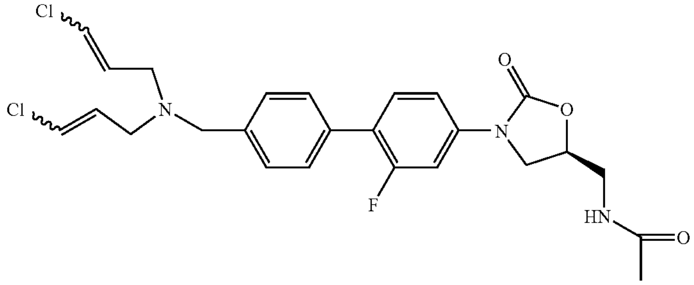 |
| 32 | 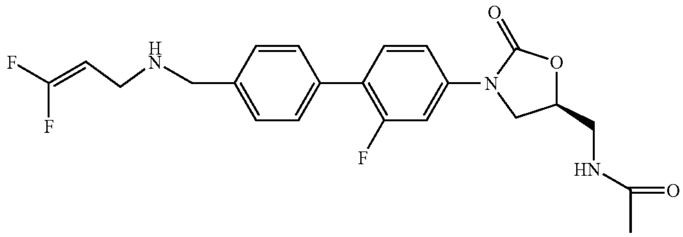 |
| 33 | 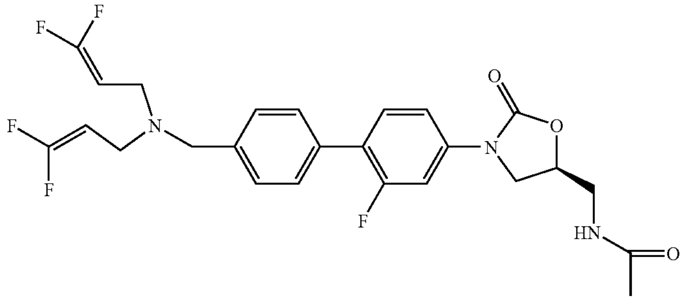 |
| 34 | 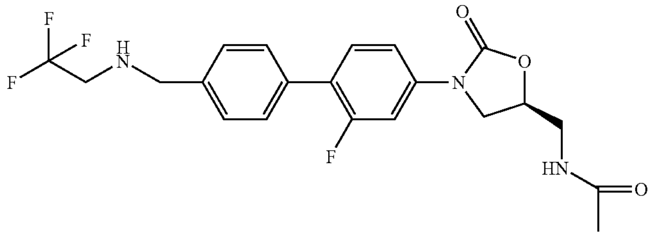 |

-continued
| Compound Number | Structure |
| --- | --- |
| 35 | 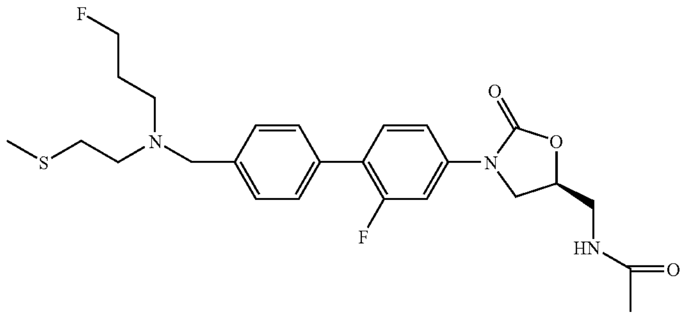 |
| 36 | 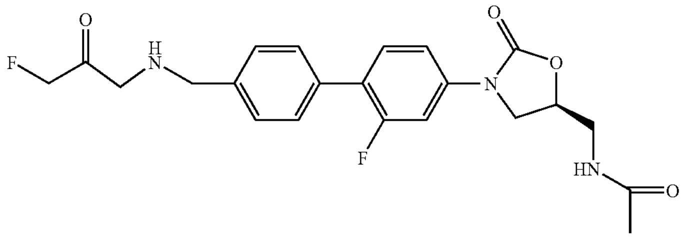 |
| 37 | 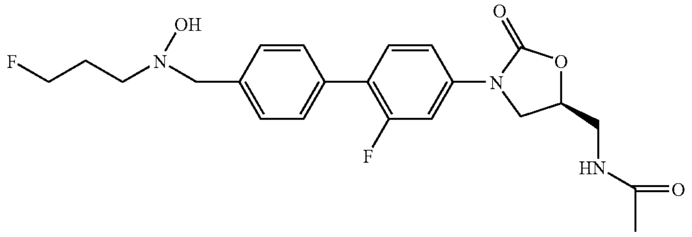 |
| 38 | 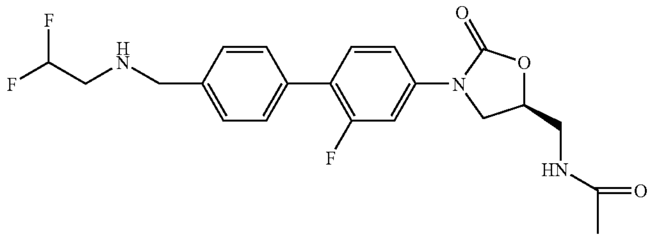 |
| 39 | 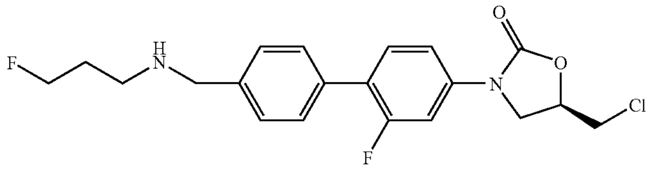 |
| 40 | 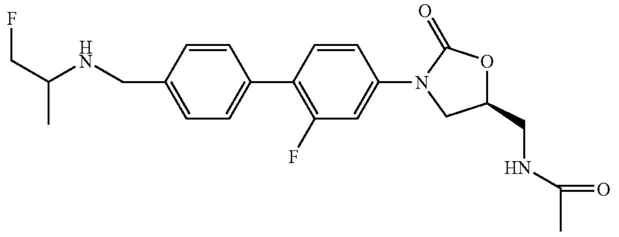 |

-continued
| Compound Number | Structure |
| --- | --- |
| 41 | 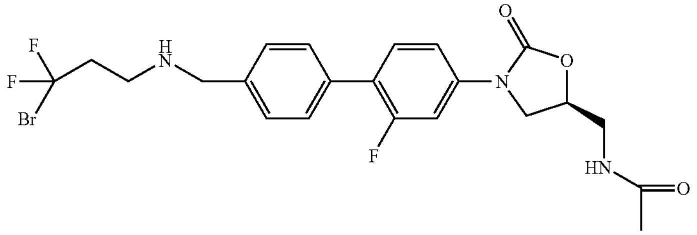 |
| 42 | 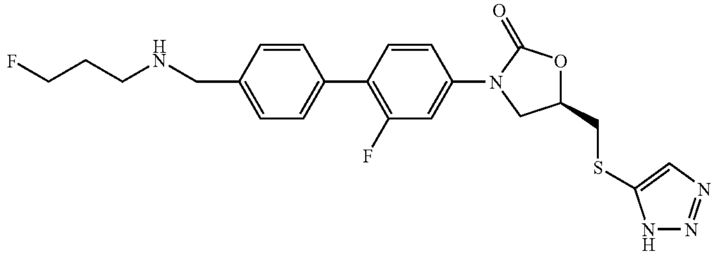 |
| 43 | 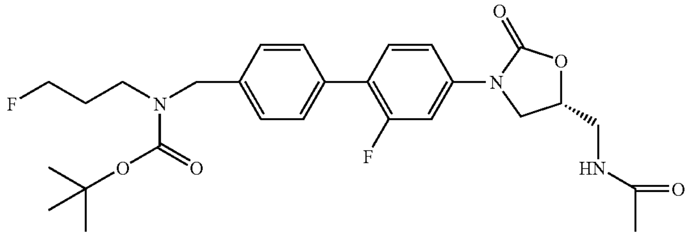 |
| 44 | 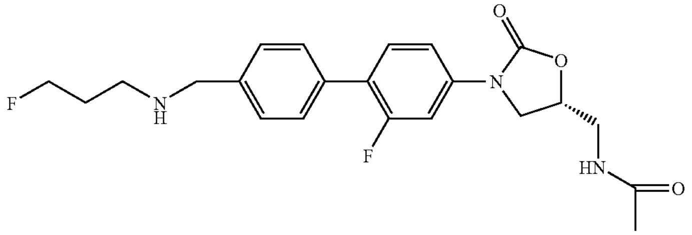 |
| 45 | 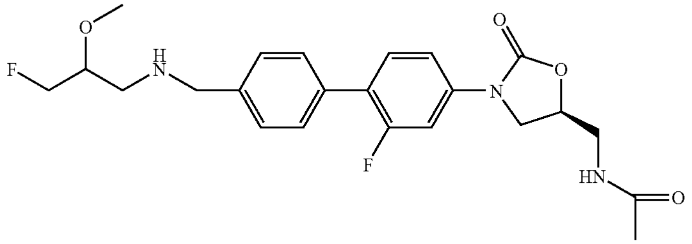 |
| 46 | 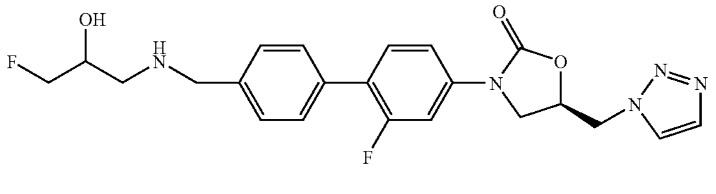 |

-continued
| Compound Number | Structure |
|---|---|
| 47 | 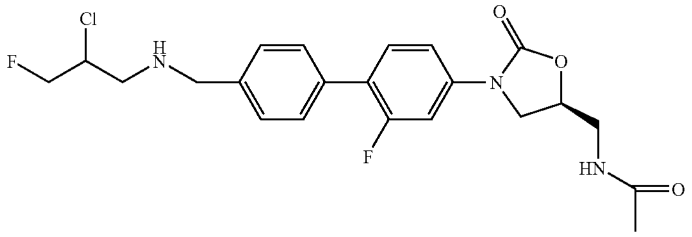 |
| 48 | 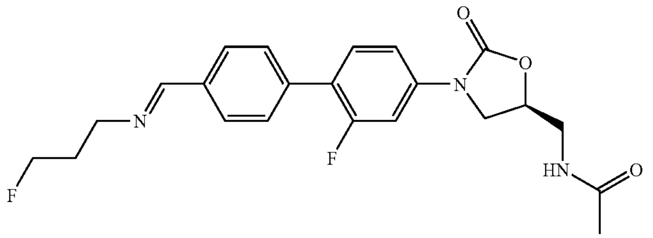 |
| 49 | 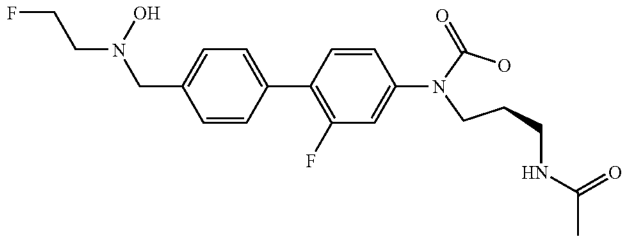 |
| 50 | 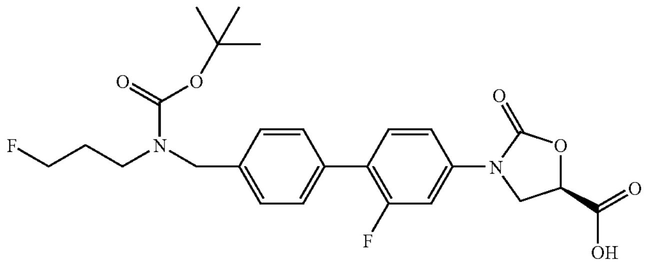 |
| 51 | 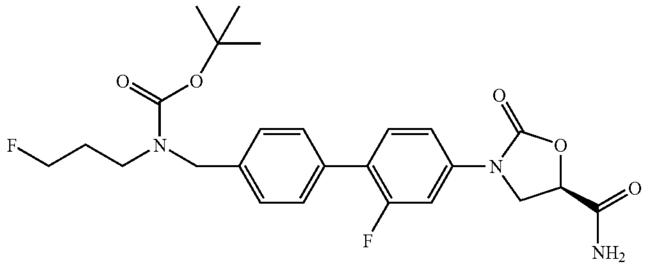 |
| 52 | 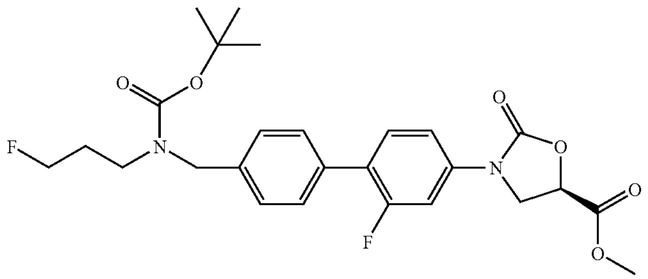

-continued
| Compound Number | Structure |
| --- | --- |
| 53 | 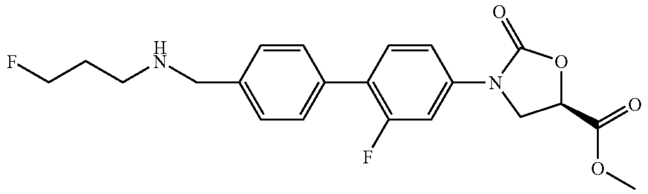 |
| 54 | 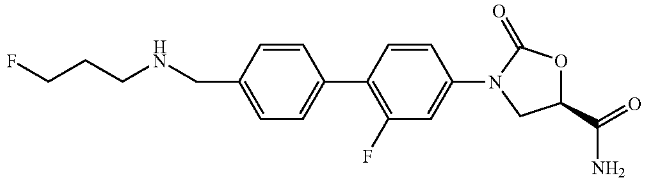 |
| 55 | 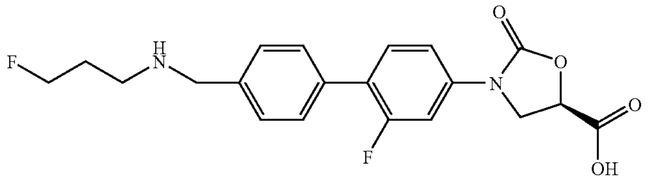 |
| 56 | 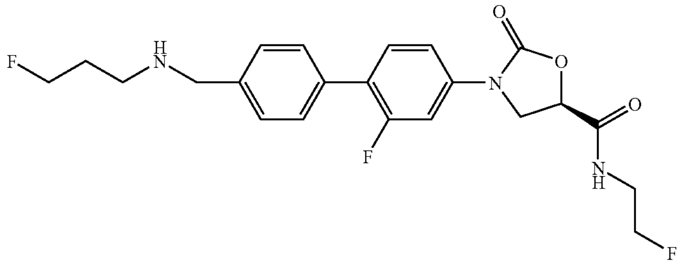 |
| 57 | 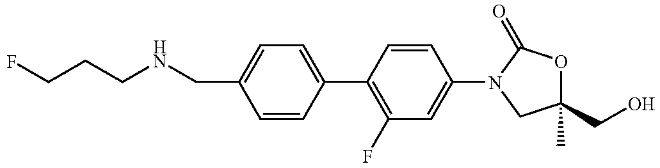 |
| 58 | 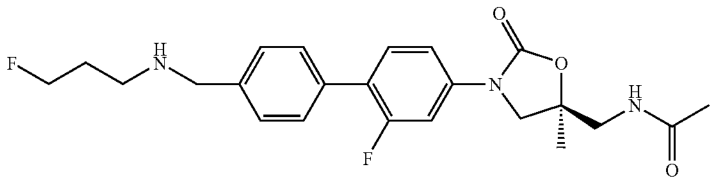 |
| 59 | 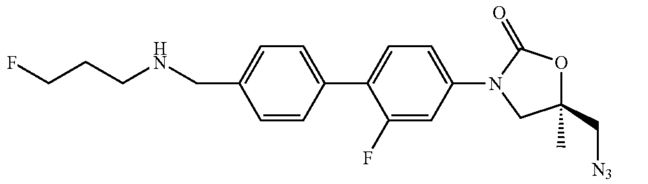 |

-continued
| Compound Number | Structure |
|---|---|
| 60 | 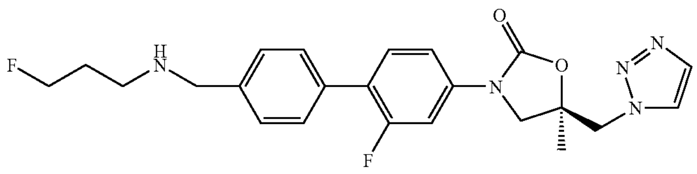 |
| 61 | 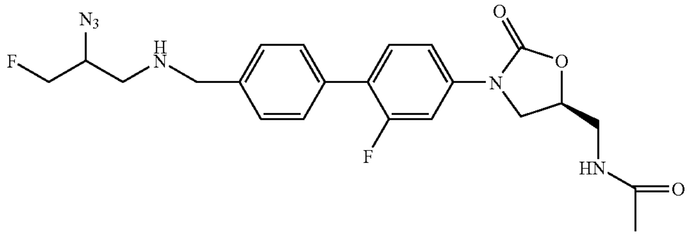 |
| 62 | 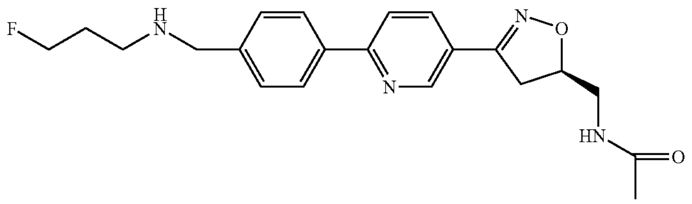 |
| 63 | 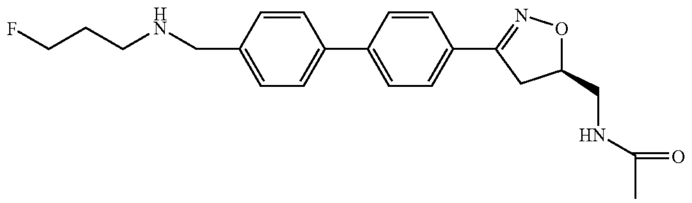 |
| 64 | 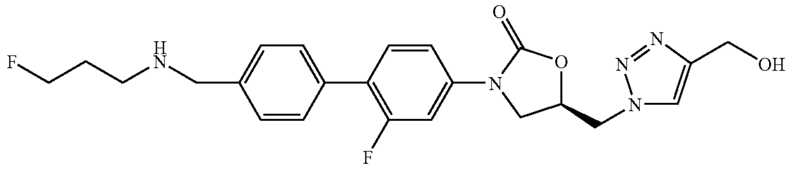 |
| 65 | 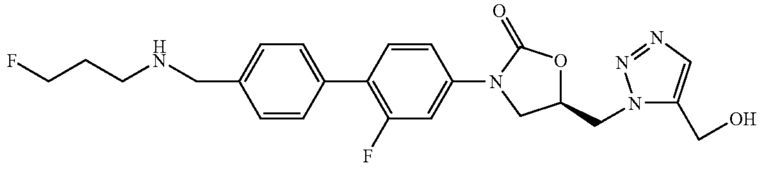 |
| 66 | 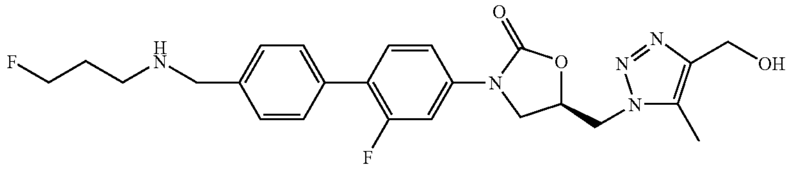 |
| 67 | 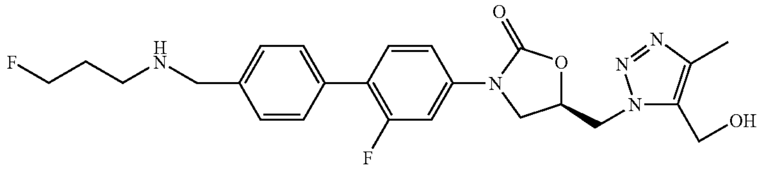 |

-continued
| Compound Number | Structure |
|---|---|
| 68 | 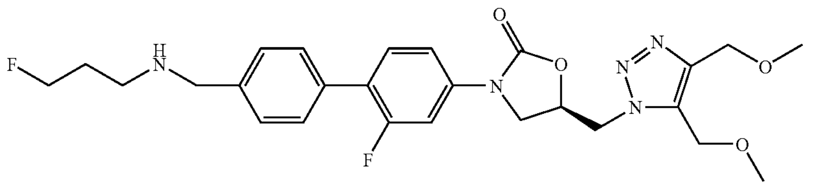 |
| 69 | 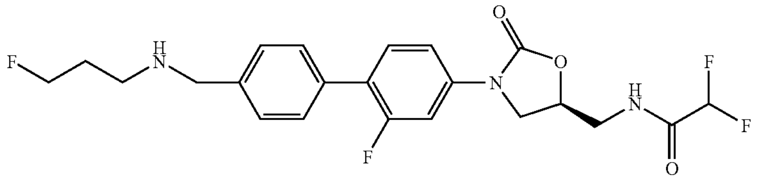 |
| 70 | 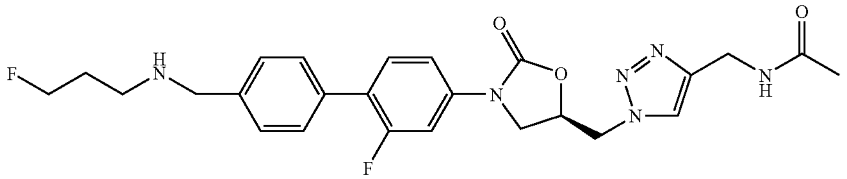 |
| 71 | 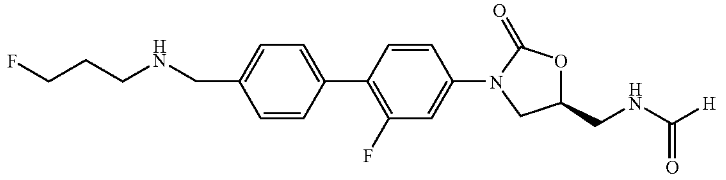 |
| 72 | 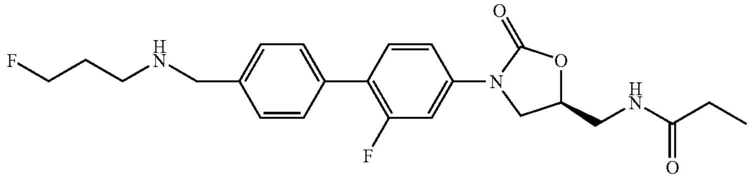 |
| 73 | 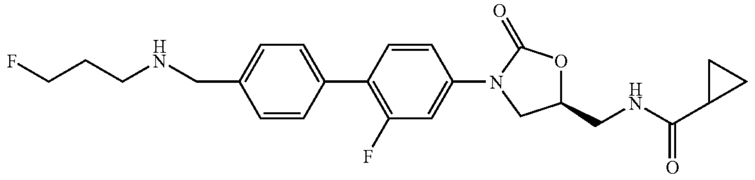 |
| 74 | 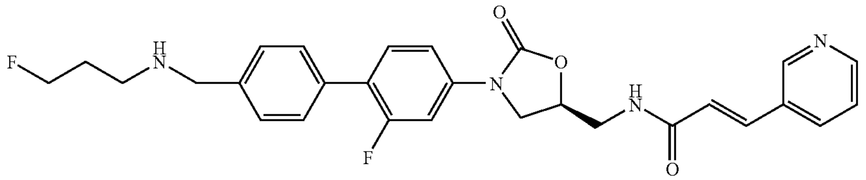 |
| 75 | 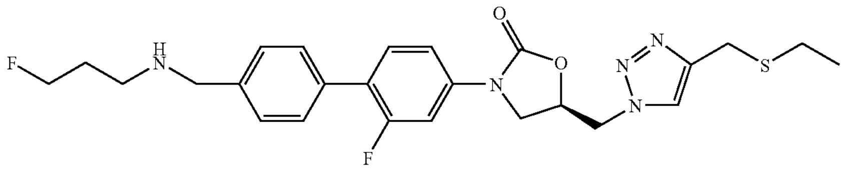 |

-continued
| Compound Number | Structure |
| --- | --- |
| 76 | 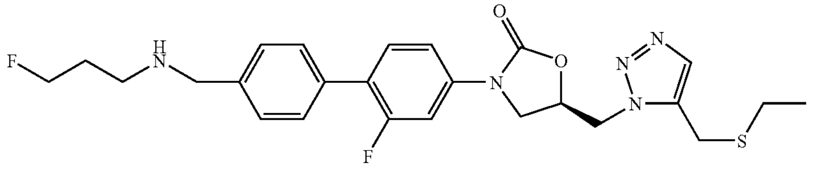 |
| 77 | 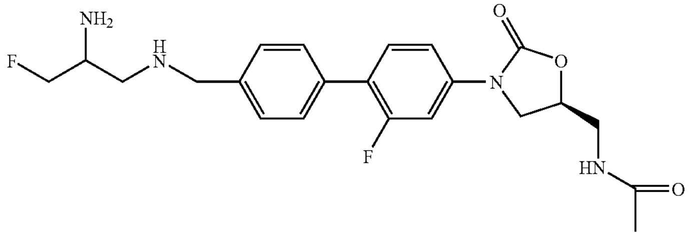 |
| 78 | 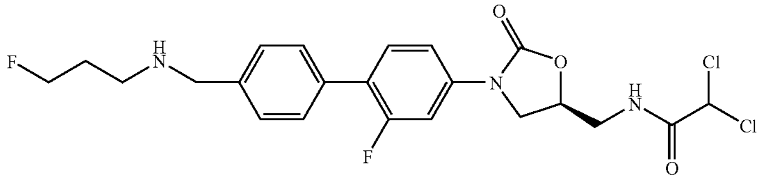 |
| 79 | 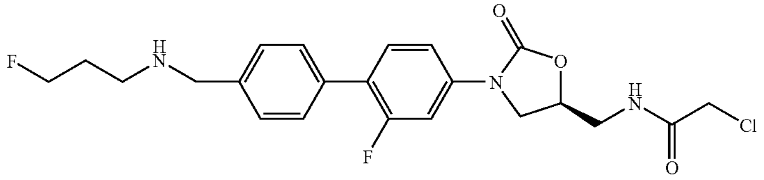 |
| 80 | 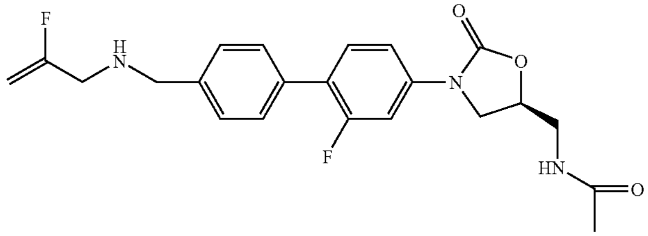 |
| 81 | 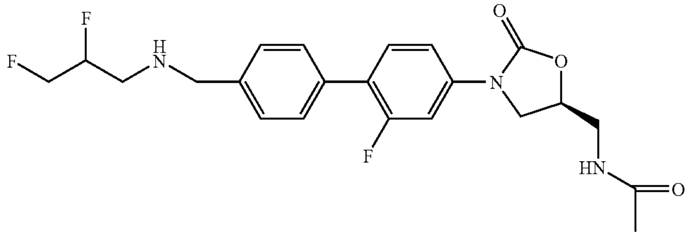 |

-continued

| Compound Number | Structure |
|---|---|
| 82 | 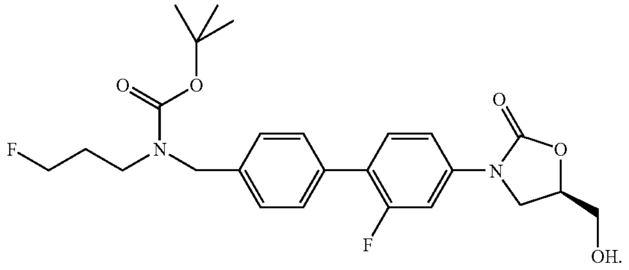 |

or a pharmaceutically acceptable salt, ester or prodrug thereof.

37. A pharmaceutically acceptable salt of a compound corresponding to any one of the compounds according to claim 36.

38. A pharmaceutically acceptable salt according to claim 37 wherein the compound corresponds to any one of compounds 1–12, 20–22, 24–42, 44–49, and 53–81 listed below:

| Compound Number | Structure |
|---|---|
| 1 | 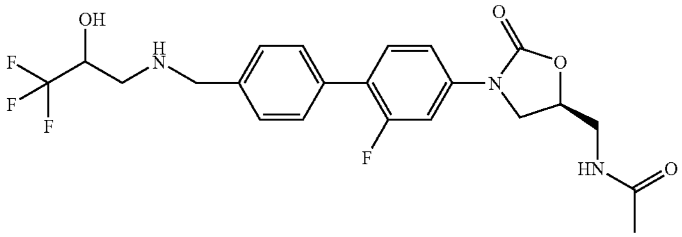 |
| 2 | 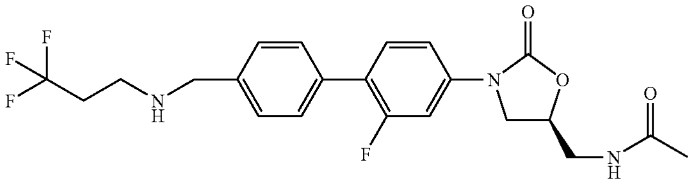 |
| 3 | 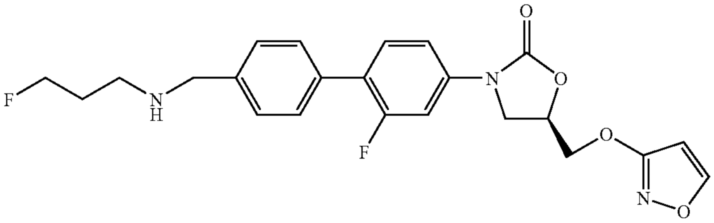 |
| 4 | 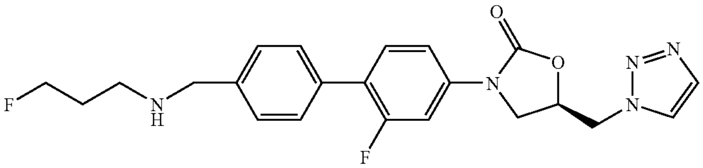 |

-continued
| Compound Number | Structure |
| --- | --- |
| 5 | 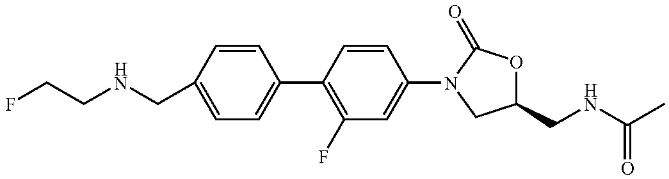 |
| 6 | 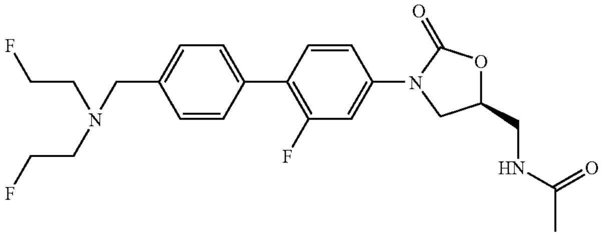 |
| 7 | 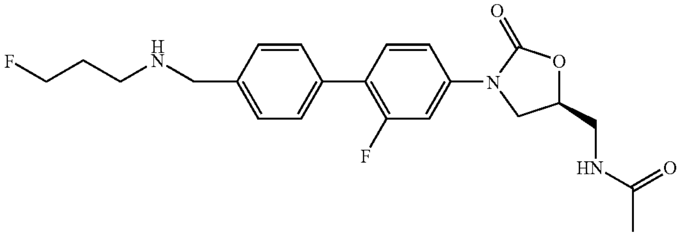 |
| 8 | 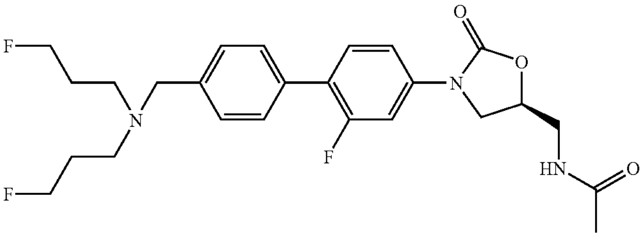 |
| 9 | 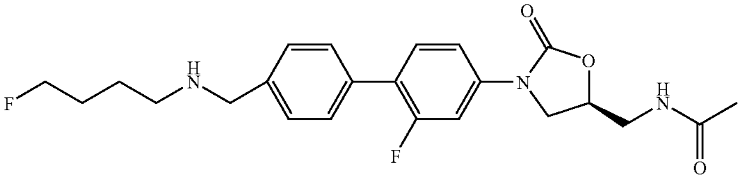 |
| 10 | 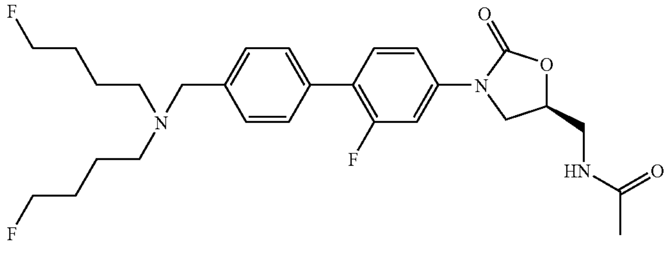 |
| 11 | 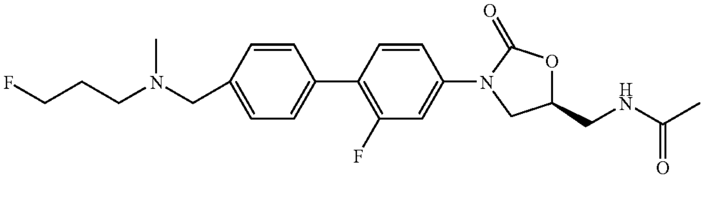 |

-continued
| Compound Number | Structure |
| --- | --- |
| 12 | 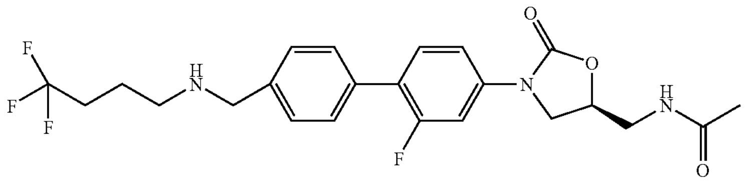 |
| 20 | 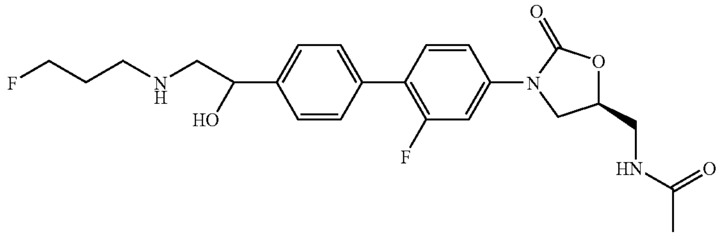 |
| 21 | 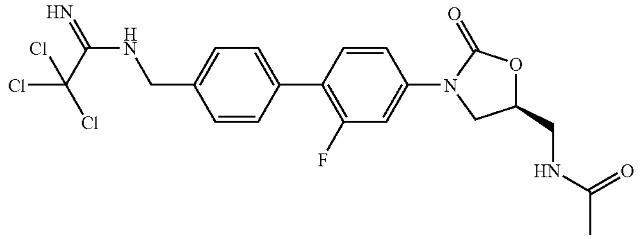 |
| 22 | 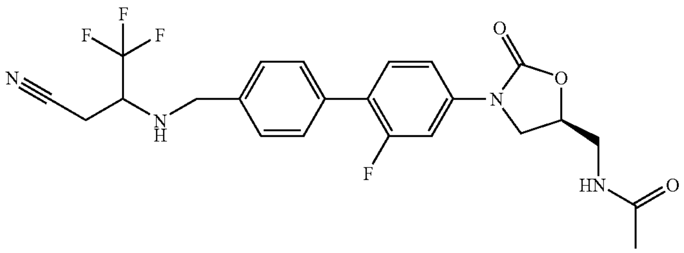 |
| 24 | 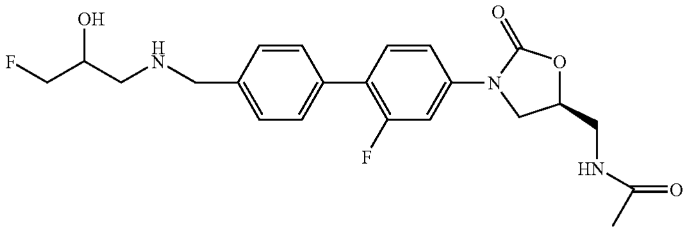 |
| 25 | 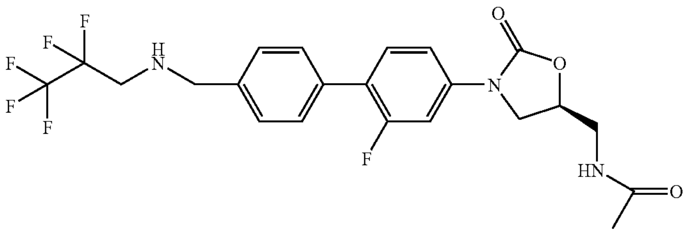 |

-continued
| Compound Number | Structure |
|---|---|
| 26 | 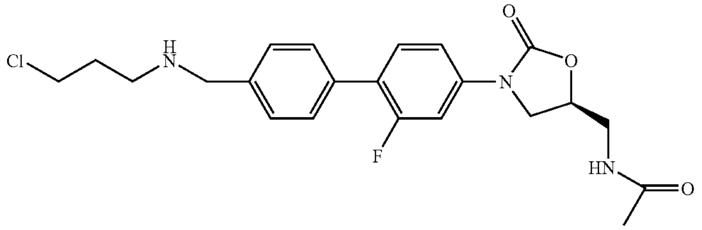 |
| 27 | 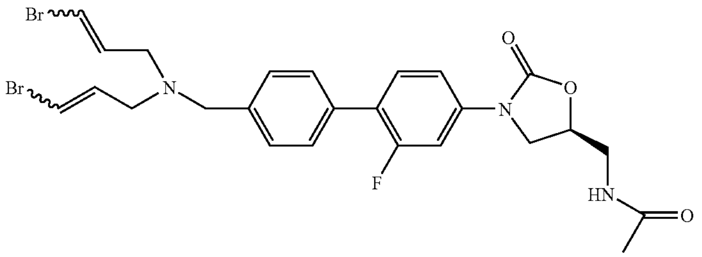 |
| 28 | 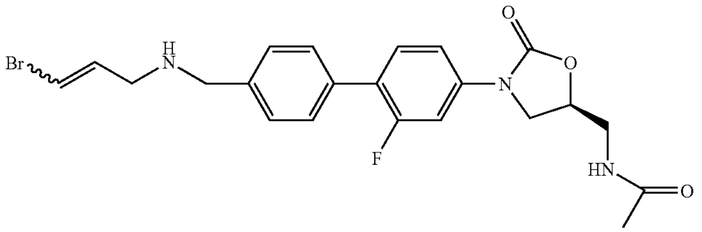 |
| 29 | 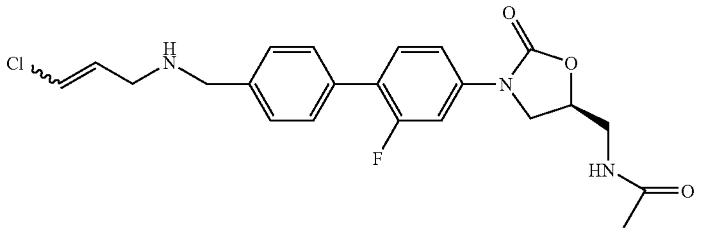 |
| 30 | 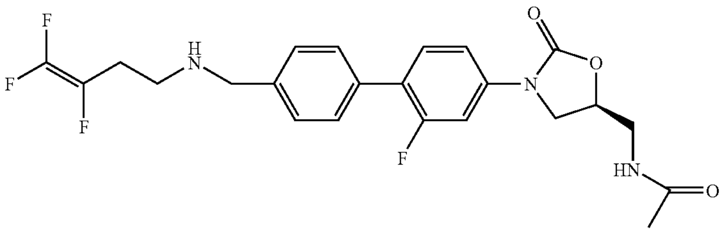 |
| 31 | 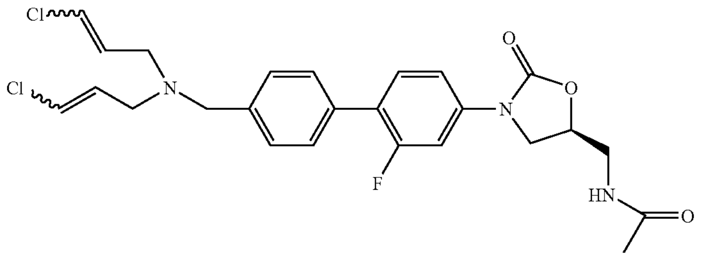 |

-continued
| Compound Number | Structure |
|---|---|
| 32 | 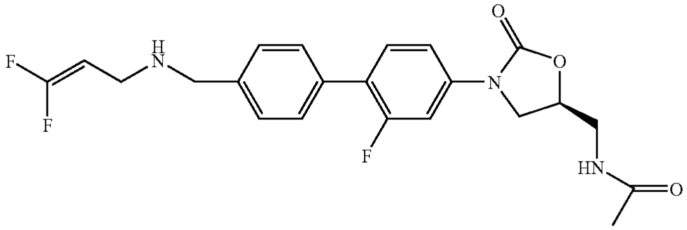 |
| 33 | 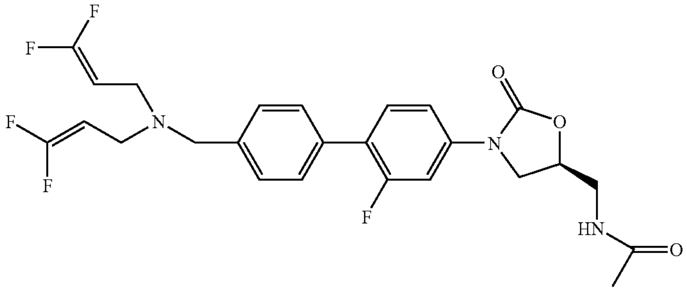 |
| 34 | 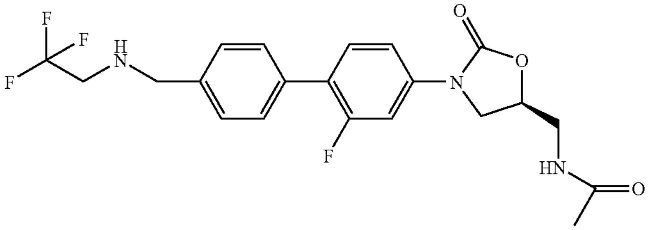 |
| 35 | 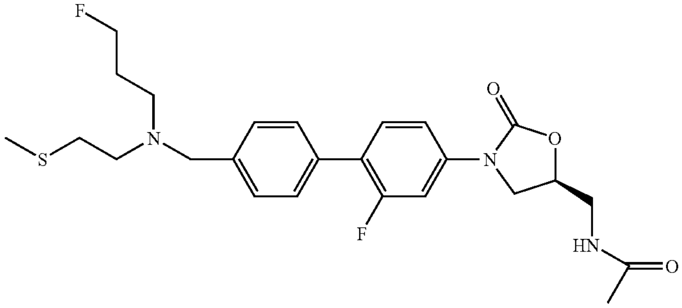 |
| 36 | 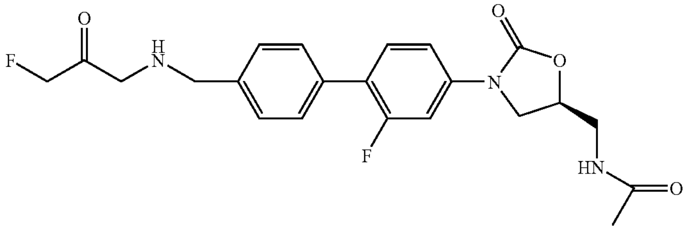 |

-continued
| Compound Number | Structure |
|---|---|
| 37 | 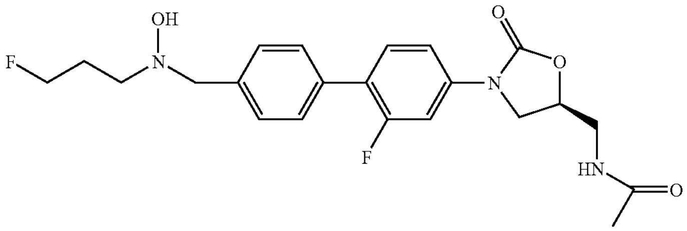 |
| 38 | 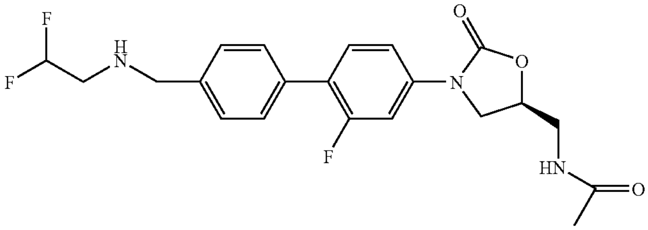 |
| 39 | 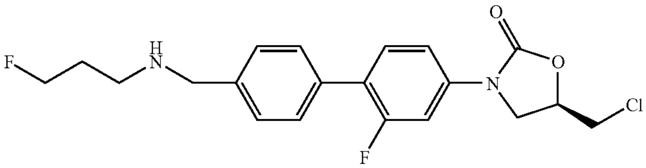 |
| 40 | 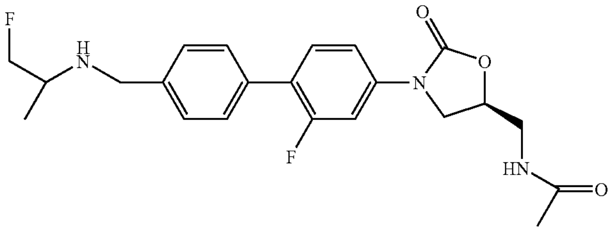 |
| 41 | 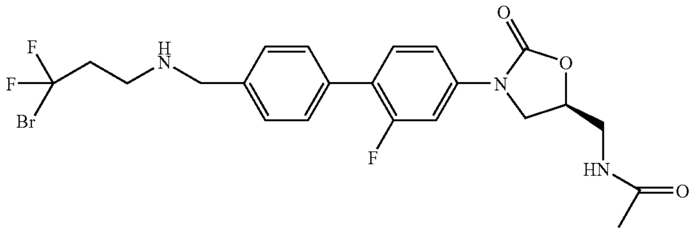 |
| 42 | 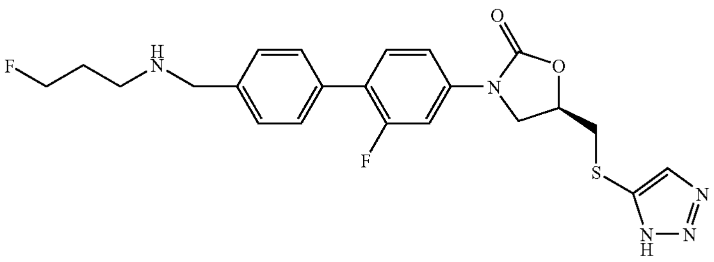 |

-continued
| Compound Number | Structure |
|---|---|
| 44 | 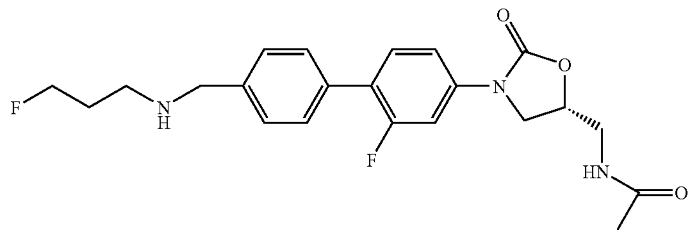 |
| 45 | 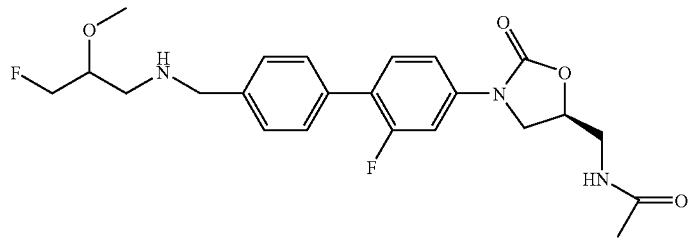 |
| 46 | 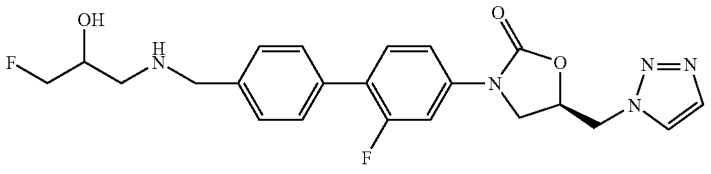 |
| 47 | 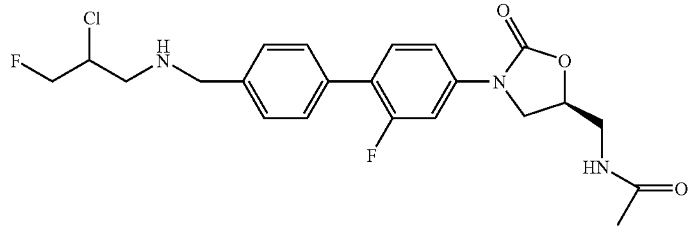 |
| 48 | 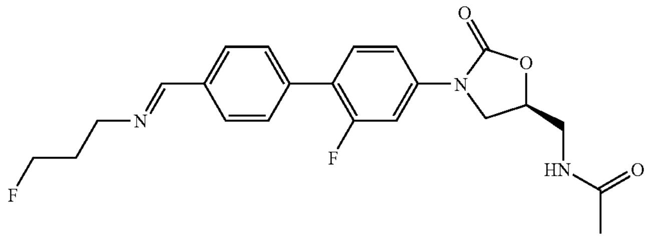 |
| 49 | 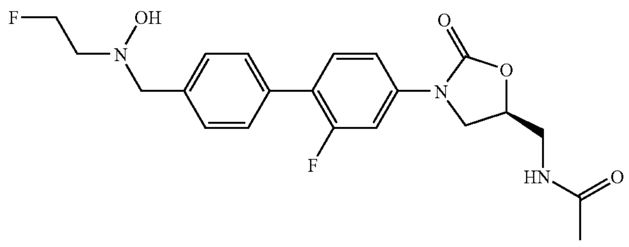 |

-continued
| Compound Number | Structure |
| --- | --- |
| 53 | 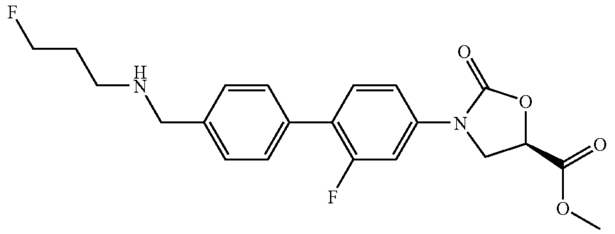 |
| 54 | 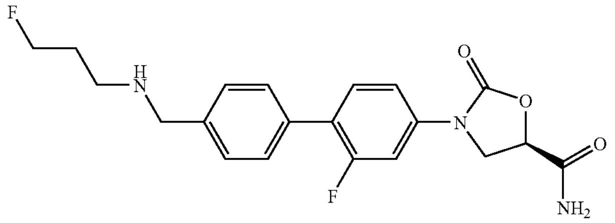 |
| 55 | 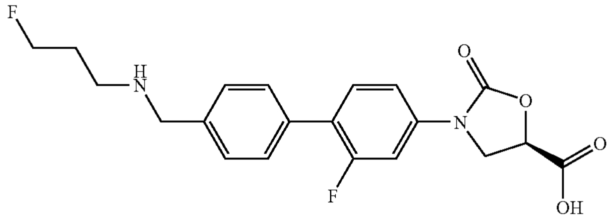 |
| 56 | 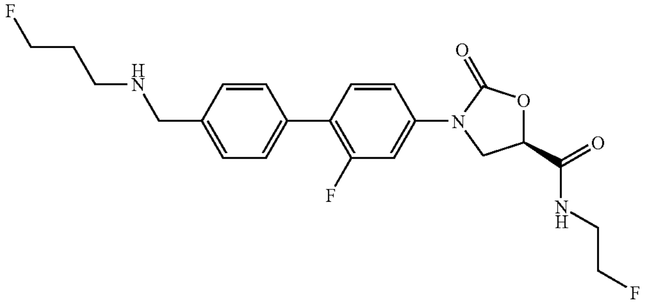 |
| 57 | 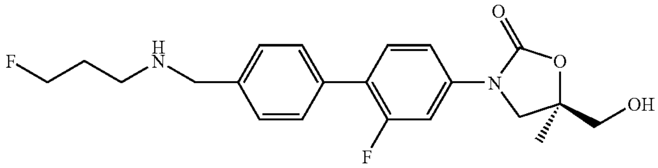 |
| 58 | 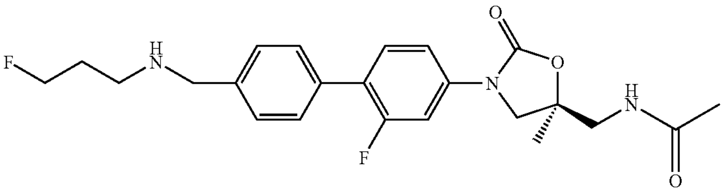 |

-continued
| Compound Number | Structure |
|---|---|
| 59 | 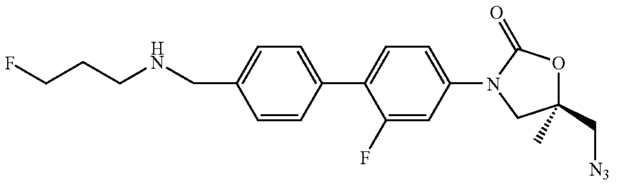 |
| 60 | 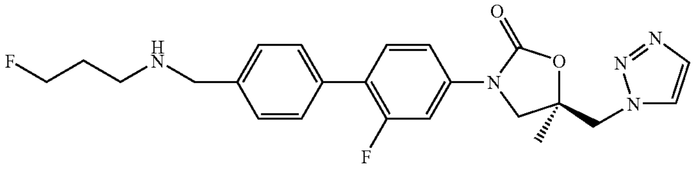 |
| 61 | 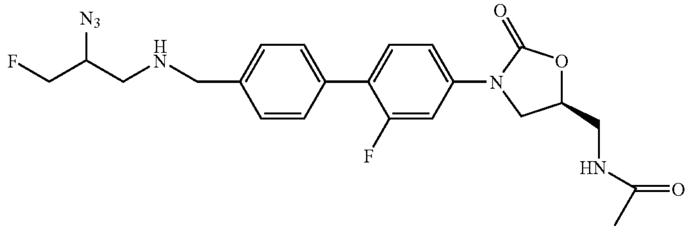 |
| 62 | 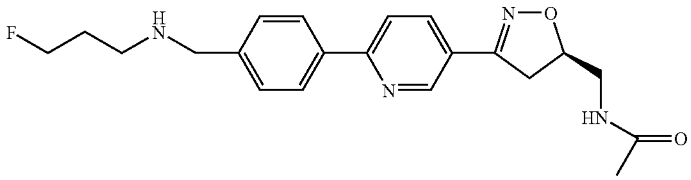 |
| 63 | 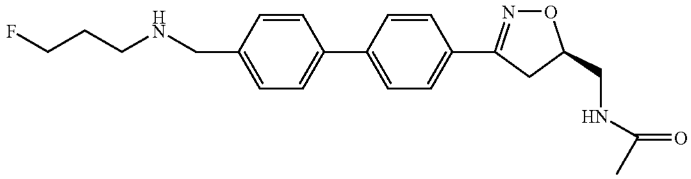 |
| 64 | 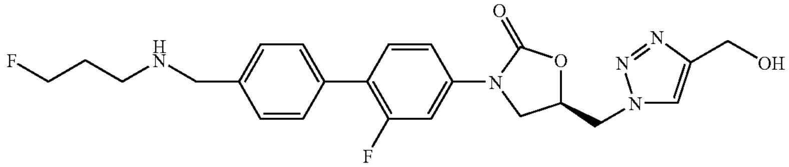 |
| 65 | 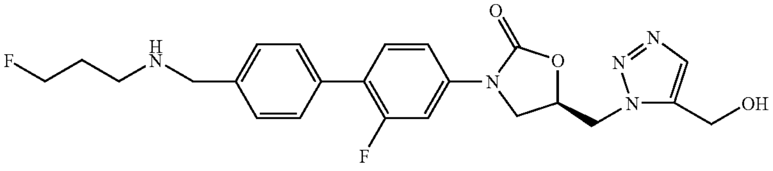 |
| 66 | 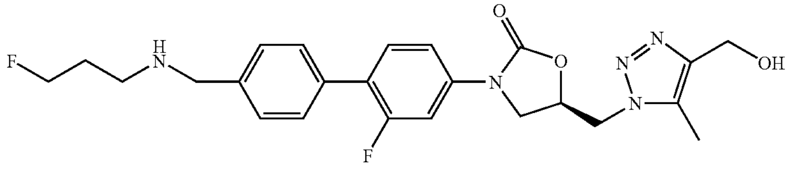 |

-continued
| Compound Number | Structure |
|---|---|
| 67 | 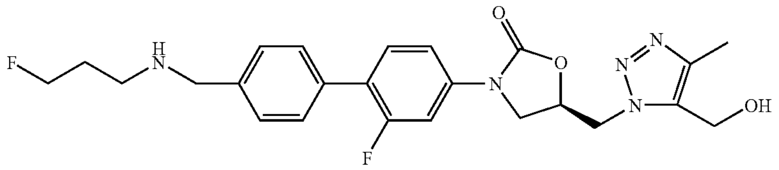 |
| 68 | 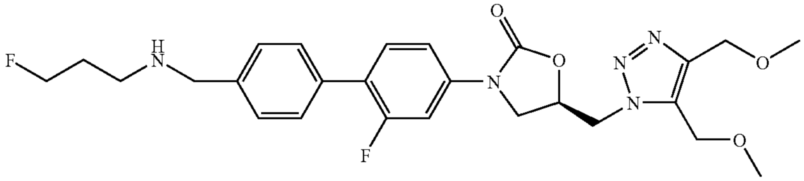 |
| 69 | 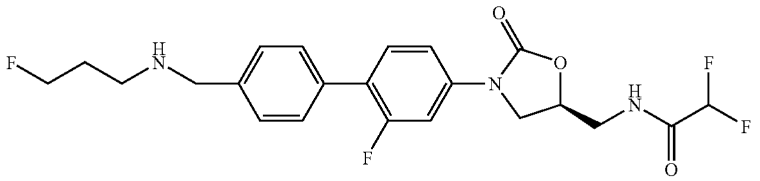 |
| 70 | 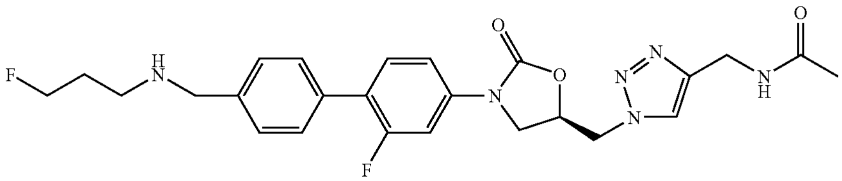 |
| 71 | 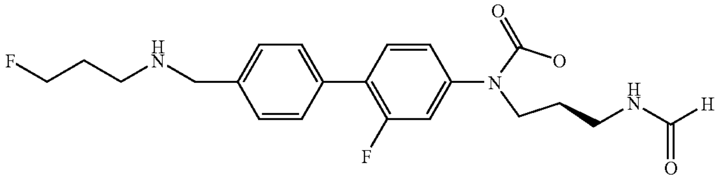 |
| 72 | 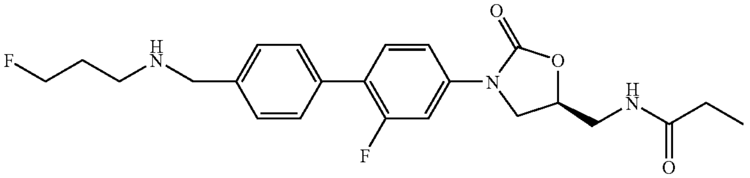 |
| 73 | 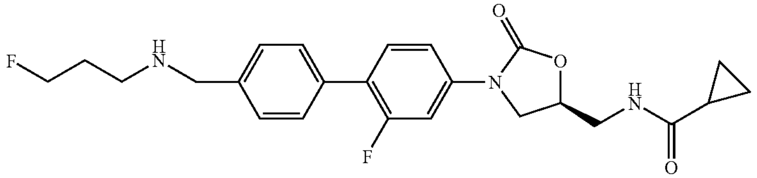 |
| 74 | 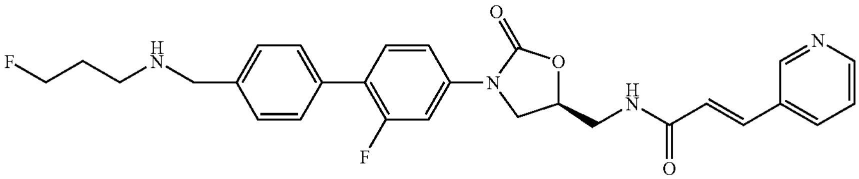 |

-continued
| Compound Number | Structure |
| --- | --- |
| 75 | 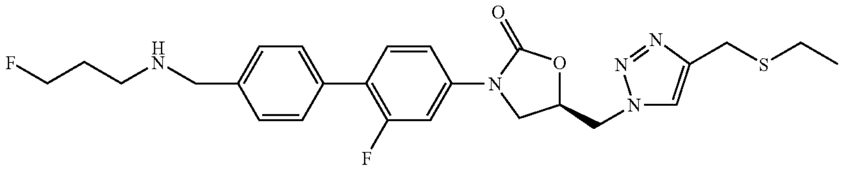 |
| 76 | 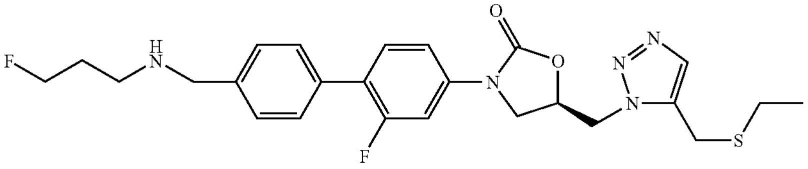 |
| 77 | 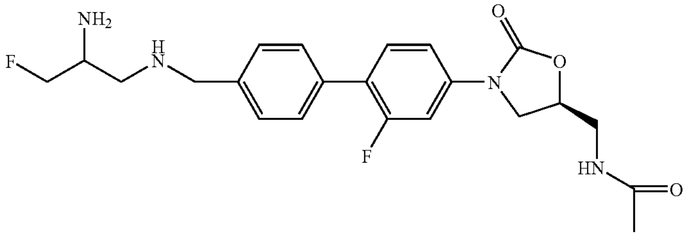 |
| 78 | 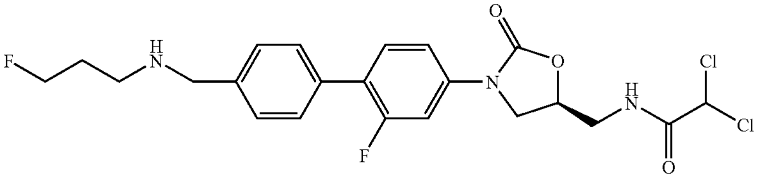 |
| 79 | 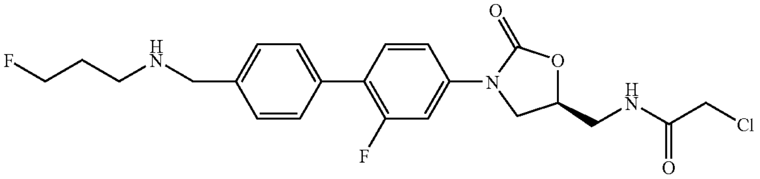 |
| 80 | 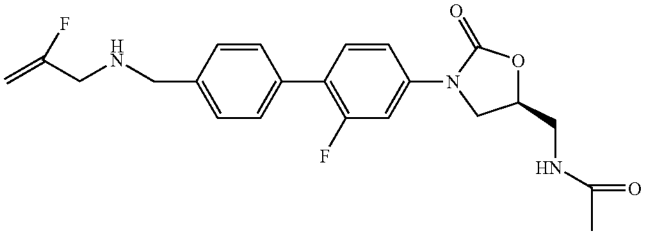 |
| 81 | 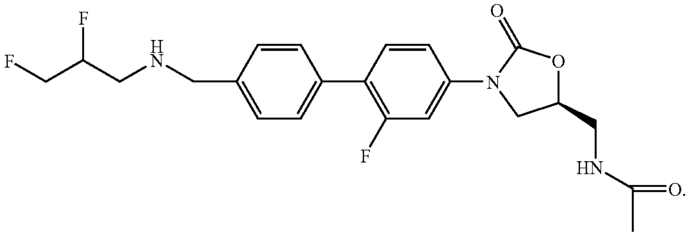 |

39. A pharmaceutically acceptable salt according to claim 38, wherein said salt is a monohydrochloride salt.

40. A pharmaceutical composition comprising one or more compounds according to claim 1 and a pharmaceutically acceptable carrier.

41. A compound having the formula:

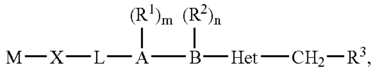

or a pharmaceutically acceptable salt, ester or prodrug thereof, wherein:

A is phenyl

B is selected from the group consisting of:

phenyl, pyridyl, pyrazinyl, pyrimidinyl, and pyridazinyl;

Het-$CH_2$—$R^3$ is selected from the group consisting of:

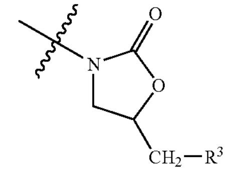
,
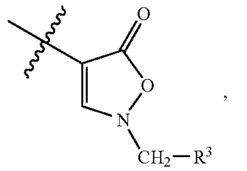
,
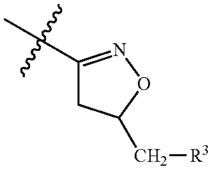
, and
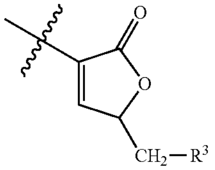
;

M is selected from the group consisting of:

a) $C_{1-6}$ alkyl, b) $C_{2-6}$ alkenyl, and c) $C_{2-6}$ alkynyl, wherein i) any of a)–c) is substituted with one or more moieties selected from the group consisting of F, Cl, Br, and I; and ii) any of a)–c) optionally is further substituted with one or more $R^4$ groups;

X is selected from the group consisting of:

a) —O—, b) —$NR^5$—, c) —N(O)—, d) —N($OR^5$)—, e) —$S(O)_p$—, f) —$NR^5$—N═, g) ═N—$NR^5$—, h) —O—N═, i) ═N—O—, j) —N═, k) ═N—, l) —$NR^5$—$NR^5$—, m) —$NR^5$C(O)O—, n) —OC(O)$NR^5$—, o) —$NR^5$C(O)$NR^5$—, p) —$NR^5$C($NR^5$)$NR^5$—, and q)

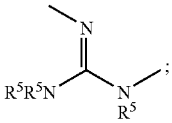
;

L is selected from the group consisting of:

a) $C_{1-6}$ alkyl, b) $C_{2-6}$ alkenyl, and c) $C_{2-6}$ alkynyl, wherein any of a)–c) optionally is substituted with one or more $R^4$ groups;

$R^1$, at each occurrence, independently is selected from the group consisting of:

a) F, b) Cl, c) Br, d) I, e) —$CF_3$, f) —$OR^7$, g) —CN, h) —$NO_2$, i) —$NR^7R^7$, j) —C(O)$R^7$, k) —C(O)$OR^7$, l) —OC(O)$R^7$, m) —C(O)$NR^7R^7$, n) —$NR^7$C(O)$R^7$, o) —OC(O)$NR^7R^7$, p) —$NR^7$C(O)$OR^7$, q) —$NR^7$C(O)$NR^7R^7$, r) —C(S)$R^7$, s) —C(S)$OR^7$, t) —OC(S)$R^7$, u) —C(S)$NR^7R^7$, v) —$NR^7$C(S)$R^7$, w) —OC(S)$NR^7R^7$, x) —$NR^7$C(S)$OR^7$, y) —$NR^7$C(S)$NR^7$, $R^7$, z) —$NR^7$C($NR^7$)$NR^7R^7$, aa) —$S(O)_pR^7$, bb) —$SO_2NR^7R^7$, and cc) $R^7$;

$R^2$, at each occurrence, independently is selected from the group consisting of:

a) F, b) Cl, c) Br, d) I, e) —$CF_3$, f) —$OR^7$, g) —CN, h) —$NO_2$, i) —$NR^7R^7$, j) —C(O)$R^7$, k) —C(O)$OR^7$, l) —OC(O)$R^7$, m) —C(O)$NR^7R^7$, n) —$NR^7$C(O)$R^7$, o) —OC(O)$NR^7R^7$, p) —$NR^7$C(O)$OR^7$, q) $NR^7$C(O)$NR^7R^7$, r) —C(S)$R^7$, s) —C(S)$R^7$, t) —OC(S)$R^7$, u) —C(S)$NR^7R^7$, v) —$NR^7$C(S)$R^7$, w) —OC(S)$NR^7R^7$, x) —$NR^7$C(S)$OR^7$, y) —$NR^7$C(S)$NR^7R^7$, z) —$NR^7$C($NR^7$)$NR^7R^7$, aa) —$S(O)_pR^7$, bb) —$SO_2NR^7R^7$, and cc) $R^7$;

$R^3$ is selected from the group consisting of:

a) —$NR^7R^7$, b) —C(O)$R^7$, c) —C(O)$OR^7$, d) —OC(O)$R^7$, e) —C(O)$NR^7R^7$, f) —$NR^7$C(O)$R^7$, g) —OC(O)$NR^7R^7$, h) —$NR^7$C(O)$OR^7$, i) —$NR^7$C(O)$NR^7R^7$, j) —C(S)$R^7$, k) —C(S)$OR^7$, l) —OC(S)$R^7$, m) —(S)$NR^7R^7$, n) —$NR^7$C(S)$R^7$, o) —OC(S)$NR^7R^7$, p) —$NR^7$C(S)$OR^7$, q) —$NR^7$C(S)$NR^7R^7$, r) —$NR^7$C($NR^7$)$NR^7R^7$, s) —$SOR^7$, t) $SO_2R^7$, u)—$SO_2NR^7R^7$, and v) $R^7$;

$R^4$, at each occurrence, independently is selected from the group consisting of:

a) H, b) F, c) Cl, d) Br, e) I, f) ═O, g) ═S, h) ═$NR^5$, i) ═$NOR^5$, j) ═N—$NR^5R^5$, k) —$CF_3$, l) —$OR^5$, m) —CN, n) —$NO_2$, o) —$NR^5R^5$, p) —C(O)$R^5$, q) —C(O)$OR^5$, r) —OC(O)$R^5$, s) —C(O)$NR^5R^5$, t) —$NR^5$C(O)$R^5$, u) —OC(O)$NR^5R^5$, v) —$NR^5$C(O)$OR^5$, w) —$NR^5$C(O)$NR^5R^5$, x) —C(S)$R^5$, y) —C(S)$OR^5$, z) —OC(S)$R^5$, aa) —C(S)$NR^5R^5$, bb) —$NR^5$C(S)$R^5$, cc) —OC(S)$NR^5R^5$, dd) —$NR^5$C(S)$OR^5$, ee) —$NR^5$C(S)$NR^5R^5$, ff) —$NR^5$C($NR^5$)$NR^5$, $R^5$, gg) —$S(O)_pR^5$, and hh) $R^5$;

$R^5$, at each occurrence, independently is selected from the group consisting of:

a) H, b) $C_{1-6}$ alkyl, c) $C_{2-6}$ alkenyl, d) $C_{2-6}$ alkynyl, e) —C(O)—$C_{1-6}$ alkyl, f) —C(O)—$C_{2-6}$ alkenyl, g) —C(O)—$C_{2-6}$ alkynyl, h) —C(O)O—$C_{1-6}$ alkyl, i) —C(O)O—$C_{2-6}$ alkenyl, and j) —C(O)O—$C_{2-6}$ alkynyl, wherein any of b)–j) optionally is substituted with one or more $R^6$ groups;

$R^6$, at each occurrence, independently is selected from the group consisting of:

a) F, b) Cl, c) Br, d) I, e) —$CF_3$, f) —OH, g) —$OC_{1-6}$ alkyl, h) —SH, i) —$SC_{1-6}$ alkyl, j) —CN, k) —$NO_2$, l) —$NH_2$, m) —$NHC_{1-6}$ alkyl, n) —N($C_{1-6}$ alkyl)$_2$, o) —C(O)$C_{1-6}$ alkyl, p) —C(O)$OC_{1-6}$ alkyl, q) —C(O)$NH_2$, r) —C(O)$NHC_{1-6}$ alkyl, s) —C(O)N($C_{1-6}$ alkyl)$_2$, t) —NHC(O)$C_{1-6}$ alkyl, and u) —$S(O)_pC_{1-6}$ alkyl;

$R^7$, at each occurrence, independently is selected from the group consisting of:

a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3–14 membered saturated, unsaturated, or aromatic heterocycle consisting one or more heteroatoms selected from the group consisting of nitrogen, oxygen, and sulfur, g) —C(O)$C_{1-6}$ alkyl, h) —C(O)—$C_{2-6}$ alkenyl, i) —C(O)—$C_{2-6}$ alkynyl, j) —C(O)$C_{3-14}$ saturated, unsaturated, or aromatic carbocycle, k) —C(O)-3–14 membered saturated, unsaturated, or aromatic heterocycle consisting one or more heteroatoms selected from the group consisting of nitrogen, oxygen, and sulfur, l) —C(O)O—$C_{1-6}$ alkyl, m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3–14 membered saturated, unsaturated, or aromatic heterocycle consisting one or more heteroatoms selected from the group consisting of nitrogen, oxygen, and sulfur, wherein any of b)–p) optionally is substituted with one or more $R^8$ groups;

$R^8$, at each occurrence, is independently selected from the group consisting of:

a) F, b) Cl, c) Br, d) I, e) =O, f) =S, g) =$NR^9$, h) =$NOR^9$, i) =N—$NR^9R^9$, j) —$CF_3$, k) —$OR^9$, l) —CN, m) —$NO_2$, n) —$NR^9R^9$, o) —C(O)$R^9$, p) —C(O)$OR^9$, q) —OC(O)$R^9$, r) —C(O)$NR^9R^9$, s) —$NR^9C(O)R^9$, t) —OC(O)$NR^9R^9$, u) —$NR^9C(O)OR^9$, v) —$NR^9C(O)NR^9R^9$, w) —C(S)$R^9$, x) —C(S)$OR^9$, y) —OC(S)$R^9$, z) —C(S)$NR^9R^9$, aa) —$NR^9C(S)R^9$, bb) —OC(S)$NR^9R^9$, cc) —$NR^9C(S)OR^9$, dd) —$NR^9C(S)NR^9R^9$, ee) —$NR^9C(NR^9)NR^9R^9$, ff) —$S(O)_pR^9$, gg) —$SO_2NR^9R^9$, and hh) $R^9$;

$R^9$, at each occurrence, independently is selected from the group consisting of:

a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3–14 membered saturated, unsaturated, or aromatic heterocycle consisting one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated, unsaturated, or aromatic carbocycle, k) —C(O)—$C_{3-14}$ membered saturated, unsaturated, or aromatic heterocycle consisting one or more heteroatoms selected from the group consisting of nitrogen, oxygen, and sulfur, l) —C(O)O—$C_{1-6}$ alkyl, m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3–14 membered saturated, unsaturated, or aromatic heterocycle consisting one or more heteroatoms selected from the group consisting of nitrogen, oxygen, and sulfur, wherein any of b)–p) optionally is substituted with one or more moieties selected from the group consisting of:

a) F, b) Cl, c) Br, d) I, e) —$CF_3$, f) —OH, g) —$OC_{1-6}$ alkyl, h) —SH, i) —$SC_{1-6}$ alkyl, j) —CN, k) —$NO_2$, l) —$NH_2$, m) —$NHC_{1-6}$ alkyl, n) —$N(C_{1-6}\ alkyl)_2$, o) —C(O)$C_{1-6}$ alkyl, p) —C(O)$OC_{1-6}$ alkyl, q) —C(O)$NH_2$, r) —C(O)$NHC_{1-6}$ alkyl, s) —C(O)$N(C_{1-6}\ alkyl)_2$, t) —NHC(O)$C_{1-6}$ alkyl, u) —$SO_2NH_2$—, v) —$SO_2NHC_{1-6}$ alkyl, w) —$SO_2N(C_{1-6}\ alkyl)_2$, and x) —$S(O)_pC_{1-6}$ alkyl;

m is 0, 1, 2, 3, or 4;

n is 0, 1, 2, 3, or 4; and p, at each occurrence, independently is 0, 1, or 2.

42. The compound according to claim 41, having the formula:

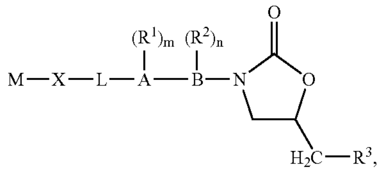

or a pharmaceutically acceptable salt, ester or prodrug thereof, wherein A, B, L, M, $R^1$, $R^2$, $R^3$, X, m, and n are defined as described in claim 41.

43. The compound according to claim 41, having the formula:

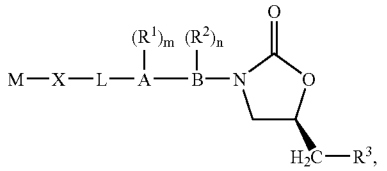

or a pharmaceutically acceptable salt, ester or prodrug thereof, wherein A, B, L, M, $R^1$, $R^2$, $R^3$, X, m, and n are defined as described in claim 41.

44. The compound according to claim 41, wherein

A is phenyl

B is selected from the group consisting of phenyl and pyridyl;

m is 0, 1, or 2; and n is 0, 1, or 2.

45. The compound according to claim 41, wherein A-B is:

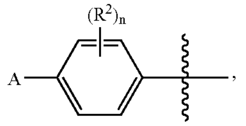

wherein A, $R^2$, and n are defined as described in claim 41.

46. The compound according to claim 45, wherein $R^2$ is selected from the group consisting of H and F, and n is 0, 1, or 2.

47. The compound according to claim 45, wherein A-B is:

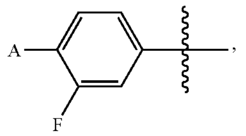

wherein A is defined as described in claim 41.

48. The compound according to claim 45, wherein A-B is:

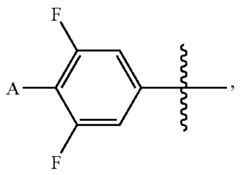

wherein A is defined as described in claim 41.

49. The compound according to claim 41, wherein A-B is:

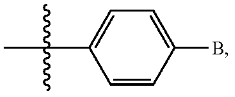

wherein B is defined as described in claim 41.

50. The compound according to claim 41, wherein $R^3$ is $—NR^7C(O)R^7$.

51. The compound according to claim 41, wherein $R^3$ is $—NHC(O)R^7$.

52. The compound according to claim 50, wherein $R^7$ is $C_{1-6}$ alkyl, optionally substituted with one or more substituents independently selected from F or Cl.

53. The compound according to claim 50 wherein $R^7$ is selected from the group consisting of $—CH_3$, $—CH_2F$, $—CHF_2$, $—CF_3$, $—CH_2Cl$, $—CHCl_2$, $—CCl_3$, $—CHFCl$, $—CF_2Cl$, and $—CFCl_2$.

54. The compound according to claim 53, wherein $R^7$ is $—CH_3$.

55. The compound according to claim 41, wherein $R^3$ is:

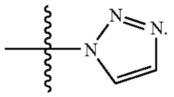

56. The compound according to claim 41, having the formula:

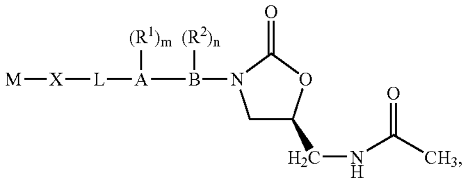

or a pharmaceutically acceptable salt, ester or prodrug thereof, wherein A, B, L, M, $R^1$, $R^2$, X, m, and n are defined as described in claim 41.

57. The compound according to claim 41, having the formula:

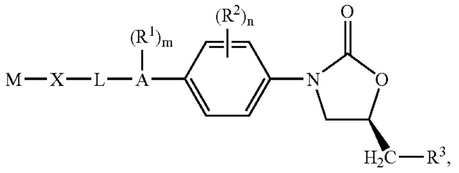

or a pharmaceutically acceptable salt, ester or prodrug thereof, wherein A, L, M, $R^1$, $R^3$, X, and m are defined as described in claim 41, $R^2$ is selected from the group consisting of H and F, and n is 0, 1, or 2.

58. The compound according to claim 41, having the formula:

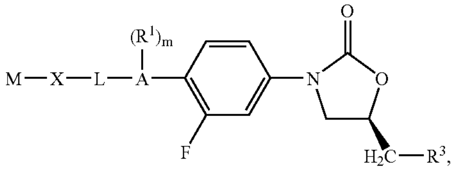

or a pharmaceutically acceptable salt, ester or prodrug thereof, wherein A, L, M, $R^1$, $R^3$, X, and m are defined as described in claim 41.

59. The compound according to claim 58, having the formula:

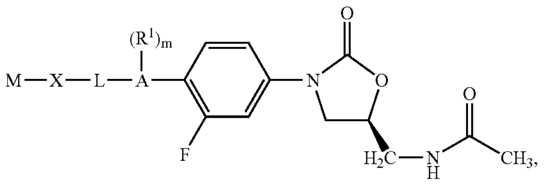

or a pharmaceutically acceptable salt, ester or prodrug thereof, wherein A, L, M, $R^1$, X, and m are defined as described in claim 41.

60. The compound according to claim 58, having the formula:

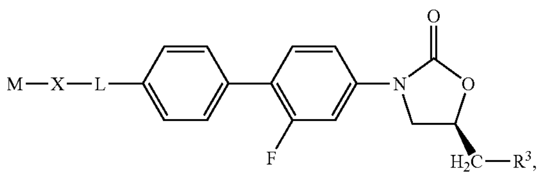

or a pharmaceutically acceptable salt, ester or prodrug thereof, wherein L, M, $R^3$, and X are defined as described in claim 41.

61. The compound according to claim 41, having the formula:

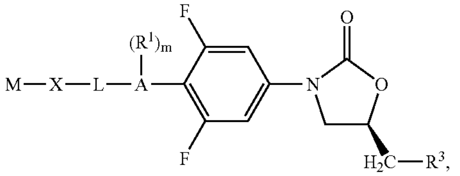

or a pharmaceutically acceptable salt, ester or prodrug thereof, wherein A, L, M, $R^1$, $R^3$, X, and m are defined as described in claim 41.

62. The compound according to claim 61, having the formula:

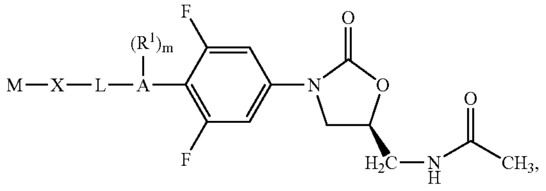

or a pharmaceutically acceptable salt, ester or prodrug thereof, wherein A, L, M, $R^1$, X, and m are defined as described in claim 41.

63. The compound according to claim 61, having the formula:

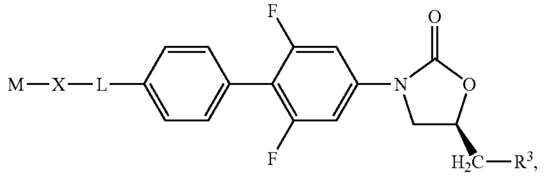

or a pharmaceutically acceptable salt, ester or prodrug thereof, wherein L, M, $R^3$, and X are defined as described in claim 41.

64. The compound according to claim 41, wherein L is $C_{1-6}$ alkyl.

65. The compound according to claim 64, wherein L is $—CH_2—$.

66. The compound according to claim 41, wherein X is selected from the group consisting of $—NR^5—$, —N(O)—, and $—N(OR^5)—$, and $R^5$ is selected from the group consisting of H and $C_{1-6}$ alkyl.

67. The compound according to claim 41, wherein X is $—NR^5—$, and $R^5$ is selected from the group consisting of H and $C_{1-6}$ alkyl.

68. The compound according to claim 67, wherein X is —NH—.

69. The compound according to claim 65, wherein X is $—NC_{1-6}$ alkyl, wherein the $C_{1-6}$ alkyl group is substituted with one or more moieties selected from the group consisting of F, Cl, Br, and I.

70. The compound according to claim 41, wherein M is $C_{1-6}$ alkyl substituted with one or more moieties selected from the group consisting of F, Cl, Br, and I.

71. The compound according to claim 70, wherein M is $C_{1-6}$ alkyl substituted with one or more F atoms.

72. The compound according to claim 71, wherein M is $—CH_2CH_2CH_2F$.

73. The compound according to claim 41, wherein M is $—CH_2CH(OH)CH_2F$.

74. A compound having the formula:

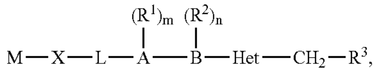

or a pharmaceutically acceptable salt, ester or prodrug thereof, wherein:

A is phenyl

B is selected from the group consisting of:

phenyl, pyridyl, pyrazinyl, pyrimidinyl, and pyridazinyl;

Het-$CH_2$—$R^3$ is selected from the group consisting of:

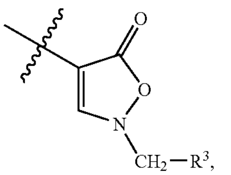

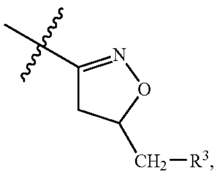

and

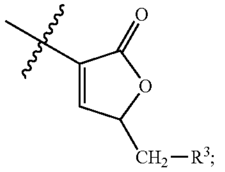

M is selected from the group consisting of:

a) $C_{1-6}$ alkyl, b) $C_{2-6}$ alkenyl, and c) $C_{2-6}$ alkynyl, wherein i) any of a)–c) is substituted with one or more moieties selected from the group consisting of F, Cl, Br, and I; and ii) any of a)–c) optionally is further substituted with one or more $R^4$ groups;

X is selected from the group consisting of:

a) —O—, b) $—NR^5—$, c) —N(O)—, d) $—N(OR^5)—$, e) $—S(O)_p—$, f) $—NR^5—N=$, g) $=N—NR^5—$, h) —O—N=, i) =N—O—, j) —N=, k) =N—, l) $—NR^5—NR^5—$, m) $—NR^5C(O)O—$, n) $—OC(O)NR^5—$, o) $—NR^5C(O)NR^5—$, p) $—NR^5C(NR^5)NR^5—$, and q)

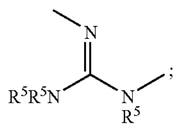

L is selected from the group consisting of:

a) $C_{1-6}$ alkyl, b) $C_{2-6}$ alkenyl, and c) $C_{2-6}$ alkynyl, wherein any of a)–c) optionally is substituted with one or more $R^4$ groups;

$R^1$, at each occurrence, independently is selected from the group consisting of:

a) F, b) Cl, c) Br, d) I, e) —$CF_3$, f) —$OR^7$, g) —CN, h) —$NO_2$, i) —$NR^7R^7$, j) —C(O)$R^7$, k) —C(O)O$R^7$, l) —OC(O)$R^7$, m) —C(O)N$R^7R^7$, n) —$NR^7$C(O)$R^7$, o) —OC(O)N$R^7R^7$, p) —$NR^7$C(O)O$R^7$, q) —$NR^7$C(O)N$R^7R^7$, r) —C(S)$R^7$, s) —C(S)O$R^7$, t) —OC(S)$R^7$, u) —C(S)N$R^7R^7$, v) —$NR^7$C(S)$R^7$, w) —OC(S)N$R^7R^7$, x) —$NR^7$C(S)O$R^7$, y) —$NR^7$C(S)N$R^7$, $R^7$, z) —$NR^7$C($NR^7$)N$R^7R^7$, aa) —S(O)$_p$$R^7$, bb) —$SO_2NR^7R^7$, and cc) $R^7$;

$R^2$, at each occurrence, independently is selected from the group consisting of:

a) F, b) Cl, c) Br, d) I, e) —$CF_3$, f) —$OR^7$, g) —CN, h) —$NO_2$, i) —$NR^7R^7$, j) —C(O)$R^7$, k) —C(O)O$R^7$, l) —OC(O)$R^7$, m) —C(O)N$R^7R^7$, n) —$NR^7$C(O)$R^7$, o) —OC(O)N$R^7R^7$, p) —$NR^7$C(O)O$R^7$, q) —$NR^7$C(O)N$R^7R^7$, r) —C(S)$R^7$, s) —C(S)$R^7$, t) —OC(S)$R^7$, u) —C(S)N$R^7R^7$, v) —$NR^7$C(S)$R^7$, w) —OC(S)N$R^7R^7$, x) —$NR^7$C(S)O$R^7$, y) —$NR^7$C(S)N$R^7R^7$, z) —$NR^7$C($NR^7$)N$R^7R^7$, aa) —S(O)$_p$$R^7$, bb) —$SO_2NR^7R^7$, and cc) $R^7$;

$R^3$ is selected from the group consisting of:

a) —$OR^7$, b) —$NR^7R^7$, c) —C(O)$R^7$, d) —C(O)O$R^7$, e) —OC(O)$R^7$, f) —C(O)N$R^7R^7$, g) —$NR^7$C(O)$R^7$, h) —OC(O)N$R^7R^7$, i) —$NR^7$C(O)O$R^7$, j) —$NR^7$C(O)N$R^7R^7$, k) —C(S)$R^7$, l) —C(S)O$R^7$, m) —OC(S)$R^7$, n) —C(S)N$R^7R^7$, o) —$NR^7$C(S)$R^7$, p) —OC(S)N$R^7R^7$, q) —$NR^7$C(S)O$R^7$, r) —$NR^7$C(S)N$R^7R^7$, s) —$NR^7$C($NR^7$)N$R^7R^7$, t) —S(O)$_p$$R^7$, u) —$SO_2NR^7R^7$, and v) $R^7$;

$R^4$, at each occurrence, independently is selected from the group consisting of:

a) H, b) F, c) Cl, d) Br, e) I, f) ═O, g) ═S, h) ═$NR^5$, i) ═NO$R^5$, j) ═N—N$R^5R^5$, k) —$CF_3$, l) —$OR^5$, m) —CN, n) —$NO_2$, o) —$NR^5R^5$, p) —C(O)$R^5$, q) —C(O)O$R^5$, r) —OC(O)$R^5$, s) —C(O)N$R^5R^5$, t) —$NR^5$C(O)$R^5$, u) —OC(O)N$R^5R^5$, v) —$NR^5$C(O)O$R^5$, w) —$NR^5$C(O)N$R^5R^5$, x) —C(S)$R^5$, y) —C(S)O$R^5$, z) —OC(S)$R^5$, aa) —C(S)N$R^5R^5$, bb) —$NR^5$C(S)$R^5$, cc) —OC(S)N$R^5R^5$, dd) —$NR^5$C(S)O$R^5$, ee) —$NR^5$C(S)N$R^5R^5$, ff) —$NR^5$C($NR^5$)N$R^5$, $R^5$, gg) —S(O)$_p$$R^5$, and hh) $R^5$;

$R^5$, at each occurrence, independently is selected from the group consisting of:

a) H, b) $C_{1-6}$ alkyl, c) $C_{2-6}$ alkenyl, d) $C_{2-6}$ alkynyl, e) —C(O)—$C_{1-6}$ alkyl, f) —C(O)—$C_{2-6}$ alkenyl, g) —C(O)—$C_{2-6}$ alkynyl, h) —C(O)O—$C_{1-6}$ alkyl, i) —C(O)O—$C_{2-6}$ alkenyl, and j) —C(O)O—$C_{2-6}$ alkynyl, wherein any of b)–j) optionally is substituted with one or more $R^6$ groups;

$R^6$, at each occurrence, independently is selected from the group consisting of:

a) F, b) Cl, c) Br, d) I, e) —$CF_3$, f) —OH, g) —O$C_{1-6}$ alkyl, h) —SH, i) —S$C_{1-6}$ alkyl, j) —CN, k) —$NO_2$, l) —$NH_2$, m) —NH$C_{1-6}$ alkyl, n) —N($C_{1-6}$ alkyl)$_2$, o) —C(O)$C_{1-6}$ alkyl, p) —C(O)O$C_{1-6}$ alkyl, q) —C(O)$NH_2$, r) —C(O)NH$C_{1-6}$ alkyl, s) —C(O)N($C_{1-6}$ alkyl)$_2$, t) —NHC(O)$C_{1-6}$ alkyl, and u) —S(O)$_p$$C_{1-6}$ alkyl;

$R^7$, at each occurrence, independently is selected from the group consisting of:

a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3–14 membered saturated, unsaturated, or aromatic heterocycle consisting one or more heteroatoms selected from the group consisting of nitrogen, oxygen, and sulfur, g) —C(O)$C_{1-6}$ alkyl, h) —C(O)—$C_{2-6}$ alkenyl, i) —C(O)—$C_{2-6}$ alkynyl, j) —C(O)$C_{3-14}$ saturated, unsaturated, or aromatic carbocycle, k) —C(O)-3–14 membered saturated, unsaturated, or aromatic heterocycle consisting one or more heteroatoms selected from the group consisting of nitrogen, oxygen, and sulfur, l) —C(O)O—$C_{1-6}$ alkyl, m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3–14 membered saturated, unsaturated, or aromatic heterocycle consisting one or more heteroatoms selected from the group consisting of nitrogen, oxygen, and sulfur, wherein any of b)–p) optionally is substituted with one or more $R^8$ groups;

$R^8$, at each occurrence, is independently selected from the group consisting of:

a) F, b) Cl, c) Br, d) I, e) ═O, f) ═S, g) ═$NR^9$, h) ═NO$R^9$, i) ═N—N$R^9R^9$, j) —$CF_3$, k) —$OR^9$, l) —CN, m) —$NO_2$, n) —$NR^9R^9$, o) —C(O)$R^9$, p) —C(O)O$R^9$, q) —OC(O)$R^9$, r) —C(O)N$R^9R^9$, s) —$NR^9$C(O)$R^9$, t) —OC(O)N$R^9R^9$, u) —$NR^9$C(O)O$R^9$, v) —$NR^9$C(O)N$R^9R^9$, w) —C(S)$R^9$, x) —C(S)O$R^9$, y) —OC(S)$R^9$, z) —C(S)N$R^9R^9$, aa) —$NR^9$C(S)$R^9$, bb) —OC(S)N$R^9R^9$, cc) —$NR^9$C(S)O$R^9$, dd) —$NR^9$C(S)N$R^9R^9$, ee) —$NR^9$C($NR^9$)N$R^9R^9$, ff) —S(O)$_p$$R^9$, gg) —$SO_2NR^9R^9$, and hh) $R^9$;

$R^9$, at each occurrence, independently is selected from the group consisting of:

a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3–14 membered saturated, unsaturated, or aromatic heterocycle consisting one or more heteroatoms selected from the group consisting of nitrogen, oxygen, and sulfur, g) —C(O)—$C_{1-6}$ alkyl, h) —C(O)$C_{2-6}$ alkenyl, i) —C(O)—$C_{2-6}$ alkynyl, j) —C(O)$C_{3-14}$ saturated, unsaturated, or aromatic carbocycle, k) —C(O)—$C_{3-14}$ membered saturated, unsaturated, or aromatic heterocycle consisting one or more heteroatoms selected from the group consisting of nitrogen, oxygen, and sulfur, l) —C(O)O—$C_{1-6}$ alkyl, m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3–14 membered saturated, unsaturated, or aromatic heterocycle consisting one or more heteroatoms selected from the group consisting of nitrogen, oxygen, and sulfur, wherein any of b)–p) optionally is substituted with one or more moieties selected from the group consisting of:

a) F, b) Cl, c) Br, d) I, e) —$CF_3$, f) —OH, g) —O$C_{1-6}$ alkyl, h) —SH, i) —S$C_{1-6}$ alkyl, j) —CN, k) —$NO_2$, l) —$NH_2$, m) —NH$C_{1-6}$ alkyl, n) —N($C_{1-6}$ alkyl)$_2$, o) —C(O)$C_{1-6}$ alkyl, p) —C(O)O$C_{1-6}$ alkyl, q) —C(O)$NH_2$, r) —C(O)NH$C_{1-6}$ alkyl, s) —C(O)N($C_{1-6}$ alkyl)$_2$, t) —NHC(O)$C_{1-6}$ alkyl, u) —$SO_2NH_2$—, v) —$SO_2$NH$C_{1-6}$ alkyl, w) —$SO_2$N($C_{1-6}$ alkyl)$_2$, and x) —S(O)$_p$$C_{1-6}$ alkyl;

m is 0, 1, 2, 3, or 4;

n is 0, 1, 2, 3, or 4; and p, at each occurrence, independently is 0, 1, or 2.

75. The compound according to claim 74, wherein

A is phenyl

B is selected from the group consisting of phenyl and pyridyl;

m is 0, 1, or 2; and n is 0, 1, or 2.

76. The compound according to claim 74, wherein A-B is:

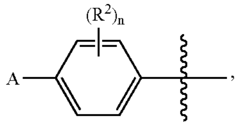

wherein A, $R^2$, and n are defined as described in claim 74.

77. The compound according to claim 76, wherein $R^2$ is selected from the group consisting of H and F, and n is 0, 1, or 2.

78. The compound according to claim 76, wherein A-B is:

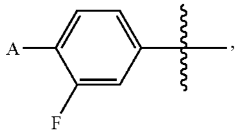

wherein A is defined as described in claim 74.

79. The compound according to claim 76, wherein A-B is:

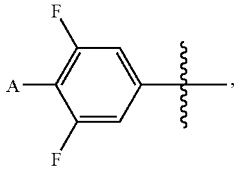

wherein A is defined as described in claim 74.

80. The compound according to claim 74, wherein A-B is:

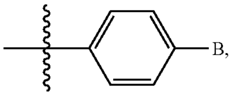

wherein B is defined as described in claim 74.

81. The compound according to claim 74, wherein $R^3$ is $—NR^7C(O)R^7$.

82. The compound according to claim 74, wherein $R^3$ is $—NHC(O)R^7$.

83. The compound according to claim 81, wherein $R^7$ is $C_{1-6}$ alkyl, optionally substituted with one or more substituents independently selected from F or Cl.

84. The compound according to claim 81 wherein $R^7$ is selected from the group consisting of $—CH_3$, $—CH_2F$, $—CHF_2$, $—CF_3$, $—CH_2Cl$, $—CHCl_2$, $—CCl_3$, $—CHFCl$, $—CF_2Cl$, and $—CFCl_2$.

85. The compound according to claim 84, wherein $R^7$ is $—CH_3$.

86. The compound according to claim 74, wherein $R^3$ is:

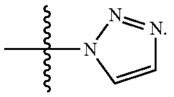

87. The compound according to claim 74, wherein L is $C_{1-6}$ alkyl.

88. The compound according to claim 87, wherein L is $—CH_2—$.

89. The compound according to claim 74, wherein X is selected from the group consisting of $—NR^5—$, $—N(O)—$, and $—N(OR^5)—$, and $R^5$ is selected from the group consisting of H and $C_{1-6}$ alkyl.

90. The compound according to claim 74, wherein X is $—NR^5—$, and $R^5$ is selected from the group consisting of H and $C_{1-6}$ alkyl.

91. The compound according to claim 90, wherein X is —NH—.

92. The compound according to claim 90, wherein X is $—NC_{1-6}$ alkyl, wherein the $C_{1-6}$ alkyl group is substituted with one or more moieties selected from the group consisting of F, Cl, Br, and I.

93. The compound according to claim 74, wherein M is $C_{1-6}$ alkyl substituted with one or more moieties selected from the group consisting of F, Cl, Br, and I.

94. The compound according to claim 93, wherein M is $C_{1-6}$ alkyl substituted with one or more F atoms.

95. The compound according to claim 94, wherein M is $—CH_2CH_2CH_2F$.

96. The compound according to claim 74, wherein M is $—CH_2CH(OH)CH_2F$.

97. A compound having the structure

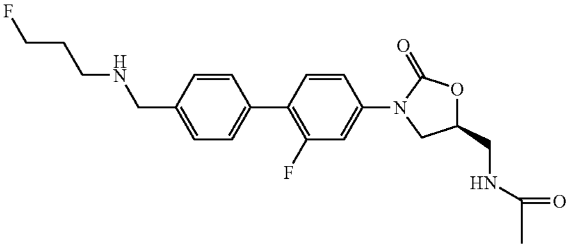

or a pharmaceutically acceptable salt or prodrug thereof.

98. A pharmaceutically acceptable salt of a compound according to claim 97.

99. A pharmaceutically acceptable salt according to claim 98, wherein said salt is a monohydrochloride salt.

100. A pharmaceutical composition comprising a compound according to claim 97 and a pharmaceutically acceptable carrier.

101. A pharmaceutical composition comprising a compound according to claim 98 and a pharmaceutically acceptable carrier.

102. A pharmaceutical composition comprising a compound according to claim 99 and a pharmaceutically acceptable carrier.

103. A compound having the structure

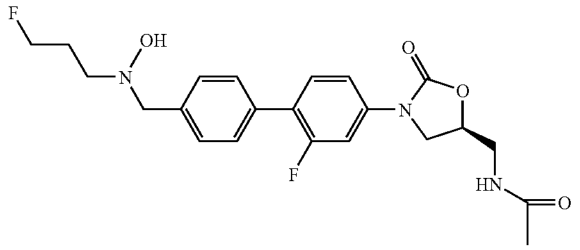

or a pharmaceutically acceptable salt, ester, or prodrug thereof.

104. A pharmaceutically acceptable salt of a compound according to claim 103.

105. A pharmaceutically acceptable salt according to claim 104, wherein said salt is a monohydrochloride salt.

106. A pharmaceutical composition comprising a compound according to claim 103 and a pharmaceutically acceptable carrier.

107. A pharmaceutical composition comprising a compound according to claim 104 and a pharmaceutically acceptable carrier.

108. A pharmaceutical composition comprising a compound according to claim 105 and a pharmaceutically acceptable carrier.

109. A pharmaceutically acceptable salt according to claim 38, wherein said salt is a hydrochloride salt.

110. A pharmaceutically acceptable salt according to claim 98, wherein said salt is a hydrochloride salt.

111. A pharmaceutically acceptable salt according to claim 104, wherein said salt is a hydrochloride salt.

* * * * *

UNITED STATES PATENT AND TRADEMARK OFFICE

CERTIFICATE OF CORRECTION

PATENT NO. : 7,129,259 B2 
APPLICATION NO. : 11/001446
DATED : October 31, 2006
INVENTOR(S) : Chen et al.

It is certified that error appears in the above-identified patent and that said Letters Patent is hereby corrected as shown below:

On Title page item 75 should read

Applicant(s)

Shili Chen, Cheshire, CT;
Jiacheng Zhou, Hockessin, DE;
Yusheng Wu, Lebanon, NJ;
Deping Wang, Cheshire, CT;
Joseph M. Salvino, Branford, CT;
Adegboyega K. Oyelere, Hamden, CT;
Rongliang Lou, Cheshire, CT;
Ashoke Bhattacharjee, West Haven, CT;
Yi Chen, Cheshire, CT.

Signed and Sealed this

Sixth Day of March, 2007

JON W. DUDAS
*Director of the United States Patent and Trademark Office*